(12) United States Patent
Seshimo et al.

(10) Patent No.: US 8,932,795 B2
(45) Date of Patent: Jan. 13, 2015

(54) RESIST COMPOSITION, METHOD OF FORMING RESIST PATTERN, NOVEL COMPOUND, AND ACID GENERATOR

(75) Inventors: Takehiro Seshimo, Kawasaki (JP); Yoshiyuki Utsumi, Kawasaki (JP); Kazushige Dohtani, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 31 days.

(21) Appl. No.: 13/106,691

(22) Filed: May 12, 2011

(65) Prior Publication Data

US 2011/0287362 A1 Nov. 24, 2011

(30) Foreign Application Priority Data

May 19, 2010 (JP) .................... 2010-115452

(51) Int. Cl.
*G03F 7/004* (2006.01)
*G03F 7/20* (2006.01)
*C07D 333/52* (2006.01)
*C07D 333/76* (2006.01)
*C07D 493/18* (2006.01)
*C07D 497/08* (2006.01)
*G03F 7/039* (2006.01)

(52) U.S. Cl.
CPC ............ *G03F 7/0045* (2013.01); *C07D 333/52* (2013.01); *C07D 333/76* (2013.01); *C07D 493/18* (2013.01); *C07D 497/08* (2013.01); *G03F 7/0046* (2013.01); *G03F 7/0397* (2013.01); *G03F 7/2041* (2013.01)
USPC ........................................ 430/270.1; 430/325

(58) Field of Classification Search
None
See application file for complete search history.

(56) References Cited

U.S. PATENT DOCUMENTS

| 5,945,517 | A | 8/1999 | Nitta et al. |
| 6,153,733 | A | 11/2000 | Yukawa et al. |
| 6,444,397 | B2 | 9/2002 | Hada et al. |
| 6,949,325 | B2 | 9/2005 | Li et al. |
| 7,074,543 | B2 | 7/2006 | Iwai et al. |
| 2008/0220369 | A1* | 9/2008 | Yamaguchi et al. ........ 430/281.1 |
| 2008/0311522 | A1* | 12/2008 | Iwai et al. ................. 430/286.1 |
| 2009/0162788 | A1* | 6/2009 | Hada et al. ................ 430/285.1 |
| 2009/0214982 | A1* | 8/2009 | Shimizu et al. ............ 430/285.1 |
| 2009/0246694 | A1* | 10/2009 | Ohsawa et al. ............ 430/285.1 |
| 2009/0317743 | A1 | 12/2009 | Shiono et al. |
| 2010/0323296 | A1* | 12/2010 | Ichikawa et al. .......... 430/286.1 |

FOREIGN PATENT DOCUMENTS

| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | 2003-241385 | 8/2003 |
| JP | A-2005-336452 | 12/2005 |
| JP | A-2006-259582 | 9/2006 |
| JP | A-2006-317803 | 11/2006 |
| JP | A-2009-258695 | 11/2009 |
| JP | A-2010-002870 | 1/2010 |
| WO | WO 2004/074242 A2 | 9/2004 |

* cited by examiner

*Primary Examiner* — Cynthia H Kelly
*Assistant Examiner* — Anna Malloy
(74) *Attorney, Agent, or Firm* — Knobbe Martens Olson & Bear LLP

(57) ABSTRACT

A resist composition including a base component (A) which exhibits changed solubility in an alkali developing solution under action of acid and an acid-generator component (B) which generates acid upon exposure, the acid-generator component (B) including an acid generator (B1) represented by general formula (b1-1) shown below (in the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; each of $R^1$ and $R^2$ independently represents a divalent linking group; and $Z^+$ represents a monovalent organic cation).

[Chemical Formula 1]

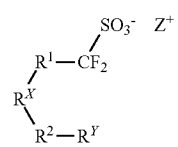

(b1-1)

6 Claims, No Drawings

RESIST COMPOSITION, METHOD OF FORMING RESIST PATTERN, NOVEL COMPOUND, AND ACID GENERATOR

TECHNICAL FIELD

The present invention relates to a resist composition, a method of forming a resist pattern using the same, a novel compound useful as an acid generator for a resist composition, and an acid generator.

Priority is claimed on Japanese Patent Application No. 2010-115452, filed May 19, 2010, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in an alkali developing solution under the action of acid and an acid-generator component that generates acid upon exposure.

For example, a chemically amplified positive resist contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid-generator component, and the action of this acid causes an increase in the solubility of the resin component in an alkali developing solution, making the exposed portions soluble in the alkali developing solution.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 1).

On the other hand, as acid generators usable in a chemically amplified resist composition, various types have been proposed including, for example, onium salt acid generators such as iodonium salts and sulfonium salts; oxime sulfonate acid generators; diazomethane acid generators; nitrobenzylsulfonate acid generators; iminosulfonate acid generators; and disulfone acid generators.

Among these, as acid generators, onium salt acid generators having an onium ion such as triphenylsulfonium as the cation moiety are particularly used. As the anion moiety for onium salt acid generators, an alkylsulfonate ion or a fluorinated alkylsulfonate ion in which part or all of the hydrogen atoms within the aforementioned alkylsulfonate ion has been substituted with fluorine atoms is typically used.

Further, a photoacid generator which generates a sulfonic acid represented by general formula (1a) shown below has also been proposed (see Patent Document 2).

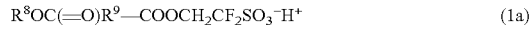

$$R^8OC(=O)R^9\text{—}COOCH_2CF_2SO_3^-H^+ \qquad (1a)$$

In the formula, $R^8O$ represents a hydroxy group or a substituted or unsubstituted linear, branched or cyclic organooxy group of 1 to 20 carbon atoms; and $R^9$ represents a divalent aliphatic group of 1 to 20 carbon atoms which may have a substituent containing a hetero atom such as an oxygen atom, a nitrogen atom or a sulfur atom, provided that $R^9$ may form a monocyclic or polycyclic structure with $R^8O$.

DOCUMENTS OF RELATED ART

Patent Document

[Patent Document 1] Japanese Unexamined Patent Application, First Publication No. 2003-241385
[Patent Document 2] Japanese Unexamined Patent Application, First Publication No. 2009-258695

SUMMARY OF THE INVENTION

Currently, among the aforementioned onium salt-based acid generators, onium salt-based acid generators having a perfluoroalkylsulfonic acid ion as the anion moiety are generally used.

However, in recent years, as miniaturization of resist patterns progress, further improvement in resist pattern shape and various lithography properties have been demanded for conventional chemically amplified resist compositions containing an onium salt-based acid generator having a perfluoroalkylsulfonic acid ion as the anion moiety. Therefore, development of a novel compound which is more favorable as an acid generator for a resist composition has been demanded.

When a resist pattern is formed using a resist composition containing the photoacid generator of Patent Document 2, the roughness, the mask reproducibility and the exposure latitude of the resist pattern was unsatisfactory, and further improvement in these properties have been demanded.

The present invention takes the above circumstances into consideration, with an object of providing a compound useful as an acid generator for a resist composition, an acid generator including the compound, a resist composition containing the acid generator, and a method of forming a resist pattern using the resist composition.

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) represented by general formula (b1-1) shown below.

[Chemical Formula 1.]

(b1-1)

In the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; each of $R^1$ and $R^2$ independently represents a divalent linking group; and $Z^+$ represents a monovalent organic cation.

A second aspect of the present invention is a method of forming a resist pattern, including forming a resist film on a substrate using a resist composition according to the first aspect, subjecting the resist film to exposure, and subjecting the resist film to alkali developing to form a resist pattern.

A third aspect of the present invention is a compound represented by general formula (b0-1) shown below.

[Chemical Formula 2.]

(b0-1)

In the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; each of $R^1$ and $R^2$ independently represents a divalent linking group; and $Z'^+$ represents a monovalent cation.

A fourth aspect of the present invention is an acid generator including the compound of the third aspect wherein $Z'^+$ in general formula (b0-1) is an organic cation.

In the present description and claims, an "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

The term "(meth)acrylic acid" is a generic term that includes either or both of acrylic acid having a hydrogen atom bonded to the α-position and methacrylic acid having a methyl group bonded to the α-position.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

According to the present invention, there are provided a compound useful as an acid generator for a resist composition, an acid generator including the compound, a resist composition containing the acid generator, and a method of forming a resist pattern using the resist composition.

According to the resist composition and method of forming a resist pattern of the present invention, a resist pattern with excellent lithography properties such as mask reproducibility and exposure latitude and reduced roughness can be formed.

DETAILED DESCRIPTION OF THE INVENTION

<<Resist Composition>>

The resist composition according to the first aspect of the present invention includes a base component (A) which exhibits changed solubility in an alkali developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

As the component (A), a resin component which exhibits changed solubility in an alkali developing solution under action of acid may be used. Alternatively, as the component (A), a low molecular weight material which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; a (meth)acrylic resin or polycycloolefin resin having a sulfoneamide group, as disclosed in U.S. Pat. No. 6,949,325; a resin having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycycloolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

When the resist composition of the present invention is a positive resist composition, as the component (A), a base component which exhibits increased solubility in an alkali developing solution by action of acid (hereafter, referred to as "component (A0)") is used.

More specifically, the component (A0) is substantially insoluble in an alkali developing solution prior to exposure, but when acid is generated from the component (B) upon exposure, the action of this acid causes an increase in the solubility of the base component in an alkali developing solution. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component (A0) which exhibits increased solubility in an alkali developing solution under action of acid. That is, the resist composition of the present invention is preferably a positive resist composition.

The component (A0) may be a resin component (A1) that exhibits increased solubility in an alkali developing solution under the action of acid (hereafter, frequently referred to as "component (A1)"), a low molecular weight material (A2) that exhibits increased solubility in an alkali developing solution under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the expression "structural unit derived from an acrylate ester" refers to a structural unit that is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. Examples of the substituent include an alkyl group of 1 to 5 carbon atoms and a halogenated alkyl group of 1 to 5 carbon atoms.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the alkyl group of 1 to 5 carbon atoms for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated alkyl group of 1 to 5 carbon atoms include groups in which part or all of the hydrogen atoms of the aforementioned "alkyl group of 1 to 5 carbon atoms for the substituent at the α-position" are substituted with halogen atoms. Examples of the halogen atom include a fluorine atom, a chlorine atom, a bromine atom and an iodine atom, and a fluorine atom is particularly desirable.

In the present invention, it is preferable that a hydrogen atom, an alkyl group of 1 to 5 carbon atoms or a halogenated alkyl group of 1 to 5 carbon atoms is bonded to the α-position of the acrylate ester, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

In the resist composition of the present invention, it is particularly desirable that the component (A1) include a structural unit (a1) derived from an acrylate ester containing an acid dissociable, dissolution inhibiting group.

Further, it is preferable that the component (A1) include a structural unit (a2) derived from an acrylate ester containing a lactone-containing cyclic group, as well as the structural unit (a1).

Furthermore, it is preferable that the component (A1) include a structural unit (a3) derived from an acrylate ester containing a polar group-containing aliphatic hydrocarbon group, as well as the structural unit (a1), or the structural unit (a1) and the structural unit (a2).

Further, in the present invention, the component (A1) may also include a structural unit other than the aforementioned structural units (a1) to (a3).

(Structural Unit (a1))

The structural unit (a1) is a structural unit derived from an acrylate ester containing an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic branched" refers to a branched structure having no aromaticity.

The "aliphatic branched, acid dissociable, dissolution inhibiting group" is not limited to be constituted of only carbon and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group.

Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be used. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be used.

[Chemical Formula 3.]

(a1"-1)

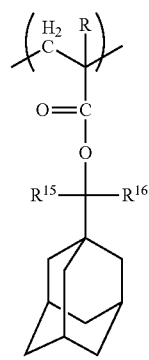

(a1″-2)

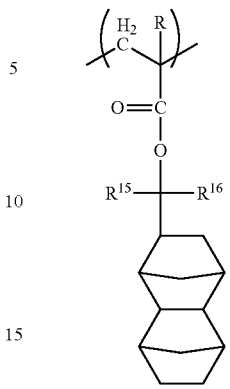

(a1″-6)

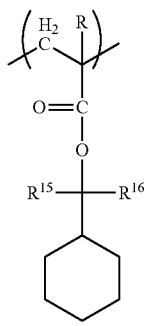

(a1″-3)

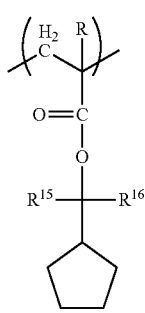

(a1″-4)

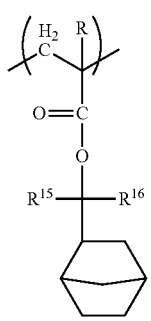

(a1″-5)

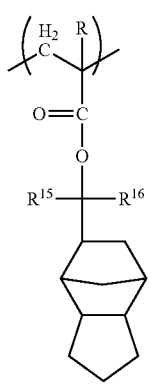

In the formulas, R represents a hydrogen atom, a lower alkyl group or a halogenated lower alkyl group; and $R^{15}$ and $R^{16}$ each independently represent an alkyl group (which may be linear or branched, and preferably has 1 to 5 carbon atoms).

In general formulas (a1″-1) to (a1″-6) above, the lower alkyl group or halogenated lower alkyl group for R are the same as the alkyl group of 1 to 5 carbon atoms or halogenated alkyl group of 1 to 5 carbon atoms which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 4.]

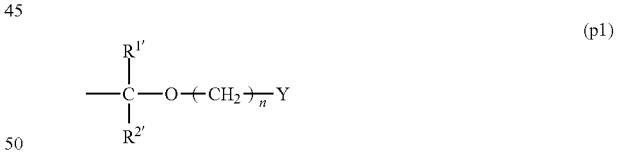

(p1)

In the formula, $R^{1\prime}$ and $R^{2\prime}$ each independently represent a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same lower alkyl groups as those described above for R can be used, although a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 5.]

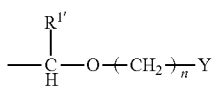
(p1-1)

In the formula, $R^{1'}$, n and Y are the same as defined above.

As the lower alkyl group for Y, the same as the lower alkyl groups for R above can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 6.]

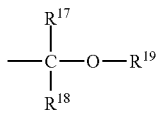
(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 7.]

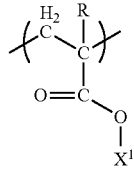
(a1-0-1)

In the formula, R represents a hydrogen atom, a lower alkyl group or a halogenated lower alkyl group; and $X^1$ represents an acid dissociable, dissolution inhibiting group.

[Chemical Formula 8.]

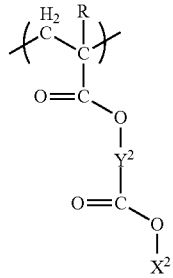
(a1-0-2)

In the formula, R represents a hydrogen atom, a lower alkyl group or a halogenated lower alkyl group; $X^2$ represents an acid dissociable, dissolution inhibiting group; and $Y^2$ represents a divalent linking group.

In general formula (a1-0-1) above, the lower alkyl group or halogenated lower alkyl group for R are the same as the alkyl group of 1 to 5 carbon atoms or halogenated alkyl group of 1 to 5 carbon atoms which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

As the divalent linking group for $Y^2$, an alkylene group, a divalent aliphatic cyclic group or a divalent linking group containing a hetero atom can be mentioned.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, and "-A-O—B— (wherein O is an oxygen atom, and each of A and B independently represents a divalent hydrocarbon group which may have a substituent)".

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent.

A hydrocarbon "has a substituent" means that part or all of the hydrogen atoms within the hydrocarbon group is substituted with groups or atoms other than hydrogen atom.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As a linear aliphatic hydrocarbon group, a linear alkylene group is preferable, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylalkylene groups, e.g., alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

As examples of the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

Examples of the hydrocarbon group for A include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

As the hydrocarbon group for B, the same divalent hydrocarbon groups as those described above for A can be used.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 9.]

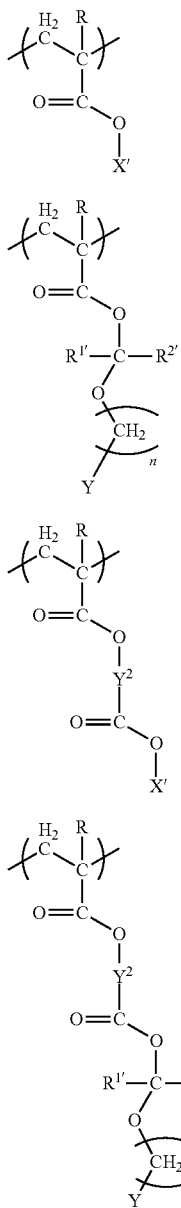

(a1-1)
(a1-2)
(a1-3)
(a1-4)

In the formulas, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents a divalent linking group; R is the same as defined above; and each of $R^{1'}$ and $R^{2'}$ independently represents a hydrogen atom or a lower alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1'}$, $R^{2'}$, n and Y are respectively the same as defined for $R^{1'}$, $R^{2'}$, n and Y in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 10.]

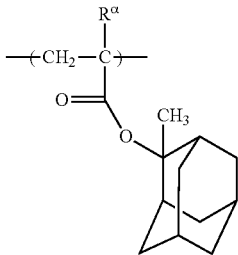

(a1-1-1)

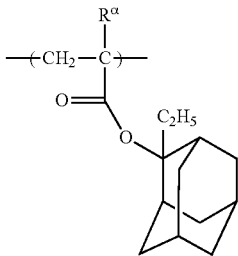

(a1-1-2)

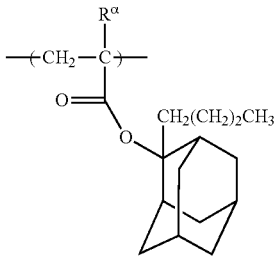

(a1-1-3)

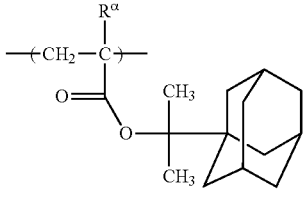

(a1-1-4)

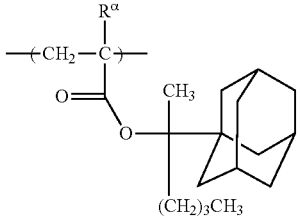

(a1-1-5)

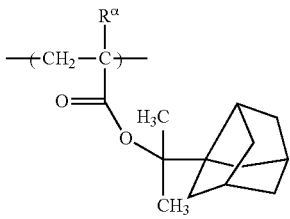

(a1-1-6)

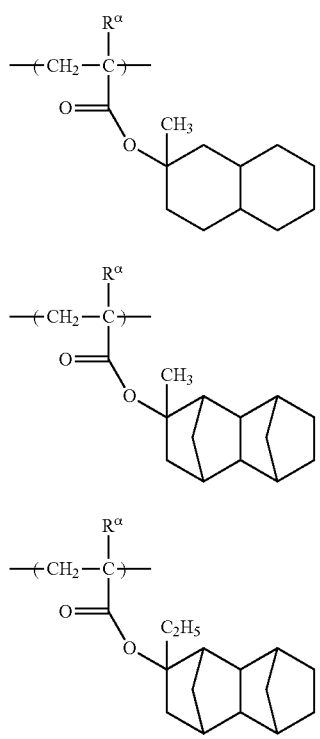
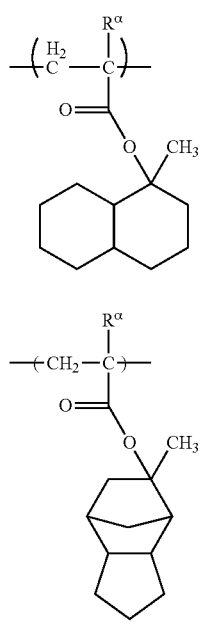
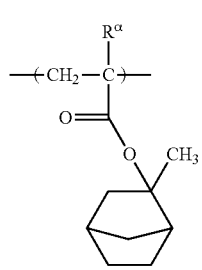
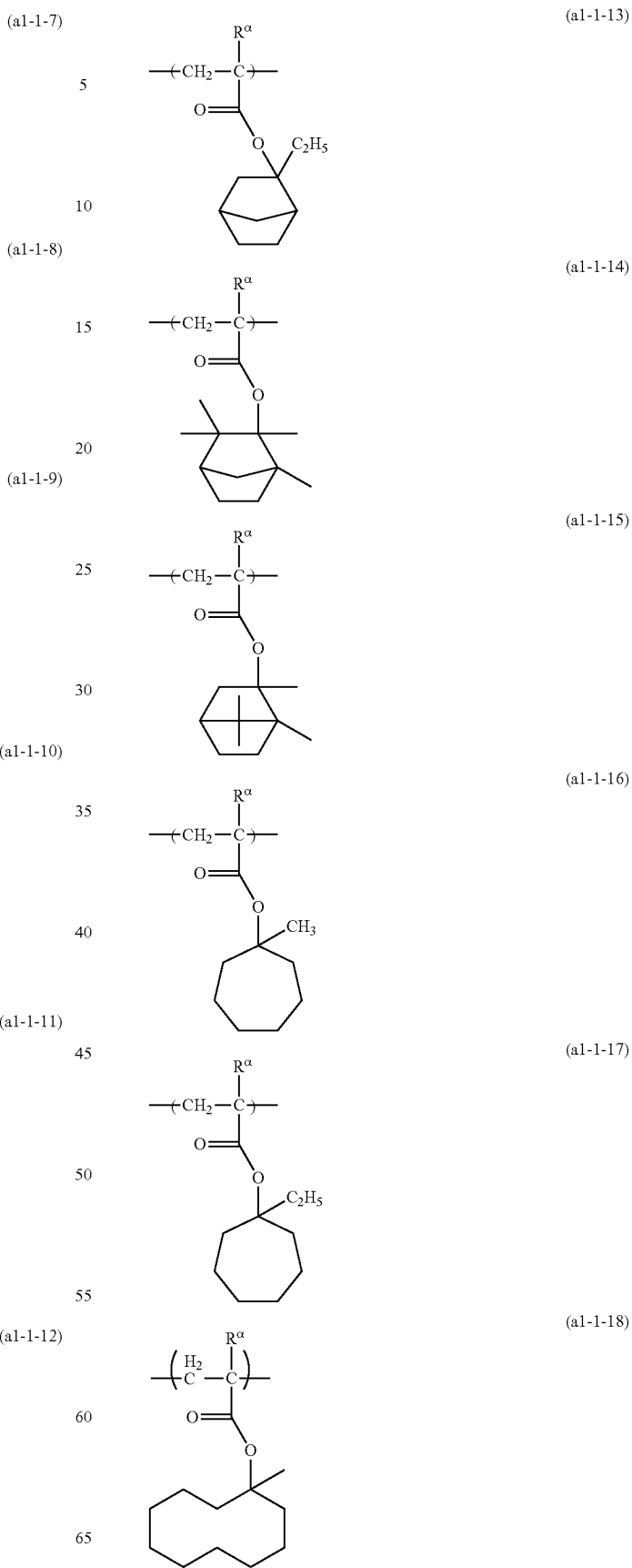

(a1-1-19) 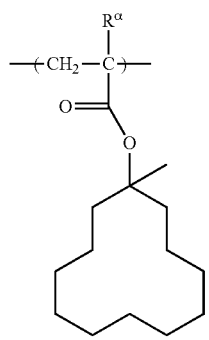
(a1-1-20) 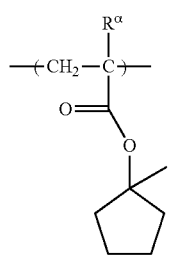
(a1-1-21) 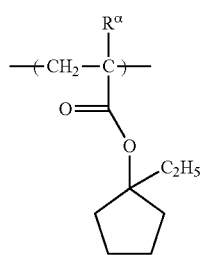
[Chemical Formula 12.]
(a1-1-22) 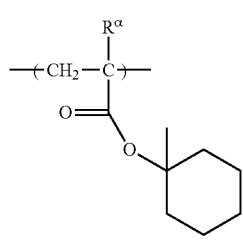
(a1-1-23) 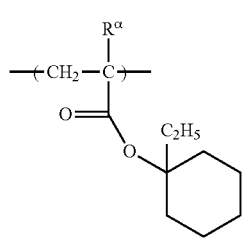
(a1-1-24) 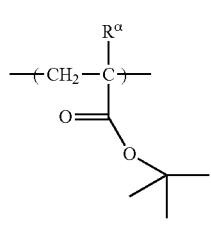
(a1-1-25) 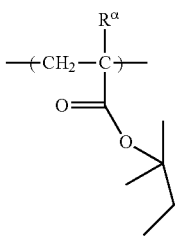
(a1-1-26) 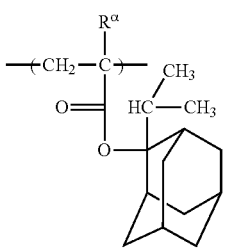
(a1-1-27) 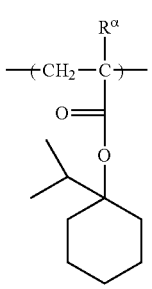
(a1-1-28) 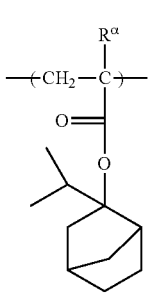
(a1-1-29) 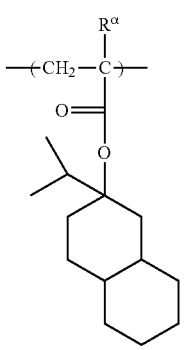

(a1-1-30)
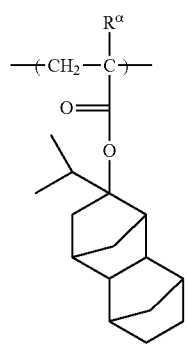
(a1-1-31)
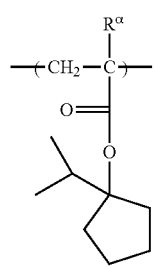
(a1-1-32)
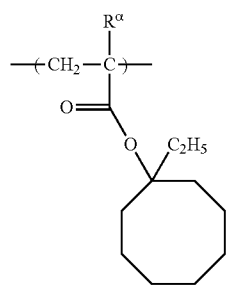
(a1-1-33)
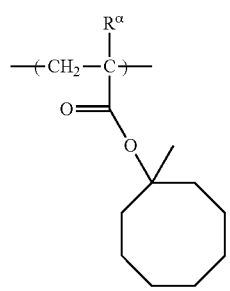
[Chemical Formula 13.]
(a1-2-1)
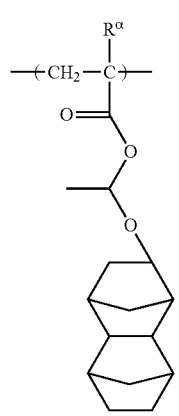
(a1-2-2)
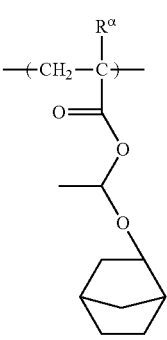
(a1-2-3)
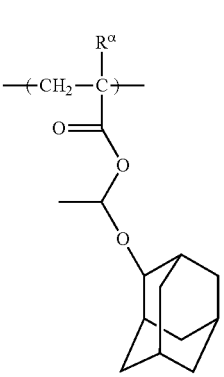
(a1-2-4)
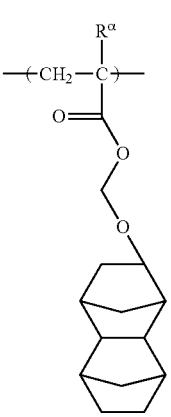
(a1-2-5)
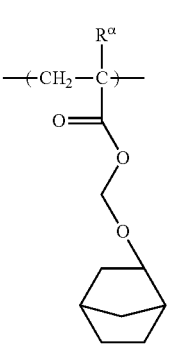

-continued
(a1-2-6)
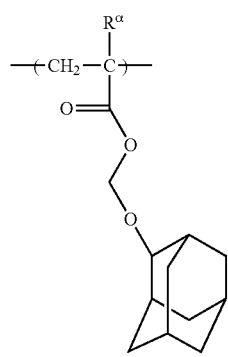
(a1-2-7)
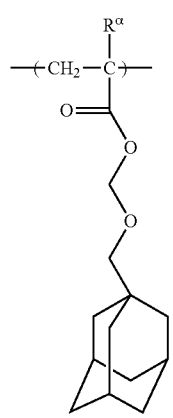
(a1-2-8)
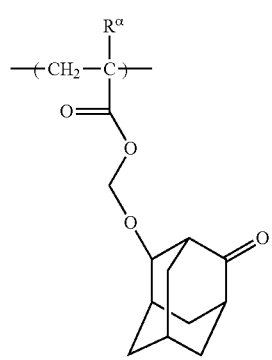
(a1-2-9)
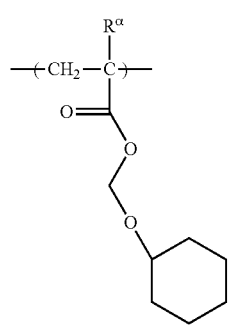
-continued
(a1-2-10)
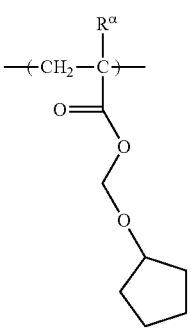
(a1-2-11)
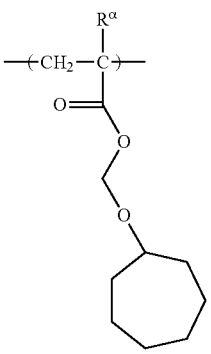
(a1-2-12)
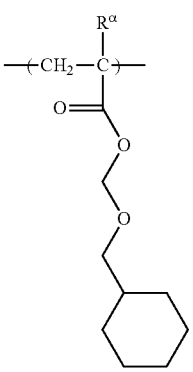
(a1-2-13)
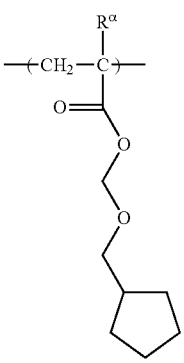

(a1-2-14)
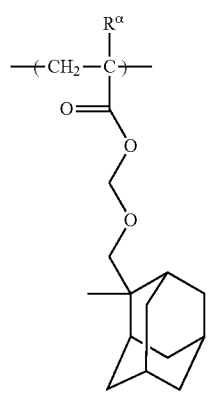
(a1-2-15)
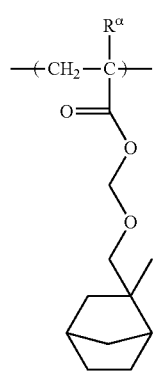
(a1-2-16)
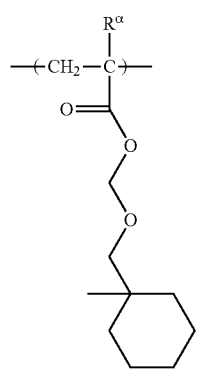
(a1-2-17)
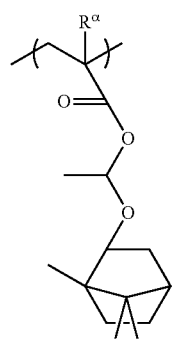
(a1-2-18)
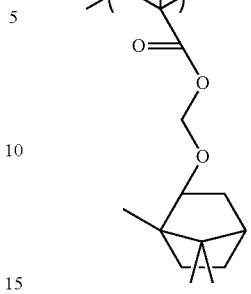
(a1-2-19)
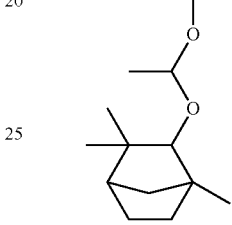
(a1-2-20)
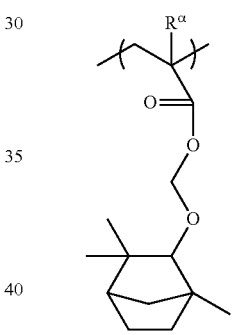
(a1-2-21)
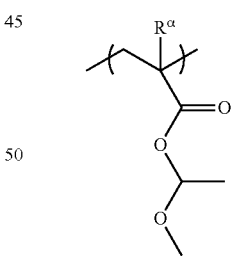
(a1-2-22)
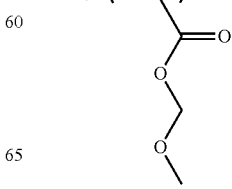

(a1-2-23) 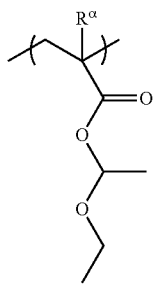
(a1-2-24) 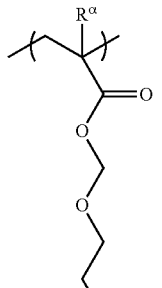
[Chemical Formula 14.]
(a1-3-1) 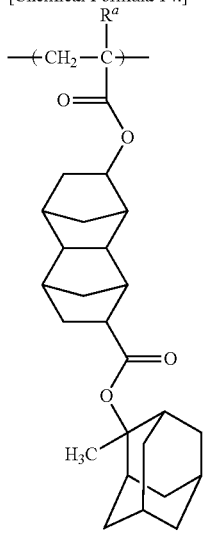
(a1-3-2) 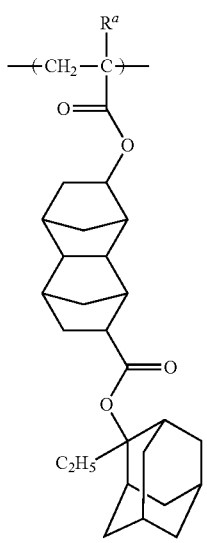
(a1-3-3) 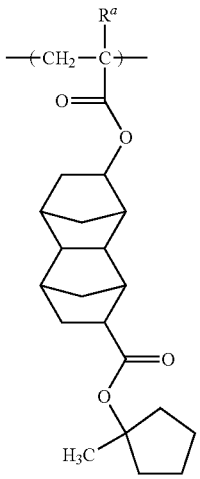
(a1-3-4) 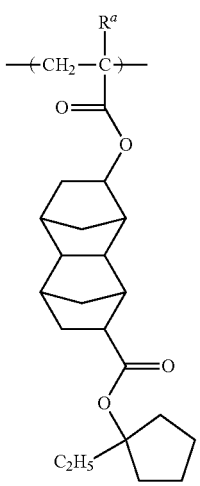
(a1-3-5) 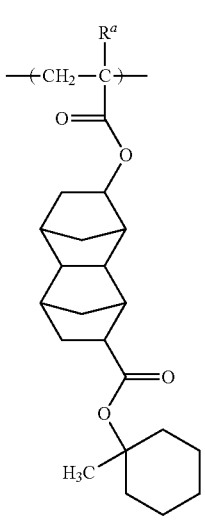

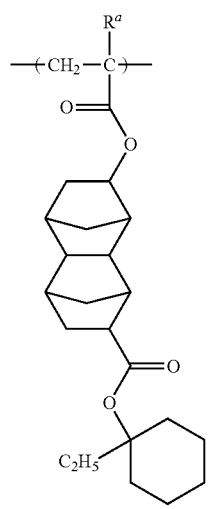
(a1-3-6)
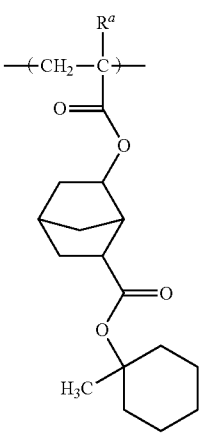
(a1-3-9)
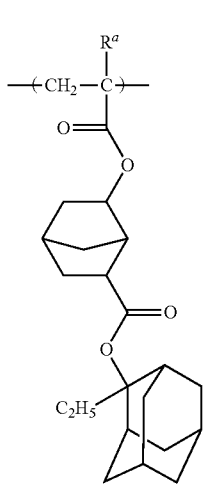
(a1-3-7)
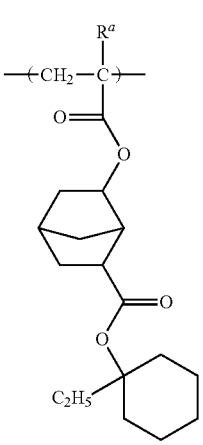
(a1-3-10)
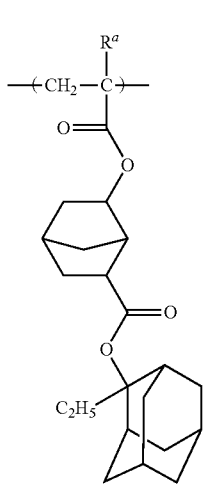
(a1-3-8)
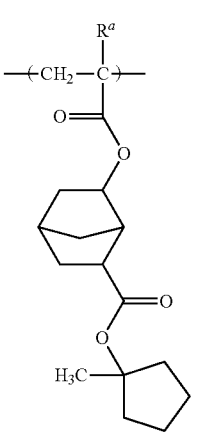
(a1-3-11)

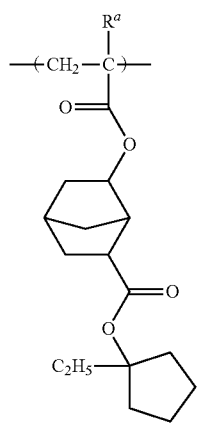
(a1-3-12)
(a1-3-13)
(a1-3-14)
(a1-3-15)
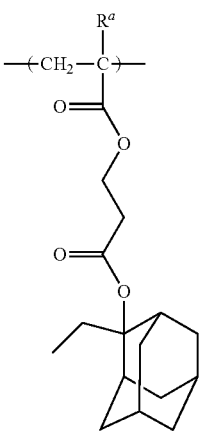
(a1-3-16)
(a1-3-17)
(a1-3-18)
[Chemical Formula 15.]
(a1-3-19)

(a1-3-20)
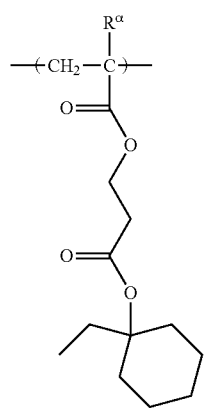
(a1-3-21)
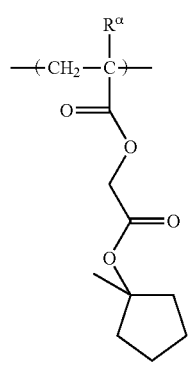
(a1-3-22)
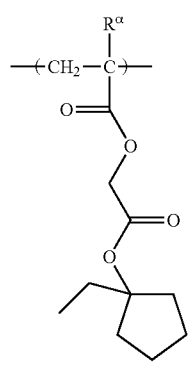
(a1-3-23)
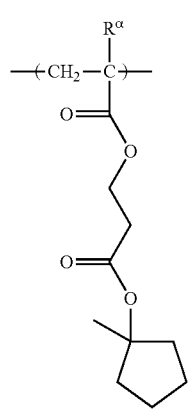
(a1-3-24)
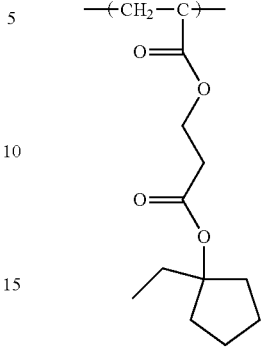
[Chemical Formula 16.]
(a1-3-25)
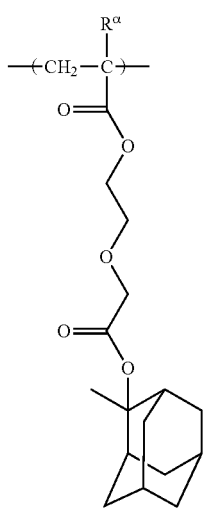
(a1-3-26)
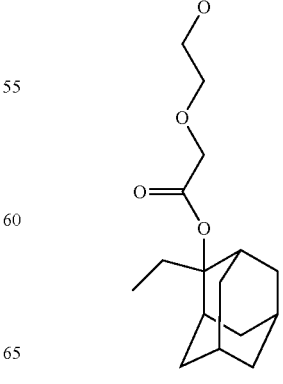

(a1-3-27) 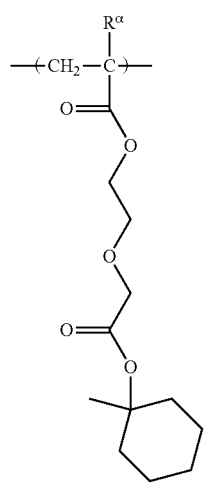
(a1-3-28) 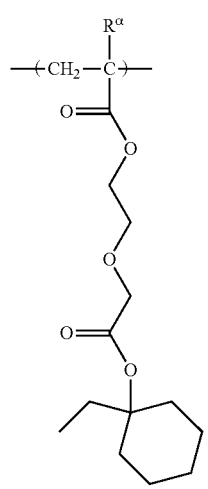
(a1-3-29) 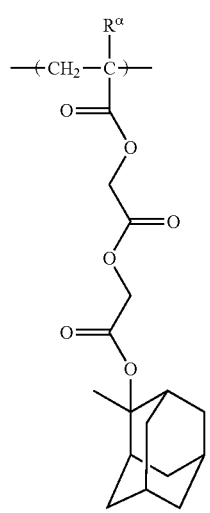
(a1-3-30) 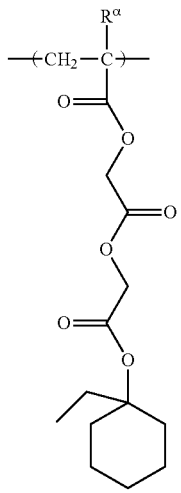
(a1-3-31) 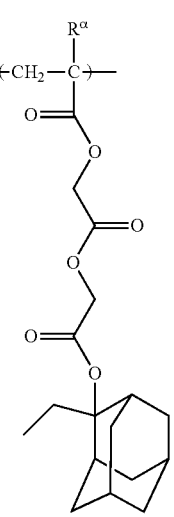
(a1-3-32) 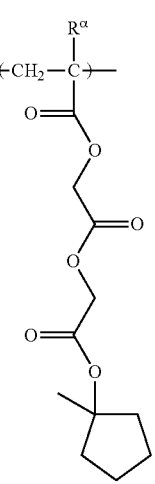

-continued
[Chemical Formula 17.]
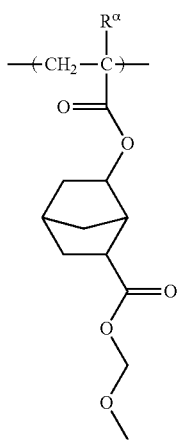
(a1-4-1)
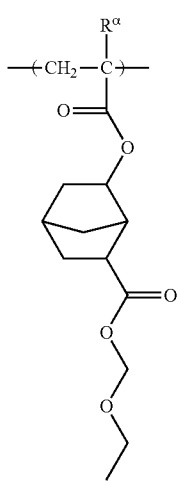
(a1-4-2)
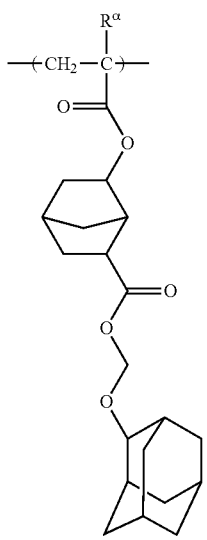
(a1-4-3)
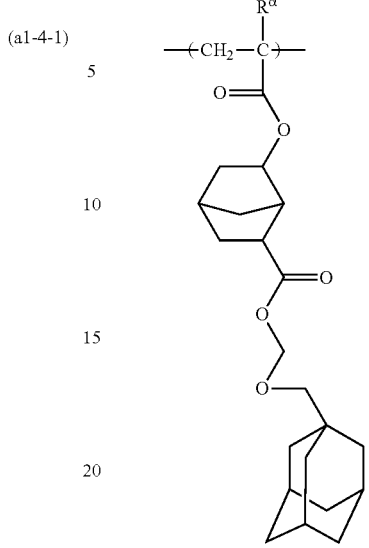
(a1-4-4)
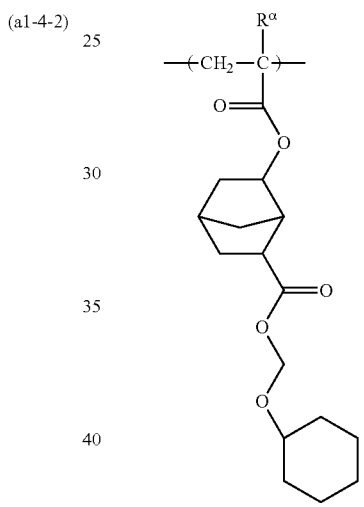
(a1-4-5)
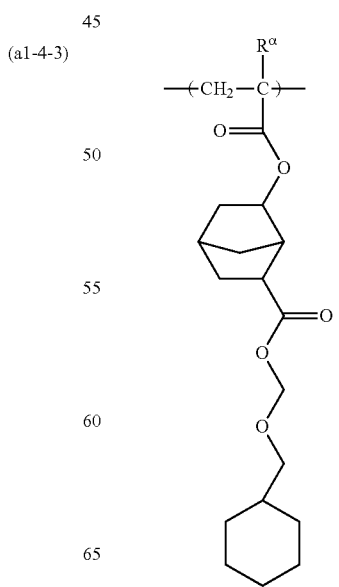
(a1-4-6)

(a1-4-7)
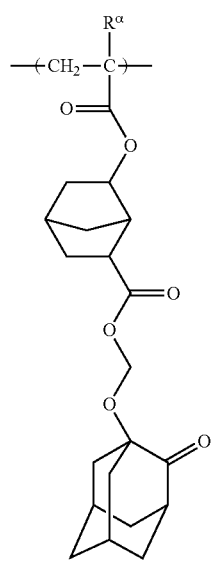
(a1-4-9)
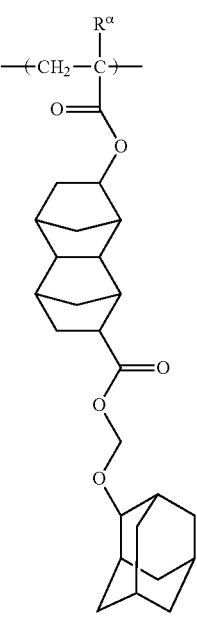
(a1-4-8)
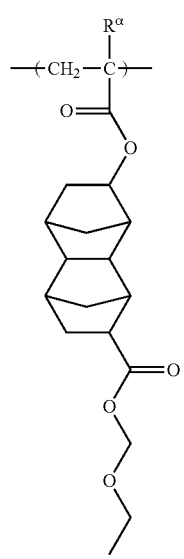
(a1-4-10)
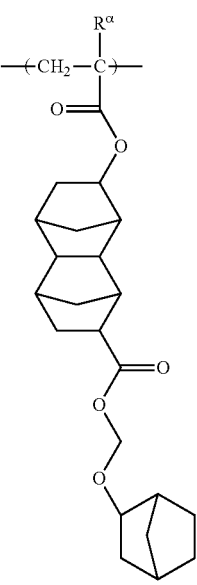

(a1-4-11)
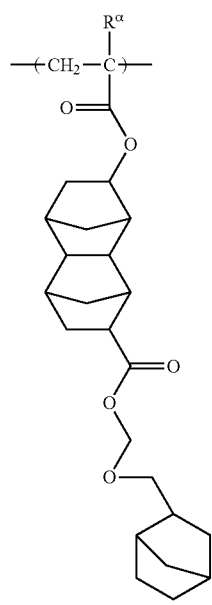
(a1-4-12)
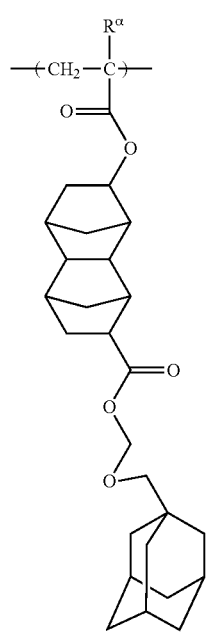
(a1-4-13)
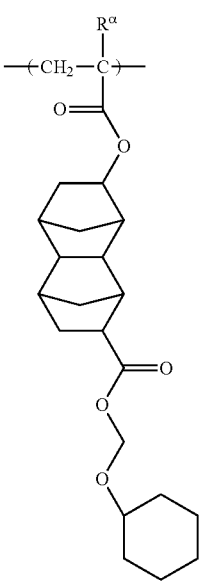
(a1-4-14)
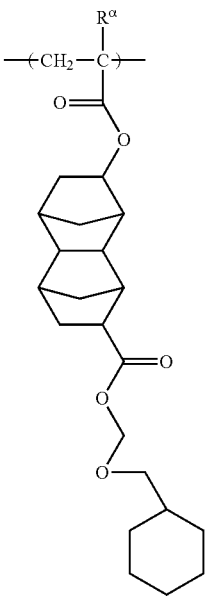

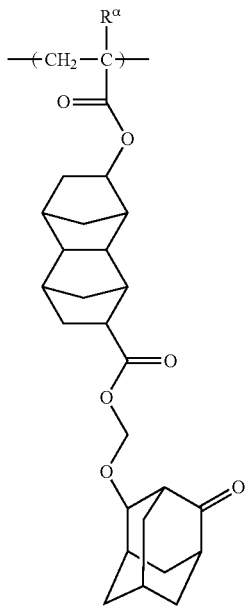

(a1-4-15)

As the structural unit (a1), one type of structural unit may be used alone, or two or more types of structural units may be used in combination.

Among these, structural units represented by general formula (a1-1) or (a1-3) are preferable. More specifically, at least one structural unit selected from the group consisting of structural units represented by formulas (a1-1-1) to (a-1-1-4), (a1-1-16), (a1-1-17), (a1-1-20) to (a1-1-23), (a1-1-26), (a1-1-32), (a1-1-33) and (a1-3-25) to (a1-3-28) is more preferable.

Further, as the structural unit (a1), structural units represented by general formula (a1-1-01) shown below which includes the structural units represented by formulas (a1-1-1) to (a1-1-3) and (a1-1-26), structural units represented by general formula (a1-1-02) shown below which includes the structural units represented by formulas (a1-1-16), (a1-1-17), (a1-1-20) to (a1-1-23), (a1-1-32) and (a1-1-33), structural units represented by general formula (a1-3-01) shown below which include the structural units represented by formulas (a1-3-25) and (a1-3-26), and structural units represented by general formula (a1-3-02) shown below which include the structural units represented by formulas (a1-3-27) and (a1-3-28) are also preferable.

[Chemical Formula 18.]

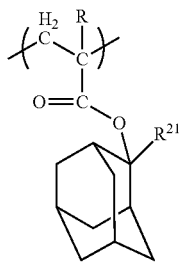

(a1-1-01)

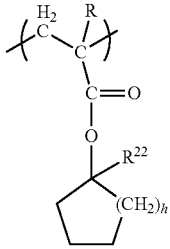

(a1-1-02)

In the formula, R represents a hydrogen atom, a lower alkyl group or a halogenated lower alkyl group; $R^{21}$ represents a lower alkyl group; $R^{22}$ represents a lower alkyl group. h represents an integer of 1 to 6.

In general formula (a1-1-01), R is the same as defined above.

The lower alkyl group for $R^{21}$ is the same as defined for the lower alkyl group for R above, a linear or branched alkyl group is preferable, and a methyl group, an ethyl group or an isopropyl group is particularly desirable.

In general formula (a1-1-02), R is the same as defined above.

The lower alkyl group for $R^{22}$ is the same as defined for the lower alkyl group for R above, a linear or branched alkyl group is preferable, and a methyl group or an ethyl group is particularly desirable.

h is preferably 1 or 2.

[Chemical Formula 19.]

(a1-3-01)

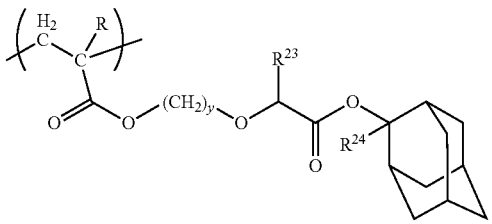

In the formula, R represents a hydrogen atom, a lower alkyl group or a halogenated lower alkyl group; $R^{24}$ represents a lower alkyl group; $R^{23}$ represents a hydrogen atom or a methyl group; and y represents an integer of 1 to 10.

[Chemical Formula 20.]

(a1-3-02)

In the formula, R represents a hydrogen atom, a lower alkyl group or a halogenated lower alkyl group; $R^{24}$ represents a lower alkyl group; $R^{23}$ represents a hydrogen atom or a methyl group; y represents an integer of 1 to 10; and n' represents an integer of 1 to 6.

In general formulas (a1-3-01) and (a1-3-02), R is the same as defined above.

$R^{23}$ is preferably a hydrogen atom.

The lower alkyl group for $R^{24}$ is the same as defined for the lower alkyl group for R, and is preferably a methyl group or an ethyl group.

y is preferably an integer of 1 to 8, more preferably an integer of 2 to 5, and most preferably 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

(Structural Unit (a2))

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 21.]

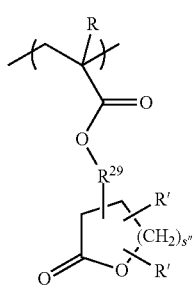
(a2-1)

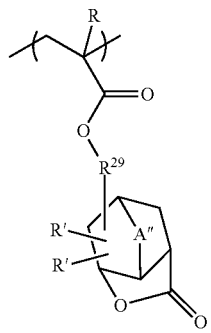
(a2-2)

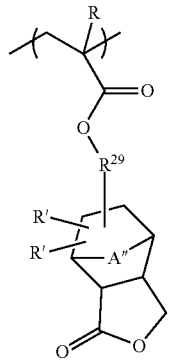
(a2-3)

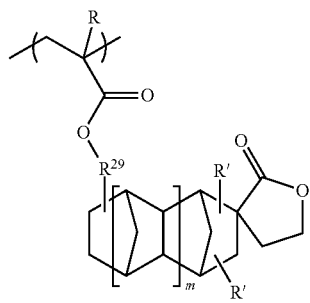
(a2-4)

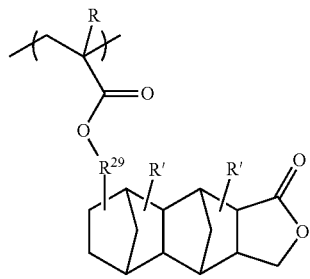
(a2-5)

In the formulas, R represents a hydrogen atom, a lower alkyl group or a halogenated lower alkyl group; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group In terms of industrial availability, R' is preferably a hydrogen atom.

R" preferably represents a hydrogen atom or a linear, branched or cyclic alkyl group of 1 to 15 carbon atoms.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As A", an alkylene group of 1 to 5 carbon atoms or —O— is preferable, more preferably an alkylene group of 1 to 5 carbon atoms, and most preferably a methylene group.

$R^{29}$ represents a single bond or a divalent linking group. Examples of divalent linking groups include the same divalent linking groups as those described above for $Y^2$ in general formula (a1-0-2). Among these, an alkylene group, an ester bond (—C(=O)—O—) or a combination thereof is preferable. The alkylene group as a divalent linking group for $R^{29}$ is preferably a linear or branched alkylene group. Specific examples include the same linear alkylene groups and branched alkylene groups as those described above for the aliphatic cyclic group A in $Y^2$.

s" is preferably 1 or 2.

Specific examples of structural units represented by general formulas (a2-1) to (a2-5) are shown below.

In the formulas shown below, $R^\alpha$ represents a hydrogen atom, a methyl group or a trifluoromethyl group.

[Chemcial Formula 22.]

(a2-1-1)

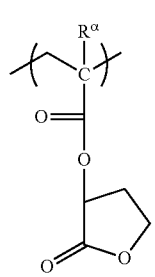

(a2-1-2)

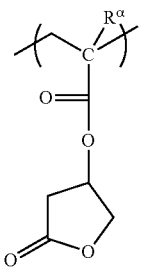

(a2-1-3)

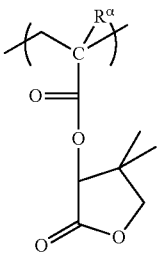

(a2-1-4)

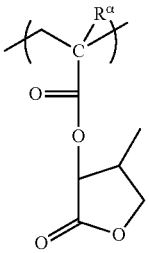

(a2-1-5)

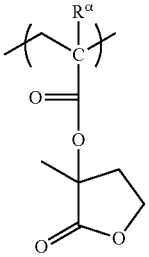

(a2-1-6)

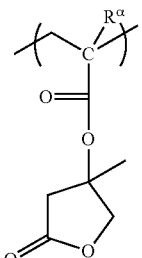

(a2-1-7)

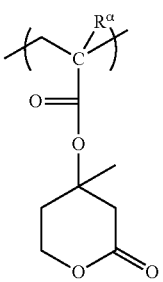

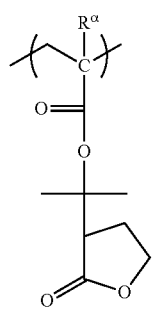 (a2-1-8)
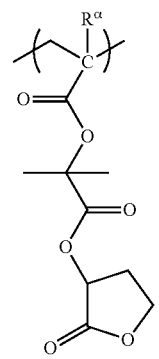 (a2-1-12)
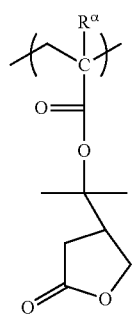 (a2-1-9)
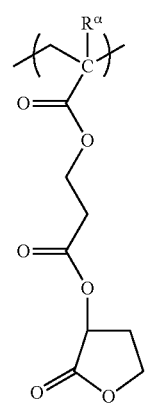 (a2-1-13)
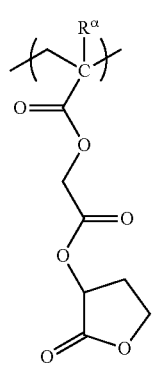 (a2-1-10)
[Chemical Formula 23.]
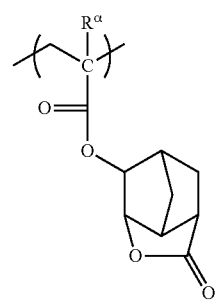 (a2-2-1)
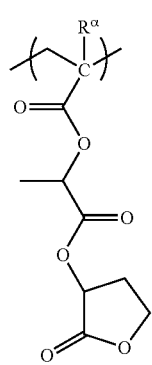 (a2-1-11)
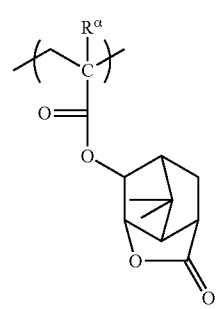 (a2-2-2)

(a2-2-3)
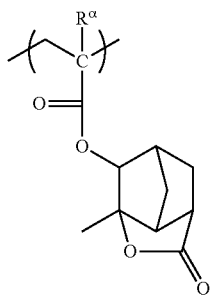
(a2-2-4)
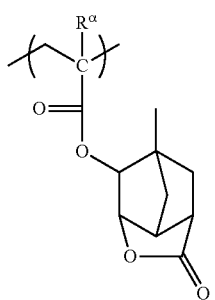
(a2-2-5)
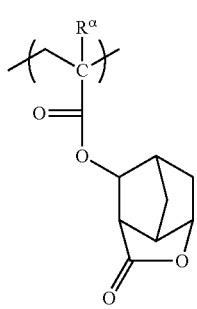
(a2-2-6)
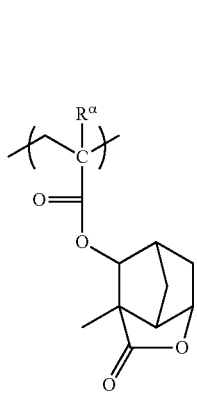
(a2-2-7)
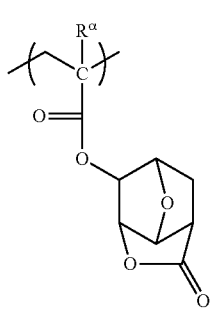
(a2-2-8)
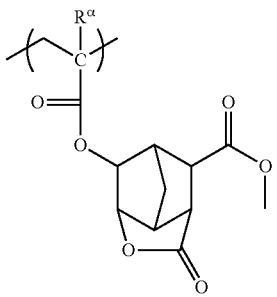
(a2-2-9)
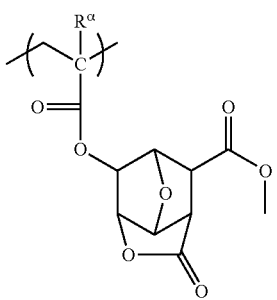
(a2-2-10)
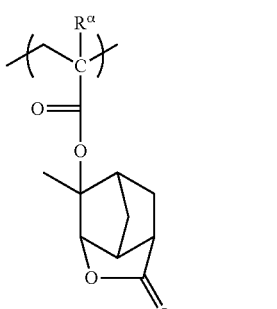
(a2-2-11)
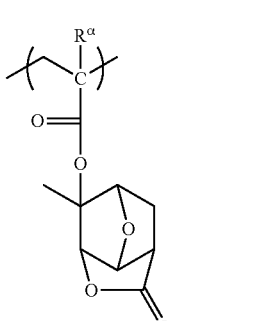
(a2-2-12)
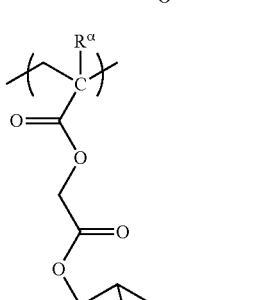
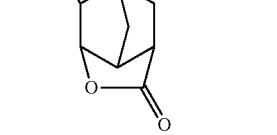

(a2-2-13)
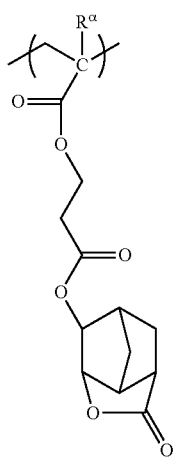
(a2-2-14)
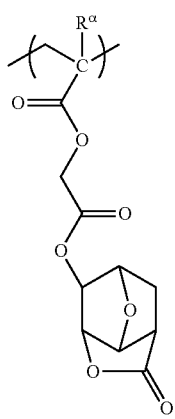
(a2-2-15)
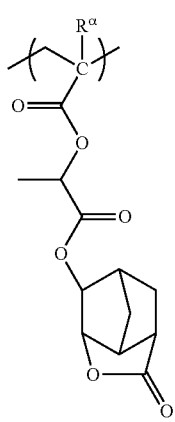
(a2-2-16)
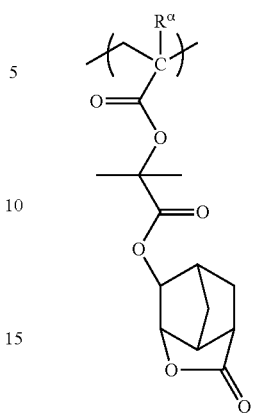
(a2-2-17)
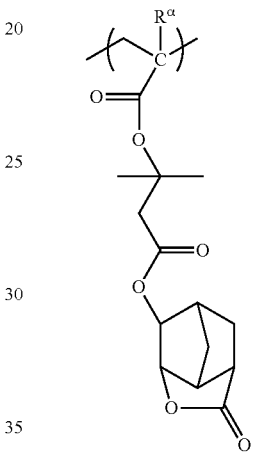
[Chemical Formula 24.]
(a2-3-1)
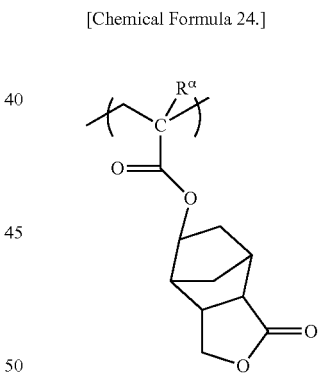
(a2-3-2)
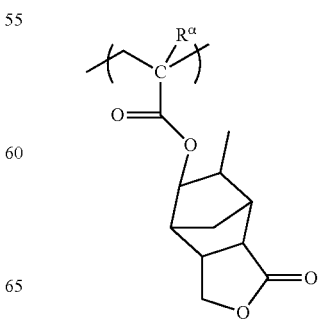

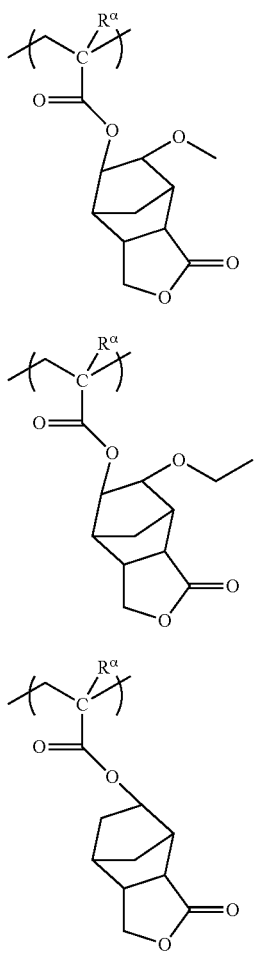
(a2-3-3)
(a2-3-4)
(a2-3-5)
[Chemical Formula 25.]
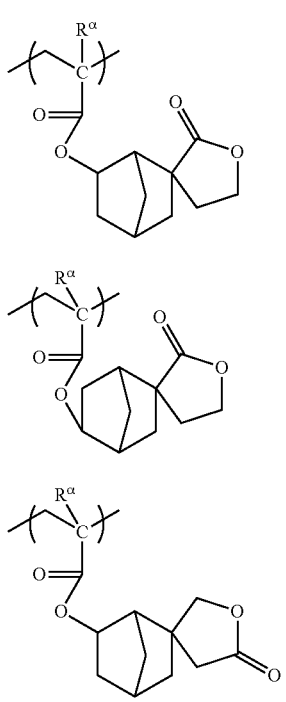
(a2-4-1)
(a2-4-2)
(a2-4-3)
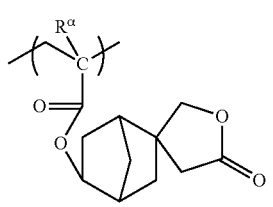
(a2-4-4)
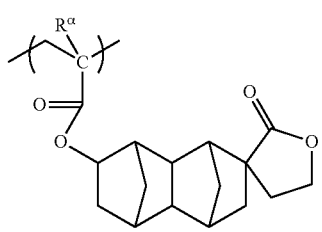
(a2-4-5)
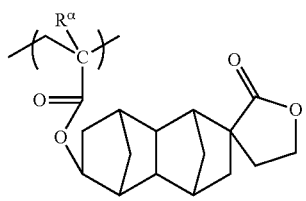
(a2-4-6)
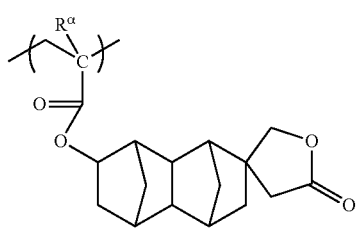
(a2-4-7)
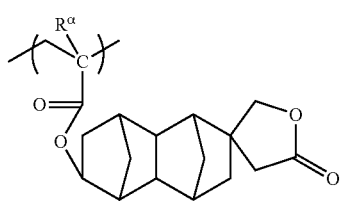
(a2-4-8)
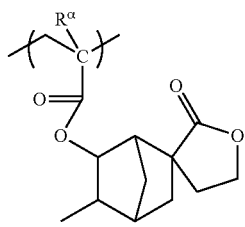
(a2-4-9)
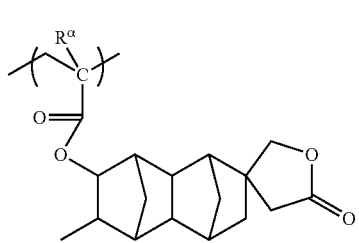
(a2-4-10)

(a2-4-11)
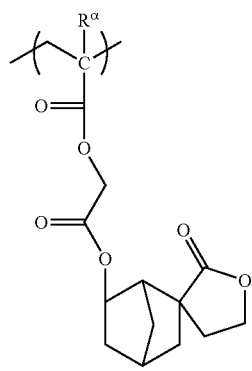
(a2-4-12)
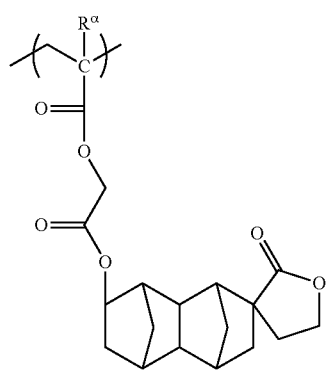
[Chemical Formula 26.]
(a2-5-1)
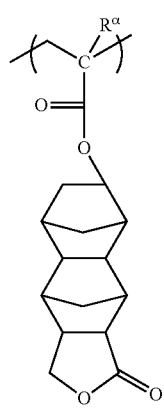
(a2-5-2)
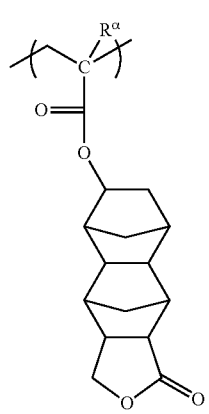
(a2-5-3)
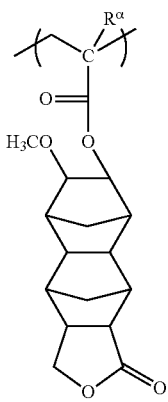
(a2-5-4)
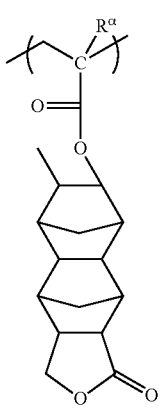
(a2-5-5)
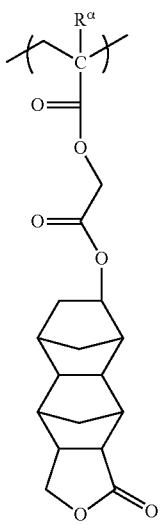

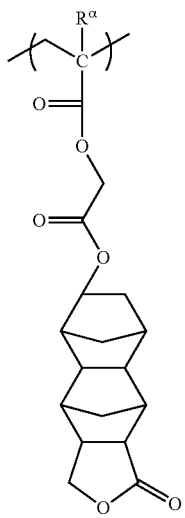

(a2-5-6)

In the component (A1), as the structural unit (a2), one type of structural unit may be used, or two or more types may be used in combination.

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is preferable to use at least one structural unit selected from the group consisting of structural units represented by formulas (a2-1-1), (a2-1-2), (a2-2-1), (a2-2-7), (a2-3-1) and (a2-3-5).

In the component (A1), the amount of the structural unit (a2) based on the combined total of all structural units constituting the component (A1) is preferably 5 to 60 mol %, more preferably 10 to 50 mol %, and still more preferably 20 to 50 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

(Structural Unit (a3))

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 27.]

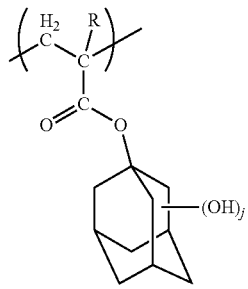

(a3-1)

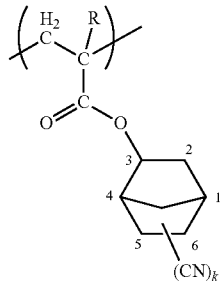

(a3-2)

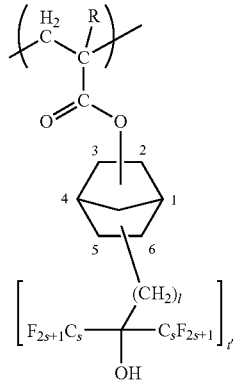

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3), one type of structural unit may be used, or two or more types may be used in combination.

The amount of the structural unit (a3) within the component (A1) based on the combined total of all structural units constituting the component (A1) is preferably 5 to 50 mol %, more preferably 5 to 40 mol %, and still more preferably 5 to 25 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) may also have a structural unit other than the above-mentioned structural units (a1) to (a3), as long as the effects of the present invention are not impaired.

As such a structural unit, any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

Examples of other structural units include a structural unit (a4) derived from an acrylate ester containing a non-acid-dissociable aliphatic polycyclic group, a structural unit (a5) derived from an acrylate ester containing a sultone structure on the side chain, a structural unit (a6) derived from hydroxystyrene or vinyl(hydroxynaphthalene), and a structural unit (a7) derived from styrene or vinylnaphthalene.

Structural Unit (a4)

The structural unit (a4) is a structural unit derived from an acrylate ester containing a non-acid dissociable, aliphatic polycyclic group.

In the structural unit (a4), examples of this polycyclic group include the same groups as those described above in relation to the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a-4-1) to (a-4-5) shown below.

[Chemical Formula 28.]

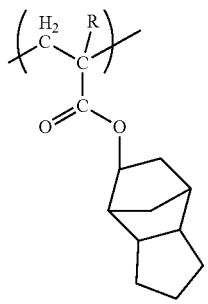
(a4-1)

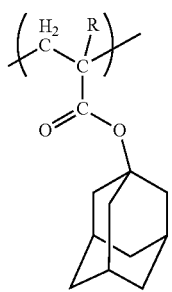
(a4-2)

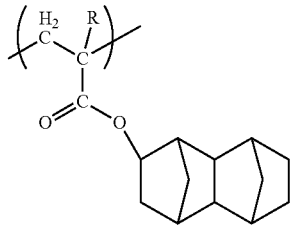
(a4-3)

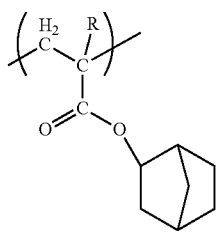
(a4-4)

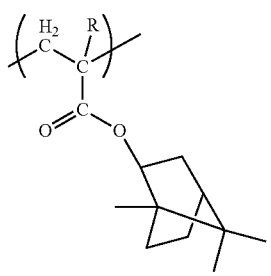
(a4-5)

In the formulas, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

Structural Unit (a5)

The structural unit (a5) is a structural unit derived from an acrylate ester having a sultone structure on the side chain thereof. By including the structural unit (a5), lithography properties such as resolution and resist pattern shape can be improved. Specific examples include structural units represented by general formula (a5-1) shown below.

[Chemical Formula 29.]

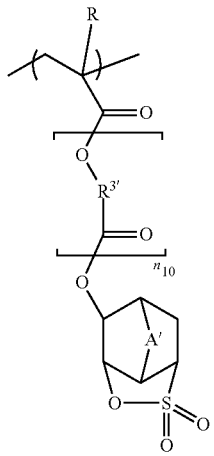

(a5-1)

In the formula, R is the same as defined above; $R^{3'}$ represents a linear or branched alkylene group; A' represents an oxygen atom, a sulfur atom or an alkylene group of 1 to 5 carbon atoms which may contain an oxygen atom or a sulfur atom; and $n_{10}$ represents 0 to 2.

The linear or branched alkylene group for $R^{3'}$ preferably has 1 to 10 carbon atoms, more preferably 1 to 8, still more preferably 1 to 5, still more preferably 1 to 3, and most preferably 1 or 2.

A' is preferably a methylene group, an oxygen atom (—O—) or a sulfur atom (—S—).

$n_{10}$ is preferably 0 or 1.

As the structural unit (a5), one type of structural unit may be used alone, or two or more types of structural units may be used in combination.

When the structural unit (a5) is included in the component (A1), the amount of the structural unit (a5) based on the combined total of all structural units constituting the component (A1) is preferably 1 to 60 mol %, more preferably 5 to 55 mol %, and still more preferably 10 to 50 mol %.

Structural Unit (a6)

A "structural unit derived from a hydroxystyrene" refers to a structural unit that is formed by the cleavage of the ethylenic double bond of a hydroxystyrene.

A hydroxystyrene is a compound which has 1 vinyl group and at least 1 hydroxy group bonded to a benzene ring. The number of hydroxy groups bonded to the benzene ring is preferably 1 to 3, and most preferably 1. The bonding position of the hydroxy group on the benzene ring is not particularly limited. When there is 1 hydroxy group, a para-4th position from the bonding position of the vinyl group is preferable. When there are 2 or more hydroxy groups, a desired combination of the bonding positions can be used.

In the present specification, a hydroxystyrene in which the hydrogen atom bonded to the carbon atom on the α position has been substituted with a substituent is referred to as an α-substituted hydroxystyrene. Further, hydroxystyrenes and α-substituted hydroxystyrenes are collectively referred to as (α-substituted) hydroxystyrene.

As the substituent to be bonded to the carbon atom on the α position of an α-substituted hydroxystyrene, the same substituents as those described above for the substituent to be bonded to the carbon atom on the α position of an α-substituted acrylate ester can be mentioned.

The substituent other than a hydroxy group which may be bonded to the benzene ring of an (α-substituted) hydroxystyrene is not particularly limited, and examples thereof include a halogen atom, an alkyl group of 1 to 5 carbon atoms and a halogneated alkyl group of 1 to 5 carbon atoms. Examples of the halogen atom include a fluorine atom, a chlorine atom, a bromine atom and an iodine atom, and a fluorine atom is particularly desirable.

A "structural unit derived from a vinyl(hydroxynaphthalene)" refers to a structural unit that is formed by the cleavage of the ethylenic double bond of a vinyl(hydroxynaphthalene).

A vinyl(hydroxynaphthalene) is a compound which has 1 vinyl group and at least 1 hydroxy group bonded to a naphthalene ring. The vinyl group may be bonded to the 1st or 2nd position of the naphthalene ring. The number of hydroxy groups bonded to the naphthalene ring is preferably 1 to 3, and most preferably 1. The bonding position of the hydroxy group on the naphthalene ring is not particularly limited. When the vinyl group is bonded to the 1st or 2nd position of the naphthalene ring, the hydroxy group is preferably bonded to either one of the 5th to 8th position of the naphthalene ring. In particular, when the number of hydroxy group is 1, the hydroxy group is preferably bonded to either one of the 5th to 7th position of the naphthalene ring, and more preferably the 5th or 6th position. When there are 2 or more hydroxy groups, a desired combination of the bonding positions can be used.

In the present specification, a vinyl(hydroxynaphthalene) in which the hydrogen atom bonded to the carbon atom on the α position has been substituted with a substituent is referred to as an α-substituted vinyl(hydroxynaphthalene). Further, vinyl(hydroxynaphthalenes) and α-substituted vinyl(hydroxynaphthalenes) are collectively referred to as (α-substituted) vinyl(hydroxynaphthalene).

As the substituent to be bonded to the carbon atom on the α position of an α-substituted vinyl(hydroxynaphthalene), the same substituents as those described above for the substituent to be bonded to the carbon atom on the α position of an α-substituted acrylate ester can be mentioned.

As the substituent other than a hydroxy group which may be bonded to the naphthanlene ring of the (α-substituted) vinyl(hydroxynaphthalene), the same substituents as those described above for the substituent other than a hydroxy group which may be bonded to the benzene ring of the (α-substituted) hydroxystyrene can be mentioned.

As the structural unit (a6), one type of structural unit may be used alone, or two or more types of structural units may be used in combination.

When the structural unit (a6) is included in the component (A1), the amount of the structural unit (a6) based on the combined total of all structural units constituting the component (A1) is preferably 10 to 90 mol %, more preferably 20 to 85 mol %, and still more preferably 30 to 80 mol %.

Structural Unit (a7)

A "structural unit derived from styrene" refers to a structural unit that is formed by the cleavage of the ethylenic double bond of styrene.

In the present specification, styrene in which the hydrogen atom bonded to the carbon atom on the α position has been substituted with a substituent is referred to as an α-substituted styrene.

As the substituent to be bonded to the carbon atom on the α position of an α-substituted styrene, the same substituents as those described above for the substituent to be bonded to the carbon atom on the α position of an α-substituted acrylate ester can be mentioned.

The benzene ring of the α-substituted styrene may have a substituent. Examples of the substituent include a fluorine atom, an alkyl group or fluorinated alkyl group of 1 to 5 carbon atoms, and a cyclic alkyl group of 3 to 20 carbon atoms.

A "structural unit derived from vinylnaphthalene" refers to a structural unit that is formed by the cleavage of the ethylenic double bond of a vinylnaphthalene.

In the present specification, a vinylnaphthalene in which the hydrogen atom bonded to the carbon atom on the α position has been substituted with a substituent is referred to as an α-substituted vinylnaphthalene.

As the substituent to be bonded to the carbon atom on the α position of an α-substituted vinylnaphthalene, the same substituents as those described above for the substituent to be bonded to the carbon atom on the α position of an α-substituted acrylate ester can be mentioned.

The naphthalene ring of the α-substituted vinylnaphthalene may have a substituent. Examples of the substituent include a fluorine atom, an alkyl group or fluorinated alkyl group of 1 to 5 carbon atoms, and a cyclic alkyl group of 3 to 15 carbon atoms.

As the structural unit (a7), one type of structural unit may be used, or two or more types may be used in combination.

When the structural unit (a7) is included in the component (A1), the amount of the structural unit (a7) based on the combined total of all the structural units that constitute the component (A1) is preferably within the range from 1 to 40 mol %, and more preferably from 1 to 30 mol %.

In the resist composition of the present invention, the component (A1) is preferably a polymeric compound having a structural unit (a1).

Examples of the component (A1) include a copolymer consisting of the structural units (a1) and (a2) and (a3), a copolymer consisting of the structural units (a1), (a2), (a3) and (a4), a copolymer consisting of the structural units (a1), (a2), (a3) and (a5), and a copolymer consisting of the structural units (a1) and (a6).

In the component (A), as the component (A1), one type may be used alone, or two or more types may be used in combination.

In the present invention, as the component (A1), a polymeric compound that includes a combination of structural units such as that shown below is particularly desirable.

[Chemical Formula 30.]

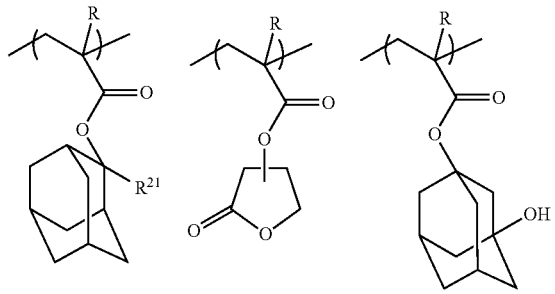

(A1-11)

In the formula, R and $R^{21}$ are the same as defined above, and the plurality of R may be the same or different from each other.

In formula (A1-11), the lower alkyl group for $R^{21}$ is the same as the lower alkyl group for R above, preferably a methyl group or an ethyl group, and most preferably a methyl group.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is preferably 1.0 to 5.0, more preferably 1.0 to 3.0, and most preferably 1.0 to 2.5. Here, Mn is the number average molecular weight.

In the resist composition of the present invention, the component (A) may contain "a base component which exhibits increased solubility in an alkali developing solution under action of acid" other than the component (A1).

Such base component other than the component (A1) is not particularly limited, and any of the multitude of conventional base components used within chemically amplified resist compositions (e.g., a novolak resin, a polyhydroxystyrene-based resin (PHS), a low molecular weight component (component (A2))) can be appropriately selected for use.

Examples of the component (A2) include low molecular weight compounds that have a molecular weight of at least 500 and less than 2,000, contains a hydrophilic group, and also contains an acid dissociable, dissolution inhibiting group described above in connection with the component (A1). Specific examples of the low molecular weight compound include compounds containing a plurality of phenol skeletons in which a part of the hydrogen atoms within hydroxyl groups have been substituted with the aforementioned acid dissociable, dissolution inhibiting groups.

In the resist composition of the present invention, as the component (A), one type may be used, or two or more types of compounds may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, a resist pattern exhibiting a high resolution and a high rectangularity can be formed.

In the resist composition of the present invention, the amount of the component (A) can be appropriately adjusted depending on the thickness of the resist film to be formed, and the like.

<Component (B)>

In the resist composition of the present invention, the component (B) includes an acid generator (B1) containing a compound represented by general formula (b1) shown below (hereafter, this acid generator (B1) is referred to as "component (B1)").

[Chemical Formula 31.]

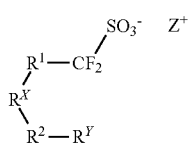

(b1-1)

In the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; each of $R^1$ and $R^2$ independently represents a divalent linking group; and $Z^+$ represents a monovalent organic cation.

Anion Moiety of Component (B1)

In formula (b1-1), $R^X$ represents a divalent aliphatic group of 3 to 20 carbon atoms.

In the present invention, the term "aliphatic group" refers to a group that has no aromaticity, and includes aliphatic hydrocarbon groups and groups containing a hetero atom within the hydrocarbon groups.

The aliphatic group for $R^X$ has 3 to 20 carbon atoms, preferably 3 to 16, more preferably 3 to 12, and most preferably 3 to 10.

Preferable examples of the aliphatic group for $R^X$ include divalent hydrocarbon groups of 3 to 20 carbon atoms. The hydrocarbon group may have a substituent, or part of the carbon atoms constituting the hydrocarbon group may be substituted with a hetero atom.

A hydrocarbon "has a substituent" means that part or all of the hydrogen atoms within the hydrocarbon group is substituted with groups or atoms other than hydrogen.

The hydrocarbon group for the aliphatic group represented by $R^X$ may be either saturated or unsaturated. As specific examples of the hydrocarbon group, a linear or branched aliphatic hydrocarbon group (chain-like group), and an aliphatic hydrocarbon group containing a ring in the structure thereof can be given.

The linear or branched aliphatic hydrocarbon group (chain-like group) preferably has 3 to 12 carbon atoms, more preferably 3 to 10, and most preferably 3 to 8.

Specific examples of the chain-like group include a linear alkylene group such as a methylene group, an ethylene group [—(CH$_2$)$_2$—], a trimethylene group [—(CH$_2$)$_3$—], a tetramethylene group [—(CH$_2$)$_4$—] or a pentamethylene group [—(CH$_2$)$_5$—]; and a branched alkylene group such as an alkylalkylene group. As the alkyl group within the alkylalkylene group, a linear alkyl group of 1 to 5 carbon atoms is preferable.

Examples of the alkylalkylene group include an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— or —C(CH$_2$CH$_3$)$_2$—; an alkylethylene group such as —CH(CH$_3$)CH$_2$—, —CH(CH$_2$CH$_3$)—, —C(CH$_3$)$_2$CH$_2$— or —CH(CH$_2$CH$_3$)CH$_2$—; an alkyltrimethylene group such as —CH(CH$_3$)CH$_2$CH$_2$—, —CH$_2$CH(CH$_3$)CH$_2$— or —CH$_2$C(CH$_3$)(CH$_3$)CH$_2$—; and an alkyltetramethylene group such as —CH(CH$_3$)CH$_2$CH$_2$CH$_2$— or —CH$_2$CH(CH$_3$)CH$_2$CH$_2$—.

The chain-like group may or may not have a substituent. Examples of the substituent include an alkoxyalkyl group of 1 to 5 carbon atoms, a fluorine atom, a fluorinated lower alkyl group of 1 to 5 carbon atoms, and an oxygen atom (=O). Further, part of the carbon atoms constituting the chain-like group may be substituted with a hetero atom.

As examples of the hydrocarbon group containing a ring in the structure thereof, a cyclic aliphatic hydrocarbon group (a group in which two hydrogen atoms have been removed from an aliphatic hydrocarbon ring, i.e., a divalent alicyclic group), and a group in which the cyclic aliphatic hydrocarbon group is bonded to the terminal of the aforementioned chain-like group or interposed within the aforementioned chain-like group, can be given.

The cyclic aliphatic hydrocarbon group (divalent alicyclic group) preferably has 3 to 16 carbon atoms, and more preferably 3 to 12 carbon atoms.

The cyclic aliphatic hydrocarbon group (divalent alicyclic group) may be either a polycyclic group or a monocyclic group. As the divalent monocyclic group, a group in which two hydrogen atoms have been removed from a monocycloalkane of 3 to 6 carbon atoms is preferable. Examples of the monocycloalkane include cyclopentane and cyclohexane. As the divalent polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The aliphatic hydrocarbon group containing a ring in the structure thereof may or may not have a substituent. Examples of substituents include lower alkyl groups of 1 to 5 carbon atoms, alkoxyalkyl groups of 1 to 5 carbon atoms, fluorine atom, fluorinated lower alkyl groups of 1 to 5 carbon atoms, and oxygen atom (=O). Further, part of the carbon atoms constituting the alicyclic group may be substituted with a hetero atom.

Among these, as $R^X$, in terms of improving the solubility in an organic solvent, a divalent alicyclic group of 3 to 20 carbon atoms is preferable, and a divalent polycyclic group of 3 to 20 carbon atoms is particularly desirable.

Specific examples of the divalent aliphatic group of 3 to 20 carbon atoms for $R^X$ are shown below. The 2 dotted lines (bonds) extending from an aliphatic group are bonded to $R^1$ and $R^2$.

[Chemical Formula 32.]

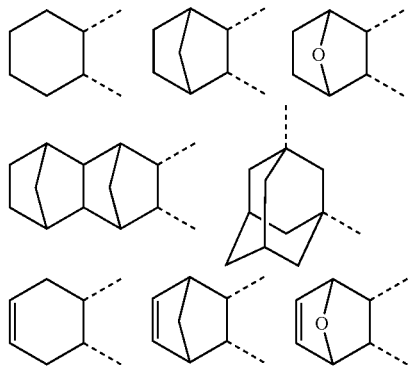

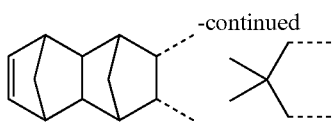

In formula (b1-1), $R^Y$ represents a monovalent aliphatic group of 3 to 20 carbon atoms having —C(=O)—O— or —S(=O)$_2$—.

The aliphatic group for $R^Y$ preferably has 3 to 16 carbon atoms, more preferably 3 to 12, and most preferably 4 to 9.

Preferable examples of the aliphatic group for $R^Y$ include a monovalent hydrocarbon group of 3 to 20 carbon atoms. The hydrocarbon group may have a substituent, or part of the carbon atoms constituting the hydrocarbon group may be substituted with a hetero atom.

A hydrocarbon "has a substituent" means that part or all of the hydrogen atoms within the hydrocarbon group is substituted with groups or atoms other than hydrogen.

The hydrocarbon group for the aliphatic group represented by $R^Y$ may be either saturated or unsaturated.

Specific examples of the hydrocarbon group include the same monovalent hydrocarbon groups as those described above for the aliphatic group represented by $R^X$, i.e., a linear or branched aliphatic hydrocarbon group (chain-like group), and an aliphatic hydrocarbon group containing a ring in the structure thereof.

When $R^Y$ represents an aliphatic hydrocarbon group containing a ring in the structure thereof, —C(=O)—O— or —S(=O)$_2$— may or may not be contained in the ring skeleton of the alicyclic group.

"—C(=O)—O— or —S(=O)$_2$— is contained in the ring skeleton of the alicyclic group" means that part of the carbon atoms constituting the alicyclic group has been substituted with —C(=O)—O—, —S(=O)$_2$— or a group containing either one of these, or part of the hydrogen atoms of the alicyclic group has been substituted with —C(=O)—O—, —S(=O)$_2$— or a group containing either one of these.

"—C(=O)—O— or —S(=O)$_2$— is not contained in the ring skeleton of the alicyclic group" means that —C(=O)—O— or —S(=O)$^2$— is present between the alicyclic group and $R_2$.

Specific examples of $R^Y$ include a monocycloalkane in which 1 hydrogen atom removed therefrom and "—CH$_2$—" constituting the ring skeleton of the monocyclic group has been substituted with "—SO$_2$—", a monocycloalkane in which 1 hydrogen atom has been removed therefrom and "—CH$_2$—CH$_2$—" constituting the ring skeleton of the monocyclic group has been substituted with "—O—SO$_2$—" and a group represented by the formula: "(a monocycloalkane having 1 hydrogen atom removed therefrom)-R$^{98}$—S(=O)$_2$—O—".

Further examples include a polycycloalkane (a bicycloalkane, a tricycloalkane, a tetracycloalkane or the like) in which 1 hydrogen atom has been removed therefrom and "—CH$_2$—" constituting the ring skeleton of the polycyclic group has been substituted with "—SO$_2$—", a polycycloalkane in which 1 hydrogen atom has been removed therefrom and "—CH$_2$—CH$_2$—" constituting the ring skeleton of the polycyclic group has been substituted with "—O—SO$_2$—", a polycycloalkane in which 1 hydrogen atom has been removed therefrom and "—CH$_2$—CH$_2$—" constituting the ring skeleton of the polycyclic group has been substituted with "—O—C(=O)—", and a group represented by the formula: "(a polycycloalkane having 1 hydrogen atom removed therefrom)-R$^{99}$—S(=O)$_2$—O—".

In the formulas, each of $R^{98}$ and $R^{99}$ independently represents a single bond or an alkylene group. The alkylene group preferably has 1 to 12 carbon atoms, more preferably 1 to 5, and most preferably 1 to 3 (a methylene group, an ethylene group or a propylene group).

Among these, as $R^Y$, a cyclic group containing —C(=O)—O— or —S(=O)$_2$— is particularly desirable, as diffusion of acid generated upon exposure can be suppressed, and lithography properties can be improved.

Specific examples of the monovalent aliphatic group of 3 to 20 carbon atoms represented by $R^Y$ having —C(=O)—O— or —S(=O)$_2$— are shown below. The dotted line (bond) extending from an aliphatic group is bonded to $R^2$.

[Chemical Formula 33.]

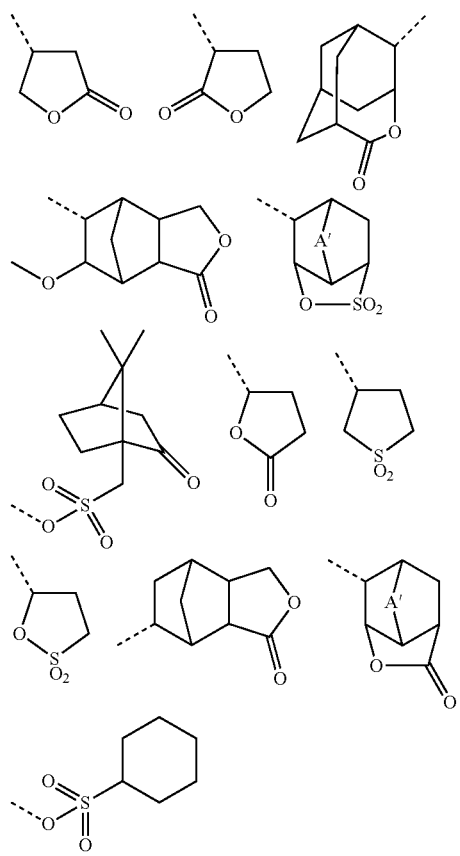

In the formulas, A' represents an oxygen atom (—O—), a sulfur atom (—S—), or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—.

As A', an alkylene group of 1 to 5 carbon atoms or —O— is preferable, more preferably an alkylene group of 1 to 5 carbon atoms, and a methylene group is particularly desirable.

In formula (b1-1), each of $R^1$ and $R^2$ independently represents a divalent linking group.

The divalent linking group for $R^1$ and $R^2$ is the same as defined for the divalent linking group for $Y^2$ in general formula (a1-0-2), and preferable examples thereof include an alkylene group, a divalent aliphatic cyclic group and a divalent linking group containing a hetero atom.

Preferable examples of the divalent linking group for $R^1$ and $R^2$ include non-hydrocarbon, oxygen atom-containing linking groups such as an ether bond (—O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, oxygen atom-containing linking groups with an alkylene group.

Specific examples of the combinations of the aforementioned non-hydrocarbon, hetero atom-containing linking groups and an alkylene group include —$R^{91}$—O—, —C(=O)—O—$R^{92}$—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, more preferably an alkylene group of 1 to 8 carbon atoms, still more preferably an alkylene group of 1 to 5 carbon atoms, and most preferably an alkylene group of 1 to 3 carbon atoms (a methylene group, an ethylene group or a propylene group).

Among these, as $R^1$ and $R^2$, an ester bond or a divalent linking group containing an ester bond is preferable, and —C(=O)—O— or —C(=O)—O—$R^{92}$— is more preferable. It is particularly desirable that $R^1$ represent —C(=O)—O—$R^{92}$— and $R^2$ represents —C(=O)—O—.

Specific examples of the anion moiety of the component (B1) are shown below.

[Chemical Formula 34.]

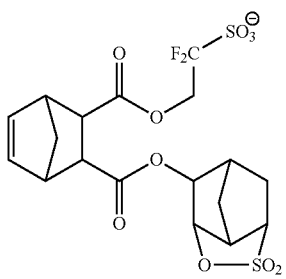

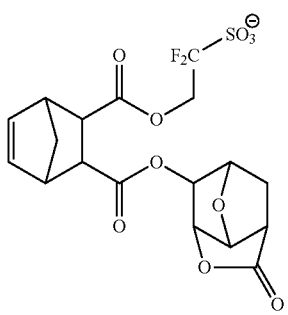

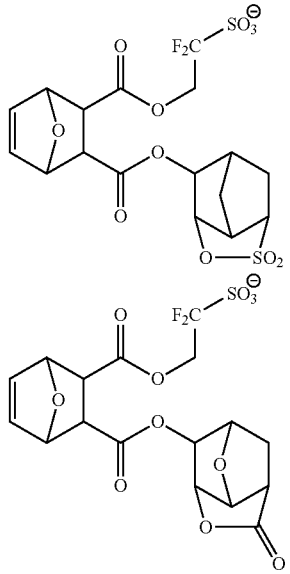

Cation Moiety of Component (B1)

In general formula (b1-1), as the monovalent organic cation for $Z^+$, there is no particular limitation, and any of those conventionally known as cation moiety for an onium salt-based acid generator can be appropriately selected for use.

As the cation moiety, a sulfonium ion or an iodonium ion is preferable, and a sulfonium ion is particularly desirable.

As a particularly preferable example of the monovalent organic cation for $Z^+$, an organic cation represented by general formula (b1-c1) or (b1-c2) shown below can be given.

[Chemical Formula 35.]

(b1-c1)

$$R^{2\prime\prime}-\underset{R^{3\prime\prime}}{\overset{R^{1\prime\prime}}{S^+}}$$

(b1-c2)

$$\underset{R^{6\prime\prime}}{\overset{R^{5\prime\prime}}{I^+}}$$

In the formulas, each of $R^{1\prime\prime}$ to $R^{3\prime\prime}$, $R^{5\prime\prime}$ and $R^{6\prime\prime}$ independently represents an aryl group, alkyl group or alkenyl group which may have a substituent, provided that at least one of $R^{1\prime\prime}$ to $R^{3\prime\prime}$ represents an aryl group, and at least one of $R^{5\prime\prime}$ and $R^{6\prime\prime}$ represents an aryl group. In formula (b1-c1), two of $R^{1\prime\prime}$ to $R^{3\prime\prime}$ may be mutually bonded to form a ring with the sulfur atom.

In formula (b1-c1), each of $R^{1\prime\prime}$ to $R^{3\prime\prime}$ independently represents an aryl group, alkyl group or alkenyl group which may have a substituent. Two of $R^{1\prime\prime}$ to $R^{3\prime\prime}$ may be mutually bonded to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

Examples of the aryl group for $R^{1\prime\prime}$ to $R^{3\prime\prime}$ include an unsubstituted aryl group of 6 to 20 carbon atoms; a substituted aryl group in which part or all of the hydrogen atoms of the aforementioned unsubstituted aryl group has been substituted with an alkyl group, an alkoxy group, an alkoxyalkyloxy group, an alkoxycarbonylalkyloxy group, a halogen atom, a hydroxy group, an oxo group (=O), an aryl group, —C(=O)—O—R$^{6'}$, —O—C(=O)—R$^{7'}$ or —O—R$^{8'}$; and —(R$^{4'}$)—C(=O)—R$^{5'}$.

R$^{4'}$ represents an alkylene group of 1 to 5 carbon atoms. R$^{5'}$ represents an aryl group. As the aryl group for R$^{5'}$, the same aryl groups as those described above for R$^{1'''}$ to R$^{3'''}$ can be mentioned.

Each of R$^{6'}$, R$^{7'}$ and R$^{8'}$ independently represents a linear or branched saturated hydrocarbon group of 1 to 15 atoms, a cyclic saturated hydrocarbon group of 3 to 20 carbon atoms or a linear or branched, aliphatic unsaturated hydrocarbon group of 2 to 5 carbon atoms.

The linear or branched saturated hydrocarbon group has 1 to 15 carbon atoms, and preferably 4 to 10 carbon atoms.

Examples of the linear, saturated hydrocarbon group include a methyl group, an ethyl group, a propyl group, a butyl group, a pentyl group, a hexyl group, a heptyl group, an octyl group, a nonyl group and a decyl group.

Examples of the branched, saturated hydrocarbon group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group, but excluding tertiary alkyl groups.

The linear or branched, saturated hydrocarbon group may have a substituent. Examples of the substituent include an alkoxy group, a halogen atom, a halogenated alkyl group, a hydroxyl group, an oxygen atom (=O), a cyano group and a carboxy group.

The alkoxy group as the substituent for the linear or branched saturated hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the linear or branched, saturated alkyl group include a fluorine atom, a chlorine atom, a bromine atom and an iodine atom, and a fluorine atom is preferable.

Example of the halogenated alkyl group as the substituent for the linear or branched, saturated hydrocarbon group includes a group in which part or all of the hydrogen atoms within the aforementioned linear or branched, saturated hydrocarbon group have been substituted with the aforementioned halogen atoms.

The cyclic saturated hydrocarbon group of 3 to 20 carbon atoms for R$^{6'}$, R$^{7'}$ and R$^{8'}$ may be either a polycyclic group or a monocyclic group, and examples thereof include groups in which one hydrogen atom has been removed from a monocycloalkane, and groups in which one hydrogen atom has been removed from a polycycloalkane (e.g., a bicycloalkane, a tricycloalkane or a tetracycloalkane). More specific examples include groups in which one hydrogen atom has been removed from a monocycloalkane such as cyclopentane, cyclohexane, cycloheptane or cyclooctane; and groups in which one or more hydrogen atoms have been removed from a polycycloalkane such as adamantane, norbornane, isobornane, tricyclodecane or tetracyclododecane.

The cyclic, saturated hydrocarbon group may have a substituent. For example, part of the carbon atoms constituting the ring within the cyclic alkyl group may be substituted with a hetero atom, or a hydrogen atom bonded to the ring within the cyclic alkyl group may be substituted with a substituent.

In the former example, a heterocycloalkane in which part of the carbon atoms constituting the ring within the aforementioned monocycloalkane or polycycloalkane has been substituted with a hetero atom such as an oxygen atom, a sulfur atom or a nitrogen atom, and one hydrogen atom has been removed therefrom, can be used. Further, the ring may contain an ester bond (—C(=O)—O—). More specific examples include a lactone-containing monocyclic group, such as a group in which one hydrogen atom has been removed from γ-butyrolactone; and a lactone-containing polycyclic group, such as a group in which one hydrogen atom has been removed from a bicycloalkane, tricycloalkane or tetracycloalkane containing a lactone ring.

In the latter example, as the substituent, the same substituent groups as those for the aforementioned linear or branched alkyl group can be used.

Alternatively, R$^{6'}$, R$^{7'}$ and R$^{8'}$ may be a combination of a linear or branched alkyl group and a cyclic group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of the linear aliphatic unsaturated hydrocarbon group for R$^{6'}$, R$^{7'}$ and R$^{8'}$ include a vinyl group, a propenyl group (an allyl group) and a butynyl group.

Examples of the branched aliphatic unsaturated hydrocarbon group for R$^{6'}$, R$^{7'}$ and R$^{8'}$ include a 1-methylpropenyl group and a 2-methylpropenyl group.

The aforementioned linear or branched, aliphatic unsaturated hydrocarbon group may have a substituent. Examples of substituents include the same substituents as those which the aforementioned linear or branched alkyl group may have.

The unsubstituted aryl group for R$^{1'''}$ to R$^{3'''}$ is preferably an aryl group having 6 to 10 carbon atoms because it can be synthesized at a low cost. Specific examples thereof include a phenyl group and a naphthyl group.

The alkyl group as the substituent for the substituted aryl group represented by R$^{1'''}$ to R$^{3'''}$ is preferably an alkyl group having 1 to 5 carbon atoms, and a methyl group, an ethyl group, a propyl group, an n-butyl group, or a tert-butyl group is particularly desirable.

The alkoxy group as the substituent for the substituted aryl group is preferably an alkoxy group having 1 to 5 carbon atoms, and a methoxy group, an ethoxy group, an n-propoxy group, an iso-propoxy group, an n-butoxy group or a tert-butoxy group is particularly desirable.

The halogen atom as the substituent for the substituted aryl group is preferably a fluorine atom.

As the aryl group within the substituted aryl group, the same aryl groups as those described above for R$^{1'''}$ to R$^{3'''}$ can be mentioned, and an aryl group of 6 to 20 carbon atoms is preferable, an aryl group of 6 to 10 carbon atoms is more preferable, and a phenyl group or a naphthyl group is still more preferable.

Examples of alkoxyalkyloxy groups as the substituent for the substituted aryl group include groups represented by a general formula shown below:

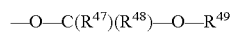

In the formula, R$^{47}$ and R$^{48}$ each independently represents a hydrogen atom or a linear or branched alkyl group; and R$^{49}$ represents an alkyl group.

The alkyl group for R$^{47}$ and R$^{48}$ preferably has 1 to 5 carbon atoms, and may be either linear or branched. As the alkyl group, an ethyl group or a methyl group is preferable, and a methyl group is most preferable.

It is preferable that at least one of $R^{47}$ and $R^{48}$ be a hydrogen atom. It is particularly desirable that at least one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Examples of the alkoxycarbonylalkyloxy group as the substituent for the substituted aryl group include groups represented by a general formula shown below:

—O—$R^{50}$—C(=O)—O—$R^{56}$

In the formula, $R^{50}$ represents a linear or branched alkylene group, and $R^{56}$ represents a tertiary alkyl group.

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

Examples of the tertiary alkyl group for $R^{56}$ include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

Furthermore, the $R^{56}$ group in the aforementioned formula may be substituted with $R^{56\prime}$. $R^{56\prime}$ represents a hydrogen atom, a fluorinated alkyl group or an aliphatic cyclic group containing a hetero atom in the ring structure. Specific examples of the aliphatic cyclic group containing a hetero atom in the ring structure include groups represented by formulas (L1) to (L6) and (S1) to (S4) described later.

The aryl group for each of $R^{1\prime\prime\prime}$ to $R^{3\prime\prime\prime}$ is preferably a phenyl group or a naphthyl group.

Examples of the alkyl group for $R^{1\prime\prime\prime}$ to $R^{3\prime\prime\prime}$ include linear, branched or cyclic alkyl groups of 1 to 10 carbon atoms. Among these, alkyl groups of 1 to 5 carbon atoms are preferable as the resolution becomes excellent. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

The alkenyl group for $R^{1\prime\prime\prime}$ to $R^{3\prime\prime\prime}$ preferably has 2 to 10 carbon atoms, more preferably 2 to 5, and still more preferably 2 to 4. Specific examples thereof include a vinyl group, a propenyl group (an allyl group), a butynyl group, a 1-methylpropenyl group and a 2-methylpropenyl group.

When two of $R^{1\prime\prime\prime}$ to $R^{3\prime\prime\prime}$ are bonded to each other to form a ring with the sulfur atom, it is preferable that the two of $R^{1\prime\prime\prime}$ to $R^{3\prime\prime\prime}$ form a 3 to 10-membered ring including the sulfur atom, and it is particularly desirable that the two of $R^{1\prime\prime\prime}$ to $R^{3\prime\prime\prime}$ form a 5 to 7-membered ring including the sulfur atom.

When two of $R^{1\prime\prime\prime}$ to $R^{3\prime\prime\prime}$ are bonded to each other to form a ring with the sulfur atom, the remaining one of $R^{1\prime\prime\prime}$ to $R^{3\prime\prime\prime}$ is preferably an aryl group. As examples of the aryl group, the same as the above-mentioned aryl groups for $R^{1\prime\prime\prime}$ to $R^{3\prime\prime\prime}$ can be given.

Specific examples of organic cation represented by general formula (b1-c1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl)diphenylsulfonium, (4-(2-methyl-2-adamantyloxycarbonylmethyloxy)phenyl)diphenylsulfonium, (4-(2-methyl-2-adamantyloxycarbonylmethyloxy)-3,5-dimethylphenyl)diphenylsulfonium, tri(4-methylphenyl)sulfonium, dimethyl(4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl)phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl)tetrahydrothiopyranium and 1-(4-methylphenyl)tetrahydrothiopyranium.

Preferable examples of the organic cation represented by formula (b1-c1) are shown below.

[Chemical Formula 36.]

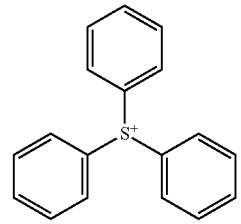
(b1-c1-1)

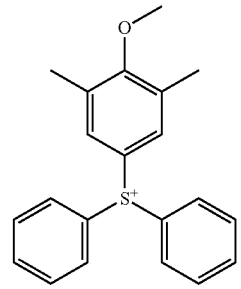
(b1-c1-2)

(b1-c1-3)
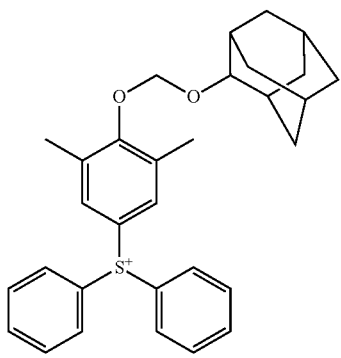
(b1-c1-4)
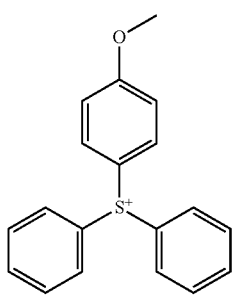
(b1-c1-5)
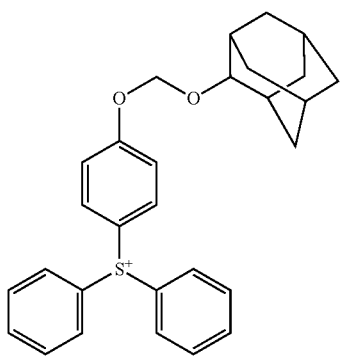
(b1-c1-6)
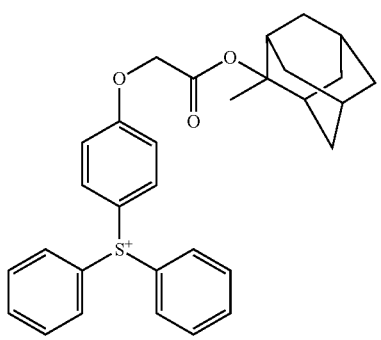
(b1-c1-7)
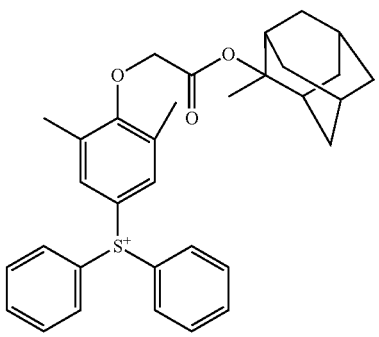
(b1-c1-8)
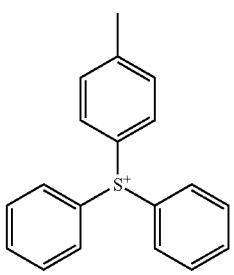
[Chemical Formula 37.]
(b1-c1-9)
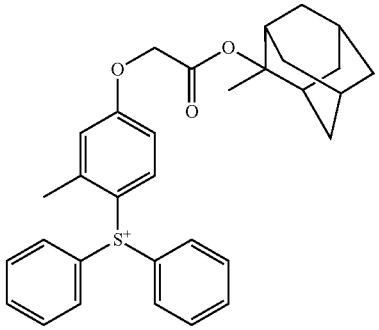
(b1-c1-10)
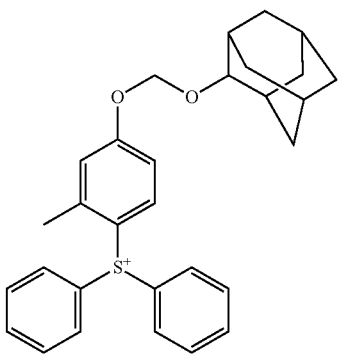

(b1-c1-11)
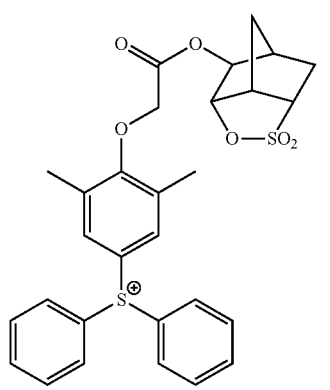
(b1-c1-12)
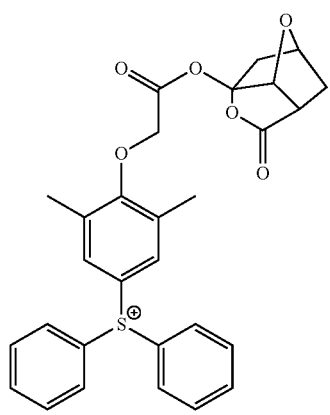
(b1-c1-13)
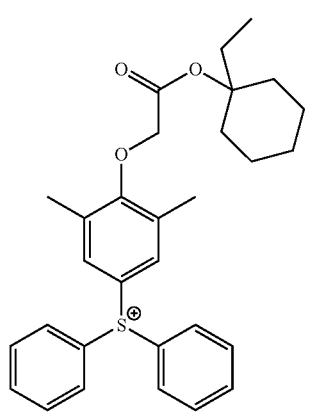
(b1-c1-14)
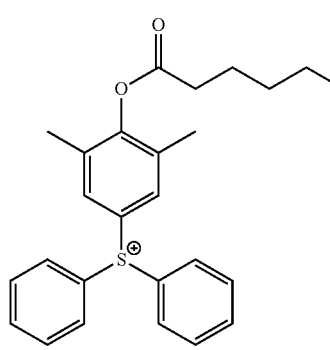
(b1-c1-15)
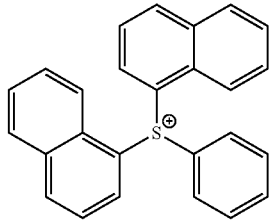
[Chemical Formula 38.]
(b1-c1-16)
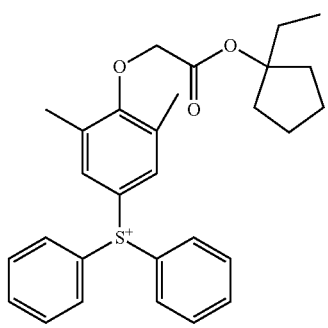
(b1-c1-17)
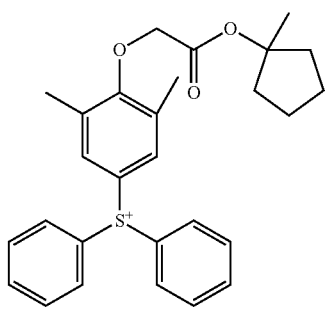
(b1-c1-18)
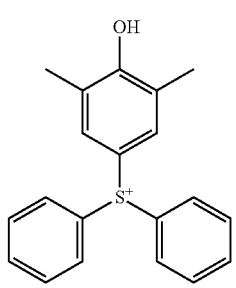
(b1-c1-19)
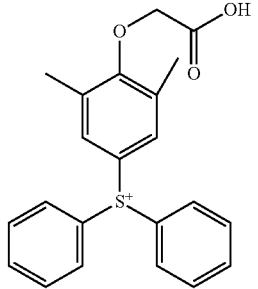

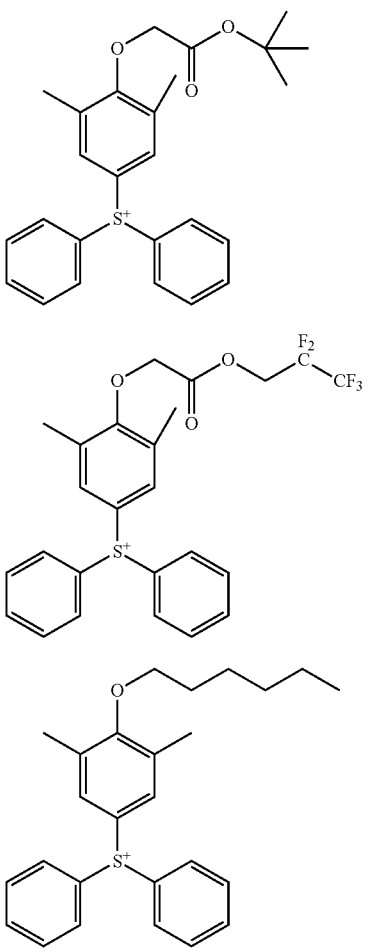

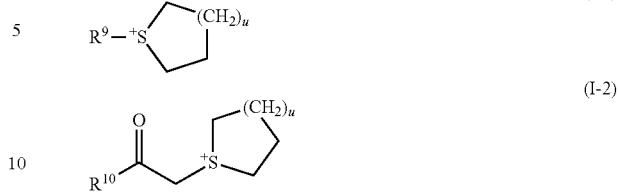

In formula (b1-c2), each of $R^{5'''}$ and $R^{6'''}$ independently represents an aryl group, alkyl group or alkenyl group which may have a substituent.

At least one of $R^{5'''}$ and $R^{6'''}$ represents an aryl group. It is preferable that both $R^{5'''}$ and $R^{6'''}$ represent an aryl group.

As the aryl group for $R^{5'''}$ and $R^{6'''}$, the same as the aryl groups for $R^{1'''}$ to $R^{3'''}$ can be used.

As the alkyl group for $R^{5'''}$ and $R^{6'''}$, the same as the alkyl groups for $R^{1'''}$ to $R^{3'''}$ can be used.

As the alkenyl group for $R^{5'''}$ and $R^{6'''}$, the same as the alkenyl groups for $R^{1'''}$ to $R^{3'''}$ can be used.

It is particularly desirable that both of $R^{5'''}$ and $R^{6'''}$ represents a phenyl group.

Specific examples of the cation moiety represented by general formula (b1-c2) include diphenyliodonium and bis (4-tert-butylphenyl)iodonium.

Furthermore, as a preferable example of the monovalent organic cation for $Z^+$, a cation represented by general formula (I-1) or (I-2) shown below can be mentioned.

In formulas (I-1) and (I-2), each of $R^9$ and $R^{19}$ independently represents a phenyl group or naphthyl group which may have a substituent, an alkyl group of 1 to 5 carbon atoms, an alkoxy group or a hydroxy group.

u is an integer of 1 to 3, and most preferably 1 or 2.

[Chemical Formula 39.]

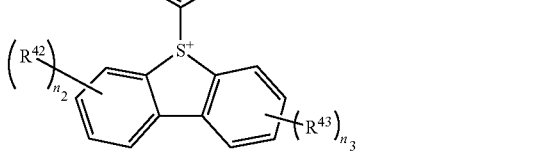

Furthermore, as a preferable example of the monovalent organic cation for $Z^+$, a cation represented by general formula (I-5) or (I-6) shown below can be mentioned.

[Chemical Formula 40.]

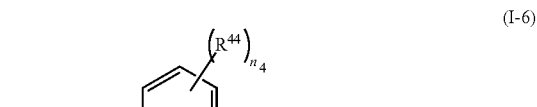

In the formulas, $R^{40}$ represents a hydrogen atom or an alkyl group; $R^{41}$ represents an alkyl group, an acetyl group, a carboxy group or a hydroxyalkyl group; each of $R^{42}$ to $R^{46}$ independently represents an alkyl group, an acetyl group, an alkoxy group, a carboxy group, or a hydroxyalkyl group; each of $n_0$ to $n_5$ independently represents an integer of 0 to 3, provided that $n_0+n_1$ is 5 or less; and $n_6$ represents an integer of 0 to 2.

In general formula (I-5), the alkyl group for $R^{40}$ is preferably an alkyl group of 1 to 15 carbon atoms, more preferably an alkyl group of 1 to 10 carbon atoms, and still more preferably an alkyl group of 1 to 4 carbon atoms. Among these, a linear or branched alkyl group is preferable.

In general formulas (I-5) and (I-6), with respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of the $OR^{40}$ group, as indicated by the value of $n_0$, then the two or more of the $OR^{40}$ group may be the same or different from each other.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_0$ is preferably 0 or 1.

$n_1$ is preferably 0 to 2.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1.

Preferable examples of the organic cation represented by formula (I-5) or (I-6) are shown below.

[Chemical Formula 41.]

(I-5-1)

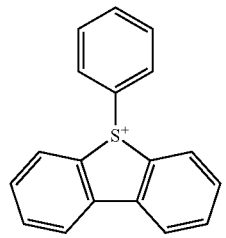

(I-5-2)

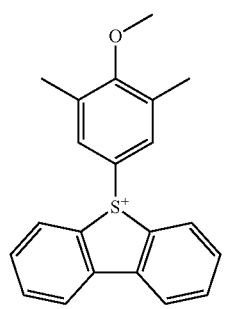

(I-5-3)

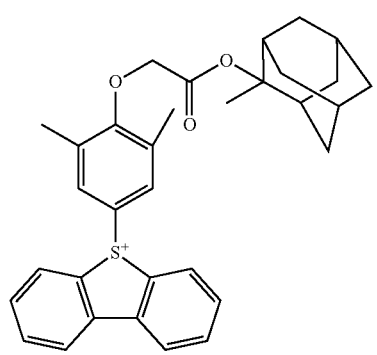

-continued (I-5-4)

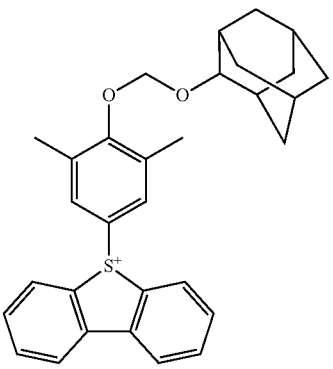

(I-5-5)

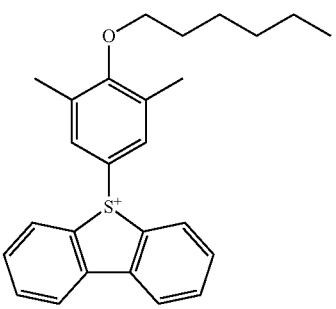

(I-5-6)

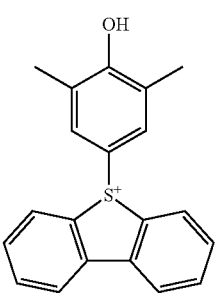

(I-6-1)

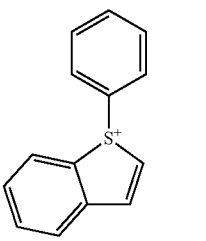

In the present invention, as the monovalent organic cation for $Z^+$, any cation other than those described above can be used, for example, the organic cations shown in the <Synthesis of novel compound> described later in the Examples can be mentioned.

Among the aforementioned examples, as the component (B1), in terms of improvement in the lithography properties and the shape of the resist pattern, a compound represented by general formula (b1-1-0) shown below is particularly desirable.

[Chemical Formula 42.]

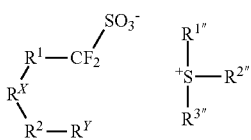

(b1-1-0)

In the formula, $R^{1'''}$ to $R^{3'''}$, $R^X$, $R^Y$, $R^1$ and $R^2$ are the same as defined above.

As the component (B1), one type of compound may be used, or two or more types of compounds may be used in combination.

In the resist composition of the present invention, the amount of the component (B1), relative to 100 parts by weight of the component (A) is preferably within the range of 0.5 to 65 parts by weight, more preferably within the range of 0.5 to 50 parts by weight, still more preferably within the range of 0.5 to 40 parts by weight, and most preferably within the range of 1 to 30 parts by weight.

When the amount of the component (B1) is at least as large as the lower limit of the above-mentioned range, various lithography properties of the resist composition are improved. Further, a resist pattern having an excellent shape can be obtained. On the other hand, when the amount is no more than the upper limit of the above-mentioned range, a uniform solution can be obtained and the storage stability becomes satisfactory.

In the component (B), the amount of the component (B1) based on the total weight of the component (B) is preferably 20% by weight or more, more preferably 40% by weight, and may be even 100% by weight. The amount of the component (B1) is most preferably 100% by weight. When the amount of the component (B1) is at least as large as the lower limit of the above-mentioned range, various lithography properties of the resist composition are improved. Further, a resist pattern having an excellent shape can be obtained.

[Component (B2)]

In the resist composition of the present invention, if desired, the component (B) may further contain an acid generator other than the component (B1) (hereafter, referred to as "component (B2)").

The component (B2) is not particularly limited as long as it is an acid generator that does not fall under the category of the component (B1). Examples of such an acid generator are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt-based acid generator which does not fall under the category of the component (B1), a compound represented by general formula (b-1) or (b-2) shown below can be used.

[Chemical Formula 43.]

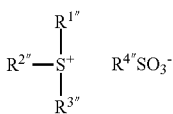

(b-1)

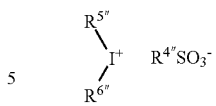

(b-2)

In formula (b-1), each of $R^{1'''}$ to $R^{3'''}$ independently represents an aryl group, alkyl group or alkenyl group which may have a substituent, provided that at least one of $R^{1'''}$ to $R^{3'''}$ represents an aryl group, and two of $R^{1'''}$ to $R^{3'''}$ may be bonded to each other to form a ring with the sulfur atom. In formula (b-2), $R^{5'''}$ and $R^{6'''}$ each independently represent an aryl group, alkyl group or alkenyl group which may have a substituent, provided that and at least one of $R^{5'''}$ and $R^{6'''}$ represents an aryl group. $R^{4'''}$ represents a halogenated alkyl group, an aryl group or an alkenyl group which may have a substituent.

In general formula (b-1), $R^{1'''}$ to $R^{3'''}$ are respectively the same as defined for $R^{1'''}$ to $R^{3'''}$ in general formula (b1-c1).

In general formula (b-2), $R^{5'''}$ and $R^{6'''}$ are respectively the same as defined for $R^{5'''}$ to $R^{6'''}$ in general formula (b1-c2).

In formulas (b-1) and (b-2), $R^{4'''}$ represents a halogenated alkyl group, an aryl group or an alkenyl group which may have a substituent.

As an example of the halogenated alkyl group for $R^{4'''}$, a group in which part of or all of the hydrogen atoms of a linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

When the alkyl group within the halogenated alkyl group is a linear or branched alkyl group, it preferably has 1 to 10 carbon atoms, more preferably 1 to 8 carbon atoms, and most preferably 1 to 4 carbon atoms. On the other hand, when the alkyl group within the halogenated alkyl group is a cyclic alkyl group, it preferably has 4 to 15 carbon atoms, more preferably 4 to 10 carbon atoms, and most preferably 6 to 10 carbon atoms.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratios are preferable, as they result in increased acid strength.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4'''}$ may have one substituent, or two or more substituents.

Examples of the substituent include a halogen atom, a hetero atom, an alkyl group, and a group represented by the formula X-$Q^2$- (in the formula, $Q^2$ represents a divalent linking group containing an oxygen atom; and X represents a hydrocarbon group of 3 to 30 carbon atoms which may have a substituent).

Examples of halogen atoms and alkyl groups as substituents for $R^{4'''}$ include the same halogen atoms and alkyl groups as those described above with respect to the halogenated alkyl group for $R^{4'''}$.

Examples of hetero atoms include an oxygen atom, a nitrogen atom, and a sulfur atom.

In the group represented by formula X-$Q^2$-, $Q^2$ represents a divalent linking group containing an oxygen atom.

$Q^2$ may contain an atom other than an oxygen atom. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ are the same as defined above, and independently represents an alkylene group).

The alkylene group for $R^{91}$ to $R^{93}$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As $Q^2$, a divalent linking group containing an ester bond or an ether bond is preferable, and —$R^{91}$—O—, —$R^{92}$—O—C(=O)— or —C(=O)—O—$R^{93}$—O—C(=O)— is more preferable.

In the group represented by the formula X-$Q^2$-, the hydrocarbon group for X may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for X, there is no particular limitation as long as it is an atom other than carbon and hydrogen. Examples of hetero atoms include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 44.]

(L1)

(L2)

(L3)

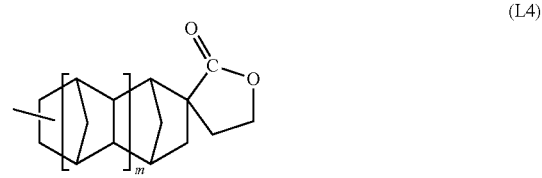
(L4)

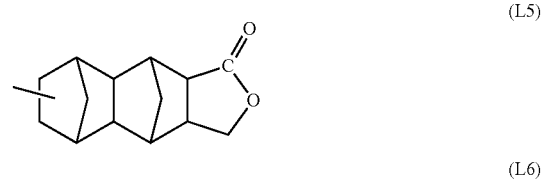
(L5)

(L6)

(S1)

(S2)

-continued

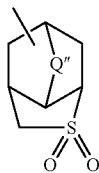
(S3)

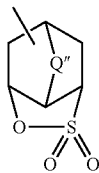
(S4)

In the formula, Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents 0 or 1.

As the alkylene group for Q", $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

Among the examples described above, as X, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by the aforementioned formulas (L2) to (L5), (S3) and (S4) are preferable.

Further, in the present invention, it is particularly desirable that X have a polar moiety, because it results in improved lithographic properties and resist pattern shape.

Specific examples of X having a polar moiety include those in which a part of the carbon atoms constituting the aliphatic hydrocarbon group for X is substituted with a substituent group containing a hetero atom such as —O—, —C(=O)—O—, —C(=O)—, —O—C(=O)—O—, —C(=O)—NH—, —NH— (wherein H may be substituted with a substituent such as an alkyl group or an acyl group), —S—, —S(=O)$_2$— and —S(=O)$_2$—O—.

In the present invention, $R^{4'''}$ preferably has X-$Q^2$- as a substituent. In this case, $R^{4'''}$ is preferably a group represented by formula X-$Q^2$-$Y^3$— [wherein $Q^2$ and X are the same as defined above; and $Y^3$ represents an alkylene group of 1 to 4 carbon atoms which may have a substituent, or a fluorinated alkylene group of 1 to 4 carbon atoms which may have a substituent].

In the group represented by the formula X-$Q^2$-$Y^3$—, as the alkylene group for $Y^3$, the same alkylene group as those described above for $Q^2$ in which the number of carbon atoms is 1 to 4 can be used.

As the fluorinated alkylene group for $Y^3$, the aforementioned alkylene group in which part or all of the hydrogen atoms has been substituted with fluorine atoms can be used.

Specific examples of $Y^3$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^3$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate such as methanesulfonate, n-propanesulfonate, n-butanesulfonate, n-octanesulfonate, 1-adamantanesulfonate, or 2-norbornanesulfonate; or a sulfonate such as d-camphor-10-sulfonate, benzenesulfonate, perfluorobenzenesulfonate, or p-toluenesulfonate.

Furthermore, onium salts in which the anion moiety of these onium salts is replaced by an anion moiety represented by any one of formulas (b1) to (b8) shown below can also be used.

[Chemical Formula 45.]

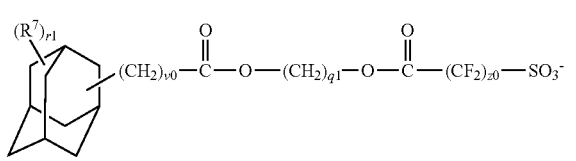

(b1)

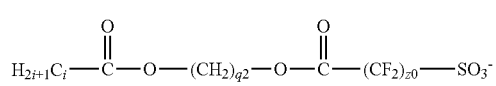

(b2)

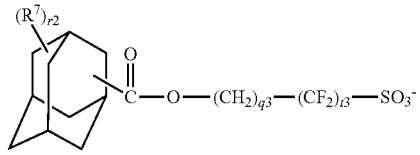

(b3)

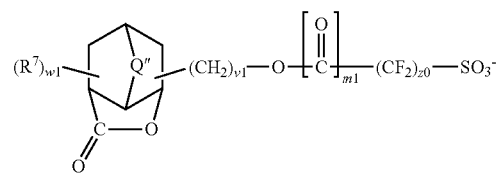

(b4)

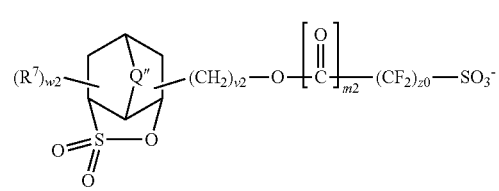

(b5)

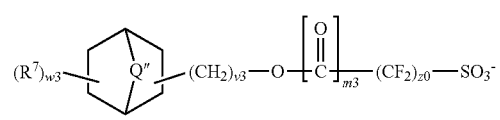

(b6)

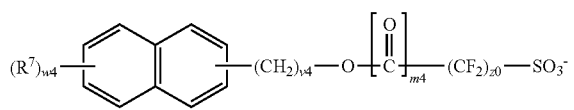

(b7)

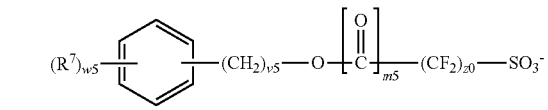

(b8)

In the formulas, z0 represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; i represents an integer of 1 to 20; $R^7$ represents a substituent; each of m1 to m5 independently represents 0 or 1; each of v0 to v5 independently represents an integer of 0 to 3; each of w1 to w5 independently represents an integer of 0 to 3; and Q" is the same as defined above.

As the substituent for $R^7$, the same groups as those which the aforementioned aliphatic hydrocarbon group or aromatic hydrocarbon group for X may have as a substituent can be used.

If there are two or more of the $R^7$ group, as indicated by the values r1, r2, and w1 to w5, then the two or more of the $R^7$ groups may be the same or different from each other.

Among the aforementioned examples, in terms of significantly improving the effects of the present invention, the onium salt-based acid generator represented by formula (b-1) or (b-2) preferably has an anion moiety in which a fluorine atom is bonded to a carbon atom adjacent to the sulfur atom of the —$SO_3^-$ group, more preferably an anion moiety in which $R^{4''}$ represents a halogenated alkyl group which may have a substituent, and most preferably an anion moiety represented by any one of formulas (b1) to (b8).

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may also be used.

[Chemical Formula 46.]

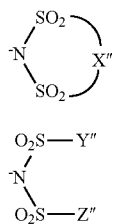

(b-3)

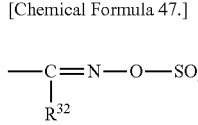

(b-4)

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Further, an onium salt-based acid generator in which the anion moiety ($R^{4"}SO_3^-$) in general formula (b-1) or (b-2) has been replaced with $R^a$—COO$^-$ (in the formula, $R^a$ represents an alkyl group or a fluorinated alkyl group) can also be used (the cation moiety is the same as that in general formula (b-1) or (b-2)).

In the formula above, as $R^a$, the same groups as those described above for $R^{4"}$ can be used.

Specific examples of the group represented by the formula "$R^a$—COO$^-$" include a trifluoroacetic acid ion, an acetic acid ion, and a 1-adamantanecarboxylic acid ion.

Further, onium salts having a cation moiety represented by general formula (I-5) or (I-6) above, and having a fluorinated alkylsulfonate ion (e.g., the anion moiety ($R^{4"}SO_3^-$) in general formula (b-1) or (b-2) above) or an anion moiety represented by general formula (b-3) or (b-4) above as the anion moiety, can be used.

In the present description, an oximesulfonate acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 47.]

$$-\underset{R^{32}}{\underset{|}{C}}=N-O-SO_2-R^{31}$$

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 48.]

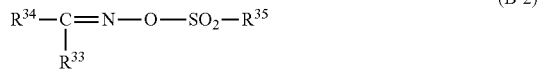

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 49.]

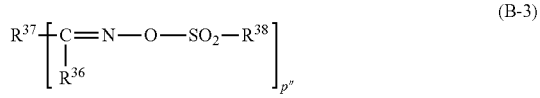

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 85) may be preferably used.

Furthermore, as preferable examples, the following can be used.

[Chemical Formula 50.]

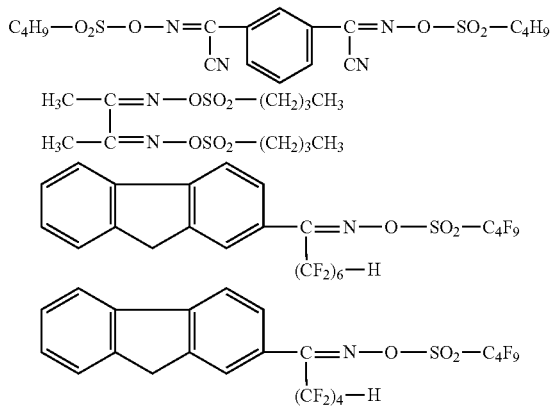

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), one type of acid generator may be used, or two or more types may be used in combination.

In the positive resist composition of the present invention, the total amount of the component (B) relative to 100 parts by weight of the component (A) is preferably 0.5 to 50 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>
[Component (D)]

It is preferable that the resist composition of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used. Among these, an aliphatic amine, particularly a secondary aliphatic amine or tertiary aliphatic amine, and an aromatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Further, aliphatic amines other than those described above can be used. Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine and tris[2-{2-(2-hydroxyethoxy)ethoxy}ethyl]amine.

Examples of aromatic amines include aniline compounds such as aniline, N,N-n-butyl-aniline, 2,6-diisopropylaniline, N-isopropylaniline, 3-isopropoxyaniline and N-ethylaniline, pyridine, 4-dimethylaminopyridine, pyrrole, indole, pyrazole, imidazole and derivatives thereof, as well as diphenylamine, triphenylamine and tribenzylamine.

As the component (D), one type of compound may be used alone, or two or more types may be used in combination.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A).

[Component (F)]

In the resist composition of the present invention, for imparting water repellency to the resist film, a fluorine additive (hereafter, referred to as "component (F)") can be added. As the component (F), for example, a fluorine-containing polymeric compound described in Japanese Unexamined Patent Application, First Publication No. 2010-002870 can be used.

More specifically, as the component (F), a polymer having a structural unit represented by formula (f1-1) shown below can be mentioned, and is preferably a polymer (homopolymer) consisting of a structural unit represented by formula (f1-1) shown below, a copolymer having a structural unit represented by formula (f1-1) shown below and the aforementioned structural unit (a1), or a copolymer having a structural unit represented by formula (f1-1) shown below, a structural unit derived from an acrylate ester or a methacrylate ester and the aforementioned structural unit (a1). As the structural unit (a1) to be copolymerized with a structural unit represented by formula (f1-1) shown below, the structural unit represented by the aforementioned formula (a1-1-32) is preferable.

[Chemical Formula 51.]

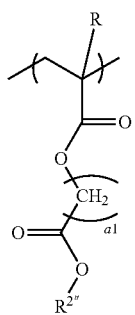

(f1-1)

In the formula, R is the same as defined above; a1 represents an integer of 1 to 5; and $R^{2'''}$ represents an organic group containing a fluorine atom.

In formula (f1-1), $R^{2'''}$ represents an organic group containing a fluorine atom, and is preferably a hydrocarbon group containing a fluorine atom. Examples of the hydrocarbon group containing a fluorine atom include linear or branched alkyl groups (preferably linear alkyl groups) in which part or all of the hydrogen atoms have been substituted with fluorine atoms.

Among these, as $R^{2'''}$, a group represented by the formula "—$(CH_2)o$-$CF_3$" (in the formula, o represents an integer of 1 to 3) is preferable.

In formula (f1-1), a1 represents an integer of 1 to 5, preferably an integer of 1 to 3, and more preferably 1 or 2.

In formula (f1-1), R is the same as defined above. As R, a hydrogen atom or a methyl group is preferable.

As the component (F), one type of compound may be used, or two or more types may be used in combination.

The amount of the compound (F) relative to 100 parts by weight of the component (A) is preferably in the range of 0.1 to 10 parts by weight.

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be produced by dissolving the materials for the resist composition in an organic solvent (hereafter, referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples of the component (S) include lactones such as γ-butyrolactone; ketones such as acetone, methyl ethyl ketone, cyclohexanone (CH), methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzyl ether, cresylmethylether, diphenylether, dibenzylether, phenetole, butylphenylether, ethylbenzene, diethylbenzene, pentylbenzene, isopropylbenzene, toluene, xylene, cymene and mesitylene.

The component (S) can be used individually, or in combination as a mixed solvent.

Among these, cyclohexanone (CH), γ-butyrolactone, propylene glycol monomethyl ether acetate (PGMEA), propylene glycol monomethyl ether (PGME) and ethyl lactate (EL) are preferable, and γ-butyrolactone, PGMEA and PGME are particularly desirable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Alternatively, when cyclohexanone (CH) is mixed as the polar solvent, the PGMEA:CH weight ratio is preferably from 1:9 to 9:1, and more preferably from 2:8 to 9:1.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is preferably within a range from 0.5 to 20% by weight, and more preferably from 1 to 15% by weight.

Dissolving of the components for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

As described above, the resist composition of the present invention is advantageous in that excellent lithography properties can be achieved, and a resist pattern having an excellent shape can be formed.

The resist composition of the present invention includes an acid generator (B1) containing a novel compound represented by general formula (b1-1).

The component (B1) has 2 aliphatic groups ($R^X$ and $R^Y$) in the anion moiety thereof.

On one terminal of the anion moiety, a monovalent aliphatic group of 3 to 20 carbon atoms ($R_Y$) having —C(=O)—O— or —S(=O)$^2$— is positioned. By virtue of this feature, diffusion of acid generated upon exposure can be suppressed, thereby improving the lithography properties of the formed resist pattern.

Further, in the anion moiety, a divalent aliphatic group of 3 to 20 carbon atoms is positioned between the linking groups ($R^1$ and $R^2$). By virtue of this feature, deterioration of solubility in an organic solvent caused by the polar group within the aliphatic group ($R^Y$) can be prevented. As a result, the solubility in an organic solvent can be improved, so that a wide variety of organic solvents can be used.

Furthermore, the anion moiety has linking groups ($R^1$ and $R^2$) so as to have an extremely bulky structure. As a result, diffusion of acid generated upon exposure can be suppressed.

For these reasons, it is presumed that the resist composition of the present invention can achieve the aforementioned effects.

The resist composition of the present invention containing the component (B1) is capable of forming a resist pattern with a high rectangularity and an excellent shape. Further, the formed resist pattern has reduced roughness (such as line width roughness (LWR)), and exhibit excellent mask reproducibility (such as mask error factor) and process margin (EL margin).

<<Method of Forming a Resist Pattern>>

The method of forming a resist pattern according to the second aspect of the present invention includes: using a resist composition according to the first aspect of the present invention to form a resist film on a substrate; conducting exposure of the resist film; and alkali-developing the resist film to form a resist pattern.

The method for forming a resist pattern according to the present invention can be performed, for example, as follows.

Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an electron lithography system or the like, the resist film is selectively exposed to an electron beam (EB) through a desired mask pattern, followed by post exposure bake (PEB) under temperature conditions of 80 to 150° C. for 40 to 120 seconds, preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the alkali developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV, and particularly effective to EB or EUV.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

The method of forming a resist pattern according to the present invention is also applicable to a double exposure method or a double patterning method.

<<Compound>>

The compound according to a third aspect of the present invention is a compound represented by general formula (b0-1) shown below.

[Chemical Formula 52.]

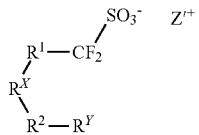

(b0-1)

In the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; each of $R^1$ and $R^2$ independently represents a divalent linking group; and $Z'^+$ represents a monovalent cation.

In formula (b0-1), $R^X$, $R^Y$, $R^1$ and $R^2$ are respectively the same as defined for $R^X$, $R^Y$, $R^1$ and $R^2$ in the aforementioned formula (b1-1).

$Z'^+$ represents a monovalent cation, and examples thereof include an alkali metal ion, an organic ammonium ion and other organic cations.

Examples of alkali metal ions include a sodium ion, a lithium ion and a potassium ion, and a sodium ion or a lithium ion is preferable.

Examples of the organic ammonium ion include those represented by general formula (b0-1-0) shown below.

[Chemical Formula 53.]

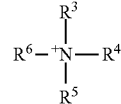

(b0-1-0)

In the formula, each of $R^3$ to $R^6$ independently represents a hydrogen atom or a hydrocarbon group which may have a substituent, provided that at least one of $R^3$ to $R^6$ represents a hydrocarbon group; and at least two of $R^3$ to $R^6$ may be mutually bonded to form a ring.

In formula (b0-1-0), each of $R^3$ to $R^6$ independently represents a hydrogen atom or a hydrocarbon group which may have a substituent, provided that at least one of $R^3$ to $R^6$ represents a hydrocarbon group.

As the hydrocarbon group for $R^3$ to $R^6$, the same hydrocarbon groups as those described above for X in the aforementioned component (B2) can be mentioned.

The hydrocarbon group may be either an aliphatic hydrocarbon group or an aromatic hydrocarbon group. When the hydrocarbon group is an aliphatic hydrocarbon group, it is particularly desirable that the hydrocarbon group is an alkyl group of 1 to 12 carbon atoms which may have a substituent.

At least one of $R^3$ to $R^6$ is a hydrocarbon group, and it is preferable that two or three groups are hydrocarbon groups.

At least two of $R^3$ to $R^6$ may be mutually bonded to form a ring. For example, two of $R^3$ to $R^6$ may be bonded to form a ring, three of $R^3$ to $R^6$ may be bonded to form a ring, or two of $R^3$ to $R^6$ may be bonded to form a ring, and the remaining two may be bonded to form another ring.

The ring which is formed by at least two of $R^3$ to $R^6$ bonded together with the nitrogen atom (i.e., the hetero ring containing nitrogen as a hetero atom) may be either an aliphatic hetero ring, or an aromatic hetero ring. Further, the hetero ring may be either a monocyclic group or a polycyclic group.

Specific examples of the ammonium ion represented by general formula (b0-1-0) include ammonium ions derived from an amine.

Here, an "ammonium ion derived from an amine" refers to an amine having a hydrogen atom bonded to the nitrogen atom to become a cation, and a tertiary ammonium ion in which a substituent has been bonded to the nitrogen atom of an amine.

The amine from which the ammonium ion is derived may be either an aliphatic amine or an aromatic amine.

As the aliphatic amine, an amine in which at least one hydrogen atom of ammonia ($NH_3$) has been substituted with an alkyl group or hydroxyalkyl group of no more than 12 carbon atoms (i.e., alkylamines or alkylalcoholamines), or a cyclic amine is particularly desirable.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo [2.2.2]octane.

Examples of aromatic amines include aniline, pyridine, 4-dimethylaminopyridine (DMAP), pyrrole, indole, pyrazole, and imidazole.

Examples of the tertiary ammonium ion include a tetramethylammonium ion, a tetraethylammonium ion and a tetrabutylammonium ion.

As the organic cation other than organic ammonium ion, the same organic cations as those described above for the monovalent organic cation represented by $Z^+$ in the aforementioned formula (b1-1) can be mentioned.

The compound of the present invention described above is a novel compound useful as a compound for deriving an acid generator for a resist composition or a precursor of a compound to be used as an acid generator.

<<Acid Generator>>

The acid generator according to a fourth aspect of the present invention is the compound according to the third aspect of the present invention in which $Z'^+$ in the aforementioned general formula (b0-1) represents an organic cation.

The explanation of the acid generator of the present invention is the same as the explanation of the aforementioned component (B1).

In the acid generator of the present invention, $R^Y$ in general formula (b0-1) preferably represents a cyclic group containing —C(=O)—O— or —S(=O)$_2$— in the ring structure thereof.

Further, in the acid generator of the present invention, $R^X$ in general formula (b0-1) preferably represents a divalent alicyclic group of 3 to 20 carbon atoms.

In the acid generator of the present invention, as a preferable example of $Z'^+$, an organic cation represented by general formula (b1-c1) or (b1-c2) shown below can be given.

[Chemical Formula 54.]

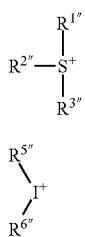

In the formulas, each of $R^{1''}$ to $R^{3''}$, $R^{5''}$ and $R^{6''}$ independently represents an aryl group, alkyl group or alkenyl group which may have a substituent, provided that at least one of $R^{1''}$ to $R^{3''}$ represents an aryl group, and at least one of $R^{5''}$ and $R^{6''}$ represents an aryl group. In formula (b1-c1), two of $R^{1''}$ to $R^{3''}$ may be mutually bonded to form a ring with the sulfur atom.

The explanation of the organic cation represented by formula (b1-c1) or (b1-c2) is the same as the explanation of the organic cation represented by formula (b1-c1) or (b1-c2) in the aforementioned component (B1).

The acid generator is useful for a chemically amplified resist composition, for example, the acid-generator component (B) of the resist composition according to the first aspect of the present invention.

(Production Method of Acid Generator)

The acid generator (B1-1-0) according to the present invention can be produced, for example by a method including the steps of:

an ester reaction step (R1) in which a compound (I) shown below is reacted with a compound (II) shown below to obtain a compound (III) shown below, an ester reaction step (R2) in which the compound (III) obtained in the ester reaction step (R1) is reacted with a compound (IV) shown below in the presence of pyridine and isopropylcarbodiimide to obtain a diester, and a salt exchange step in which the diester obtained in the ester reaction step (R2) is subjected to salt exchange.

As described above, in the second step (ester reaction step (R2)), by using diisopropylcarbodiimide as a condensing agent and pyridine as a solvent, the ester reactivity is increased, so that the diester can be obtained with a high purity.

[Chemical Formula 55.]

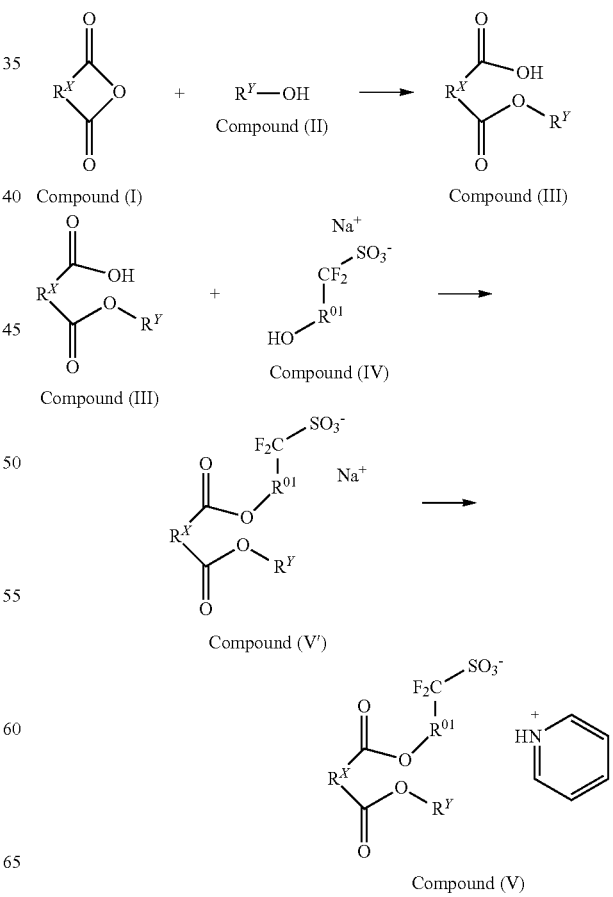

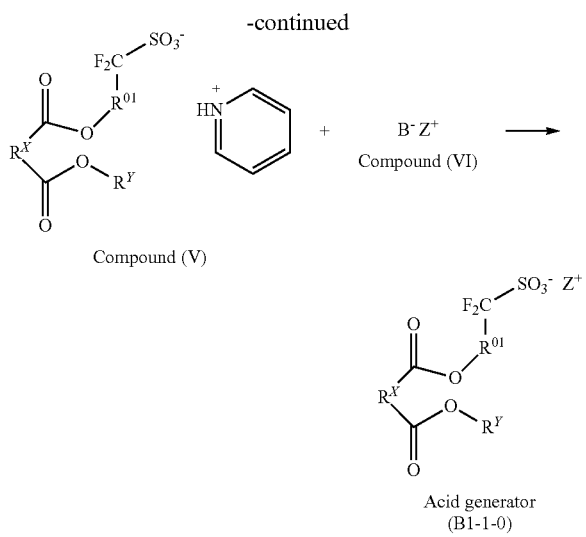

Compound (V)

Acid generator
(B1-1-0)

In the formula, $R^X$ represents a divalent aliphatic group of 3 to 20 carbon atoms; $R^Y$ represents a monovalent aliphatic group of 3 to 20 carbon atoms having —C(=O)—O— or —S(=O)$_2$—; $R^{01}$ represents a linear or branched alkylene group of 1 to 8 carbon atoms which may have a fluorine atom; $B^-$ represents a non-nucleophilic ion; and $Z^+$ is the same as defined for $Z^+$ in general formula (b1-1).

Ester Reaction Step (R1)

For example, the ester reaction step (R1) can be performed as follows.

A compound (I) and a compound (II) are dissolved in an appropriate solvent (dichloromethane, acetonitrile, chloroform, methylene chloride or the like), and a reaction is performed by stirring or the like while cooling. Then, the reaction liquid obtained by the reaction is dropwise added to a base for maturing. The maturing time is preferably 1 to 6 hours, and more preferably 2 to 4 hours. Examples of the base include inorganic bases such as sodium hydride, $K_2CO_3$ and $Cs_2CO_3$; and organic bases such as triethylamine and 4-dimethylaminopyridine (DMAP). Thereafter, an acid treatment is conducted, thereby obtaining a compound (III).

Ester Reaction Step (R2)

For example, the ester reaction step (R2) can be performed as follows.

The compound (III) obtained in the ester reaction step (R1) is dissolved in pyridine, and diisopropylcarbodiimide is added thereto, followed by stirring while cooling. While cooling, a compound (IV) is dropwise added, and maturing is conducted.

The cooling temperature is preferably 10° C. or lower, and more preferably 3 to 7° C. The maturing time is preferably 6 to 48 hours, and more preferably 8 to 24 hours.

Subsequently, the reaction liquid obtained by the maturing is washed with a solvent such as water, tert-butylmethylether (TBME) or the like.

In the ester reaction (R2), by using pyridine and diisopropylcarbodiimide, the second ester reaction can be selectively proceeded without the compound (III) obtained in the ester reaction step (R1) being decomposed. Further, after the ester reaction, diisopropylcarbodiimide can be easily removed from the reaction system. In addition, the compound (IV) exhibits a high solubility in pyridine. As a result, by using pyridine as the solvent, the ester reaction of the compound (III) and the compound (IV) can be performed by dissolving and mixing.

In the presence of pyridine and diisopropylcabodiimide, at the completion stage of the reaction between the compound (III) and the compound (IV), a compound (V') which is a sodium salt can be obtained as a diester. Thereafter, pyridine hydrochloride is added, and extraction or the like is conducted, thereby obtaining a compound (V) which is a pyridinium salt.

The compound (V') may be used as a diester in the subsequent salt exchange step. However, it is preferable to use the compound (V) which is a pyridinium salt because the salt exchange reaction can be reliably proceeded.

Salt Exchange Step

For example, the salt exchange step can be performed as follows.

A compound (VI) is dissolved in an appropriate organic solvent (e.g., dichloromethane, acetonitrile, methanol, chloroform, methylene chloride or the like), and the compound (V) is added thereto, followed by stirring or the like to effect a salt exchange reaction.

The reaction temperature is preferably 10 to 30° C., and more preferably 15 to 25° C.

The reaction time is preferably 0.5 to 3 hours, and more preferably 0.5 to 2 hours.

$B^-$ is a non-nucleophilic ion, and examples thereof include a halogen ion such as a bromine ion or a chlorine ion; an ion capable of forming an acid exhibiting a lower acidity than the compound (V); $BF_4^-$, $AsF_6^-$, $SbF_6^-$, $PF_6^-$ and $ClO_4^-$. Examples of ions which are capable of forming an acid exhibiting a lower acidity include sulfonate ions such as a p-toluenesulfonate ion, a methanesulfonate ion and a benzenesulfonate ion.

The structure of the compound obtained after each of the steps described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other formulas.

<Synthesis of Novel Compound>

The novel compounds of the present invention was synthesized in accordance with the examples shown below. Further, comparative compounds were synthesized in accordance with the comparative examples shown below.

In the NMR analysis, the internal standard for $^1$H-NMR is tetramethylsilane (TMS), and the internal standard for $^{19}$F-NMR is hexafluorobenzene (the peak of hexafluorobenzene was regarded as −160 ppm).

Example 1

Synthesis of Compound (B1-1-1)

i) Synthesis of Compound (2)

In a nitrogen atmosphere, 5.00 g of a compound (1) and 5.61 g of HIMIC anhydride were dissolved in methylene chloride and cooled to 10° C. or lower. Then, 3.53 g of 4-dimethylaminopyridine was dropwise added to the methylene chloride solution. After maturing for 3 hours, the resultant was filtered, and pure water was added to the obtained filtrate to conduct extraction with water. 31.67 g of a 5 wt % aqueous hydrochloric acid solution was added to the obtained aqueous solution, followed by filtration. The residue was collected, and subjected to disperse washing with pure water, thereby obtaining 5.12 g of a compound (2) in the form of a white solid.

[Chemical Formula 56.]

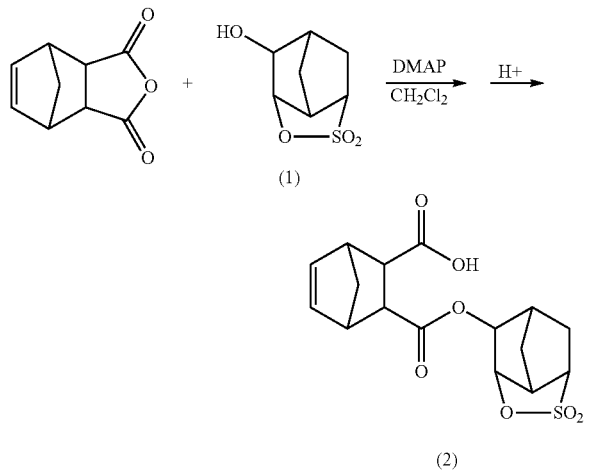

The obtained compound (2) was analyzed by $^1$H-NMR, and the structure thereof was identified by the following results.

$^1$H-NMR (400 MHz, DMSO-d6): δ (ppm)=6.23 (m, 1H, A), 6.06 (m, 1H, A'), 4.78 (m, 1H, N1), 4.43 (m, 1H, N2), 3.81 (m, 1H, N3), 3.42-3.21 (m, 3H, B+N4), 3.07-3.01 (m, 2H, C), 2.38 (m, 1H, N5), 2.11 (m, 1H, N6), 1.84-1.72 (m, 3H, N7-9), 1.31-1.28 (m, 2H, D)

[Chemical Formula 57.]

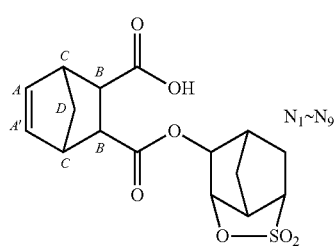

ii) Synthesis of Compound (4)

In a nitrogen atmosphere, 5.00 g of a compound (2) was dissolved in pyridine, and 2.32 g of diisopropylcarbodiimide was added thereto, followed by cooling the resulting liquid to 10° C. or lower. While maintaining the liquid temperature at 10° C. or lower, a pyridine solution containing 1.30 g of a compound (3) was gradually added in a dropwise manner. After maturing at 10° C. or lower for 15 hours, the resultant was subjected to filtration, and the filtrate was collected. Then, water and tert-butylmethylether was added to the filtrate, and a TBME washing was conducted. Thereafter, 1.63 g of pyridine hydrochloride was added, and extraction was conducted with methylene chloride. The obtained methylene chloride phase was washed with water and concentrated, thereby obtaining 2.20 g of a compound (4) in the form of a white powder.

[Chemical Formula 58.]

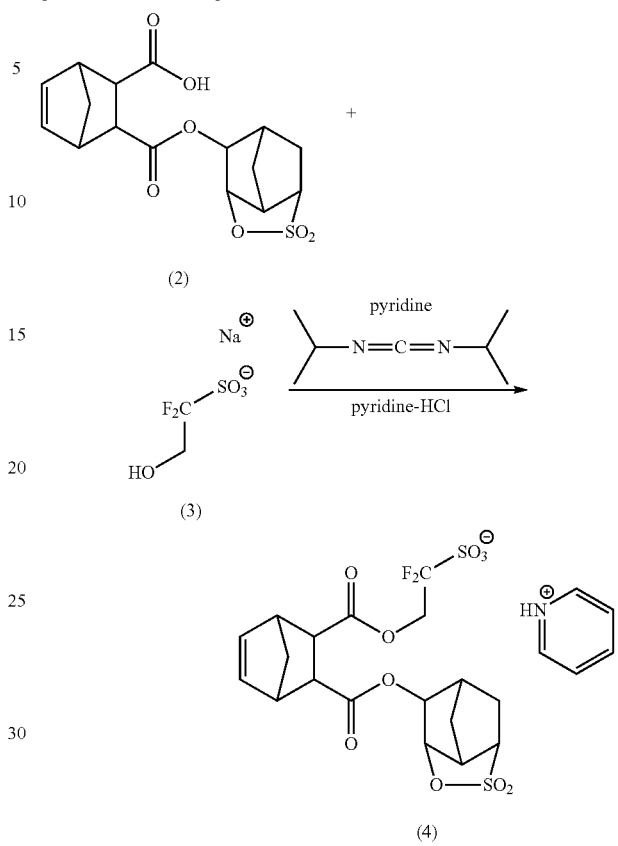

The obtained compound (4) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.22 (m, 1H, A), 6.07 (m, 1H, A'), 4.76 (m, 1H, N1), 4.65-4.34 (m, 3H, E+N2), 3.87 (m, 1H, N3), 3.58-3.39 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-118.9 (m, 2F)

[Chemical Formula 59.]

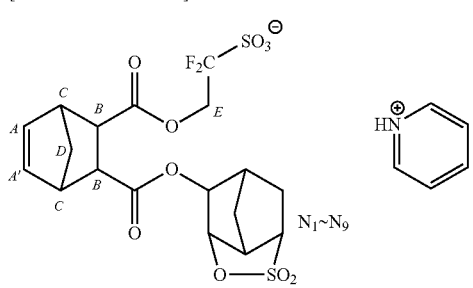

iii) Synthesis of Compound (B1-1-1)

1.03 g of 4-methylphenyldiphenylsulfonium bromide was dissolved in methylene chloride, and 2.00 g of the compound (4) and pure water (PW) were added thereto, followed by stirring at room temperature for 1 hour. Thereafter, the organic phase was washed with a 1 wt % aqueous hydrochloric acid and water, and the resulting organic phase was concentrated, thereby obtaining 2.20 g of a compound (B1-1-1) in the form of a white solid.

The obtained compound (B1-1-1) was analyzed by $^{1}$H-NMR and $^{19}$F-NMR, and the structure thereof was identified by the following results.

$^{1}$H-NMR (400 MHz, DMSO-d6): δ (ppm)=7.84-7.72 (m, 12H, ArH), 7.56 (d, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.54 (s, 3H, CationCH3), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-118.9 (m, 2F)

[Chemical Formula 60.]

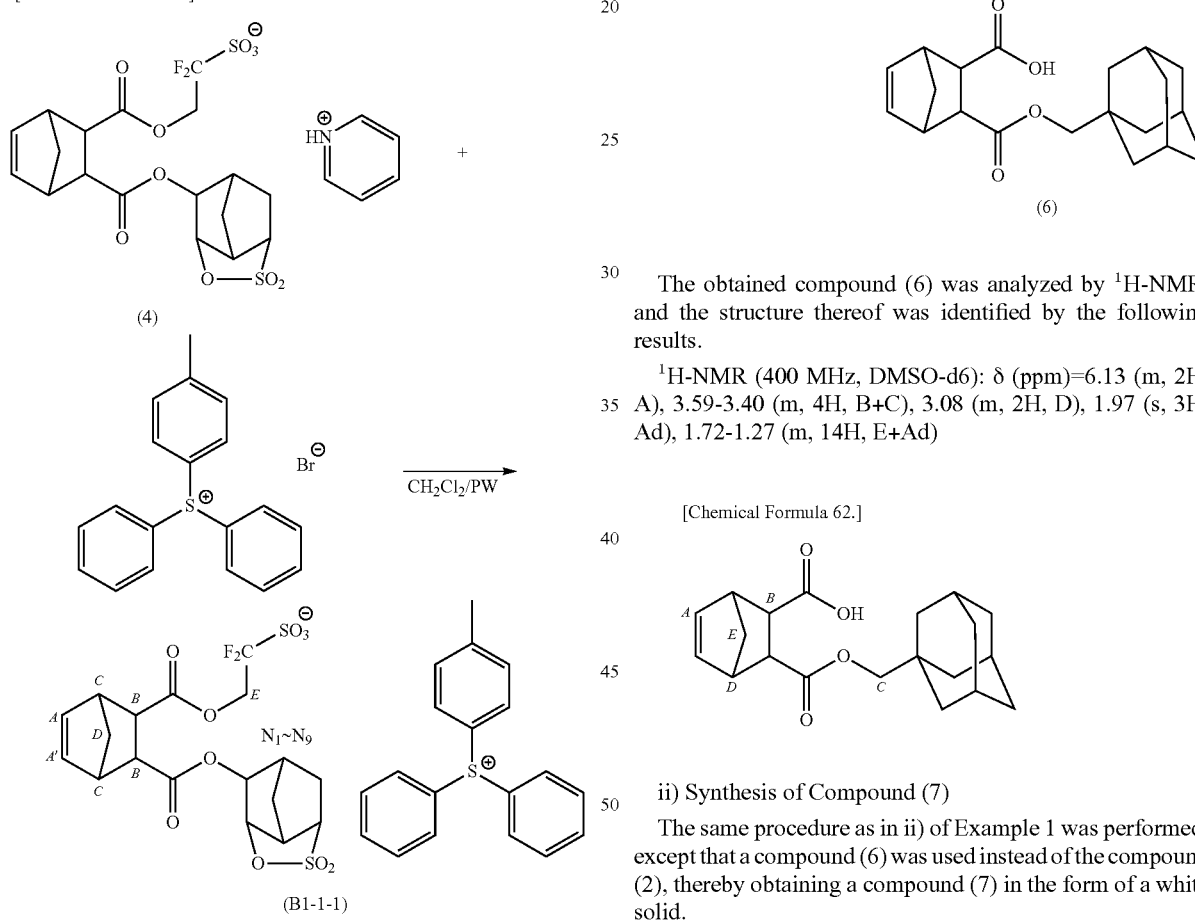

(B1-1-1)

Comparative Example 1

Synthesis of Compound (B2-1)

i) Synthesis of Compound (6)

The same procedure as in i) of Example 1 was performed, except that a compound (5) (1-adamantanemethanol) was used instead of the compound (1), thereby obtaining a compound (6) in the form of a white solid.

[Chemical Formula 61.]

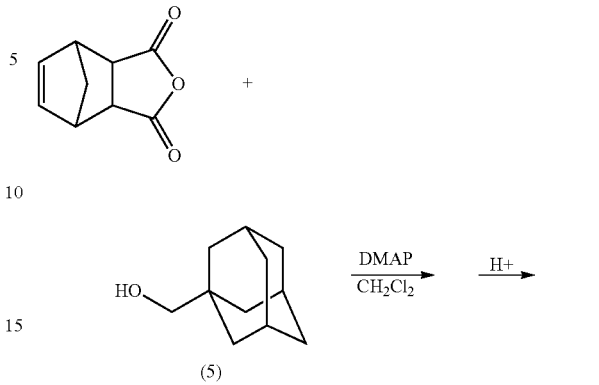

The obtained compound (6) was analyzed by $^{1}$H-NMR, and the structure thereof was identified by the following results.

$^{1}$H-NMR (400 MHz, DMSO-d6): δ (ppm)=6.13 (m, 2H, A), 3.59-3.40 (m, 4H, B+C), 3.08 (m, 2H, D), 1.97 (s, 3H, Ad), 1.72-1.27 (m, 14H, E+Ad)

[Chemical Formula 62.]

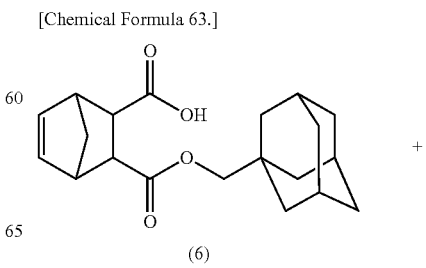

ii) Synthesis of Compound (7)

The same procedure as in ii) of Example 1 was performed, except that a compound (6) was used instead of the compound (2), thereby obtaining a compound (7) in the form of a white solid.

[Chemical Formula 63.]

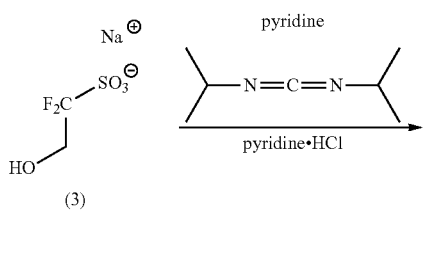

(3)

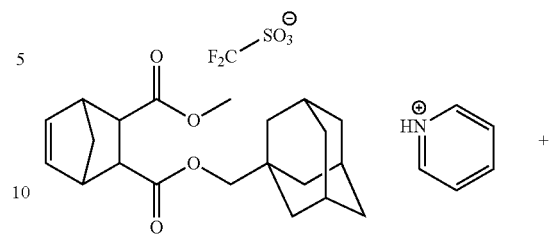

(7)

The obtained compound (7) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.13 (m, 2H, A), 4.63-4.40 (m, 2H, F), 3.59-3.40 (m, 4H, B+C), 3.08 (m, 2H, D), 1.97 (s, 3H, Ad), 1.72-1.27 (m, 14H, E+Ad)

$^{19}$F-NMR (376 MHz, DMSO-d6): δ (ppm)=−111.1−−111.5 (m, 2F)

[Chemical Formula 64.]

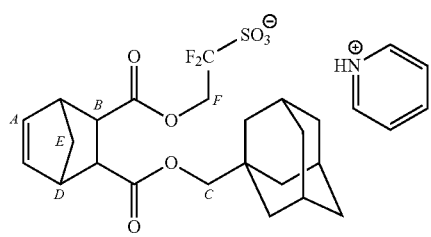

iii) Synthesis of Compound (B2-1)

The same procedure as in iii) of Example 1 was performed, except that a compound (7) was used instead of the compound (4), thereby obtaining a compound (B2-1) in the form of a white solid.

The obtained compound (B2-1) was analyzed by $^1$H-NMR and $^{19}$F-NMR, and the structure thereof was identified by the following results.

$^1$H-NMR (400 MHz, DMSO-d6): δ (ppm)=7.85-7.72 (m, 12H, ArH), 7.56 (d, 2H, ArH), 6.13 (m, 2H, A), 4.63-4.40 (m, 2H, F), 3.59-3.40 (m, 4H, B+C), 3.08 (m, 2H, D), 2.45 (s, 3H, CationCH3), 1.97 (s, 3H, Ad), 1.72-1.27 (m, 14H, E+Ad)

$^{19}$F-NMR (376 MHz, DMSO-d6): δ (ppm)=−111.1−−111.5 (m, 2F)

[Chemical Formula 65.]

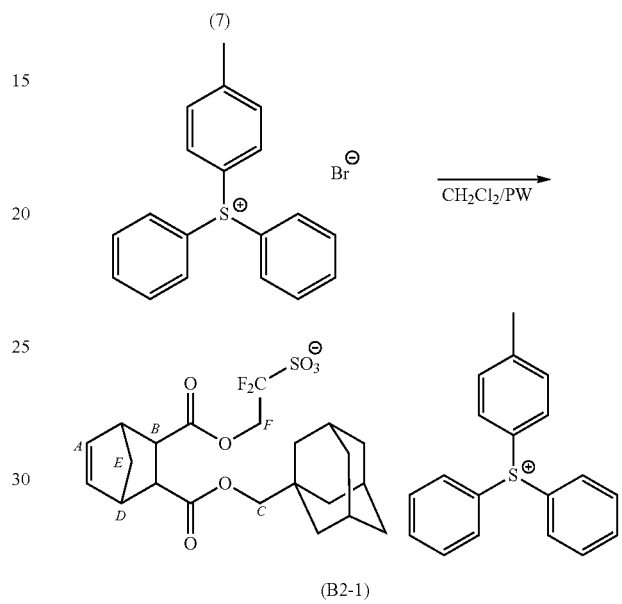

(B2-1)

Comparative Example 2

Synthesis of Compound (B2-2)

i) Synthesis of Compound (8)

The same procedure as in ii) of Example 1 was performed, except that monomethyl HIMIC acid was used instead of the compound (2), thereby obtaining a compound (8) in the form of a white solid.

[Chemical Formula 66.]

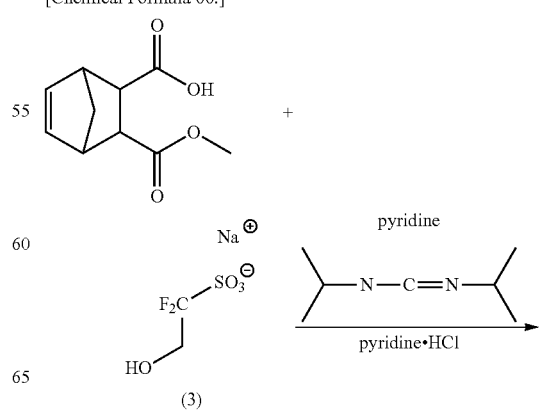

(3)

-continued

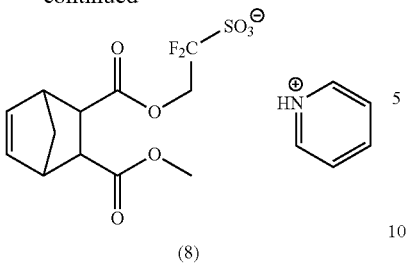

(8)

The obtained compound (8) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.14 (m, 2H, A), 4.61-4.42 (m, 2H, B), 3.52-3.39 (m, 5H, C+D), 3.12 (m, 2H, E), 1.46-1.21 (m, 2H, F)

$^{19}$F-NMR (376 MHz, DMSO-d6): δ (ppm)=−111.2-−111.4 (m, 2F)

[Chemical Formula 67.]

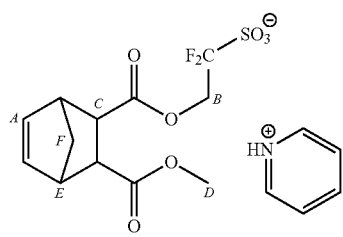

iii) Synthesis of Compound (B2-2)

The same procedure as in iii) of Example 1 was performed, except that a compound (8) was used instead of the compound (4), thereby obtaining a compound (B2-2) in the form of a white solid.

The obtained compound (B2-2) was analyzed by $^1$H-NMR and $^{19}$F-NMR, and the structure thereof was identified by the following results.

$^1$H-NMR (400 MHz, DMSO-d6): δ (ppm)=7.84-7.73 (m, 12H, ArH), 7.56 (d, 2H, ArH), 6.14 (m, 2H, A), 4.61-4.42 (m, 2H, B), 3.52-3.39 (m, 5H, C+D), 3.12 (m, 2H, E), 2.45 (m, 3H, CationCH3), 1.46-1.21 (m, 2H, F)

$^{19}$F-NMR (376 MHz, DMSO-d6): δ (ppm)=−111.2-−111.4 (m, 2F)

[Chemical Formula 68.]

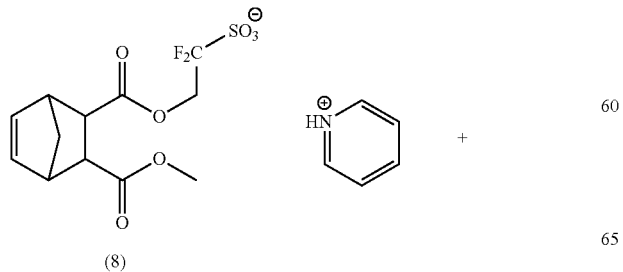

(8)

-continued

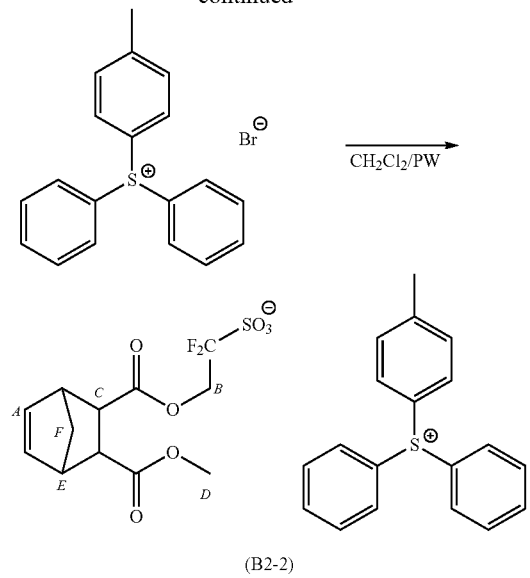

(B2-2)

Example 2

Synthesis of Compound (B1-1-2)

i) Synthesis of Compound (10)

The same procedure as in i) of Example 1 was performed, except that a compound (9) was used instead of the compound (1), thereby obtaining a compound (10) in the form of a white solid.

[Chemical Formula 69.]

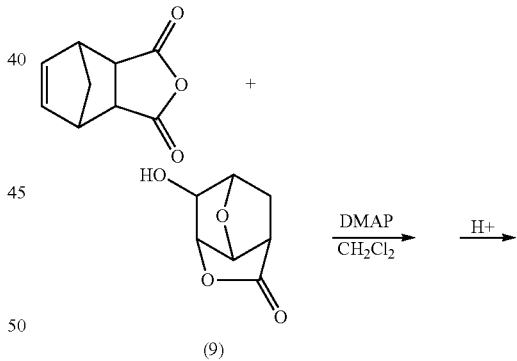

(9)

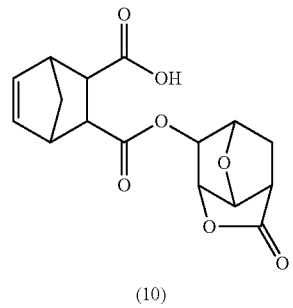

(10)

The obtained compound (10) was analyzed by $^1$H-NMR, and the structure thereof was identified by the following results.

$^1$H-NMR (400 MHz, DMSO-d6): δ (ppm)=6.22 (m, 1H, A), 6.06 (m, 1H, A'), 5.41 (m, 1H, O1), 4.66 (m, 3H, O2-4), 3.33-3.22 (m, 2H, B), 3.08-3.01 (m, 2H, C), 2.72 (m, 1H, O5), 2.11-2.04 (m, 2H, O6-7), 1.31-1.28 (m, 2H, D)

[Chemical Formula 70.]

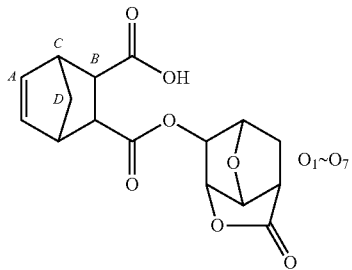

$O_1$~$O_7$ ii) Synthesis of Compound (11)

The same procedure as in ii) of Example 1 was performed, except that a compound (10) was used instead of the compound (2), thereby obtaining a compound (11) in the form of a white solid.

[Chemical Formula 71.]

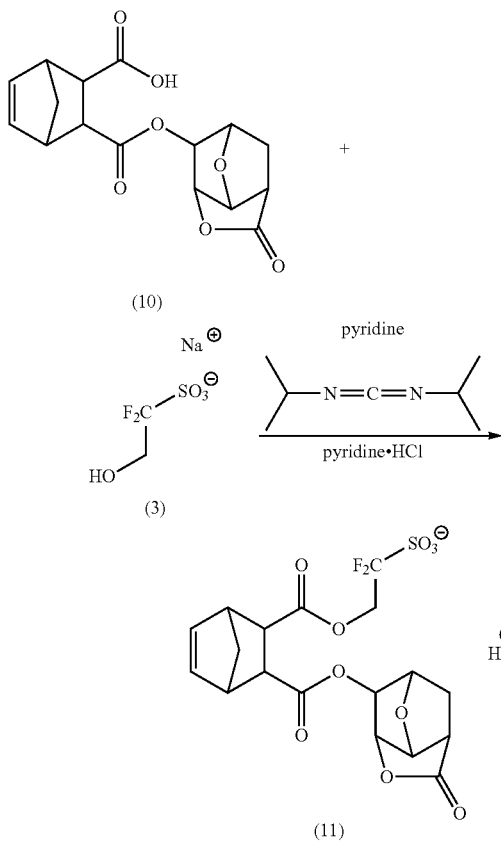

The obtained compound (11) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.24 (m, 1H, A), 6.07 (m, 1H, A'), 5.41 (m, 1H, O1), 4.67-4.33 (m, 5H, E+O2-4), 3.36- 3.24 (m, 2H, B), 3.09-3.03 (m, 2H, C), 2.74 (m, 1H, O5), 2.11-2.05 (m, 2H, O6-7), 1.33-1.29 (m, 2H, D)

$^{19}$F-NMR (376 MHz, DMSO-d6): δ (ppm)=−118.6−−118.9 (m, 2F)

[Chemical Formula 72.]

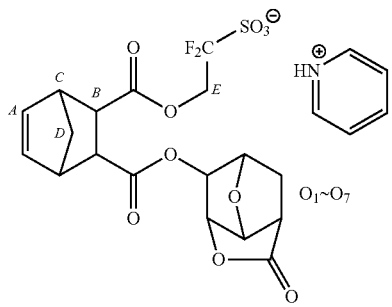

$O_1$~$O_7$ iii) Synthesis of Compound (B1-1-2)

The same procedure as in iii) of Example 1 was performed, except that a compound (11) was used instead of the compound (4), thereby obtaining a compound (B1-1-2) in the form of a white solid.

The obtained compound (B1-1-2) was analyzed by $^1$H-NMR and $^{19}$F-NMR, and the structure thereof was identified by the following results.

$^1$H-NMR (400 MHz, DMSO-d6): δ (ppm)=7.84-7.72 (m, 12H, ArH), 7.56 (d, 2H, ArH), 6.24 (m, 1H, A), 6.07 (m, 1H, A'), 5.41 (m, 1H, O1), 4.67-4.34 (m, 5H, E+O2-4), 3.36-3.24 (m, 2H, B), 3.09-3.03 (m, 2H, C), 2.74 (m, 1H, O5), 2.54 (s, 3H, CationCH3), 2.11-2.05 (m, 2H, O6-7), 1.33-1.29 (m, 2H, D)

$^{19}$F-NMR (376 MHz, DMSO-d6): δ (ppm)=−118.6−−118.9 (m, 2F)

[Chemical Formula 73.]

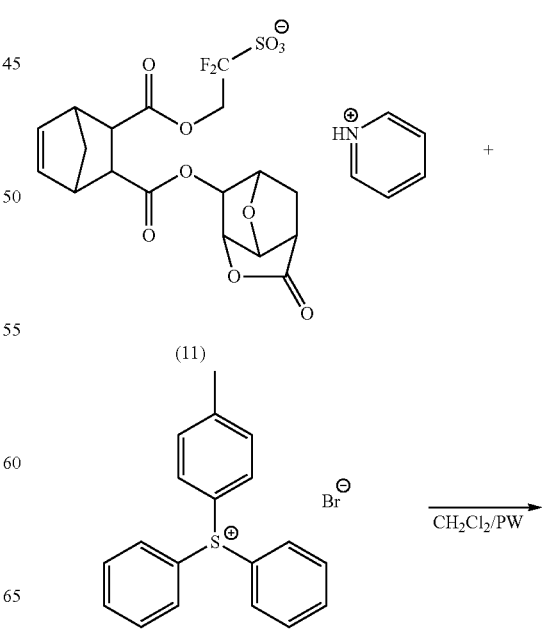

-continued

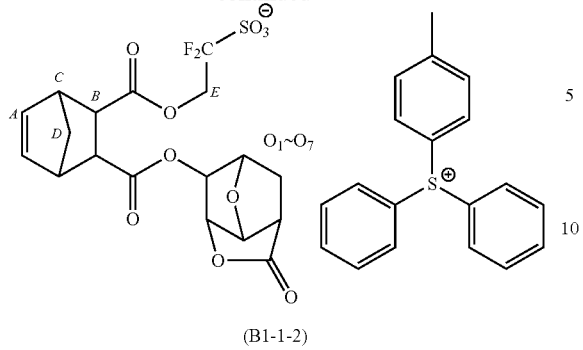

(B1-1-2)

Example 3

Synthesis of Compound (B1-1-3)

i) Synthesis of Compound (12)

The same procedure as in i) of Example 1 was performed, except that exo-3,6-epoxy-1,2,3,5-tetrahydrophthalic acid anhydride was used instead of HIMIC anhydride, thereby obtaining a compound (12) in the form of a white solid.

[Chemical Formula 74.]

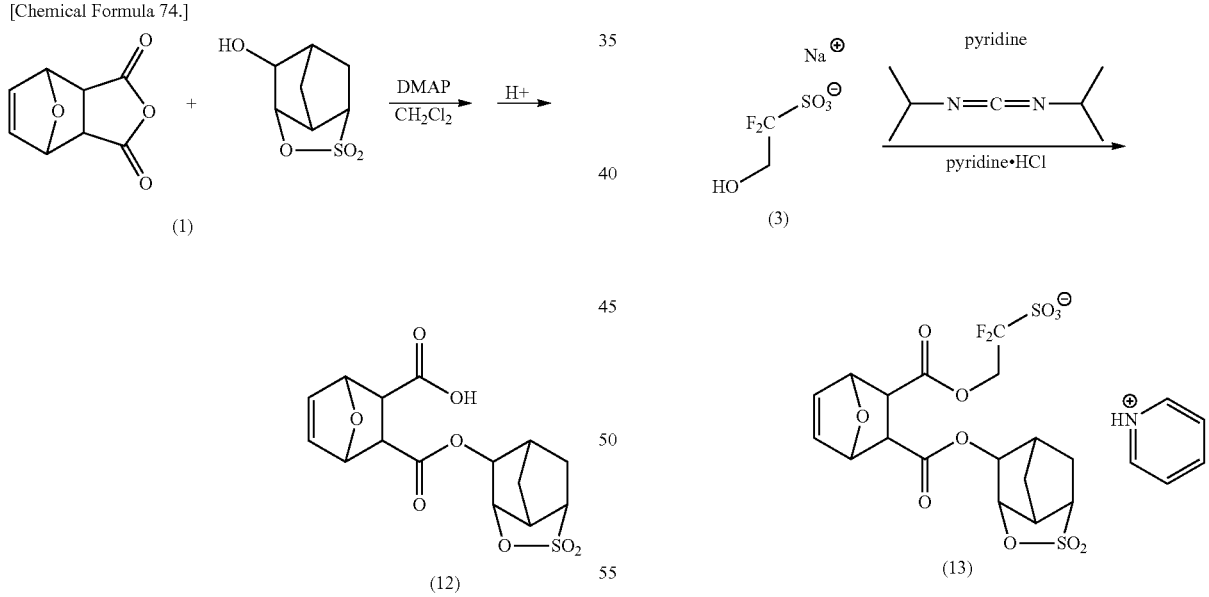

The obtained compound (12) was analyzed by $^1$H-NMR, and the structure thereof was identified by the following results.

$^1$H-NMR (400 MHz, DMSO-d6): δ (ppm)=6.44 (m, 2H, A), 5.12-5.06 (m, 2H, B), 4.74 (m, 1H, N1), 4.47 (m, 1H, N2), 3.86 (m, 1H, N3), 3.42 (m, 1H, N4), 2.73 (m, 2H, C), 2.42 (m, 1H, N5), 2.14 (m, 1H, N6), 1.87-1.74 (m, 3H, N7-9)

[Chemical Formula 75.]

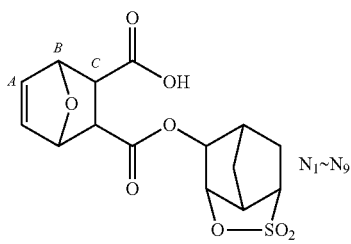

ii) Synthesis of Compound (13)

The same procedure as in ii) of Example 1 was performed, except that a compound (12) was used instead of the compound (2), thereby obtaining a compound (13) in the form of a white solid.

[Chemical Formula 76.]

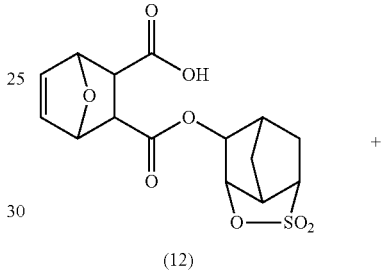

The obtained compound (13) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.46 (m, 2H, A), 5.14-5.07 (m, 2H, B), 4.75 (m, 1H, N1), 4.66-4.33 (m, 3H, E+N2), 3.86 (m, 1H, N3), 3.43 (m, 1H, N4), 2.72 (m, 2H, C), 2.42 (m, 1H, N5), 2.13 (m, 1H, N6), 1.87-1.76 (m, 3H, N7-9)

$^{19}$F-NMR (376 MHz, DMSO-d6): δ (ppm)=−118.5-118.9 (m, 2F)

[Chemical Formula 77.]

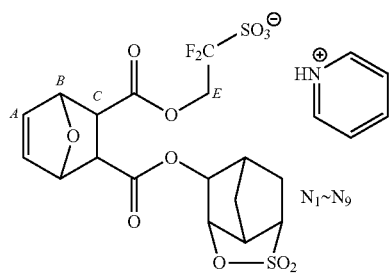

iii) Synthesis of Compound (B1-1-3)

The same procedure as in iii) of Example 1 was performed, except that a compound (13) was used instead of the compound (4), thereby obtaining a compound (B1-1-3) in the form of a white solid.

The obtained compound (B1-1-3) was analyzed by $^1$H-NMR and $^{19}$F-NMR, and the structure thereof was identified by the following results.

$^1$H-NMR (400 MHz, DMSO-d6): δ (ppm)=7.84-7.72 (m, 12H, ArH), 7.56 (d, 2H, ArH), 6.46 (m, 2H, A), 5.14-5.07 (m, 2H, B), 4.75 (m, 1H, N1), 4.66-4.33 (m, 3H, E+N2), 3.86 (m, 1H, N3), 3.43 (m, 1H, N4), 2.72 (m, 2H, C), 2.54 (s, 3H, CationCH3), 2.42 (m, 1H, N5), 2.13 (m, 1H, N6), 1.87-1.76 (m, 3H, N7-9)

$^{19}$F-NMR (376 MHz, DMSO-d6): δ (ppm)=−118.5-−119.0 (m, 2F)

[Chemical Formula 78.]

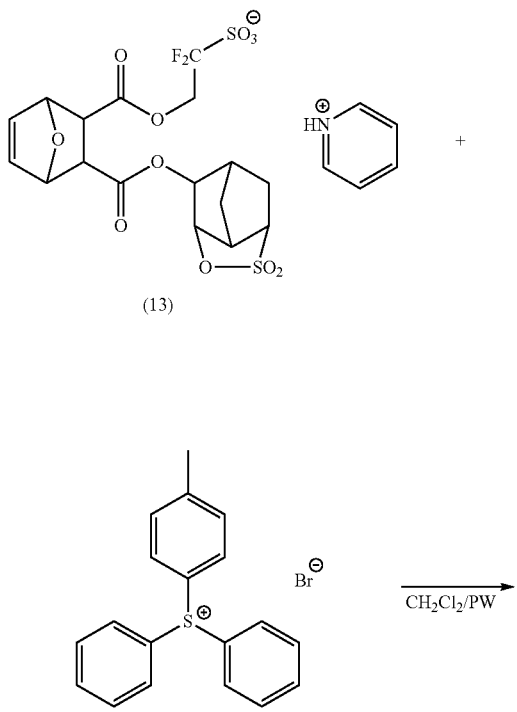

(B1-1-3)

Example 4

Synthesis of Compound (B1-1-4)

i) Synthesis of Compound (14)

The same procedure as in i) of Example 2 was performed, except that exo-3,6-epoxy-1,2,3,5-tetrahydrophthalic acid anhydride was used instead of HIMIC anhydride, thereby obtaining a compound (14) in the form of a white solid.

[Chemical Formula 79.]

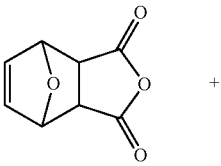

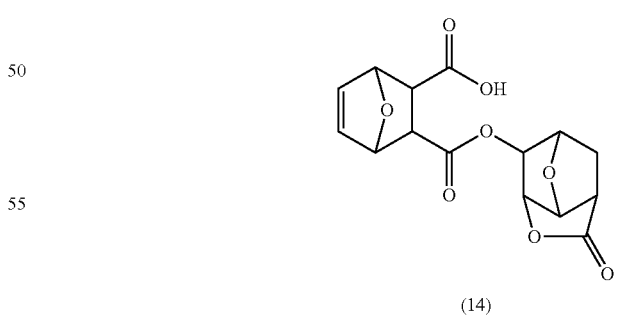

The obtained compound (14) was analyzed by $^1$H-NMR, and the structure thereof was identified by the following results.

$^1$H-NMR (400 MHz, DMSO-d6): δ (ppm)=6.45 (m, 2H, A), 5.41 (m, 1H, O1), 5.13-5.08 (m, 2H, B), 4.66 (m, 3H, O2-4), 2.75-2.71 (m, 3H, C+O5), 2.13-2.04 (m, 2H, O6-7)

[Chemical Formula 80.]

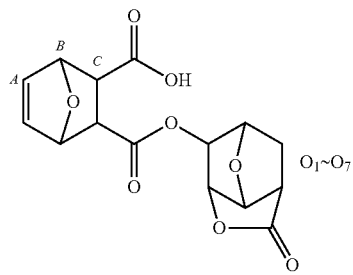

ii) Synthesis of Compound (15)

The same procedure as in ii) of Example 1 was performed, except that a compound (14) was used instead of the compound (2), thereby obtaining a compound (15) in the form of a white solid.

[Chemical Formula 81.]

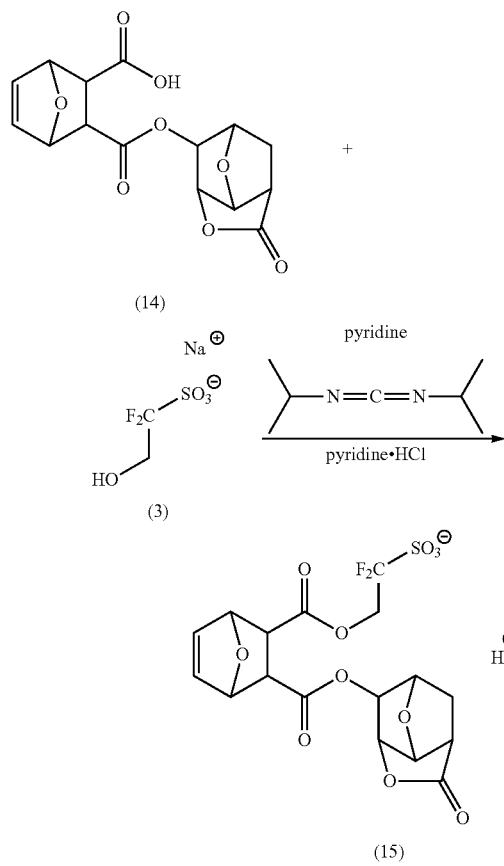

The obtained compound (15) was analyzed by $^1$H-NMR and $^{19}$F-NMR, and the structure thereof was identified by the following results.

$^1$H-NMR (400 MHz, DMSO-d6): δ (ppm)=8.94 (d, 2H, Pr), 8.63 (t, 1H, Pr), 8.09 (t, 2H, Pr), 6.44 (m, 2H, A), 5.42 (m, 1H, O1), 5.12-5.08 (m, 2H, B), 4.67-4.35 (m, 5H, E+O2-4), 2.75-2.70 (m, 3H, C+O5), 2.16-2.04 (m, 2H, O6-7)

$^{19}$F-NMR (376 MHz, DMSO-d6): δ (ppm)=−118.5-−119.0 (m, 2F)

[Chemical Formula 82.]

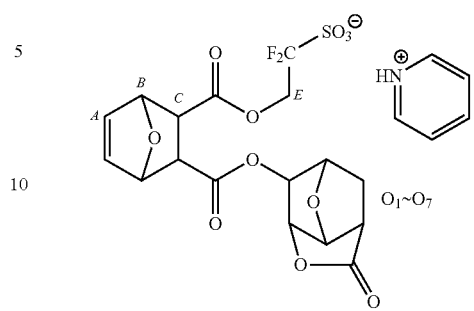

iii) Synthesis of Compound (B1-1-4)

The same procedure as in iii) of Example 1 was performed, except that a compound (15) was used instead of the compound (4), thereby obtaining a compound (B1-1-4) in the form of a white solid.

The obtained compound (B1-1-4) was analyzed by $^1$H-NMR and $^{19}$F-NMR, and the structure thereof was identified by the following results.

$^1$H-NMR (400 MHz, DMSO-d6): δ (ppm)=7.83-7.72 (m, 12H, ArH), 7.56 (d, 2H, ArH), 6.44 (m, 2H, A), 5.42 (m, 1H, O1), 5.12-5.08 (m, 2H, B), 4.67-4.35 (m, 5H, E+O2-4), 2.75-2.70 (m, 3H, C+O5), 2.54 (s, 3H, CationCH3), 2.16-2.04 (m, 2H, O6-7)

$^{19}$F-NMR (376 MHz, DMSO-d6): δ (ppm)=−118.5-−119.0 (m, 2F)

[Chemical Formula 83.]

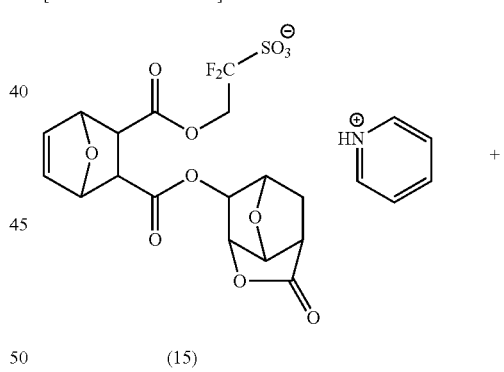

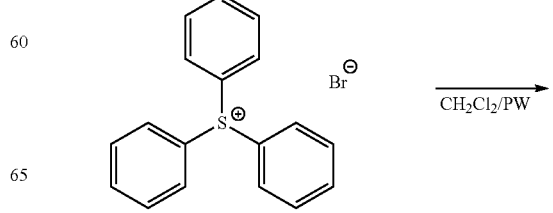

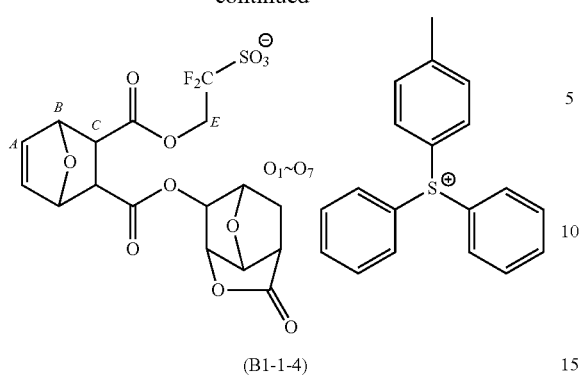

(B1-1-4)

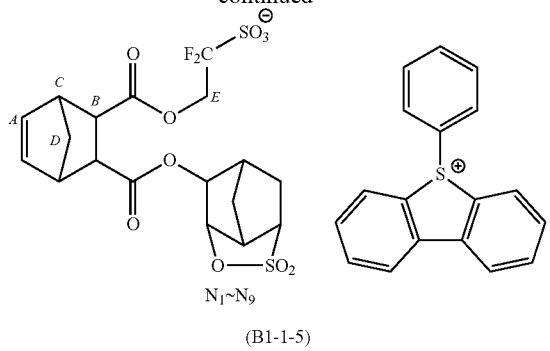

(B1-1-5)

Example 5

Synthesis of Compound (B1-1-5)

The same procedure as in iii) of Example 1 was performed, except that a compound (16) was used instead of 4-methylphenyldiphenylsulfonium bromide, thereby obtaining a compound (B1-1-5) in the form of a white solid.

The obtained compound (B1-1-5) was analyzed by $^1$H-NMR and $^{19}$F-NMR, and the structure thereof was identified by the following results.

$^1$H-NMR (400 MHz, DMSO-d6): δ (ppm)=8.50 (d, 2H, ArH), 8.37 (d, 2H, ArH), 7.93 (t, 2H, ArH), 7.75-7.55 (m, 7H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.39 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5--118.9 (m, 2F)

Example 6

Synthesis of Compound (B1-1-6)

The same procedure as in iii) of Example 1 was performed, except that a compound (17) was used instead of 4-methylphenyldiphenylsulfonium bromide, thereby obtaining a compound (B1-1-6) in the form of a white solid.

The obtained compound (B1-1-6) was analyzed by $^1$H-NMR and $^{19}$F-NMR, and the structure thereof was identified by the following results.

$^1$H-NMR (400 MHz, DMSO-d6): δ (ppm)=7.86-7.75 (m, 10H, ArH), 7.61 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.39 (m, 3H, B+N4), 3.11 (m, 2H, C), 2.37 (m, 1H, N5), 2.31 (s, 6H, CationCH3), 2.16 (m, 1H, N6), 1.98-1.21 (m, 22H, D+N7-9+Adamantane)

$^{19}$F-NMR (376 MHz, DMSO-d6): δ (ppm)=−118.5--118.9 (m, 2F)

[Chemical Formula 84.]

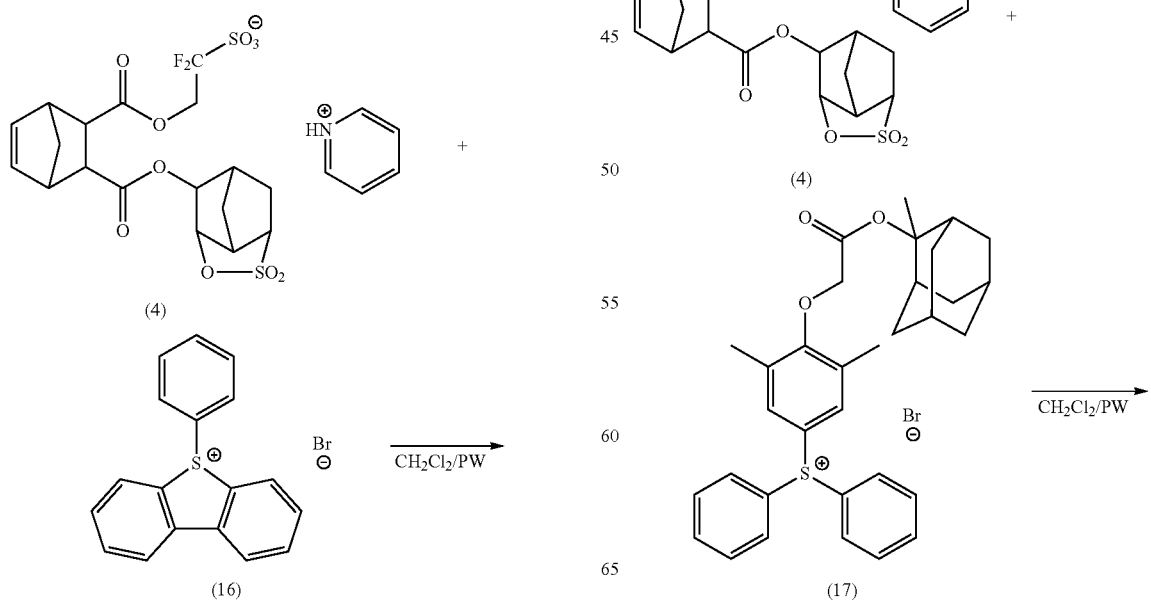

[Chemical Formula 85.]

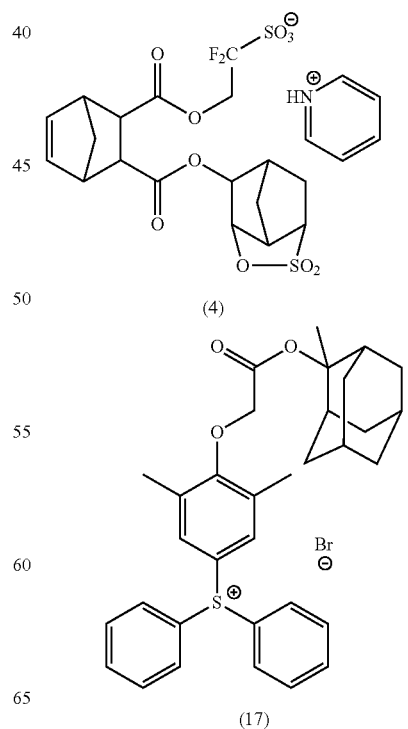

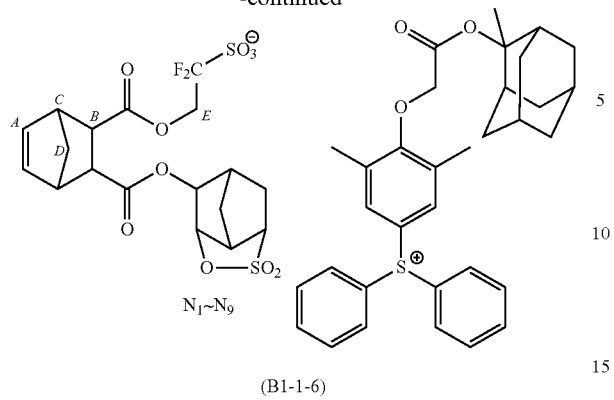

(B1-1-6)

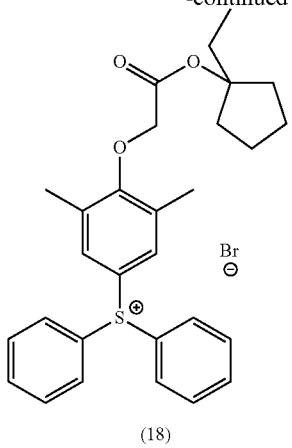

(18)

Example 7

Synthesis of Compound (B1-1-7)

The same procedure as in iii) of Example 1 was performed, except that a compound (18) was used instead of 4-methylphenyldiphenylsulfonium bromide, thereby obtaining a compound (B1-1-7) in the form of a white solid.

The obtained compound (B1-1-7) was analyzed by $^1$H-NMR and $^{19}$F-NMR, and the structure thereof was identified by the following results.

$^1$H-NMR (400 MHz, DMSO-d6): δ (ppm)=7.82-7.76 (m, 10H, ArH), 7.59 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.39 (m, 3H, B+N4), 3.11 (m, 2H, C), 2.37 (m, 1H, N5), 2.29 (m, 6H, CationCH3), 2.16 (m, 1H, N6), 1.89-1.50 (m, 13H, N7-9+CationCH2+cyclopentyl), 1.44-1.21 (m, 2H, D), 0.81-0.77 (t, 3H, CationCH3)

$^{19}$F-NMR (376 MHz, DMSO-d6): δ (ppm)=−118.5-−118.9 (m, 2F)

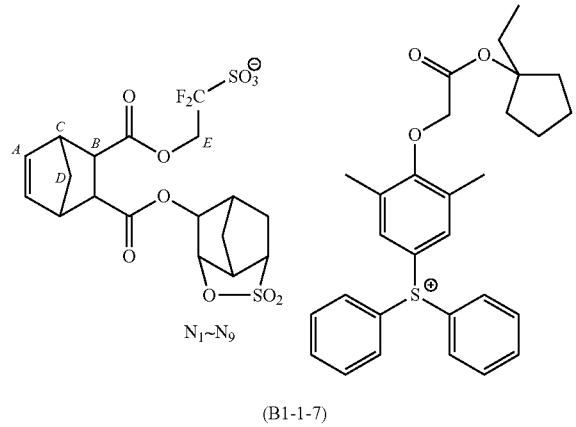

(B1-1-7)

Example 8

Synthesis of Compound (B1-1-8)

The same procedure as in iii) of Example 1 was performed, except that a compound (19) was used instead of 4-methylphenyldiphenylsulfonium bromide, thereby obtaining a compound (B1-1-8) in the form of a white solid.

The obtained compound (B1-1-8) was analyzed by $^1$H-NMR and $^{19}$F-NMR, and the structure thereof was identified by the following results.

$^1$H-NMR (400 MHz, DMSO-d6): δ (ppm)=7.83-7.73 (m, 10H, ArH), 7.59 (s, 2H, ArH), 6.22 (m, 1H, A), 6.07 (m, 1H, A'), 4.90 (m, 1H, Cationsultone), 4.76 (m, 1H, N1), 4.68-4.34 (m, 6H, E+N2+Cationsultone), 3.87 (m, 2H, N3+Cationsultone), 3.58-3.39 (m, 4H, B+N4+Cationsultone), 3.11 (m, 2H, C), 2.49-1.66 (m, 16H, N5-9+Cationsultone+CationCH3), 1.44-1.21 (m, 2H, D)

$^{19}$F-NMR (376 MHz, DMSO-d6): δ (ppm)=−118.5-−118.9 (m, 2F)

[Chemical Formula 86.]

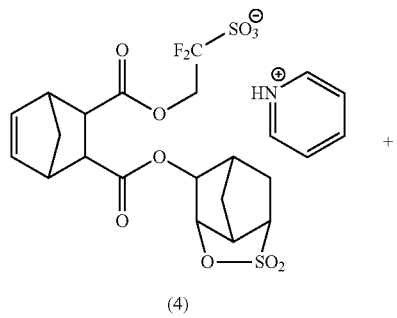

(4)

[Chemical Formula 87.]

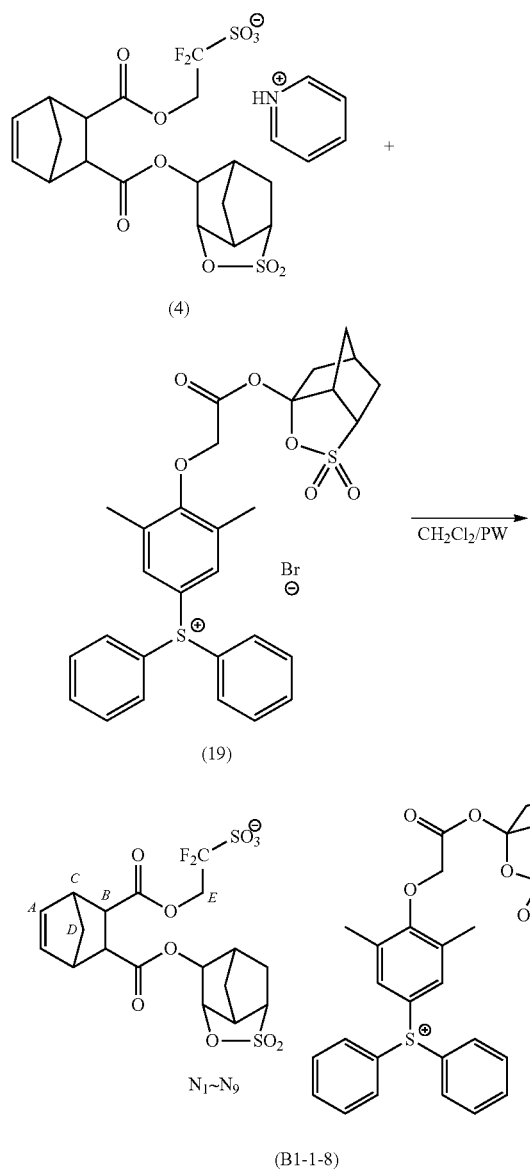

(B1-1-8)

Example 9

Synthesis of Compound (B1-1-9)

The same procedure as in iii) of Example 1 was performed, except that a compound (20) was used instead of 4-methylphenyldiphenylsulfonium bromide, thereby obtaining a compound (B1-1-9) in the form of a white solid.

The obtained compound (B1-1-9) was analyzed by $^1$H-NMR and $^{19}$F-NMR, and the structure thereof was identified by the following results.

$^1$H-NMR (400 MHz, DMSO-d6): δ (ppm)=8.01-7.99 (d, 2H, Ar), 7.76-7.73 (t, 1H, Ar), 7.61-7.58 (t, 2H, Ar), 6.22 (m, 1H, A), 6.07 (m, 1H, A'), 5.31 (s, 2H, SCH2C=O), 4.76 (m, 1H, N1), 4.65-4.34 (m, 3H, E+N2), 3.87 (m, 1H, N3), 3.63-3.39 (m, 7H, B+N4+CationCH2), 3.11 (m, 2H, C), 2.49-2.16 (m, 6H, N5-6+CationCH2S), 1.89-1.66 (m, 3H, N7-9), 1.44-1.21 (m, 2H, D)

$^{19}$F-NMR (376 MHz, DMSO-d6): δ (ppm)=−118.5--118.9 (m, 2F)

[Chemical Formula 88.]

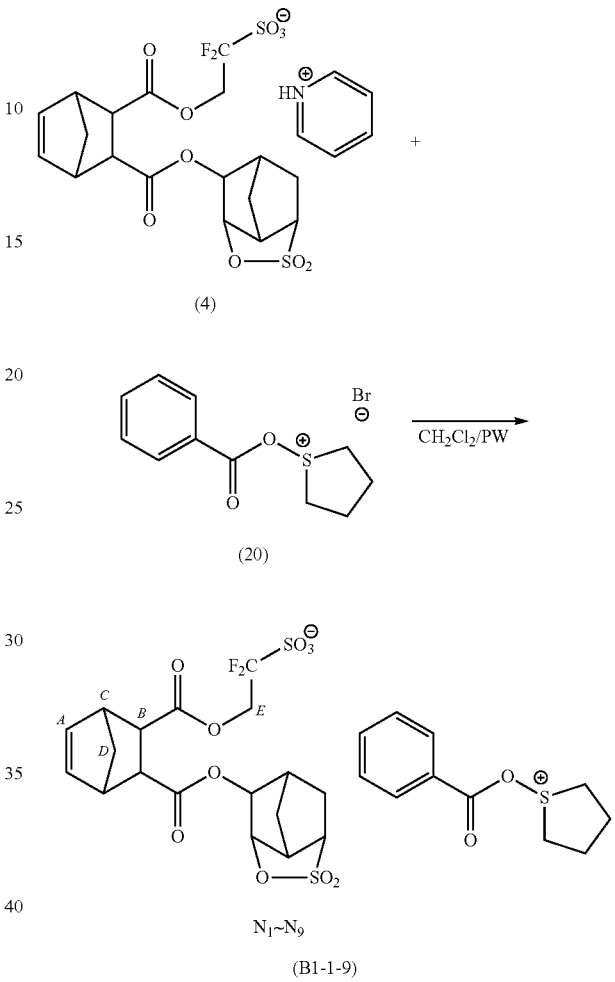

(B1-1-9)

Example 10

Synthesis of Compound (B1-1-10)

The same procedure as in iii) of Example 1 was performed, except that a compound (21) was used instead of 4-methylphenyldiphenylsulfonium bromide, thereby obtaining a compound (B1-1-10) in the form of a white solid.

The obtained compound (B1-1-10) was analyzed by $^1$H-NMR and $^{19}$F-NMR, and the structure thereof was identified by the following results.

$^1$H-NMR (400 MHz, DMSO-d6): δ (ppm)=8.06-8.02 (m, 2H, ArH), 7.73-7.63 (m, 3H, ArH), 6.22 (m, 1H, A), 6.07 (m, 1H, A'), 4.76 (m, 1H, N1), 4.65-4.34 (m, 3H, E+N2), 3.87-3.76 (m, 5H, N3+SCH2), 3.58-3.39 (m, 3H, B+N4), 3.11 (m, 2H, C), 2.37 (m, 1H, N5), 2.16-2.11 (m, 3H, N6+CationCH2), 1.94-1.60 (m, 7H, N7-9+CationCH2), 1.44-1.21 (m, 2H, D)

$^{19}$F-NMR (376 MHz, DMSO-d6): δ (ppm)=−118.5--118.9 (m, 2F)

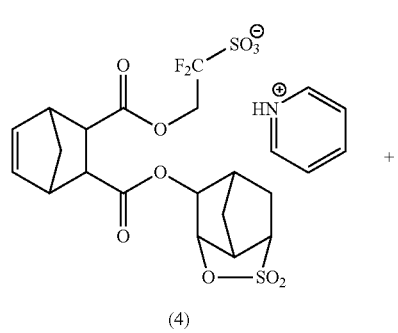

(4)

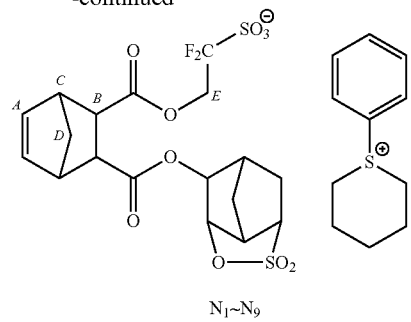

(B1-1-10)

Example 11
Synthesis of Compound (B1-1-11)

The same procedure as in iii) of Example 1 was performed, except that a compound (22) was used instead of 4-methylphenyldiphenylsulfonium bromide, thereby obtaining a compound (B1-1-11) in the form of a white solid.

The obtained compound (B1-1-11) was analyzed by $^1$H-NMR and $^{19}$F-NMR, and the structure thereof was identified by the following results.

$^1$H-NMR (400 MHz, DMSO-d6): δ (ppm)=7.93-7.79 (m, 12H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.39 (m, 3H, B+N4), 3.11 (m, 2H, C), 2.37 (m, 1H, N5), 2.73 (t, 2H, CationCH2), 2.20-2.16 (m, 7H, N6+CationCH3), 1.89-1.66 (m, 5H, N7-9+CationCH2), 1.44-1.20 (m, 16H, D+CationCH2), 0.85 (t, 3H, CationCH3)

$^{19}$F-NMR (376 MHz, DMSO-d6): δ (ppm)=−118.5-−118.9 (m, 2F)

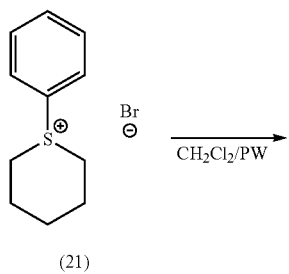

(21)

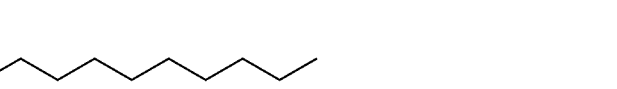

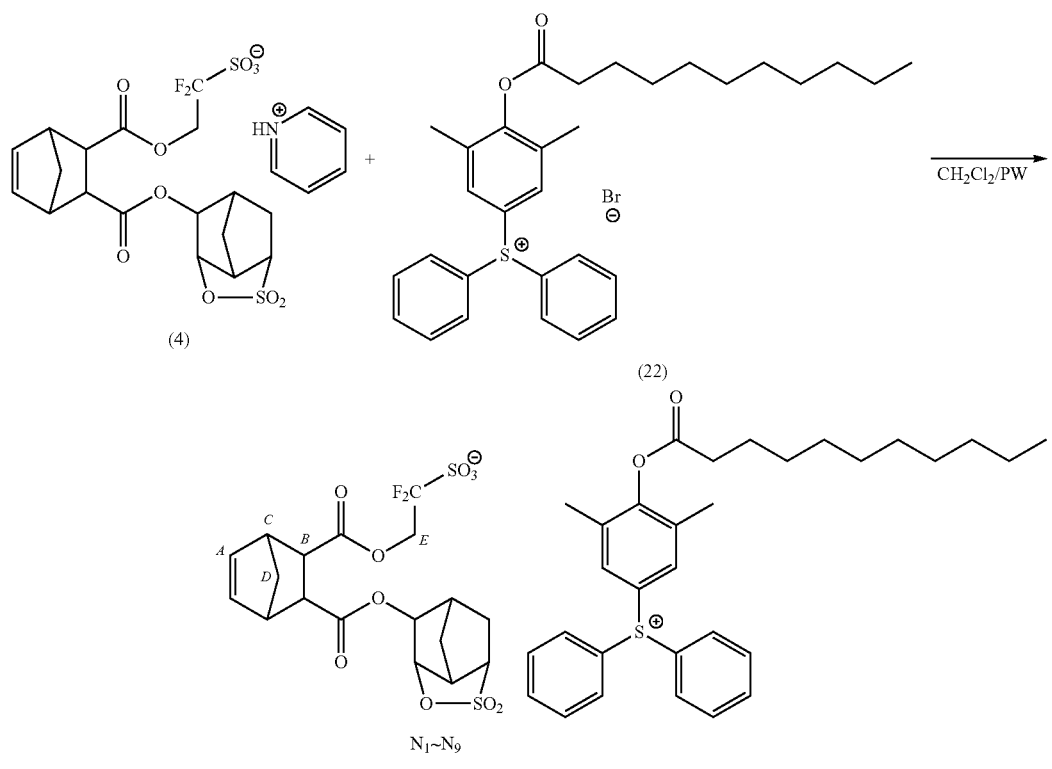

(B1-1-11)

Example 12

Synthesis of Compound (B1-1-12)

The same procedure as in iii) of Example 1 was performed, except that a compound (23) was used instead of 4-methylphenyldiphenylsulfonium bromide, thereby obtaining a compound (B1-1-12) in the form of a white solid.

The obtained compound (B1-1-12) was analyzed by $^1$H-NMR and $^{19}$F-NMR, and the structure thereof was identified by the following results.

$^1$H-NMR (400 MHz, DMSO-d6): δ (ppm)=8.28 (d, 2H, ArH), 8.11 (d, 1H, ArH), 7.86 (t, 1H, ArH), 7.81-7.64 (m, 7H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.39 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F)

[Chemical Formula 91.]

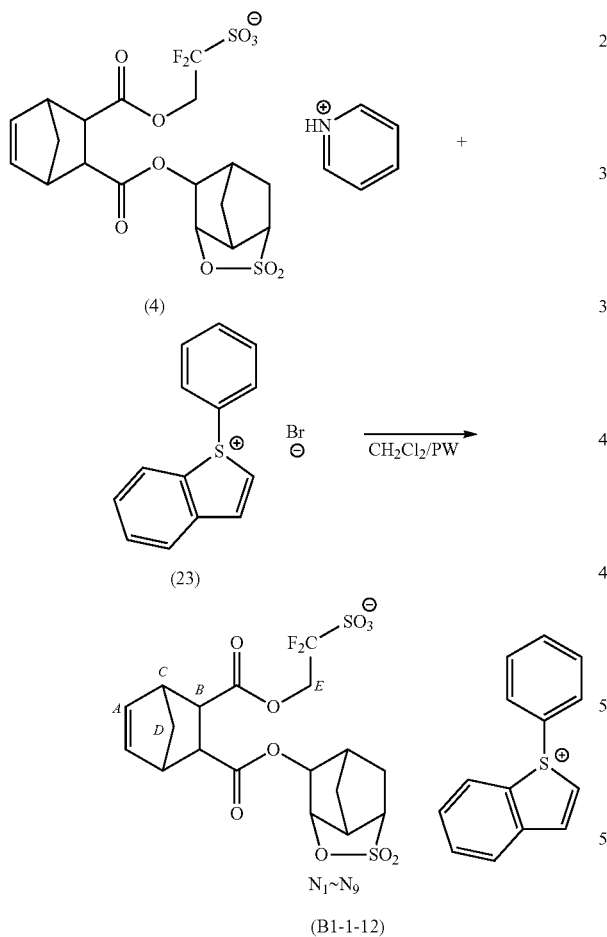

(B1-1-12)

Example 13

Synthesis of Compound (B1-1-13)

The same procedure as in iii) of Example 2 was performed, except that a compound (16) was used instead of 4-methylphenyldiphenylsulfonium bromide, thereby obtaining a compound (B1-1-13) in the form of a white solid.

The obtained compound (B1-1-13) was analyzed by $^1$H-NMR and $^{19}$F-NMR, and the structure thereof was identified by the following results.

$^1$H-NMR (400 MHz, DMSO-d6): δ (ppm)=8.50 (d, 2H, ArH), 8.37 (d, 2H, ArH), 7.93 (t, 2H, ArH), 7.75-7.56 (m, 7H, ArH), 6.24 (m, 1H, A), 6.07 (m, 1H, A'), 5.41 (m, 1H, O1), 4.67-4.34 (m, 5H, E+O2-4), 3.36-3.24 (m, 2H, B), 3.09-3.03 (m, 2H, C), 2.74 (m, 1H, O5), 2.11-2.05 (m, 2H, O6-7), 1.33-1.29 (m, 2H, D)

$^{19}$F-NMR (376 MHz, DMSO-d6): δ (ppm)=−118.6−−118.9 (m, 2F)

[Chemical Formula 92.]

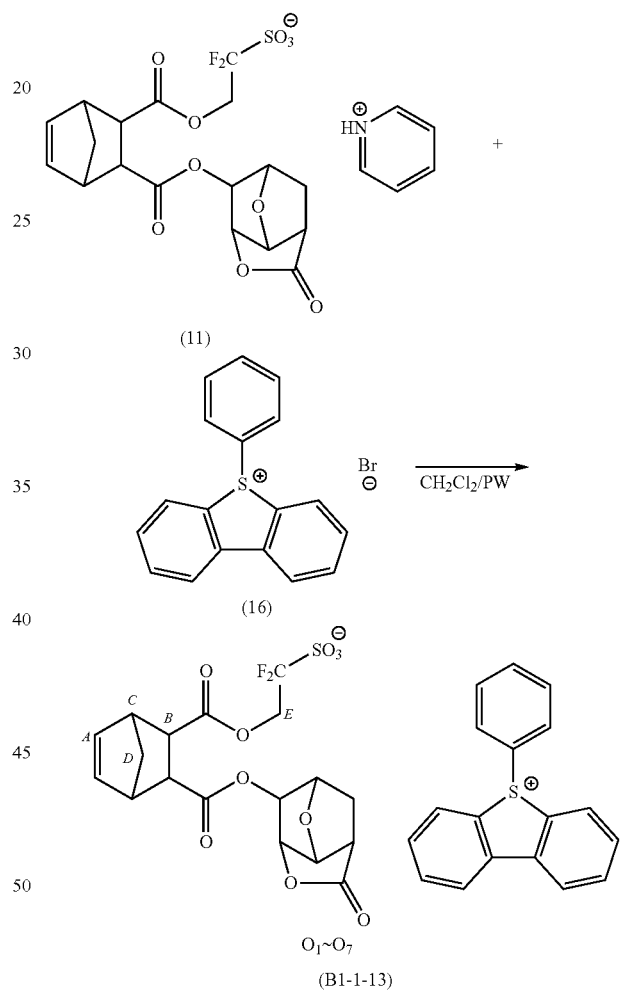

(B1-1-13)

Example 14

Synthesis of Compound (B1-1-14)

The same procedure as in iii) of Example 2 was performed, except that a compound (17) was used instead of 4-methylphenyldiphenylsulfonium bromide, thereby obtaining a compound (B1-1-14) in the form of a white solid.

The obtained compound (B1-1-14) was analyzed by $^1$H-NMR and $^{19}$F-NMR, and the structure thereof was identified by the following results.

$^1$H-NMR (400 MHz, DMSO-d6): δ (ppm)=7.86-7.76 (m, 10H, ArH), 7.61 (s, 2H, ArH), 6.24 (m, 1H, A), 6.07 (m, 1H, A'), 5.41 (m, 1H, O1), 4.67-4.34 (m, 7H, E+O2-4+CationCH2), 3.36-3.24 (m, 2H, B), 3.09-3.03 (m, 2H, C), 2.31 (s, 6H, CationCH3), 2.74 (m, 1H, O5), 2.11-1.50 (m, 19H, O6-7+Adamantane), 1.33-1.29 (m, 2H, D)

$^{19}$F-NMR (376 MHz, DMSO-d6): δ (ppm)=−118.6-−118.9 (m, 2F)

$^1$H-NMR (400 MHz, DMSO-d6): δ (ppm)=7.81-7.76 (m, 10H, ArH), 7.59 (s, 2H, ArH), 6.24 (m, 1H, A), 6.07 (m, 1H, A'), 5.41 (m, 1H, O1), 4.67-4.33 (m, 7H, E+O2-4+CationCH2), 3.36-3.24 (m, 2H, B), 3.09-3.03 (m, 2H, C), 2.74 (m, 1H, O5), 2.29 (m, 6H, CationCH3), 2.11-2.05 (m, 2H, O6-7), 1.95-1.90 (m, 4H, CationCH2+cyclopentyl), 1.78-1.42 (m, 6H, cyclopentyl), 1.33-1.29 (m, 2H, D), 0.81-0.76 (t, 3H, CationCH3)

$^{19}$F-NMR (376 MHz, DMSO-d6): δ (ppm)=−118.6-−118.9 (m, 2F)

[Chemical Formula 93.]

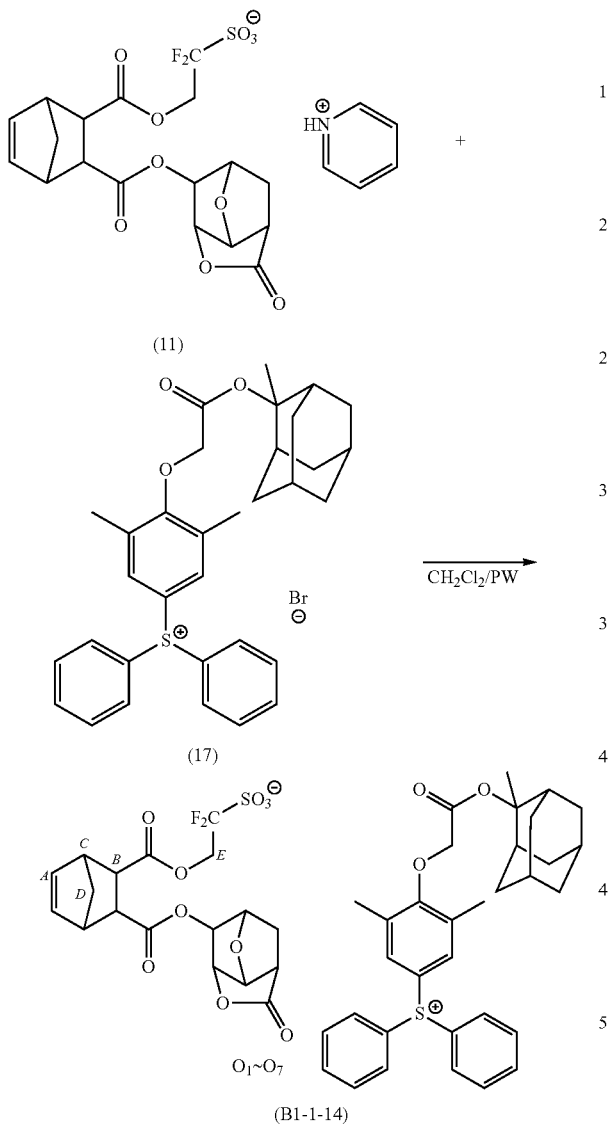

[Chemical Formula 94.]

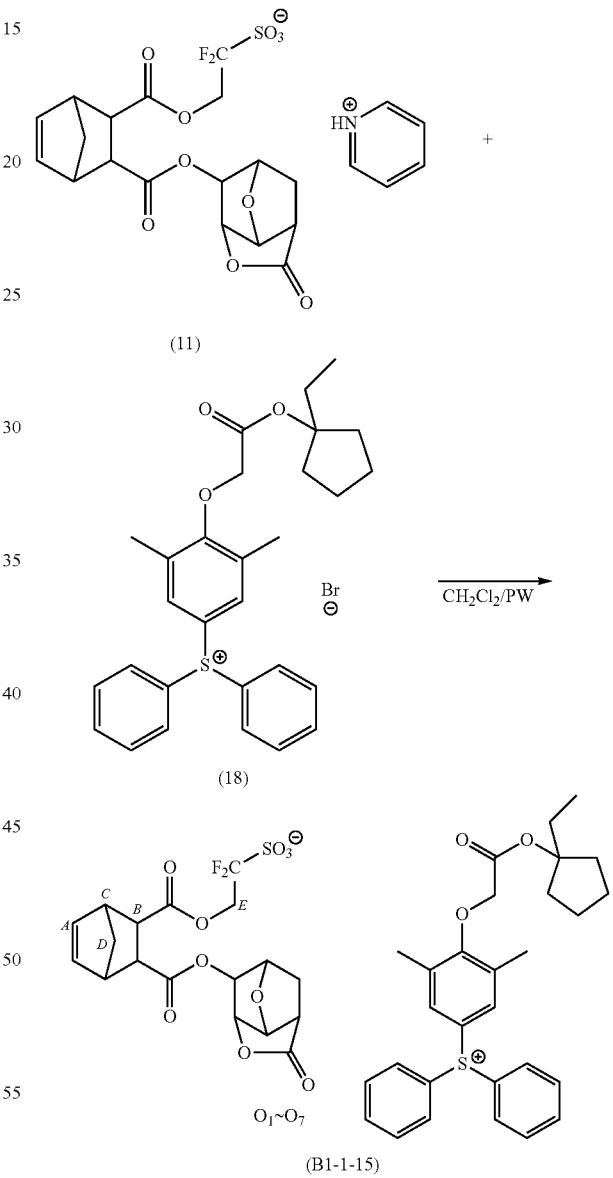

Example 15

Synthesis of Compound (B1-1-15)

The same procedure as in iii) of Example 2 was performed, except that a compound (18) was used instead of 4-methylphenyldiphenylsulfonium bromide, thereby obtaining a compound (B1-1-15) in the form of a white solid.

The obtained compound (B1-1-15) was analyzed by $^1$H-NMR and $^{19}$F-NMR, and the structure thereof was identified by the following results.

Example 16

Synthesis of Compound (B1-1-16)

The same procedure as in iii) of Example 2 was performed, except that a compound (19) was used instead of 4-methylphenyldiphenylsulfonium bromide, thereby obtaining a compound (B1-1-16) in the form of a white solid.

The obtained compound (B1-1-16) was analyzed by $^1$H-NMR and $^{19}$F-NMR, and the structure thereof was identified by the following results.

$^1$H-NMR (400 MHz, DMSO-d6): δ (ppm)=7.83-7.74 (m, 10H, ArH), 7.59 (s, 2H, ArH), 6.24 (m, 1H, A), 6.07 (m, 1H, A'), 5.41 (m, 1H, O1), 4.90 (m, 1H, Cationsultone), 4.70-4.34 (m, 8H, E+O2-4+CH2O+Cationsultone), 3.88-3.82 (m, 1H, Cationsultone), 3.44-3.24 (m, 3H, B+Cationsultone), 3.09-3.03 (m, 2H, C), 2.74 (m, 1H, O5), 2.50-1.77 (m, 13H, O6-7+Cationsultone+CationCH3), 1.33-1.29 (m, 2H, D)

$^{19}$F-NMR (376 MHz, DMSO-d6): δ (ppm)=−118.6-−118.9 (m, 2F)

[Chemical Formula 95.]

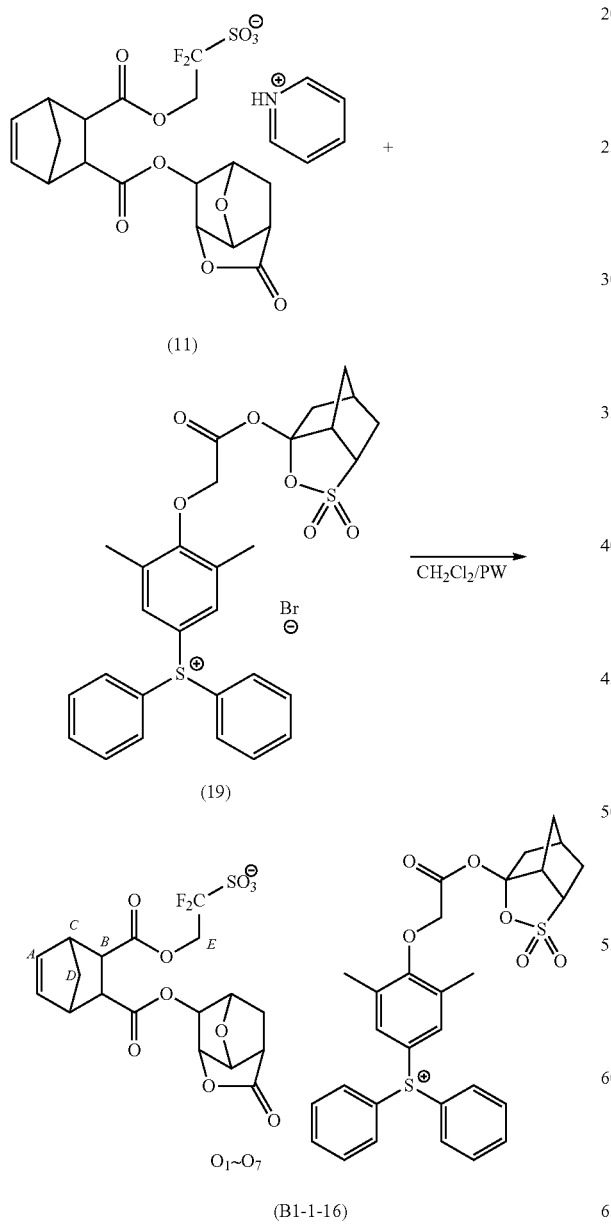

(B1-1-16)

Example 17

Synthesis of Compound (B1-1-17)

The same procedure as in iii) of Example 2 was performed, except that a compound (20) was used instead of 4-methylphenyldiphenylsulfonium bromide, thereby obtaining a compound (B1-1-17) in the form of a white solid.

The obtained compound (B1-1-17) was analyzed by $^1$H-NMR and $^{19}$F-NMR, and the structure thereof was identified by the following results.

$^1$H-NMR (400 MHz, DMSO-d6): δ (ppm)=8.01-7.98 (d, 2H, ArH), 7.76-7.73 (t, 1H, ArH), 7.61-7.58 (t, 2H, Ar), 6.24 (m, 1H, A), 6.07 (m, 1H, A'), 5.41 (m, 1H, O1), 5.31 (s, 2H, SCH2C=O), 4.67-4.33 (m, 5H, E+O2-4), 3.61-3.51 (m, 4H, CationCH2), 3.36-3.24 (m, 2H, B), 3.09-3.03 (m, 2H, C), 2.74 (m, 1H, O5), 2.51-2.06 (m, 6H, O6-7+CH2S), 1.33-1.29 (m, 2H, D)

$^{19}$F-NMR (376 MHz, DMSO-d6): δ (ppm)=−118.6-−118.9 (m, 2F)

[Chemical Formula 96.]

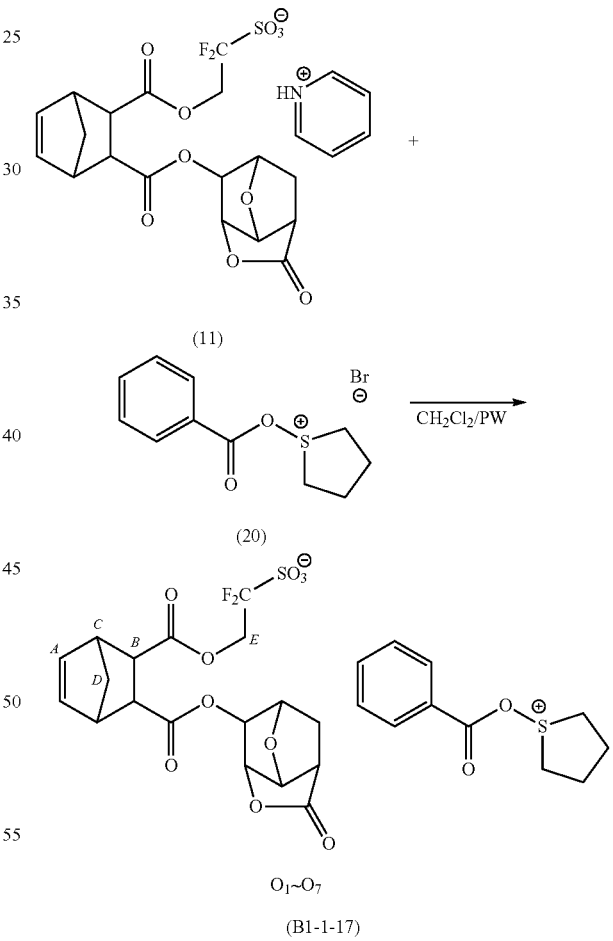

(B1-1-17)

Example 18

Synthesis of Compound (B1-1-18)

The same procedure as in iii) of Example 2 was performed, except that a compound (21) was used instead of 4-methylphenyldiphenylsulfonium bromide, thereby obtaining a compound (B1-1-18) in the form of a white solid.

The obtained compound (B1-1-18) was analyzed by $^1$H-NMR and $^{19}$F-NMR, and the structure thereof was identified by the following results.

$^1$H-NMR (400 MHz, DMSO-d6): δ (ppm)=8.05-8.02 (m, 2H, ArH), 7.73-7.61 (m, 3H, ArH), 6.24 (m, 1H, A), 6.07 (m, 1H, A'), 5.41 (m, 1H, O1), 4.67-4.33 (m, 5H, E+O2-4), 3.88-3.76 (m, 4H, SCH2), 3.36-3.24 (m, 2H, B), 3.09-3.03 (m, 2H, C), 2.74 (m, 1H, O5), 2.15-2.05 (m, 4H, O6-7+CationCH2), 1.92-1.84 (m, 2H, CationCH2), 1.71-1.60 (m, 2H, CationCH2) 1.33-1.29 (m, 2H, D)

$^{19}$F-NMR (376 MHz, DMSO-d6): δ (ppm)=−118.6-−118.9 (m, 2F)

[Chemical Formula 97.]

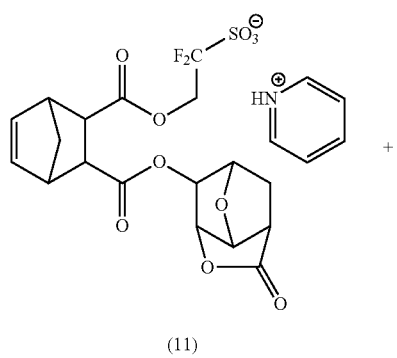

(11)

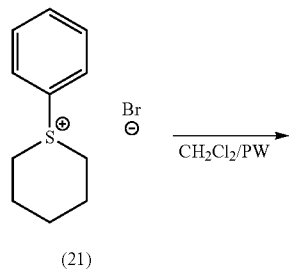

(21)

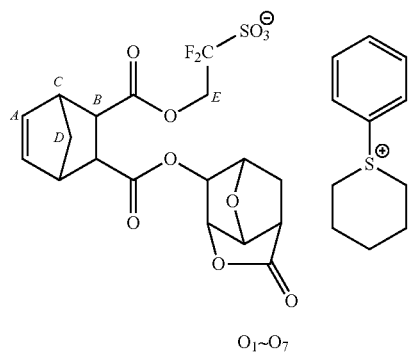

($O_1$~$O_7$)

(B1-1-18)

Example 19

Synthesis of Compound (B1-1-19)

The same procedure as in iii) of Example 2 was performed, except that a compound (22) was used instead of 4-methylphenyldiphenylsulfonium bromide, thereby obtaining a compound (B1-1-19) in the form of a white solid.

The obtained compound (B1-1-19) was analyzed by $^1$H-NMR and $^{19}$F-NMR, and the structure thereof was identified by the following results.

$^1$H-NMR (400 MHz, DMSO-d6): δ (ppm)=7.93-7.73 (m, 12H, ArH), 6.24 (m, 1H, A), 6.07 (m, 1H, A'), 5.41 (m, 1H, O1), 4.67-4.33 (m, 5H, E+O2-4), 3.36-3.24 (m, 2H, B), 3.09-3.03 (m, 2H, C), 2.76-2.73 (m, 3H, O5+CationCH2), 2.18-2.05 (m, 8H, O6-7+CationCH3), 1.71-1.65 (m, 2H, CationCH2), 1.39-1.29 (m, 16H, D+CationCH2), 0.85 (t, 3H, CationCH3)

$^{19}$F-NMR (376 MHz, DMSO-d6): δ (ppm)=−118.6-−118.9 (m, 2F)

[Chemical Formula 98.]

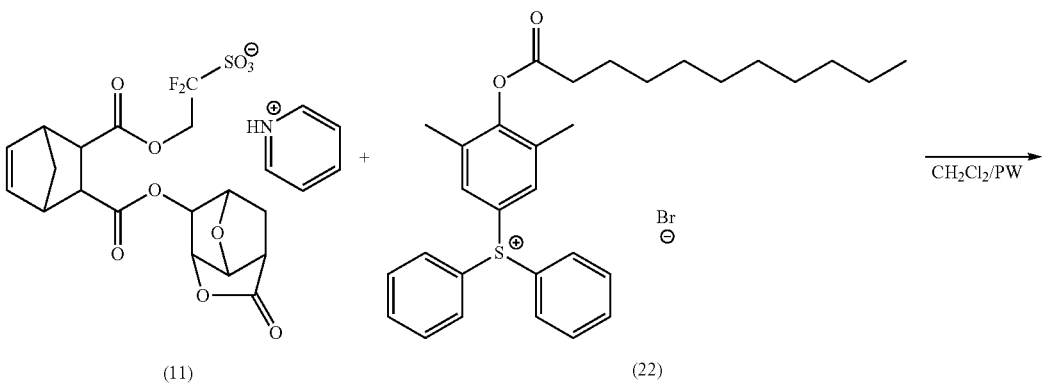

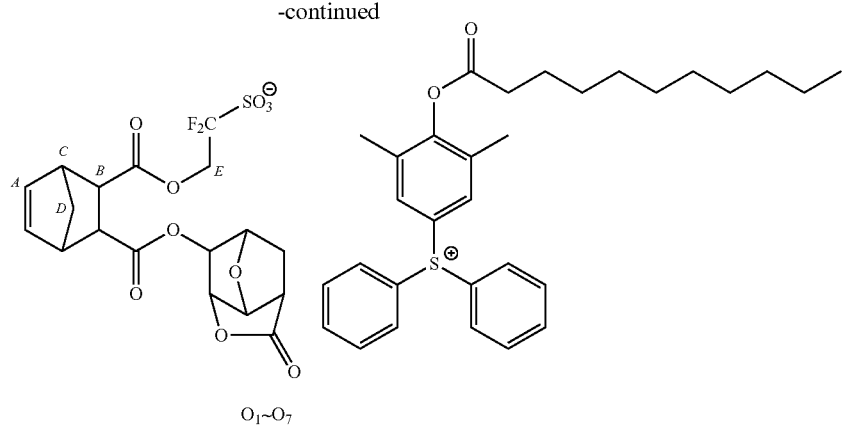

(B1-1-19)

Example 20

Synthesis of Compound (B1-1-20)

The same procedure as in iii) of Example 2 was performed, except that a compound (23) was used instead of 4-methylphenyldiphenylsulfonium bromide, thereby obtaining a compound (B1-1-20) in the form of a white solid.

The obtained compound (B1-1-20) was analyzed by $^1$H-NMR and $^{19}$F-NMR, and the structure thereof was identified by the following results.

$^1$H-NMR (400 MHz, DMSO-d6): δ (ppm)=8.28 (d, 2H, ArH), 8.11 (d, 1H, ArH), 7.86 (t, 1H, ArH), 7.82-7.64 (m, 7H, ArH), 6.24 (m, 1H, A), 6.07 (m, 1H, A'), 5.41 (m, 1H, O1), 4.67-4.33 (m, 5H, E+O2-4), 3.36-3.24 (m, 2H, B), 3.09-3.03 (m, 2H, C), 2.74 (m, 1H, O5), 2.11-2.05 (m, 2H, O6-7), 1.33-1.29 (m, 2H, D)

$^{19}$F-NMR (376 MHz, DMSO-d6): δ (ppm)=−118.6-−118.9 (m, 2F)

[Chemical Formula 99.]

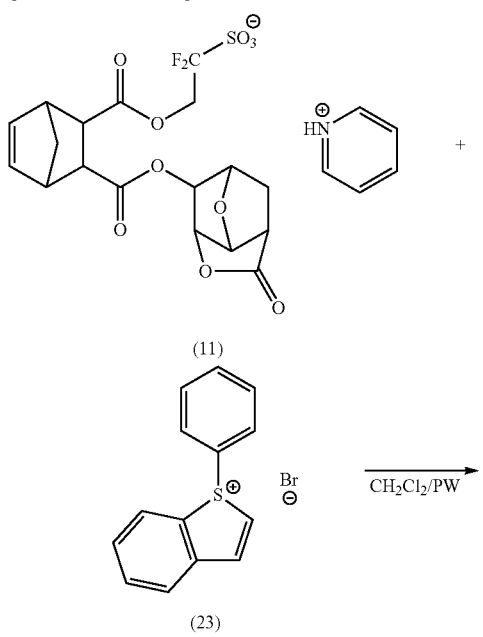

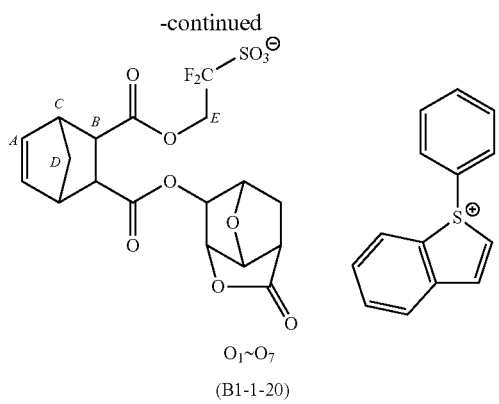

(B1-1-20)

Example 21

Synthesis of Compound (B1-1-21)

The same procedure as in iii) of Example 3 was performed, except that a compound (16) was used instead of 4-methylphenyldiphenylsulfonium bromide, thereby obtaining a compound (B1-1-21) in the form of a white solid.

The obtained compound (B1-1-21) was analyzed by $^1$H-NMR and $^{19}$F-NMR, and the structure thereof was identified by the following results.

$^1$H-NMR (400 MHz, DMSO-d6): δ (ppm)=8.50 (d, 2H, ArH), 8.37 (d, 2H, ArH), 7.93 (t, 2H, ArH), 7.75-7.55 (m, 7H, ArH), 6.46 (m, 2H, A), 5.14-5.07 (m, 2H, B), 4.75 (m, 1H, N1), 4.66-4.33 (m, 3H, E+N2), 3.86 (m, 1H, N3), 3.43 (m, 1H, N4), 2.72 (m, 2H, C), 2.42 (m, 1H, N5), 2.13 (m, 1H, N6), 1.87-1.76 (m, 3H, N7-9)

$^{19}$F-NMR (376 MHz, DMSO-d6): δ (ppm)=−118.5-−119.0 (m, 2F)

[Chemical Formula 100.]

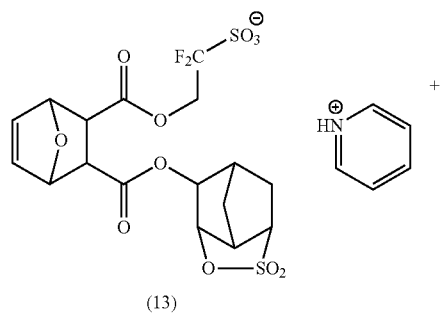

(13)

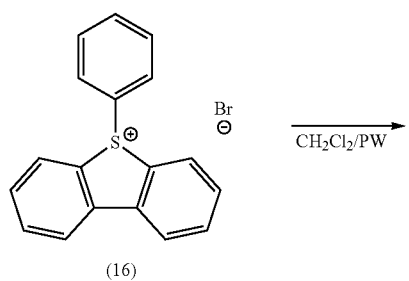

(16)

CH₂Cl₂/PW →

(B1-1-21)

Example 22

Synthesis of Compound (B1-1-22)

The same procedure as in iii) of Example 3 was performed, except that a compound (17) was used instead of 4-methylphenyldiphenylsulfonium bromide, thereby obtaining a compound (B1-1-22) in the form of a white solid.

The obtained compound (B1-1-22) was analyzed by $^1$H-NMR and $^{19}$F-NMR, and the structure thereof was identified by the following results.

$^1$H-NMR (400 MHz, DMSO-d6): δ (ppm)=7.86-7.75 (m, 10H, ArH), 7.61 (s, 2H, ArH), 6.46 (m, 2H, A), 5.14-5.07 (m, 2H, B), 4.75 (m, 1H, N1), 4.66-4.33 (m, 5H, E+N2+CationCH2), 3.86 (m, 1H, N3), 3.43 (m, 1H, N4), 2.72 (m, 2H, C), 2.42 (m, 1H, N5), 2.31 (s, 6H, CationCH3), 2.13 (m, 1H, N6), 1.97-1.49 (m, 20H, N7-9+Adamantane)

$^{19}$F-NMR (376 MHz, DMSO-d6): δ (ppm)=−118.5--119.0 (m, 2F)

[Chemical Formula 101.]

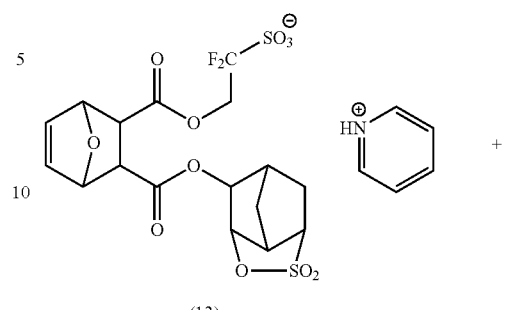

(13)

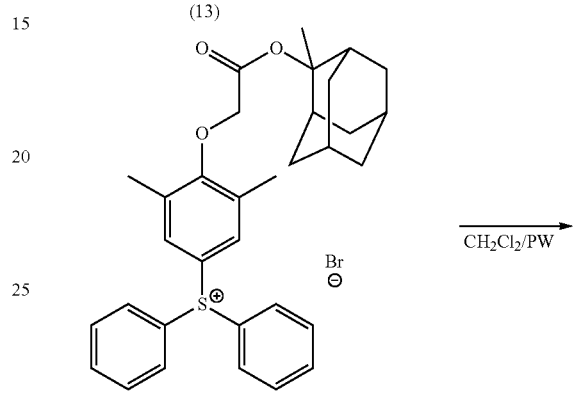

(17)

CH₂Cl₂/PW →

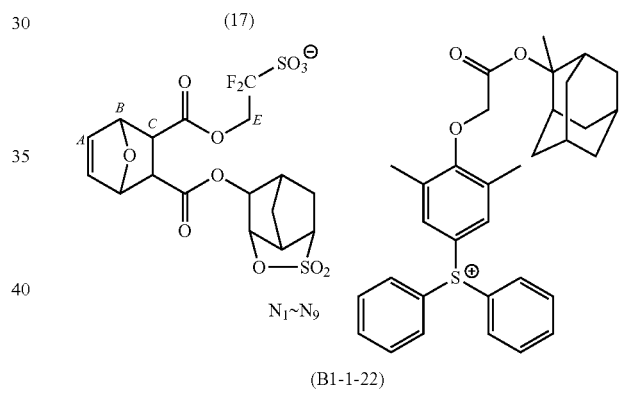

(B1-1-22)

Example 23

Synthesis of Compound (B1-1-23)

The same procedure as in iii) of Example 3 was performed, except that a compound (18) was used instead of 4-methylphenyldiphenylsulfonium bromide, thereby obtaining a compound (B1-1-23) in the form of a white solid.

The obtained compound (B1-1-23) was analyzed by $^1$H-NMR and $^{19}$F-NMR, and the structure thereof was identified by the following results.

$^1$H-NMR (400 MHz, DMSO-d6): δ (ppm)=7.82-7.76 (m, 10H, ArH), 7.59 (s, 2H, ArH), 6.46 (m, 2H, A), 5.14-5.07 (m, 2H, B), 4.75 (m, 1H, N1), 4.66-4.33 (m, 5H, E+N2+CationCH2), 3.86 (m, 1H, N3), 3.43 (m, 1H, N4), 2.72 (m, 2H, C), 2.42 (m, 1H, N5), 2.29 (m, 6H, CationCH3), 2.13 (m, 1H, N6), 1.94-1.45 (m, 13H, N7-9+CationCH2+cyclopentyl), 0.81-0.75 (t, 3H, CationCH3)

$^{19}$F-NMR (376 MHz, DMSO-d6): δ (ppm)=−118.5--119.0 (m, 2F)

[Chemical Formula 102.]

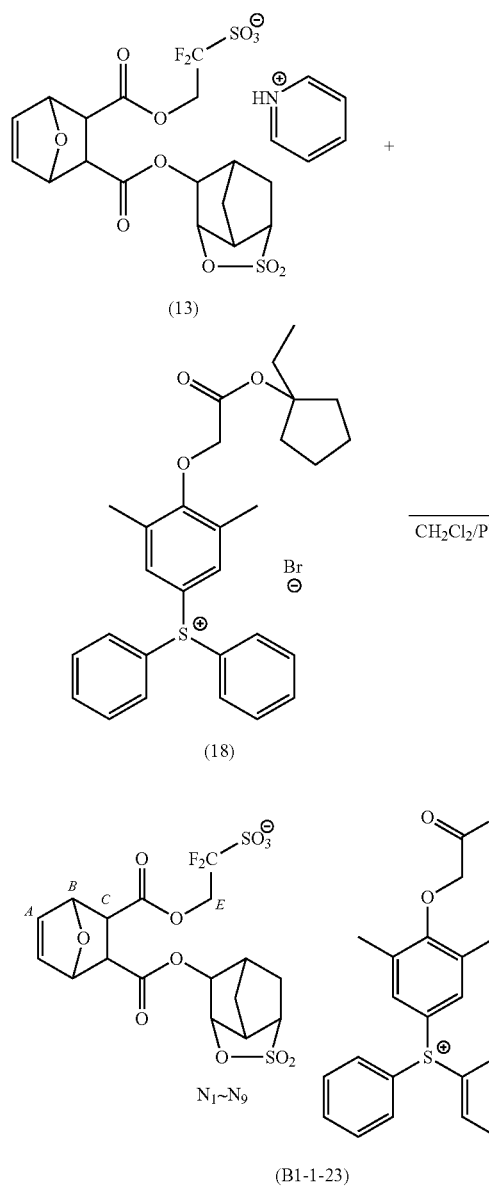

(B1-1-23)

Example 24

Synthesis of Compound (B1-1-24)

The same procedure as in iii) of Example 3 was performed, except that a compound (19) was used instead of 4-methylphenyldiphenylsulfonium bromide, thereby obtaining a compound (B1-1-24) in the form of a white solid.

The obtained compound (B1-1-24) was analyzed by $^1$H-NMR and $^{19}$F-NMR, and the structure thereof was identified by the following results.

$^1$H-NMR (400 MHz, DMSO-d6): δ (ppm)=7.83-7.72 (m, 10H, ArH), 7.59 (s, 2H, ArH), 6.46 (m, 2H, A), 5.14-5.07 (m, 2H, B), 4.90 (m, 1H, Cationsultone), 4.75 (m, 1H, N1), 4.69-4.33 (m, 6H, E+N2+CationCH2O+Cationsultone), 3.90-3.83 (m, 2H, N3+Cationsultone), 3.44-3.42 (m, 2H, N4+Cationsultone), 2.72 (m, 2H, C), 2.49-1.76 (m, 16H, N5-9+Cationsultone+CationCH3)

$^{19}$F-NMR (376 MHz, DMSO-d6): δ (ppm)=-118.5--119.0 (m, 2F)

[Chemical Formula 103.]

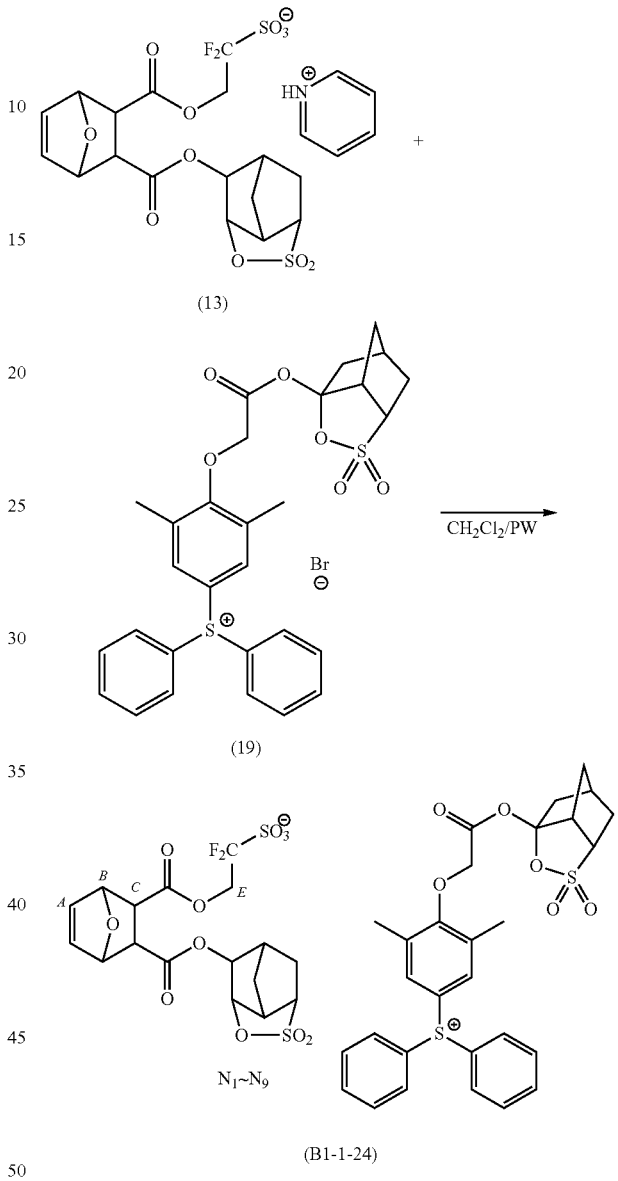

(B1-1-24)

Example 25

Synthesis of Compound (B1-1-25)

The same procedure as in iii) of Example 3 was performed, except that a compound (20) was used instead of 4-methylphenyldiphenylsulfonium bromide, thereby obtaining a compound (B1-1-25) in the form of a white solid.

The obtained compound (B1-1-25) was analyzed by $^1$H-NMR and $^{19}$F-NMR, and the structure thereof was identified by the following results.

$^1$H-NMR (400 MHz, DMSO-d6): δ (ppm)=8.02-7.99 (d, 2H, ArH), 7.76-7.73 (t, 1H, ArH), 7.61-7.56 (t, 2H, ArH), 6.46 (m, 2H, A), 5.31 (s, 2H, SCH2C=O), 5.14-5.07 (m, 2H, B), 4.75 (m, 1H, N1), 4.66-4.33 (m, 3H, E+N2), 3.86 (m, 1H, N3), 3.62-3.49 (m, 4H, CationCH2), 3.43 (m, 1H, N4), 2.72 (m, 2H, C), 2.49-2.19 (m, 5H, N5+CationCH2S), 2.13 (m, 1H, N6), 1.87-1.76 (m, 3H, N7-9)

$^{19}$F-NMR (376 MHz, DMSO-d6): δ (ppm)=−118.5-−119.0 (m, 2F)

[Chemical Formula 104.]

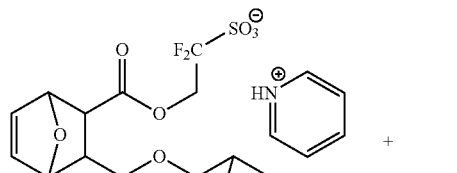

(13)

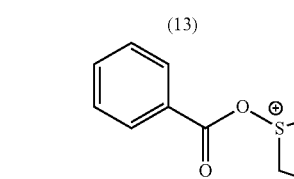

(20)

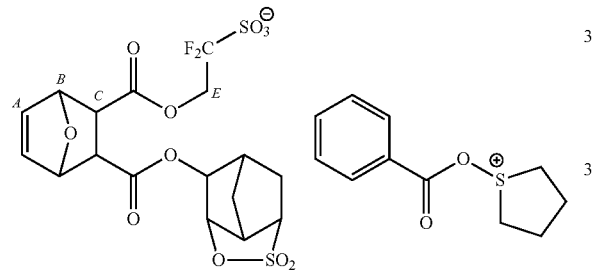

(B1-1-25)

[Chemical Formula 105.]

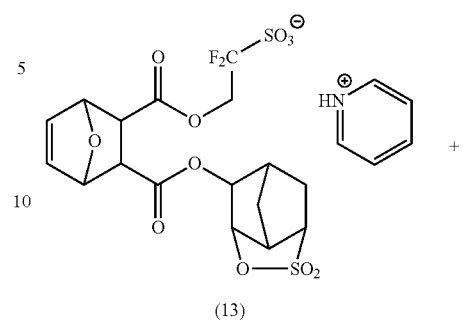

(13)

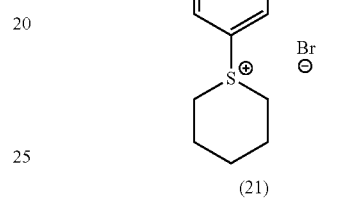

(21)

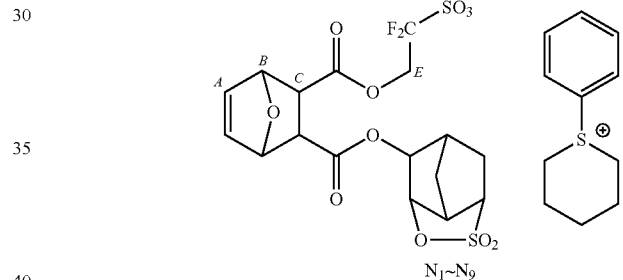

(B1-1-26)

Example 26

Synthesis of Compound (B1-1-26)

The same procedure as in iii) of Example 3 was performed, except that a compound (21) was used instead of 4-methylphenyldiphenylsulfonium bromide, thereby obtaining a compound (B1-1-26) in the form of a white solid.

The obtained compound (B1-1-26) was analyzed by $^1$H-NMR and $^{19}$F-NMR, and the structure thereof was identified by the following results.

$^1$H-NMR (400 MHz, DMSO-d6): δ (ppm)=8.05-8.02 (m, 2H, ArH), 7.73-7.61 (m, 3H, ArH), 6.46 (m, 2H, A), 5.14-5.07 (m, 2H, B), 4.75 (m, 1H, N1), 4.66-4.33 (m, 3H, E+N2), 3.87-3.76 (m, 5H, N3+CationSCH2), 3.43 (m, 1H, N4), 2.72 (m, 2H, C), 2.42 (m, 1H, N5), 2.15-2.09 (m, 3H, N6+CationCH2), 1.94-1.76 (m, 5H, N7-9+CationCH2), 1.71-1.60 (m, 2H, CationCH2)

$^{19}$F-NMR (376 MHz, DMSO-d6): δ (ppm)=−118.5-−119.0 (m, 2F)

Example 27

Synthesis of Compound (B1-1-27)

The same procedure as in iii) of Example 3 was performed, except that a compound (22) was used instead of 4-methylphenyldiphenylsulfonium bromide, thereby obtaining a compound (B1-1-27) in the form of a white solid.

The obtained compound (B1-1-27) was analyzed by $^1$H-NMR and $^{19}$F-NMR, and the structure thereof was identified by the following results.

$^1$H-NMR (400 MHz, DMSO-d6): δ (ppm)=7.93-7.79 (m, 12H, ArH), 6.46 (m, 2H, A), 5.14-5.07 (m, 2H, B), 4.75 (m, 1H, N1), 4.66-4.33 (m, 3H, E+N2), 3.86 (m, 1H, N3), 3.43 (m, 1H, N4), 2.74-2.71 (m, 4H, C+CationCH2), 2.42 (m, 1H, N5), 2.19 (s, 6H, CationCH3), 2.13 (m, 1H, N6), 1.87-1.76 (m, 3H, N7-9), 1.71-1.65 (m, 2H, CationCH2) 1.38-1.26 (m, 14H, CationCH2), 0.85 (t, 3H, CationCH3)

$^{19}$F-NMR (376 MHz, DMSO-d6): δ (ppm)=−118.5-−119.0 (m, 2F)

[Chemical Formula 106.]

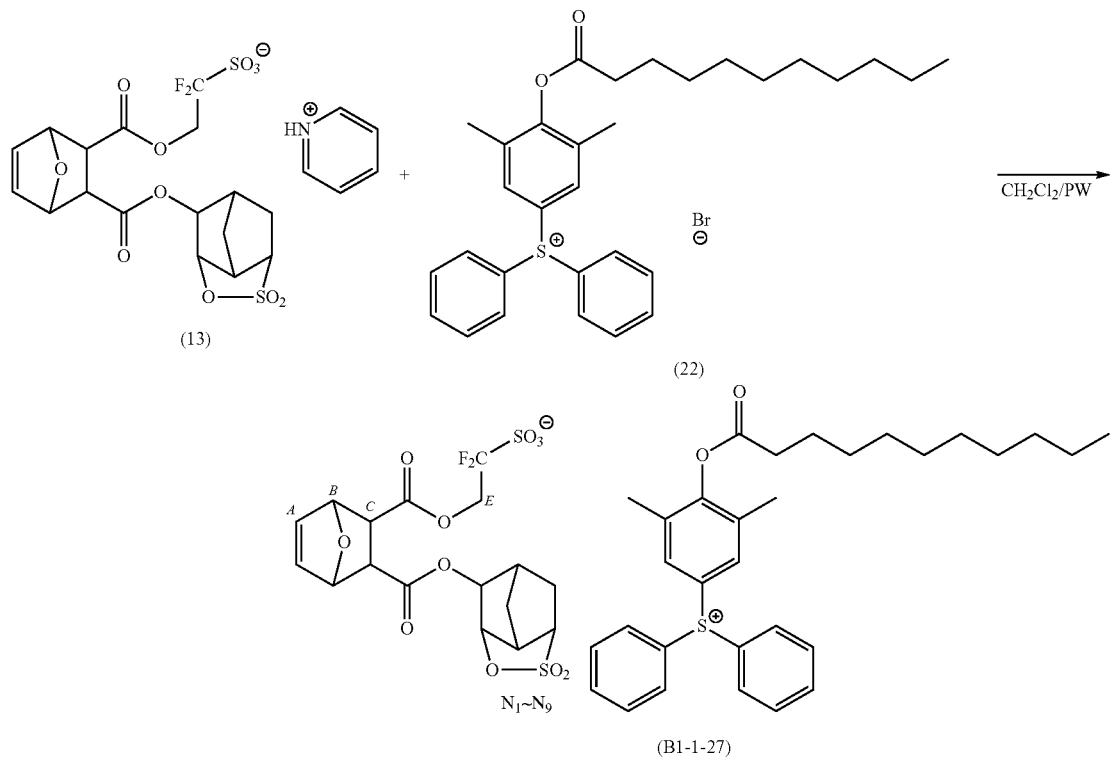

Example 28

Synthesis of Compound (B1-1-28)

The same procedure as in iii) of Example 3 was performed, except that a compound (23) was used instead of 4-methylphenyldiphenylsulfonium bromide, thereby obtaining a compound (B1-1-28) in the form of a white solid.

The obtained compound (B1-1-28) was analyzed by $^{1}$H-NMR and $^{19}$F-NMR, and the structure thereof was identified by the following results.

$^{1}$H-NMR (400 MHz, DMSO-d6): δ (ppm)=8.28 (d, 2H, ArH), 8.11 (d, 1H, ArH), 7.86 (t, 1H, ArH), 7.81-7.63 (m, 7H, ArH), 6.46 (m, 2H, A), 5.14-5.07 (m, 2H, B), 4.75 (m, 1H, N1), 4.66-4.33 (m, 3H, E+N2), 3.86 (m, 1H, N3), 3.43 (m, 1H, N4), 2.72 (m, 2H, C), 2.42 (m, 1H, N5), 2.13 (m, 1H, N6), 1.87-1.76 (m, 3H, N7-9)

$^{19}$F-NMR (376 MHz, DMSO-d6): δ (ppm)=−118.5−−119.0 (m, 2F)

[Chemical Formula 107.]

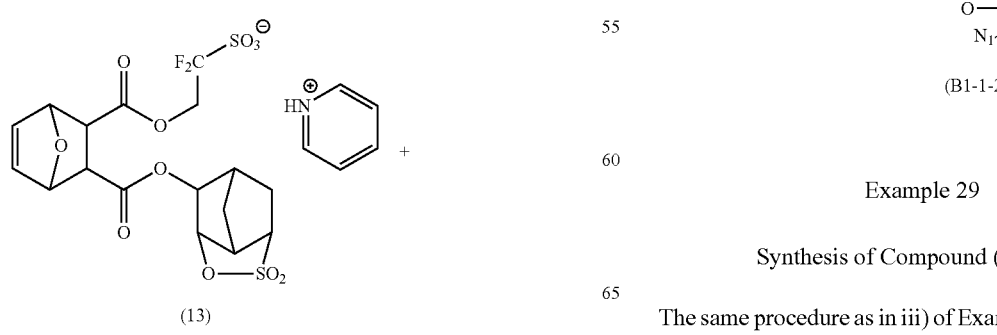

Example 29

Synthesis of Compound (B1-1-29)

The same procedure as in iii) of Example 4 was performed, except that a compound (16) was used instead of 4-methylphenyldiphenylsulfonium bromide, thereby obtaining a compound (B1-1-29) in the form of a white solid.

The obtained compound (B1-1-29) was analyzed by $^1$H-NMR and $^{19}$F-NMR, and the structure thereof was identified by the following results.

$^1$H-NMR (400 MHz, DMSO-d6): δ (ppm)=8.50 (d, 2H, ArH), 8.37 (d, 2H, ArH), 7.93 (t, 2H, ArH), 7.75-7.55 (m, 7H, ArH), 6.44 (m, 2H, A), 5.42 (m, 1H, O1), 5.12-5.08 (m, 2H, B), 4.67-4.35 (m, 5H, E+O2-4), 2.75-2.70 (m, 3H, C+O5), 2.16-2.04 (m, 2H, O6-7)

$^{19}$F-NMR (376 MHz, DMSO-d6): δ (ppm)=−118.5−−119.0 (m, 2F)

$^1$H-NMR (400 MHz, DMSO-d6): δ (ppm)=7.88-7.75 (m, 10H, ArH), 7.61 (s, 2H, ArH), 6.44 (m, 2H, A), 5.42 (m, 1H, O1), 5.12-5.08 (m, 2H, B), 4.67-4.35 (m, 7H, E+O2-4+CationCH2), 2.75-2.70 (m, 3H, C+O5), 2.31 (s, 6H, CH3), 2.16-2.04 (m, 2H, O6-7), 1.97-1.48 (m, 17H, Adamantane)

$^{19}$F-NMR (376 MHz, DMSO-d6): δ (ppm)=−118.5−−119.0 (m, 2F)

[Chemical Formula 109.]

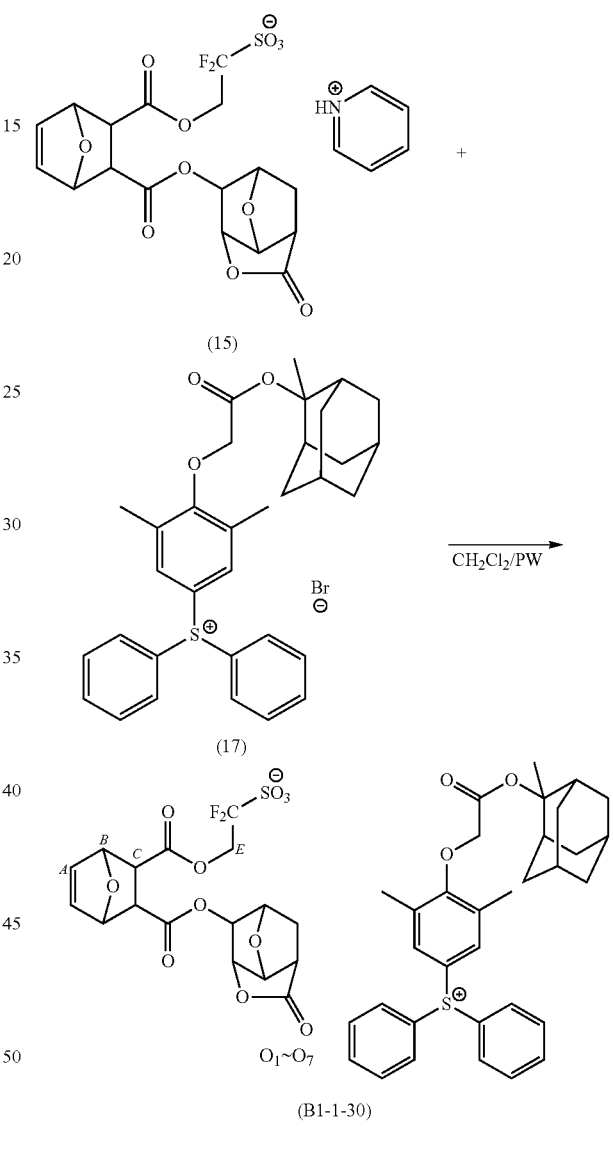

[Chemical Formula 108.]

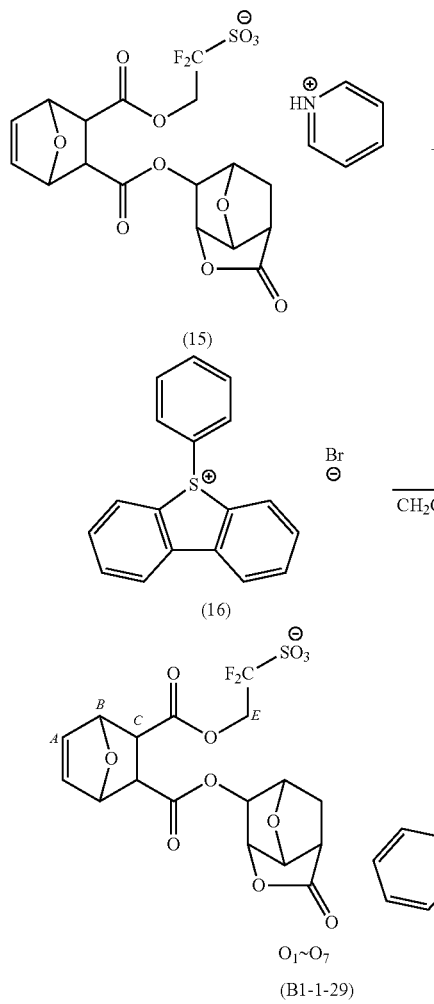

Example 30

Synthesis of Compound (B1-1-30)

The same procedure as in iii) of Example 4 was performed, except that a compound (17) was used instead of 4-methylphenyldiphenylsulfonium bromide, thereby obtaining a compound (B1-1-30) in the form of a white solid.

The obtained compound (B1-1-30) was analyzed by $^1$H-NMR and $^{19}$F-NMR, and the structure thereof was identified by the following results.

Example 31

Synthesis of Compound (B1-1-31)

The same procedure as in iii) of Example 4 was performed, except that a compound (18) was used instead of 4-methylphenyldiphenylsulfonium bromide, thereby obtaining a compound (B1-1-31) in the form of a white solid.

The obtained compound (B1-1-31) was analyzed by $^1$H-NMR and $^{19}$F-NMR, and the structure thereof was identified by the following results.

$^1$H-NMR (400 MHz, DMSO-d6): δ (ppm)=7.83-7.77 (m, 10H, ArH), 7.59 (s, 2H, ArH), 6.44 (m, 2H, A), 5.42 (m, 1H, O1), 5.12-5.08 (m, 2H, B), 4.67-4.35 (m, 2H, E+O2-4+CationCH2), 2.75-2.70 (m, 3H, C+O5), 2.29 (m, 6H, CationCH3), 2.16-2.04 (m, 2H, O6-7), 1.95-1.91 (m, 4H, CH2, cyclopentyl), 1.77-1.50 (m, 6H, cyclopentyl), 0.81-0.76 (t, 3H, CationCH3)

$^{19}$F-NMR (376 MHz, DMSO-d6): δ (ppm)=−118.5−−119.0 (m, 2F)

[Chemical Formula 110.]

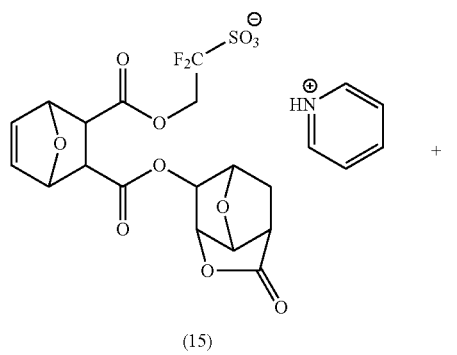

Example 32

Synthesis of Compound (B1-1-32)

The same procedure as in iii) of Example 4 was performed, except that a compound (19) was used instead of 4-methylphenyldiphenylsulfonium bromide, thereby obtaining a compound (B1-1-32) in the form of a white solid.

The obtained compound (B1-1-32) was analyzed by $^1$H-NMR and $^{19}$F-NMR, and the structure thereof was identified by the following results.

$^1$H-NMR (400 MHz, DMSO-d6): δ (ppm)=7.82-7.73 (m, 10H, ArH), 7.59 (s, 2H, ArH), 6.44 (m, 2H, A), 5.42 (m, 1H, O1), 5.12-5.08 (m, 2H, B), 4.90 (m, 1H, Cationsultone), 4.68-4.35 (m, 8H, E+O2-4+CationCH2O+Cationsultone), 3.89-3.83 (m, 1H, Cationsultone), 3.43 (m, 1H, Cationsultone), 2.75-2.70 (m, 3H, C+O5), 2.49-1.76 (m, 13H, O6-7+Cationsultone+CationCH3)

$^{19}$F-NMR (376 MHz, DMSO-d6): δ (ppm)=−118.5−−119.0 (m, 2F)

[Chemical Formula 111.]

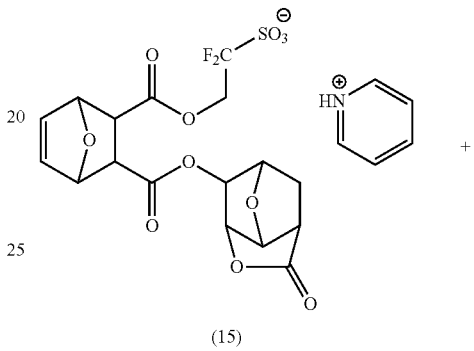

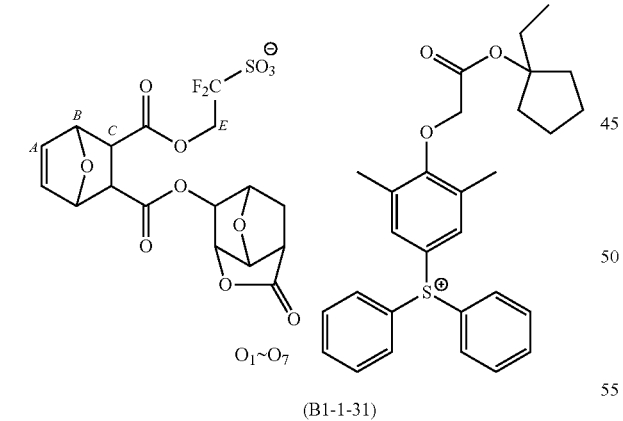

Example 33

Synthesis of Compound (B1-1-33)

The same procedure as in iii) of Example 4 was performed, except that a compound (20) was used instead of 4-methylphenyldiphenylsulfonium bromide, thereby obtaining a compound (B1-1-33) in the form of a white solid.

The obtained compound (B1-1-33) was analyzed by $^1$H-NMR and $^{19}$F-NMR, and the structure thereof was identified by the following results.

$^1$H-NMR (400 MHz, DMSO-d6): δ (ppm)=8.01-7.99 (d, 2H, ArH), 7.76-7.73 (t, 1H, ArH), 7.62-7.58 (t, 2H, ArH), 6.44 (m, 2H, A), 5.42 (m, 1H, O1), 5.31 (s, 2H, CationSCH2C=O), 5.12-5.08 (m, 2H, B), 4.67-4.35 (m, 5H, E+O2-4), 3.62-3.49 (m, 4H, CationCH2), 2.75-2.70 (m, 3H, C+O5), 2.49-2.04 (m, 6H, O6-7+CationCH2S)

$^{19}$F-NMR (376 MHz, DMSO-d6): δ (ppm)=−118.5--119.0 (m, 2F)

[Chemical Formula 112.]

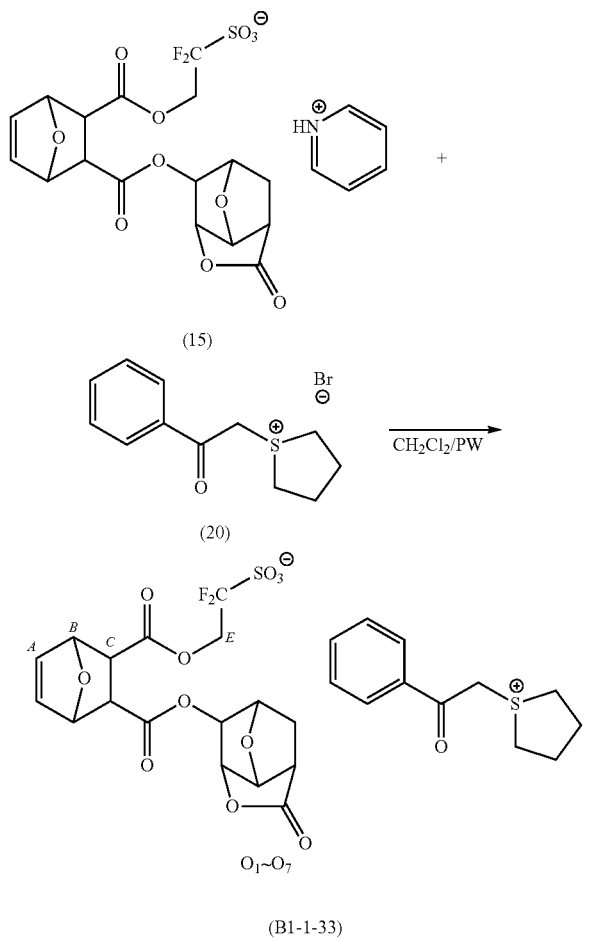

(B1-1-33)

Example 34

Synthesis of Compound (B1-1-34)

The same procedure as in iii) of Example 4 was performed, except that a compound (21) was used instead of 4-methylphenyldiphenylsulfonium bromide, thereby obtaining a compound (B1-1-34) in the form of a white solid.

The obtained compound (B1-1-34) was analyzed by $^1$H-NMR and $^{19}$F-NMR, and the structure thereof was identified by the following results.

$^1$H-NMR (400 MHz, DMSO-d6): δ (ppm)=8.05-8.02 (m, 2H, ArH), 7.73-7.61 (m, 3H, ArH), 6.44 (m, 2H, A), 5.42 (m, 1H, O1), 5.12-5.08 (m, 2H, B), 4.67-4.35 (m, 5H, E+O2-4), 3.86-3.76 (m, 4H, CationSCH2), 2.75-2.70 (m, 3H, C+O5), 2.16-2.04 (m, 4H, O6-7+CationCH2), 1.94-1.83 (m, 2H, CationCH2), 1.71-1.60 (m, 2H, CationCH2)

$^{19}$F-NMR (376 MHz, DMSO-d6): δ (ppm)=−118.5--119.0 (m, 2F)

[Chemical Formula 113.]

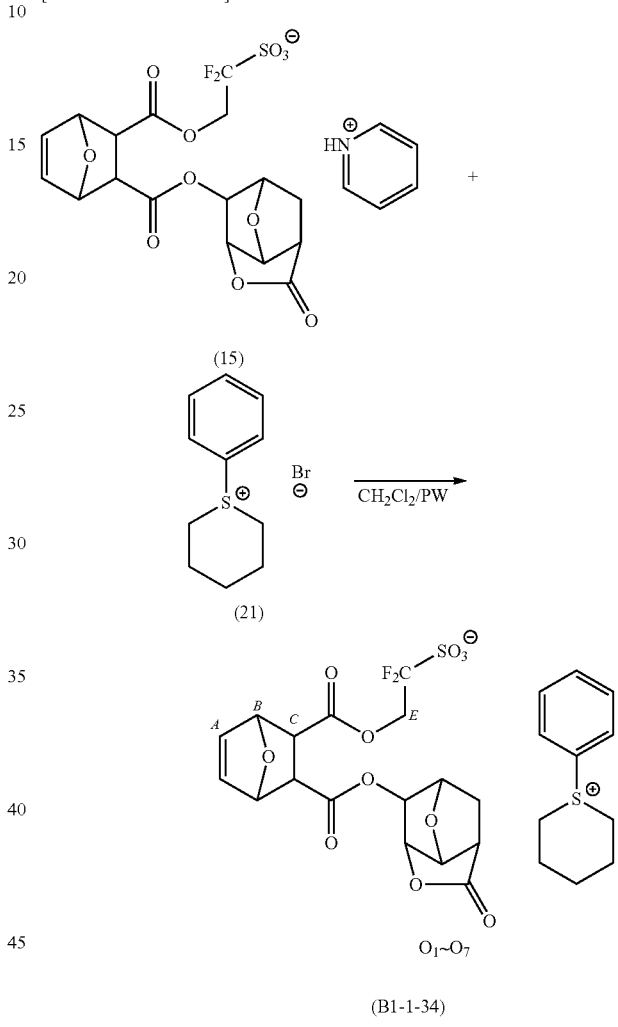

(B1-1-34)

Example 35

Synthesis of Compound (B1-1-35)

The same procedure as in iii) of Example 4 was performed, except that a compound (22) was used instead of 4-methylphenyldiphenylsulfonium bromide, thereby obtaining a compound (B1-1-35) in the form of a white solid.

The obtained compound (B1-1-35) was analyzed by $^1$H-NMR and $^{19}$F-NMR, and the structure thereof was identified by the following results.

$^1$H-NMR (400 MHz, DMSO-d6): δ (ppm)=7.93-7.79 (m, 12H, ArH), 6.44 (m, 2H, A), 5.42 (m, 1H, O1), 5.12-5.08 (m, 2H, B), 4.67-4.35 (m, 5H, E+O2-4), 2.75-2.70 (m, 5H, C+O5+CationCH2), 2.20-2.04 (m, 8H, O6-7+CationCH3), 1.71-1.65 (m, 2H, CH2), 1.38-1.26 (m, 14H, CH2), 0.85 (t, 3H, CH3)

$^{19}$F-NMR (376 MHz, DMSO-d6): δ (ppm)=−118.5--119.0 (m, 2F)

[Chemical Formula 114.]

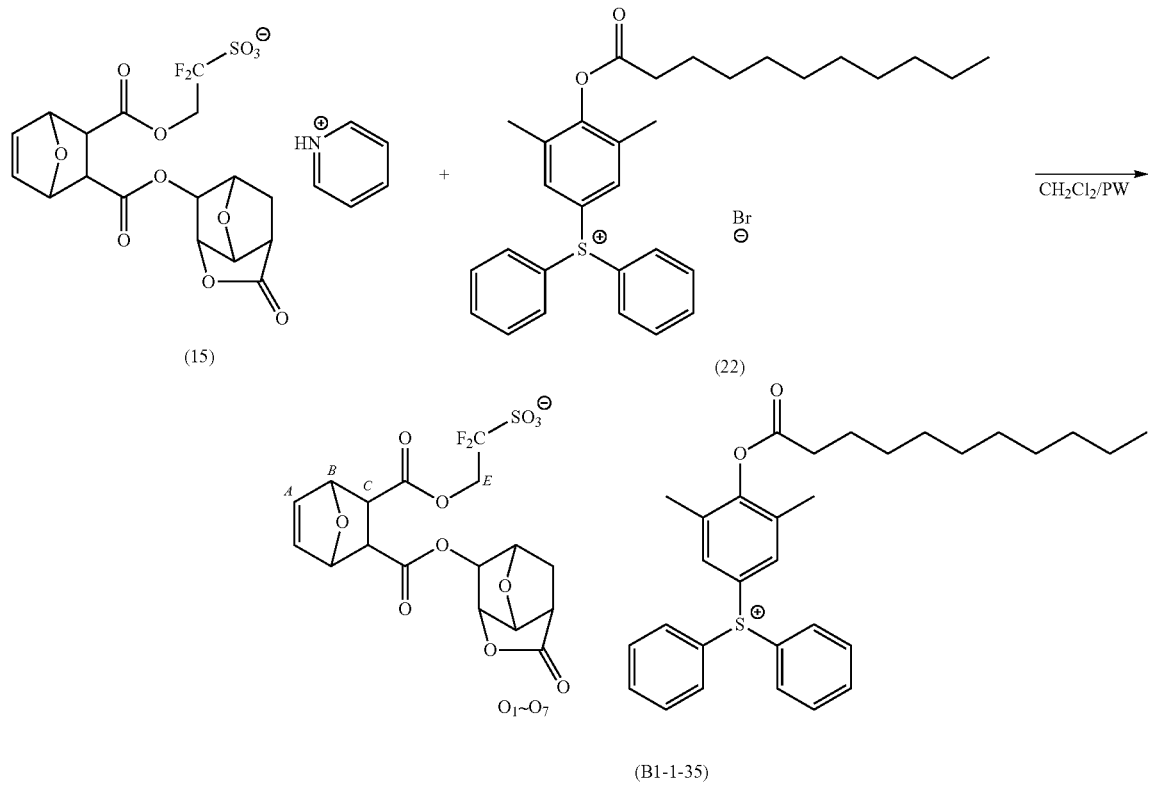

(B1-1-35)

Example 36

Synthesis of Compound (B1-1-36)

The same procedure as in iii) of Example 4 was performed, except that a compound (23) was used instead of 4-methylphenyldiphenylsulfonium bromide, thereby obtaining a compound (B1-1-36) in the form of a white solid.

The obtained compound (B1-1-36) was analyzed by $^1$H-NMR and $^{19}$F-NMR, and the structure thereof was identified by the following results.

$^1$H-NMR (400 MHz, DMSO-d6): δ (ppm)=8.28 (d, 2H, ArH), 8.11 (d, 1H, ArH), 7.86 (t, 1H, ArH), 7.81-7.64 (m, 7H, ArH), 6.44 (m, 2H, A), 5.42 (m, 1H, O1), 5.12-5.08 (m, 2H, B), 4.67-4.35 (m, 5H, E+O2-4), 2.75-2.70 (m, 3H, C+O5), 2.16-2.04 (m, 2H, O6-7)

$^{19}$F-NMR (376 MHz, DMSO-d6): δ (ppm)=-118.5--119.0 (m, 2F)

[Chemical Formula 115.]

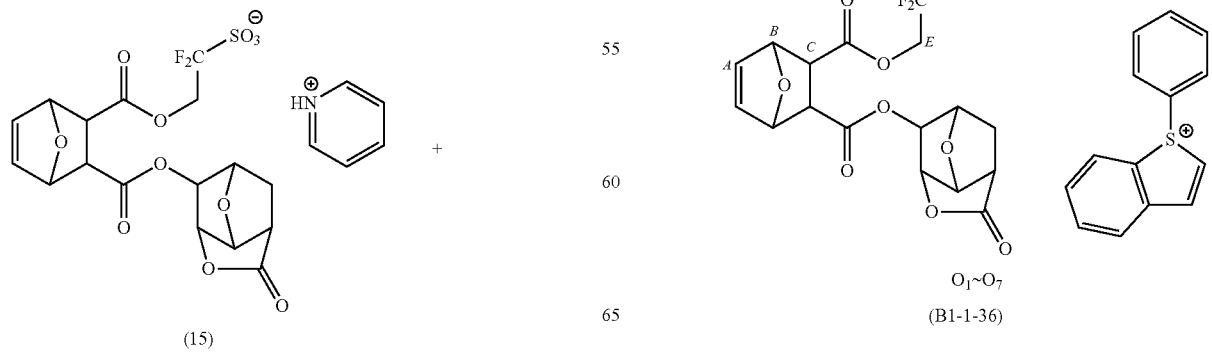

(B1-1-36)

Example 37

Synthesis of Compound (B1-1-37)

The same procedure as in iii) of Example 1 was performed, except that a compound (24) was used instead of 4-methylphenyldiphenylsulfonium bromide, thereby obtaining a compound (B1-1-37) in the form of a white solid.

The obtained compound (B1-1-37) was analyzed by $^1$H-NMR and $^{19}$F-NMR, and the structure thereof was identified by the following results.

$^1$H-NMR (400 MHz, DMSO-d6): δ (ppm)=7.82-7.76 (m, 10H, ArH), 7.59 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.38 (m, 3H, B+N4), 3.11 (m, 2H, C), 2.37 (m, 1H, N5), 2.29 (m, 6H, CH3), 2.16 (m, 1H, N6), 2.09-1.22 (m, 7H, N7-9+D+CationCH3+cyclopentyl)

$^{19}$F-NMR (376 MHz, DMSO-d6): δ (ppm)=−118.5−−118.9 (m, 2F)

Example 38

Synthesis of Compound (B1-1-38)

The same procedure as in iii) of Example 1 was performed, except that a compound (25) was used instead of 4-methylphenyldiphenylsulfonium bromide, thereby obtaining a compound (B1-1-38) in the form of a white solid.

The obtained compound (B1-1-38) was analyzed by $^1$H-NMR and $^{19}$F-NMR, and the structure thereof was identified by the following results.

$^1$H-NMR (400 MHz, DMSO-d6): δ (ppm)=10.05 (s, 1H, OH), 7.87-7.64 (m, 10H, ArH), 7.56 (s, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.22 (m, 6H, CH3), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F)

[Chemical Formula 116.]

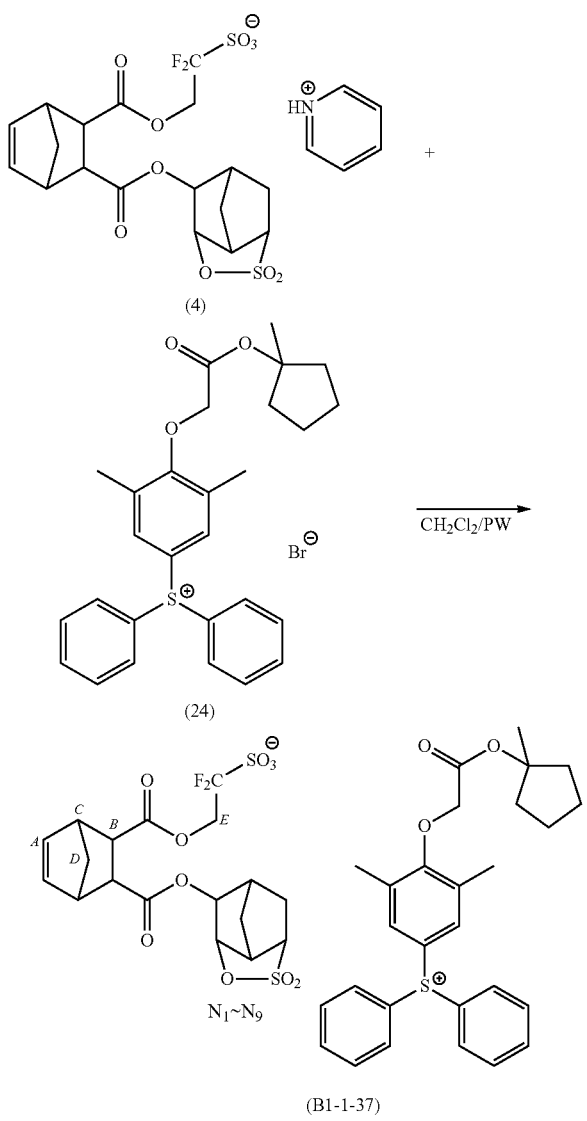

(B1-1-37)

[Chemical Formula 117.]

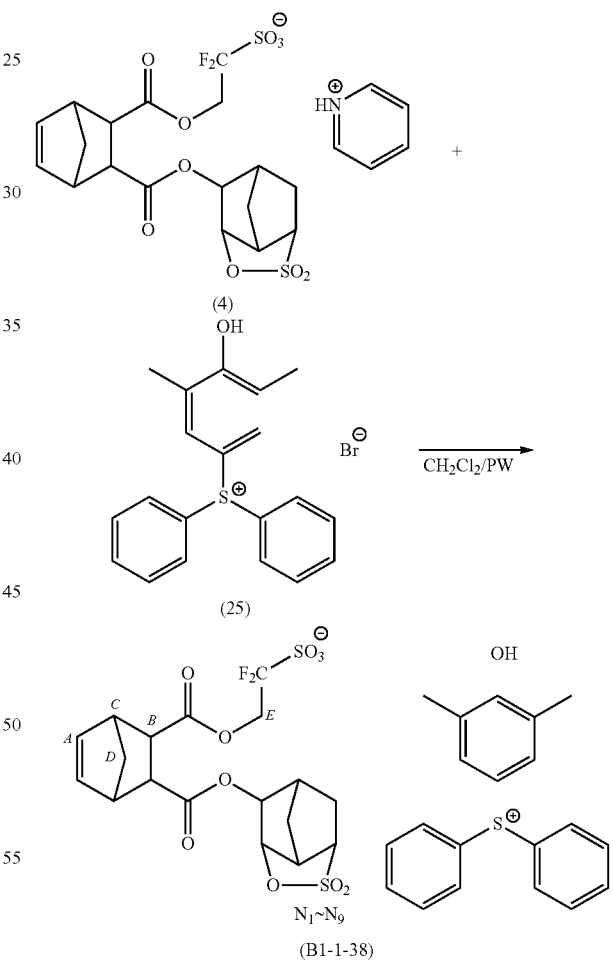

(B1-1-38)

Example 39

Synthesis of Compound (B1-1-39)

The same procedure as in iii) of Example 1 was performed, except that a compound (26) was used instead of 4-methylphenyldiphenylsulfonium bromide, thereby obtaining a compound (B1-1-39) in the form of a white solid.

The obtained compound (B1-1-39) was analyzed by $^1$H-NMR and $^{19}$F-NMR, and the structure thereof was identified by the following results.

$^1$H-NMR (400 MHz, DMSO-d6): δ (ppm)=7.89-7.72 (m, 10H, ArH), 7.59 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.38 (m, 3H, B+N4), 3.11 (m, 2H, C), 2.37 (m, 1H, N5), 2.30 (d, 6H, CationCH3), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

ylphenyldiphenylsulfonium bromide, thereby obtaining a compound (B1-1-40) in the form of a white solid.

The obtained compound (B1-1-40) was analyzed by $^1$H-NMR and $^{19}$F-NMR, and the structure thereof was identified by the following results.

$^1$H-NMR (400 MHz, DMSO-d6): δ (ppm)=7.86-7.76 (m, 10H, ArH), 7.63 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.38 (m, 3H, B+N4), 3.11 (m, 2H, C), 2.37 (m, 1H, N5), 2.30 (s, 6H, CationCH3), 2.16 (m, 1H, N6), 1.89-1.66 (m, 3H, N7-9), 1.44-1.21 (m, 11H, D+t-Butyl)

$^{19}$F-NMR (376 MHz, DMSO-d6): δ (ppm)=−118.5-−118.9 (m, 2F)

[Chemical Formula 118.]

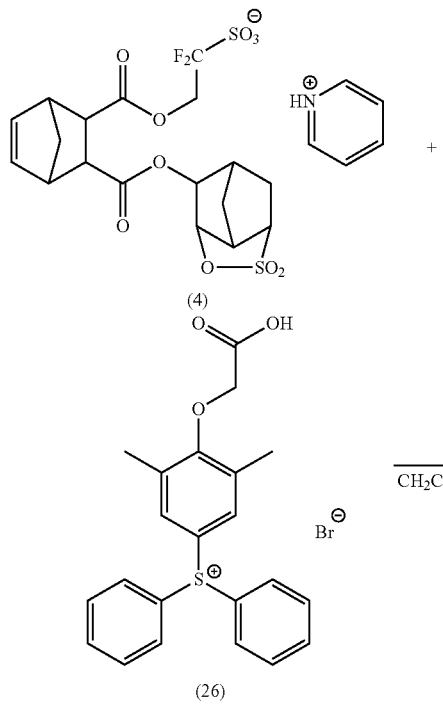

[Chemical Formula 119.]

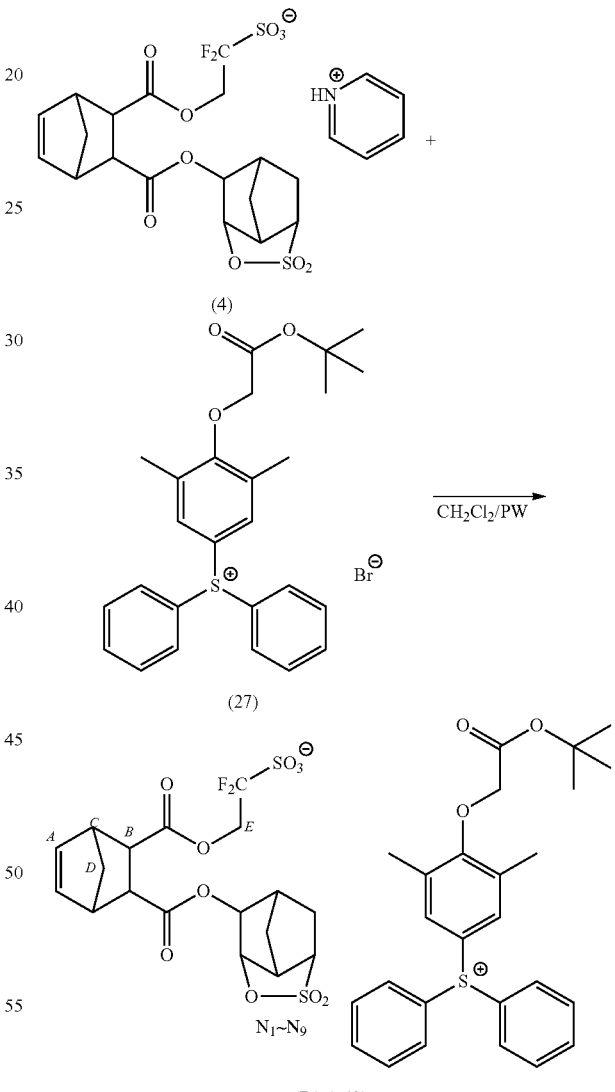

Example 40

Synthesis of Compound (B1-1-40)

The same procedure as in iii) of Example 1 was performed, except that a compound (27) was used instead of 4-meth- Example 41

Synthesis of Compound (B1-1-41)

The same procedure as in iii) of Example 1 was performed, except that a compound (28) was used instead of 4-methylphenyldiphenylsulfonium bromide, thereby obtaining a compound (B1-1-41) in the form of a white solid.

The obtained compound (B1-1-41) was analyzed by $^1$H-NMR and $^{19}$F-NMR, and the structure thereof was identified by the following results.

$^1$H-NMR (400 MHz, DMSO-d6): δ (ppm)=7.87-7.77 (m, 10H, ArH), 7.63 (s, 2H, ArH), 6.22 (m, 1H, A), 6.07 (m, 1H, A'), 4.94 (t, 2H, CationOCH2CF2), 4.84 (s, 2H, CationOCH2), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 7H, N5+CationCH3), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−119.7 (m, 2F), −118.5−−118.9 (m, 2F), −80.4 (t, 3F)

[Chemical Formula 120.]

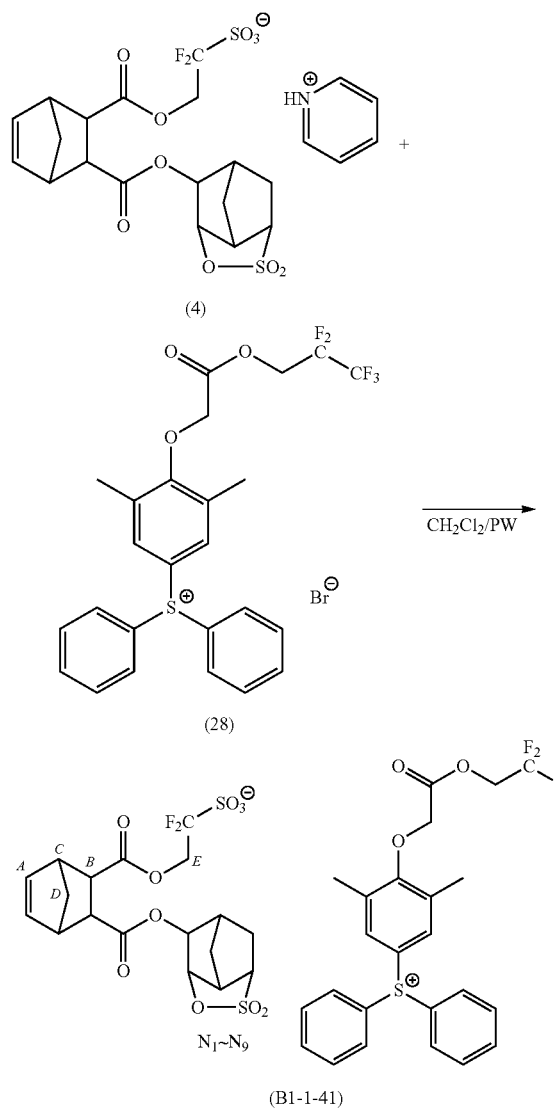

Example 42

Synthesis of Compound (B1-1-42)

The same procedure as in iii) of Example 1 was performed, except that a compound (29) was used instead of 4-meth-ylphenyldiphenylsulfonium bromide, thereby obtaining a compound (B1-1-42) in the form of a white solid.

The obtained compound (B1-1-42) was analyzed by $^1$H-NMR and $^{19}$F-NMR, and the structure thereof was identified by the following results.

$^1$H-NMR (400 MHz, DMSO-d6): δ (ppm)=7.84-7.74 (m, 10H, ArH), 7.61 (s, 2H, ArH), 6.22 (m, 1H, A), 6.07 (m, 1H, A'), 5.42 (t, 1H, oxo-norbornane), 4.97 (s, 1H, oxo-norbornane), 4.76-4.67 (m, 5H, N1+CationCH2+oxo-norbornane), 4.65-4.34 (m, 3H, E+N2), 3.87 (m, 1H, N3), 3.58-3.38 (m, 3H, B+N4), 3.11 (m, 2H, C), 2.73-2.69 (m, 1H, oxo-norbornane), 2.37 (m, 1H, N5), 2.32 (s, 6H, CationCH3), 2.16-2.06 (m, 3H, N6+oxo-norbornane), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F)

[Chemical Formula 121.]

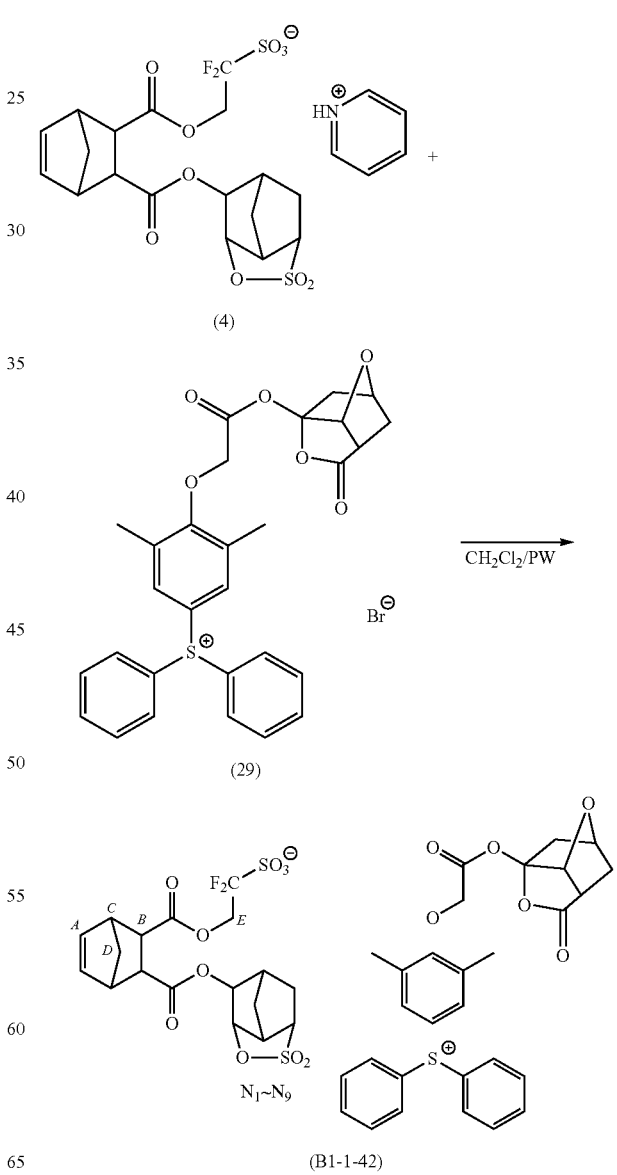

Example 43

Synthesis of Compound (B1-1-43)

The same procedure as in iii) of Example 1 was performed, except that a compound (30) was used instead of 4-methylphenyldiphenylsulfonium bromide, thereby obtaining a compound (B1-1-43) in the form of a white solid.

The obtained compound (B1-1-43) was analyzed by $^1$H-NMR and $^{19}$F-NMR, and the structure thereof was identified by the following results.

$^1$H-NMR (400 MHz, DMSO-d6): δ (ppm)=7.85-7.73 (m, 10H, ArH), 7.59 (S, 2H, ArH), 6.22 (m, 1H, A), 6.07 (m, 1H, A'), 4.76 (m, 1H, N1), 4.65-4.34 (m, 3H, E+N2), 3.87-3.83 (m, 3H, N3+CationOCH2), 3.58-3.38 (m, 3H, B+N4), 3.11 (m, 2H, C), 2.37-2.33 (m, 7H, N5+CationCH3), 2.16 (m, 1H, N6), 1.89-1.66 (m, 3H, N7-9), 1.47-1.21 (m, 10H, D+CationCH2), 0.87 (t, 3H, CationCH3)

$^{19}$F-NMR (376 MHz, DMSO-d6): δ (ppm)=-118.5--118.9 (m, 2F)

[Chemical Formula 122.]

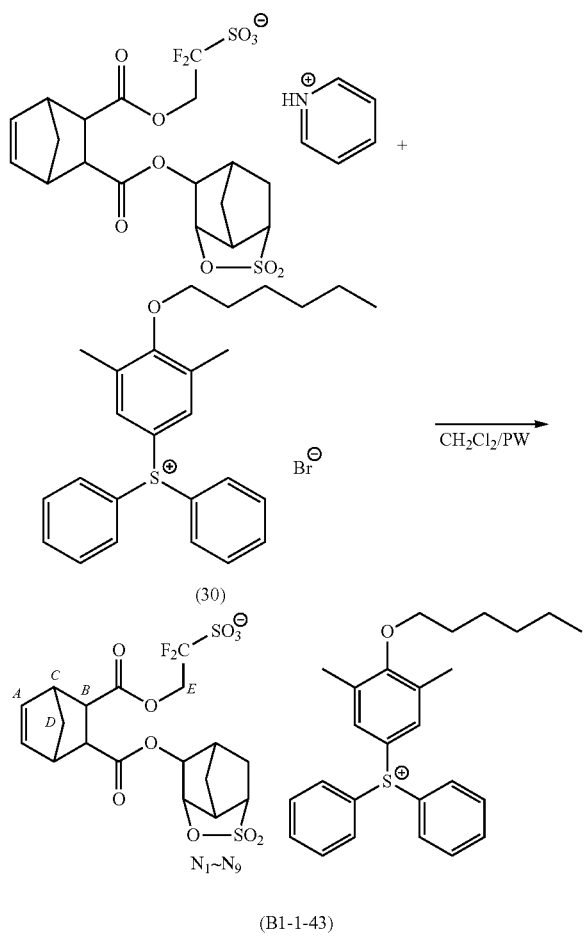

(B1-1-43)

Example 44

Synthesis of Compound (B1-1-44)

The same procedure as in iii) of Example 1 was performed, except that a compound (31) was used instead of 4-methylphenyldiphenylsulfonium bromide, thereby obtaining a compound (B1-1-44) in the form of a white solid.

The obtained compound (B1-1-44) was analyzed by $^1$H-NMR and $^{19}$F-NMR, and the structure thereof was identified by the following results.

$^1$H-NMR (400 MHz, DMSO-d6): δ (ppm)=8.53 (d, 2H, ArH), 8.27 (d, 2H, ArH), 7.95 (t, 2H, ArH), 7.74 (t, 2H, ArH), 7.20 (s, 1H, ArH), 6.38 (s, 1H, ArH), 6.22 (m, 1H, A), 6.07 (m, 1H, A'), 4.76 (m, 1H, N1), 4.65-4.34 (m, 3H, E+N2), 4.05 (t, 2H, cationOCH2), 3.87 (m, 1H, N3), 3.58-3.38 (m, 3H, B+N4), 3.11 (m, 2H, C), 2.86 (s, 3H, CationCH3), 2.37 (m, 1H, N5), 2.16 (m, 1H, N6), 1.89-1.65 (m, 8H, N7-9+CationCH3+CationCH2), 1.44-1.21 (m, 4H, D+CationCH2), 1.26-1.23 (m, 4H, CH2), 0.82 (t, 3H, CH3)

$^{19}$F-NMR (376 MHz, DMSO-d6): δ (ppm)=-118.5--118.9 (m, 2F)

[Chemical Formula 123.]

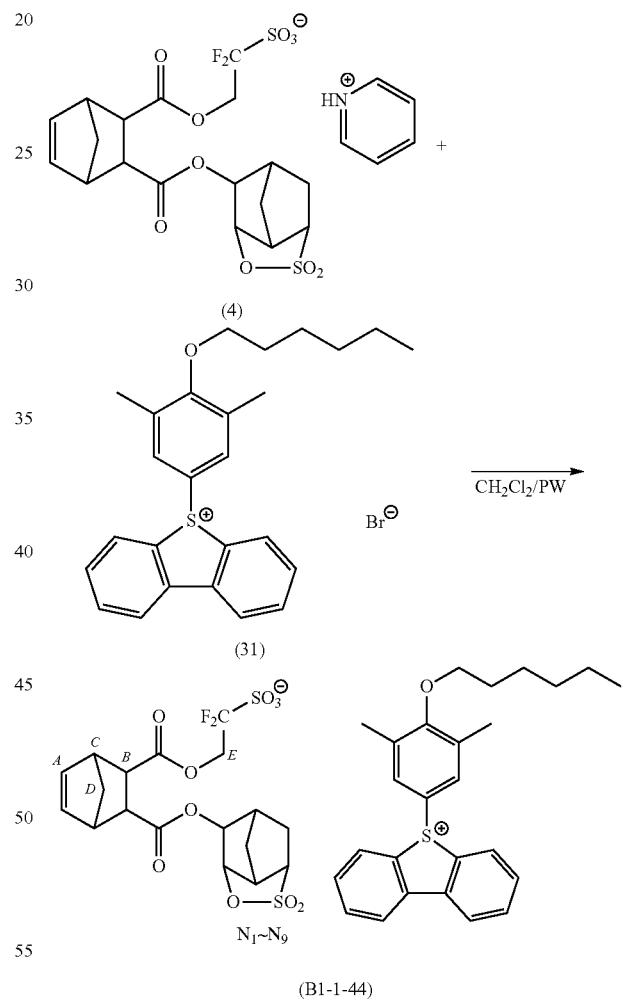

(B1-1-44)

Example 45

Synthesis of Compound (B1-1-45)

The same procedure as in iii) of Example 1 was performed, except that a compound (32) was used instead of 4-methylphenyldiphenylsulfonium bromide, thereby obtaining a compound (B1-1-45) in the form of a white solid.

The obtained compound (B1-1-45) was analyzed by $^1$H-NMR and $^{19}$F-NMR, and the structure thereof was identified by the following results.

$^1$H-NMR (400 MHz, DMSO-d6): δ (ppm)=8.09-8.04 (m, 2H, ArH), 7.79-7.69 (m, 3H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.29 (s, 6H, CationCH3), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

[Chemical Formula 124.]

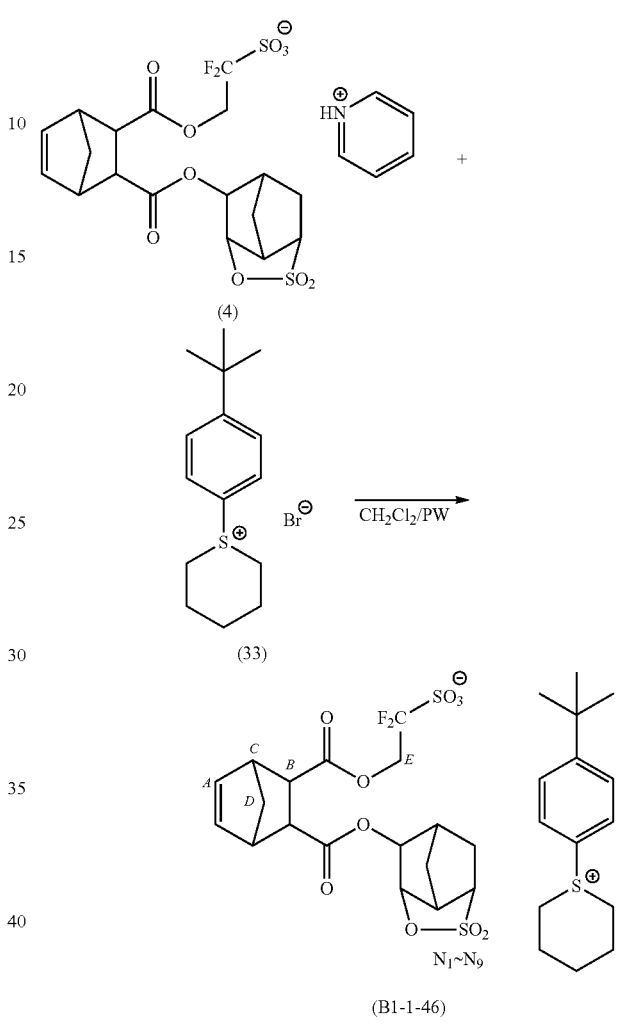

Example 46

Synthesis of Compound (B1-1-46)

The same procedure as in iii) of Example 1 was performed, except that a compound (33) was used instead of 4-methylphenyldiphenylsulfonium bromide, thereby obtaining a compound (B1-1-46) in the form of a white solid.

The obtained compound (B1-1-46) was analyzed by $^1$H-NMR and $^{19}$F-NMR, and the structure thereof was identified by the following results.

$^1$H-NMR (400 MHz, DMSO-d6): δ (ppm)=8.07 (d, 2H, ArH), 7.81 (d, 2H, ArH), 6.22 (m, 1H, A), 6.07 (m, 1H, A'), 4.76 (m, 1H, N1), 4.65-4.34 (m, 3H, E+N2), 4.10 (t, 2H, CationCH2), 3.87 (m, 1H, N3), 3.61-3.38 (m, 5H, B+N4+CationCH2), 3.11 (m, 2H, C), 2.37 (m, 1H, N5), 2.20-1.66 (m, 10H, N6-9+CationCH2), 1.89-1.66 (m, 3H, N7-9), 1.44-1.21 (m, 11H, D+t-Butyl)

$^{19}$F-NMR (376 MHz, DMSO-d6): δ (ppm)=−118.5-−118.9 (m, 2F)

[Chemical Formula 125.]

Example 47

Synthesis of Compound (B1-1-47)

The same procedure as in iii) of Example 1 was performed, except that a compound (34) was used instead of 4-methylphenyldiphenylsulfonium bromide, thereby obtaining a compound (B1-1-47) in the form of a white solid.

The obtained compound (B1-1-47) was analyzed by $^1$H-NMR and $^{19}$F-NMR, and the structure thereof was identified by the following results.

$^1$H-NMR (400 MHz, DMSO-d6): δ (ppm)=7.89-7.77 (m, 10H, ArH), 7.70 (s, 2H, ArH), 6.22 (m, 1H, A), 6.07 (m, 1H, A'), 5.10 (s, 2H, OCOCH2O), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.19-2.07 (m, 10H, N6+CationCH3), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

[Chemical Formula 126.]

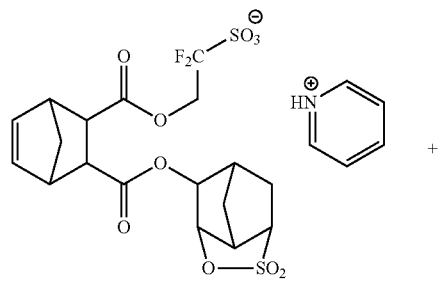

[Chemical Formula 127.]

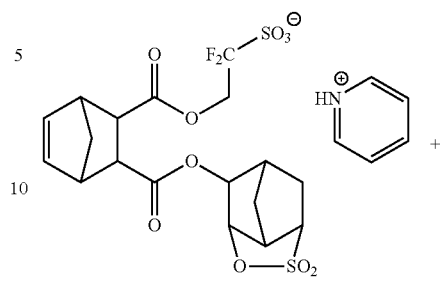

Example 48

Synthesis of Compound (B1-1-48)

The same procedure as in iii) of Example 1 was performed, except that a compound (35) was used instead of 4-methylphenyldiphenylsulfonium bromide, thereby obtaining a compound (B1-1-48) in the form of a white solid.

The obtained compound (B1-1-48) was analyzed by $^1$H-NMR and $^{19}$F-NMR, and the structure thereof was identified by the following results.

$^1$H-NMR (400 MHz, DMSO-d6): δ (ppm)=7.84 (d, 6H, ArH), 7.78 (d, 6H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 29H, D+t-Butyl)

$^{19}$F-NMR (376 MHz, DMSO-d6): δ (ppm)=−118.5−−118.9 (m, 2F)

Example 49

Synthesis of Compound (B1-1-49)

The same procedure as in iii) of Example 1 was performed, except that a compound (36) was used instead of 4-methylphenyldiphenylsulfonium bromide, thereby obtaining a compound (B1-1-49) in the form of a white solid.

The obtained compound (B1-1-49) was analyzed by $^1$H-NMR and $^{19}$F-NMR, and the structure thereof was identified by the following results.

$^1$H-NMR (400 MHz, DMSO-d6): δ (ppm)=7.89-7.73 (m, 12H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.39-2.36 (m, 7H, N5+CationCH3), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F), 70.2 (s, 3F)

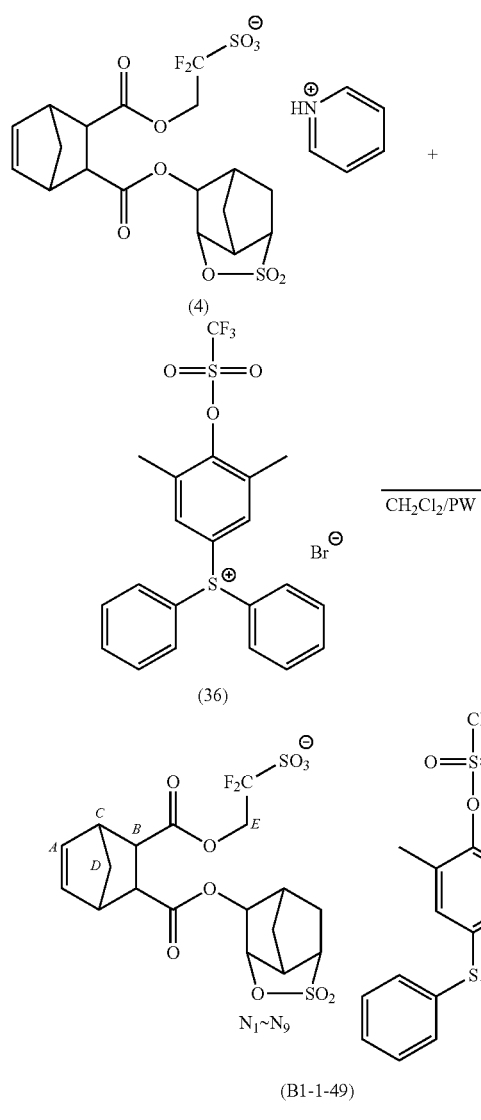

(B1-1-49)

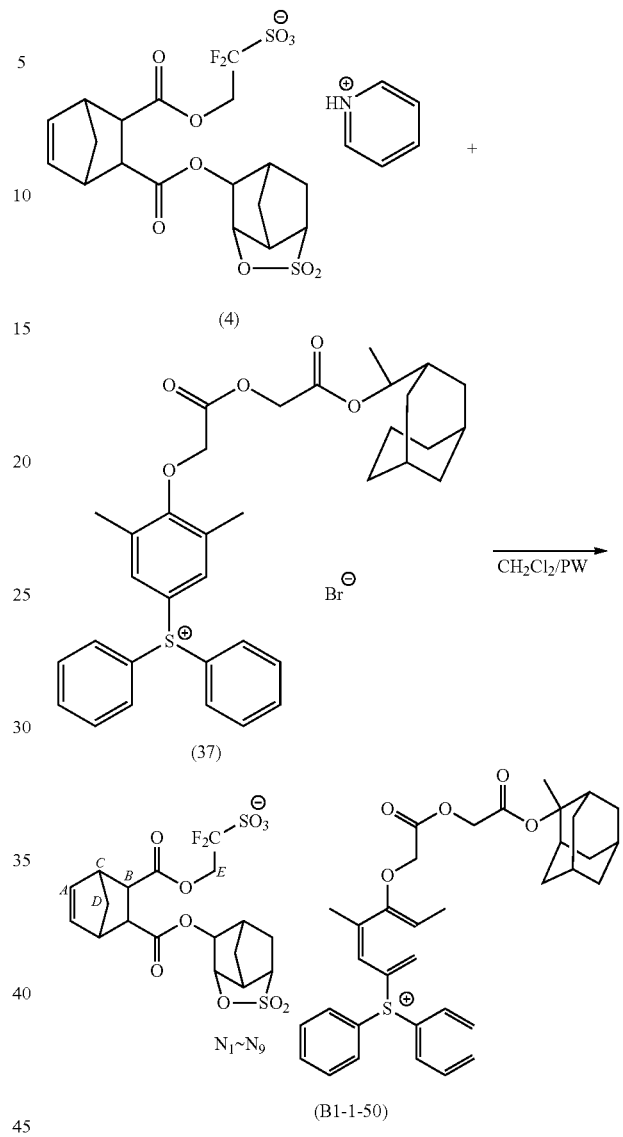

(B1-1-50)

Example 50

Synthesis of Compound (B1-1-50)

The same procedure as in iii) of Example 1 was performed, except that a compound (37) was used instead of 4-methylphenyldiphenylsulfonium bromide, thereby obtaining a compound (B1-1-50) in the form of a white solid.

The obtained compound (B1-1-50) was analyzed by $^1$H-NMR and $^{19}$F-NMR, and the structure thereof was identified by the following results.

$^1$H-NMR (400 MHz, DMSO-d6): δ (ppm)=7.85-7.69 (m, 10H, ArH), 7.56 (s, 2H, ArH), 6.22 (m, 1H, A), 6.07 (m, 1H, A'), 4.78-4.74 (m, 5H, N1+CationCH2), 4.65-4.34 (m, 3H, E+N2), 3.87 (m, 1H, N3), 3.58-3.38 (m, 3H, B+N4), 3.11 (m, 2H, C), 2.37-2.30 (m, 7H, N5+CationCH3), 2.20-2.14 (m, 3H, N6+Adamantane), 1.98-1.20 (m, 20H, N7-9+D+Adamantane)

$^{19}$F-NMR (376 MHz, DMSO-d6): δ (ppm)=−118.5-−118.9 (m, 2F)

Example 51

Synthesis of Compound (B1-1-51)

The same procedure as in iii) of Example 1 was performed, except that a compound (38) was used instead of 4-methylphenyldiphenylsulfonium bromide, thereby obtaining a compound (B1-1-51) in the form of a white solid.

The obtained compound (B1-1-51) was analyzed by $^1$H-NMR and $^{19}$F-NMR, and the structure thereof was identified by the following results.

$^1$H-NMR (400 MHz, DMSO-d6): δ (ppm)=7.84-7.72 (m, 10H, ArH), 7.59 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.58-3.38 (m, 3H, B+N4), 3.11 (m, 2H, C), 2.49 (m, 2H, Adamantane), 2.37-2.25 (m, 14H, N5+Adamantane), 2.16 (m, 1H, N6), 1.99-1.66 (m, 7H, N7-9+Adamantane), 1.44-1.21 (m, 2H, D)

$^{19}$F-NMR (376 MHz, DMSO-d6): δ (ppm)=−118.5-−118.9 (m, 2F)

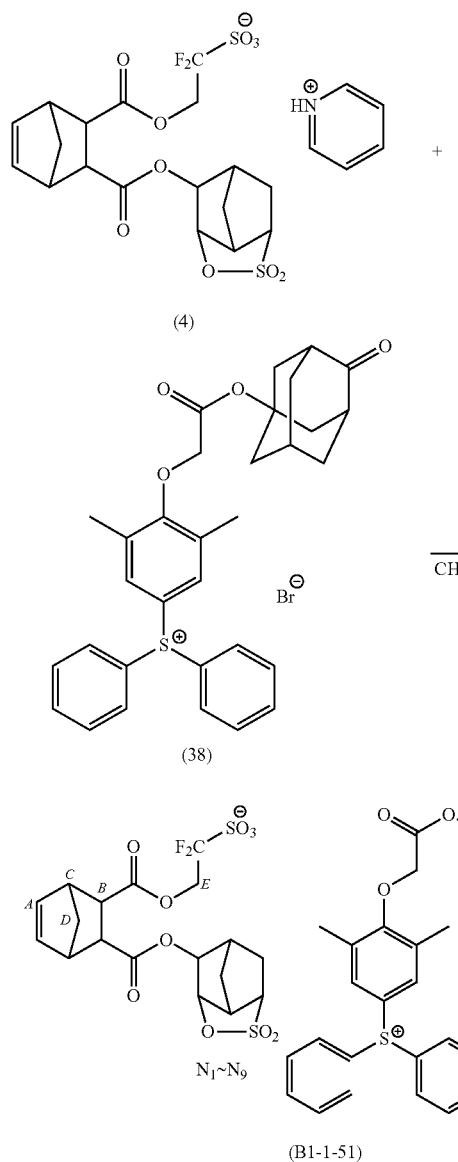

(B1-1-51)

Example 52

Synthesis of Compound (B1-1-52)

The same procedure as in iii) of Example 1 was performed, except that a compound (39) was used instead of 4-methylphenyldiphenylsulfonium bromide, thereby obtaining a compound (B1-1-52) in the form of a white solid.

The obtained compound (B1-1-52) was analyzed by $^1$H-NMR and $^{19}$F-NMR, and the structure thereof was identified by the following results.

$^1$H-NMR (400 MHz, DMSO-d6): δ (ppm)=7.84-7.73 (m, 10H, ArH), 7.59 (s, 2H, ArH), 6.22 (m, 1H, A), 6.07 (m, 1H, A'), 4.76 (m, 1H, N1), 4.65-4.34 (m, 5H, E+N2+CationCH2), 3.87 (m, 1H, N3), 3.70 (s, 3H, OCH3), 3.58-3.38 (m, 3H, B+N4), 3.11 (m, 2H, C), 2.37 (m, 1H, N5), 2.29 (s, 6H, CationCH3) 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

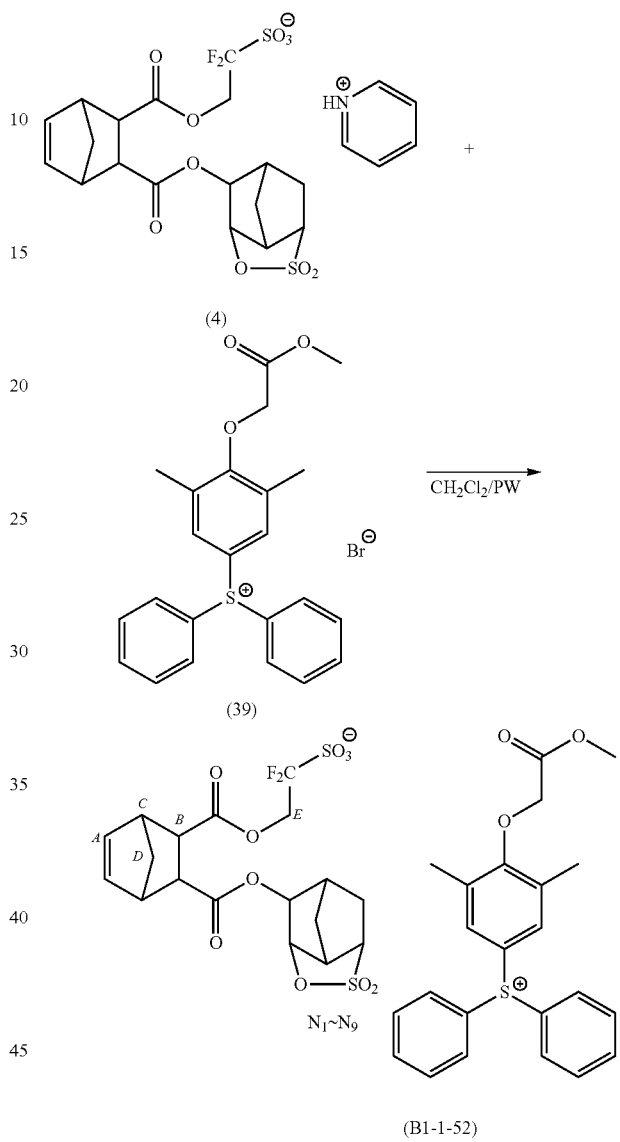

(B1-1-52)

Example 53

Synthesis of Compound (B1-1-53)

The same procedure as in iii) of Example 1 was performed, except that a compound (40) was used instead of 4-methylphenyldiphenylsulfonium bromide, thereby obtaining a compound (B1-1-53) in the form of a white solid.

The obtained compound (B1-1-53) was analyzed by $^1$H-NMR and $^{19}$F-NMR, and the structure thereof was identified by the following results.

$^1$H-NMR (400 MHz, DMSO-d6): δ (ppm)=7.89-7.78 (m, 10H, ArH), 7.64 (s, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.79 (s, 3H, OCH3), 3.58-3.38 (m, 3H, B+N4), 3.11 (m, 2H, C), 2.37 (m, 1H, N5), 2.32 (s, 6H, CationCH3), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

[Chemical Formula 132.]

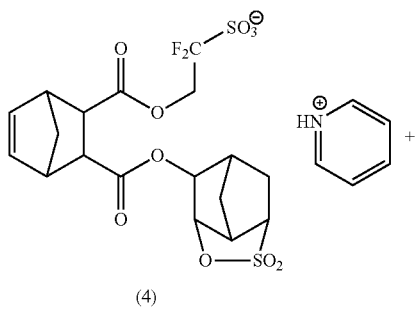

(4)

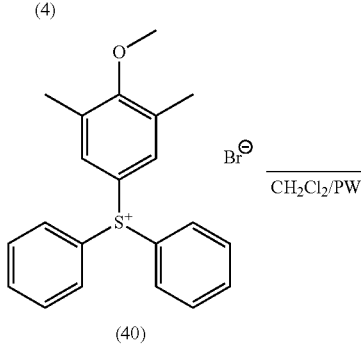

(40)

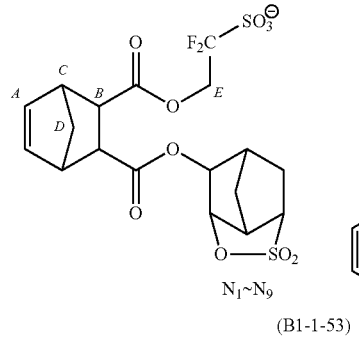

(B1-1-53)

Example 54

Synthesis of Compound (B1-1-54)

The same procedure as in iii) of Example 1 was performed, except that a compound (41) was used instead of 4-methylphenyldiphenylsulfonium bromide, thereby obtaining a compound (B1-1-54) in the form of a white solid.

The obtained compound (B1-1-54) was analyzed by $^1$H-NMR and $^{19}$F-NMR, and the structure thereof was identified by the following results.

$^1$H-NMR (400 MHz, DMSO-d6): δ (ppm)=7.87-7.76 (m, 10H, ArH), 7.69 (s, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.17-2.10 (m, 7H, N6+CationCH3), 2.04-1.66 (m, 18H, N7-9+Adamantane), 1.44-1.21 (m, 2H, D)

$^{19}$F-NMR (376 MHz, DMSO-d6): δ (ppm)=−118.5-−118.9 (m, 2F)

[Chemical Formula 133.]

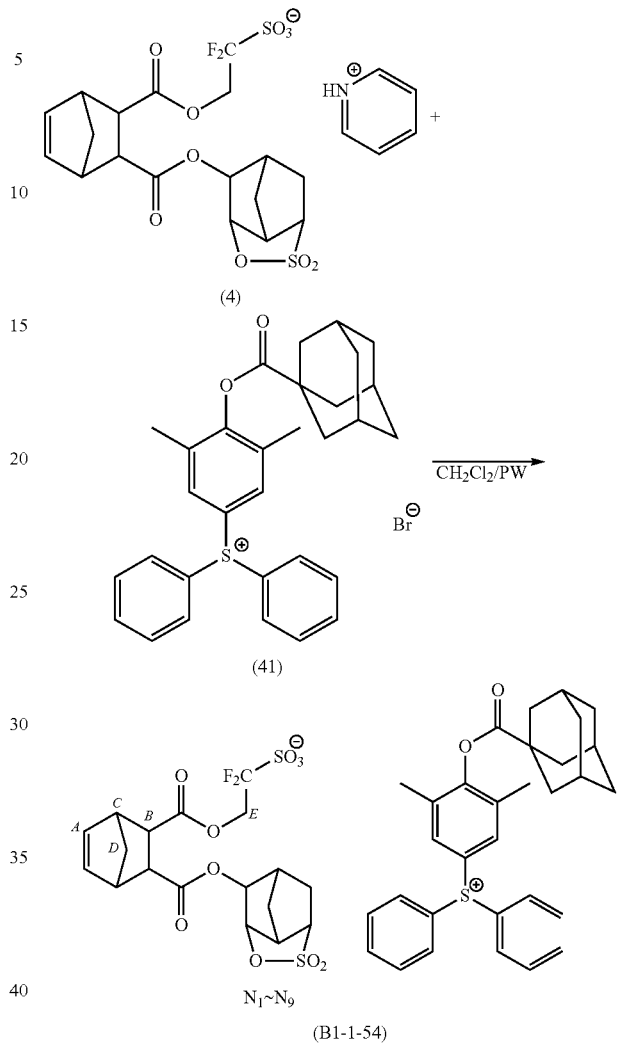

Example 55

Synthesis of Compound (B1-1-55)

The same procedure as in iii) of Example 1 was performed, except that a compound (42) was used instead of 4-methylphenyldiphenylsulfonium bromide, thereby obtaining a compound (B1-1-55) in the form of a white solid.

The obtained compound (B1-1-55) was analyzed by $^1$H-NMR and $^{19}$F-NMR, and the structure thereof was identified by the following results.

$^1$H-NMR (400 MHz, DMSO-d6): δ (ppm)=8.76 (s, 1H, ArH), 8.64-8.59 (m, 1H, ArH), 8.42 (t, 2H, ArH), 8.19-8.30 (m, 5H, ArH), 7.81 (t, 1H, ArH), 7.69 (t, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F), 62.1 (s, 3F)

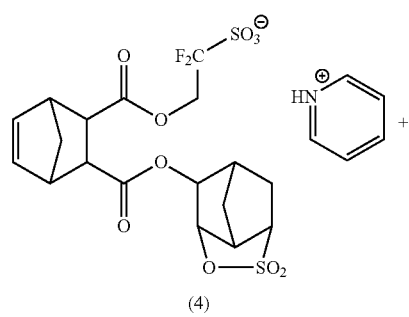

(4)

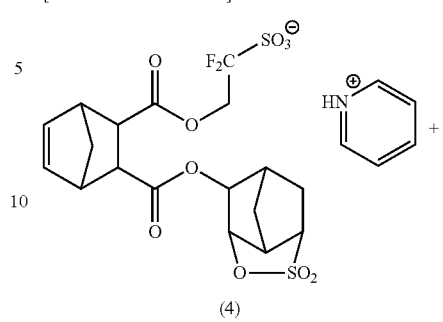

(4)

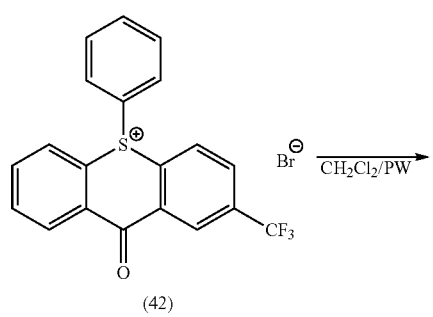

(42)

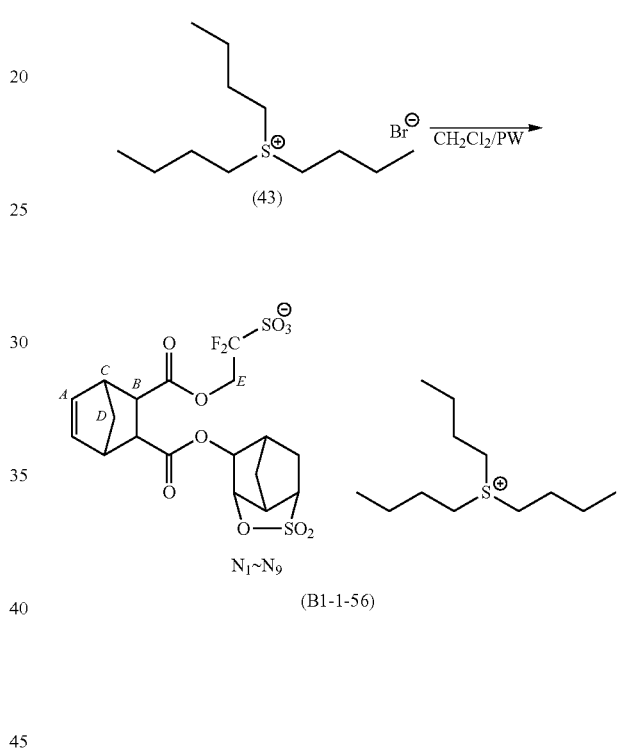

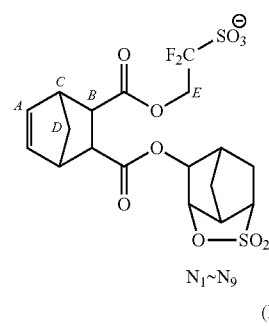

(B1-1-55)

Example 56

Synthesis of Compound (B1-1-56)

The same procedure as in iii) of Example 1 was performed, except that a compound (43) was used instead of 4-methylphenyldiphenylsulfonium bromide, thereby obtaining a compound (B1-1-56) in the form of a white solid.

The obtained compound (B1-1-56) was analyzed by $^1$H-NMR and $^{19}$F-NMR, and the structure thereof was identified by the following results.

$^1$H-NMR (400 MHz, DMSO-d6): δ (ppm)=6.22 (m, 1H, A), 6.07 (m, 1H, A'), 4.76 (m, 1H, N1), 4.65-4.34 (m, 3H, E+N2), 3.87 (m, 1H, N3), 3.58-3.35 (m, 91-1, B+N4+CationCH2), 3.11 (m, 2H, C), 2.37 (m, 1H, N5), 2.16 (m, 1H, N6), 1.89-1.66 (m, 9H, N7-9+CationCH2), 1.44-1.21 (m, 8H, D+CationCH2), 0.93-0.80 (m, 9H, CationCH3)

$^{19}$F-NMR (376 MHz, DMSO-d6): δ (ppm)=−118.5-−118.9 (m, 2F)

Example 57

Synthesis of Compound (B1-1-57)

The same procedure as in iii) of Example 1 was performed, except that a compound (44) was used instead of 4-methylphenyldiphenylsulfonium bromide, thereby obtaining a compound (B1-1-57) in the form of a white solid.

The obtained compound (B1-1-57) was analyzed by $^1$H-NMR and $^{19}$F-NMR, and the structure thereof was identified by the following results.

$^1$H-NMR (400 MHz, DMSO-d6): δ (ppm)=8.29 (d, 4H, ArH), 8.09-7.93 (m, 6H, ArH), 6.22 (m, 1H, A); 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F), −47.9 (s, 3F)

[Chemical Formula 136.]

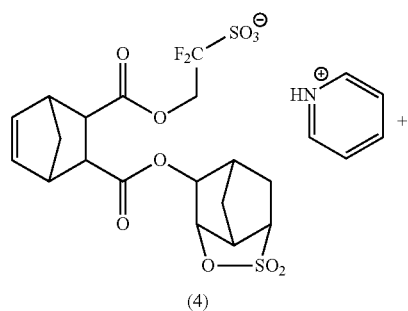

[Chemical Formula 137.]

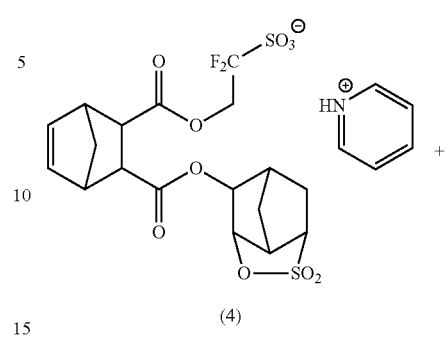

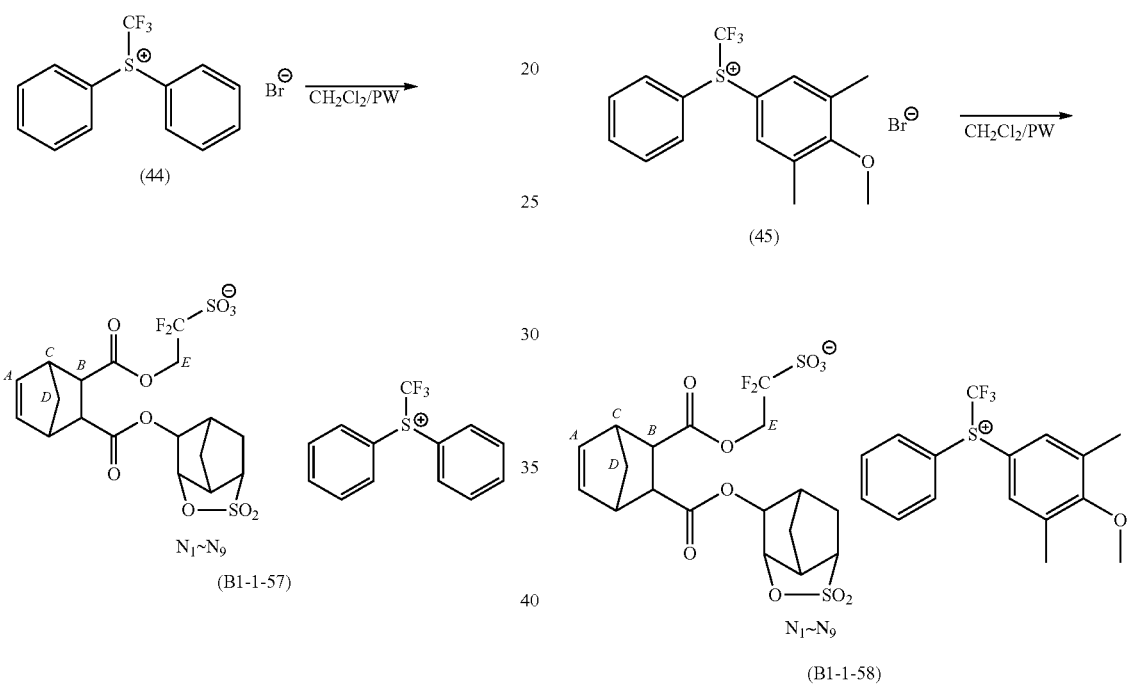

Example 58

Synthesis of Compound (B1-1-58)

The same procedure as in iii) of Example 1 was performed, except that a compound (45) was used instead of 4-methylphenyldiphenylsulfonium bromide, thereby obtaining a compound (B1-1-58) in the form of a white solid.

The obtained compound (B1-1-58) was analyzed by $^1$H-NMR and $^{19}$F-NMR, and the structure thereof was identified by the following results.

$^1$H-NMR (400 MHz, DMSO-d6): δ (ppm)=8.24-7.90 (m, 7H, ArH), 6.22 (m, 1H, A), 6.07 (m, 1H, A'), 4.76 (m, 1H, N1), 4.65-4.34 (m, 3H, E+N2), 3.87-3.84 (m, 4H, N3+OCH3), 3.58-3.38 (m, 3H, B+N4), 3.11 (m, 2H, C), 2.41-2.37 (m, 7H, N5+CationCH2), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F), 48.8 (s, 3F)

Example 59

Synthesis of Compound (B1-1-59)

The same procedure as in iii) of Example 1 was performed, except that a compound (46) was used instead of 4-methylphenyldiphenylsulfonium bromide, thereby obtaining a compound (B1-1-59) in the form of a white solid.

The obtained compound (B1-1-59) was analyzed by $^1$H-NMR and $^{19}$F-NMR, and the structure thereof was identified by the following results.

$^1$H-NMR (400 MHz, DMSO-d6): δ (ppm)=8.49 (d, 2H, ArH), 8.30 (d, 2H, ArH), 7.93 (t, 2H, ArH), 7.73 (t, 2H, ArH), 7.30 (s, 2H, ArH), 6.22 (m, 1H, A), 6.07 (m, 1H, A'), 4.76 (m, 1H, N1), 4.65-4.34 (m, 5H, E+N2+OCH2), 3.87 (m, 1H, N3), 3.58-3.38 (m, 3H, B+N4), 3.11 (m, 2H, C), 2.37 (m, 1H, N5), 2.25-2.16 (m, 9H, N6+CationCH3+Adamantane), 1.93-1.21 (m, 20H, N7-9+D+Adamantane+CationCH3)

$^{19}$F-NMR (376 MHz, DMSO-d6): δ (ppm)=−118.5-−118.9 (m, 2F)

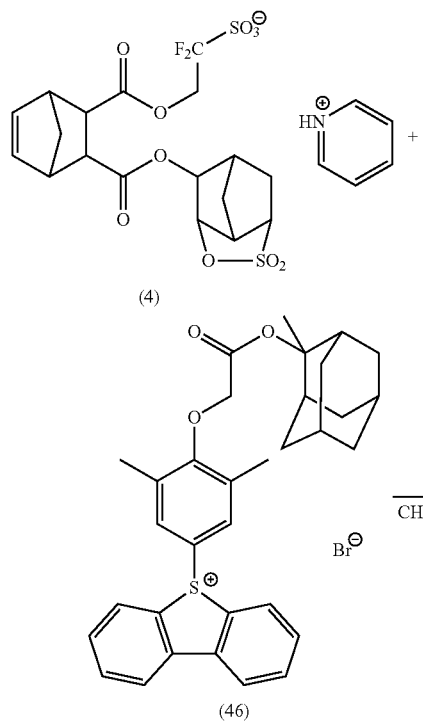

(4)

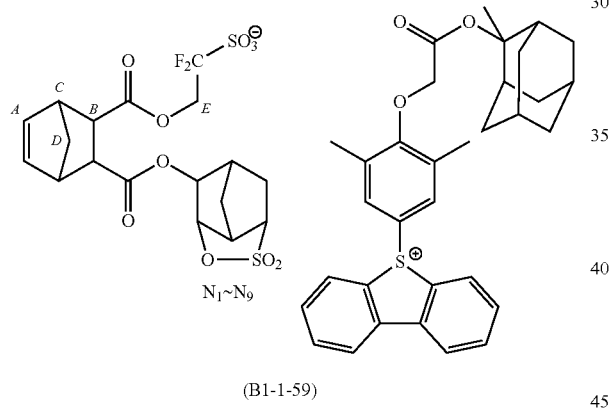

(B1-1-59)

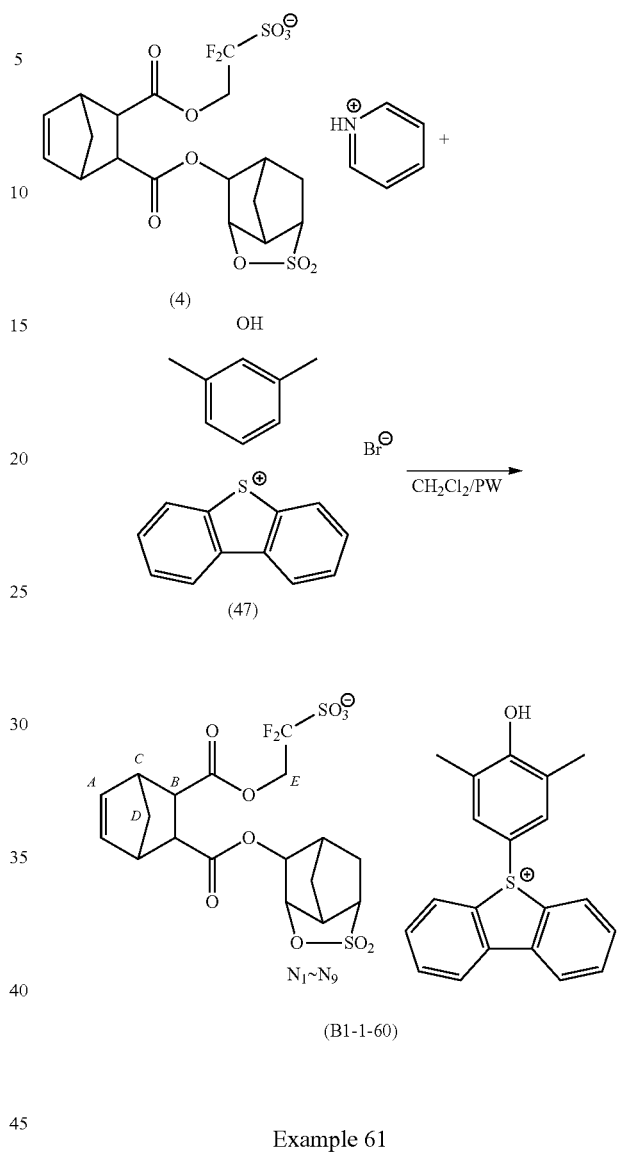

(B1-1-60)

Example 60

Synthesis of Compound (B1-1-60)

The same procedure as in iii) of Example 1 was performed, except that a compound (47) was used instead of 4-methylphenyldiphenylsulfonium bromide, thereby obtaining a compound (B1-1-60) in the form of a white solid.

The obtained compound (B1-1-60) was analyzed by $^1$H-NMR and $^{19}$F-NMR, and the structure thereof was identified by the following results.

$^1$H-NMR (400 MHz, DMSO-d6): δ (ppm)=9.73 (s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 2.10 (s, 6H, CationCH3) 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F)

Example 61

Synthesis of Compound (B1-1-61)

The same procedure as in iii) of Example 1 was performed, except that a compound (48) was used instead of 4-methylphenyldiphenylsulfonium bromide, thereby obtaining a compound (B1-1-61) in the form of a white solid.

The obtained compound (B1-1-61) was analyzed by $^1$H-NMR and $^{19}$F-NMR, and the structure thereof was identified by the following results.

$^1$H-NMR (400 MHz, DMSO-d6): δ (ppm)=7.87-7.75 (m, 10H, ArH), 7.62 (s, 2H, ArH), 6.22 (m, 1H, A), 6.07 (m, 1H, A'), 4.76 (m, 1H, N1), 4.65-4.34 (m, 3H, E+N2), 3.97 (t, 2H, CationCH2), 3.87 (m, 1H, N3), 3.58-3.38 (m, 3H, B+N4), 3.11 (m, 2H, C), 2.57-2.03 (m, 12H, N5-6+CationCH2+CationCH3), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F), −123.5 (m, 2F), −121.8 (m, 2F), −111.6 (m, 2F), −78.3 (t, 3F)

185

[Chemical Formula 140.]

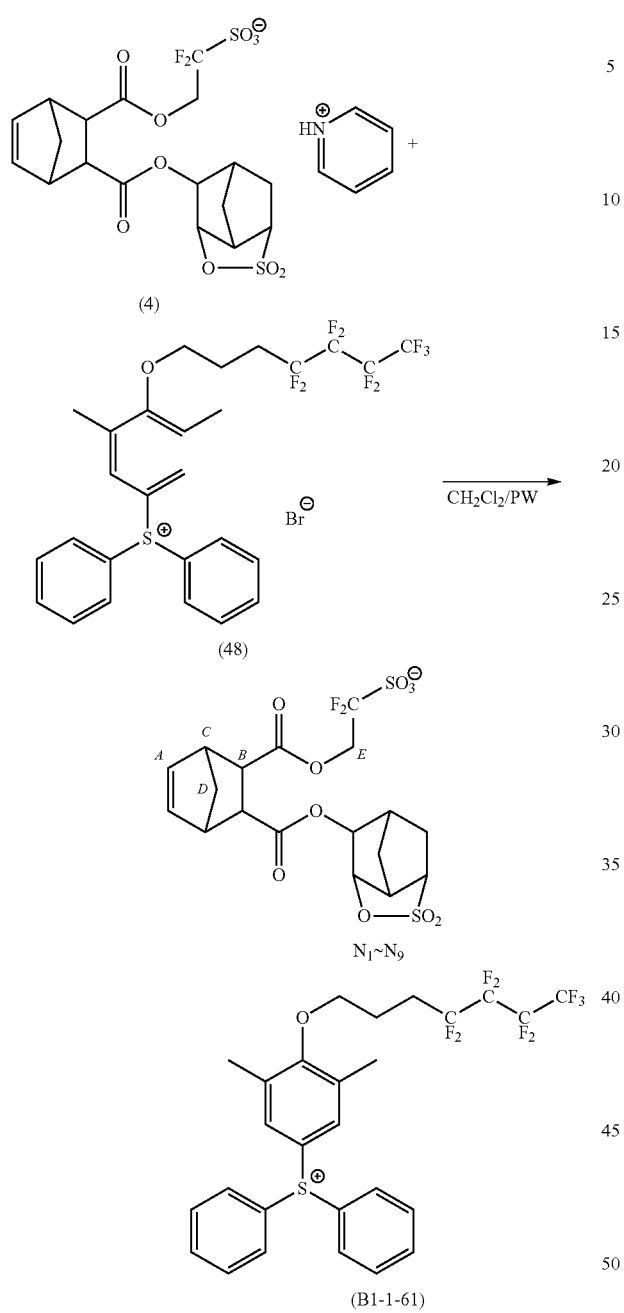

(4)

(48)

(B1-1-61)

Example 62

Synthesis of Compound (B1-1-62)

The same procedure as in iii) of Example 1 was performed, except that a compound (49) was used instead of 4-methylphenyldiphenylsulfonium bromide, thereby obtaining a compound (B1-1-62) in the form of a white solid.

The obtained compound (B1-1-62) was analyzed by $^1$H-NMR and $^{19}$F-NMR, and the structure thereof was identified by the following results.

$^1$H-NMR (400 MHz, DMSO-d6): δ (ppm)=7.86-7.76 (m, 10H, ArH), 7.60 (s, 2H, ArH), 6.22 (m, 1H, A), 6.07 (m, 1H, A'), 4.76 (m, 1H, N1), 4.65-4.34 (m, 3H, E+N2), 3.87 (m, 3H, N3+CationCH2), 3.58-3.38 (m, 3H, B+N4), 3.11 (m, 2H, C), 2.41-2.24 (m, 9H, N5+CationCH2), 2.16-2.11 (m, 7H, N6+N—CH3), 1.89-1.66 (m, 5H, N7-9+CationCH2), 1.44-1.21 (m, 2H, D)

$^{19}$F-NMR (376 MHz, DMSO-d6): δ (ppm)=−118.5-−118.9 (m, 2F)

[Chemical Formula 141.]

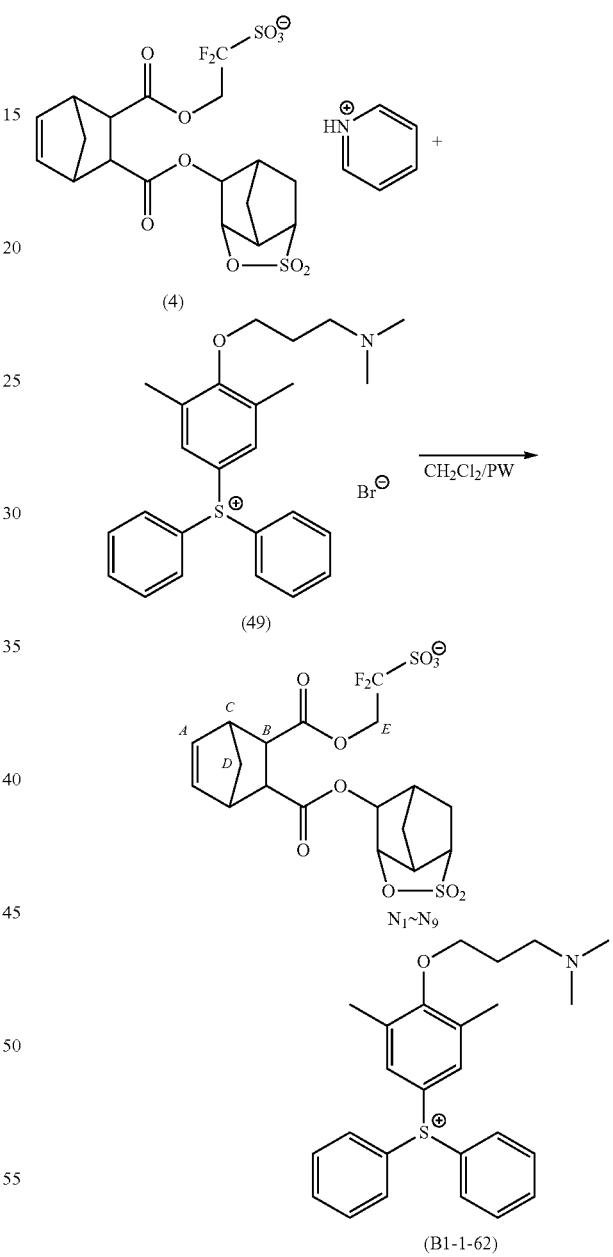

(4)

(49)

(B1-1-62)

Example 63

Synthesis of Compound (B1-1-63)

The same procedure as in iii) of Example 1 was performed, except that a compound (50) was used instead of 4-methylphenyldiphenylsulfonium bromide, thereby obtaining a compound (B1-1-63) in the form of a white solid.

The obtained compound (B1-1-63) was analyzed by $^1$H-NMR and $^{19}$F-NMR, and the structure thereof was identified by the following results.

$^1$H-NMR (400 MHz, DMSO-d6): δ (ppm)=7.89-7.77 (m, 10H, ArH), 7.71 (s, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.51 (s, 2H, CationCH2), 2.37 (m, 1H, N5), 2.21-2.15 (m, 7H, N6+CationCH3), 1.97 (s, 3H, Adamantane), 1.89-1.62 (m, 15H, N7-9+Adamantane), 1.44-1.21 (m, 2H, D)

$^{19}$F-NMR (376 MHz, DMSO-d6): δ (ppm)=–118.5-–118.9 (m, 2F)

The obtained compound (B1-1-64) was analyzed by $^1$H-NMR and $^{19}$F-NMR, and the structure thereof was identified by the following results.

$^1$H-NMR (400 MHz, DMSO-d6): δ (ppm)=7.84-7.74 (m, 10H, ArH), 7.61 (s, 2H, ArH), 6.22 (m, 1H, A), 6.07 (m, 1H, A'), 4.76 (m, 1H, N1), 4.67-4.34 (m, 7H, E+N2+norbornane+OCH2), 3.87 (m, 1H, N3), 3.58-3.38 (m, 3H, B+N4), 3.24 (m, 1H, norbornane), 3.11 (m, 2H, C), 2.54-2.44 (m, 2H, norbornane), 2.37 (m, 7H, N5+CationCH3), 2.16 (m, 1H, N6), 2.08-1.64 (m, 7H, N7-9+norbornane), 1.44-1.21 (m, 2H, D)

$^{19}$F-NMR (376 MHz, DMSO-d6): δ (ppm)=–118.5-–118.9 (m, 2F)

[Chemical Formula 142.]

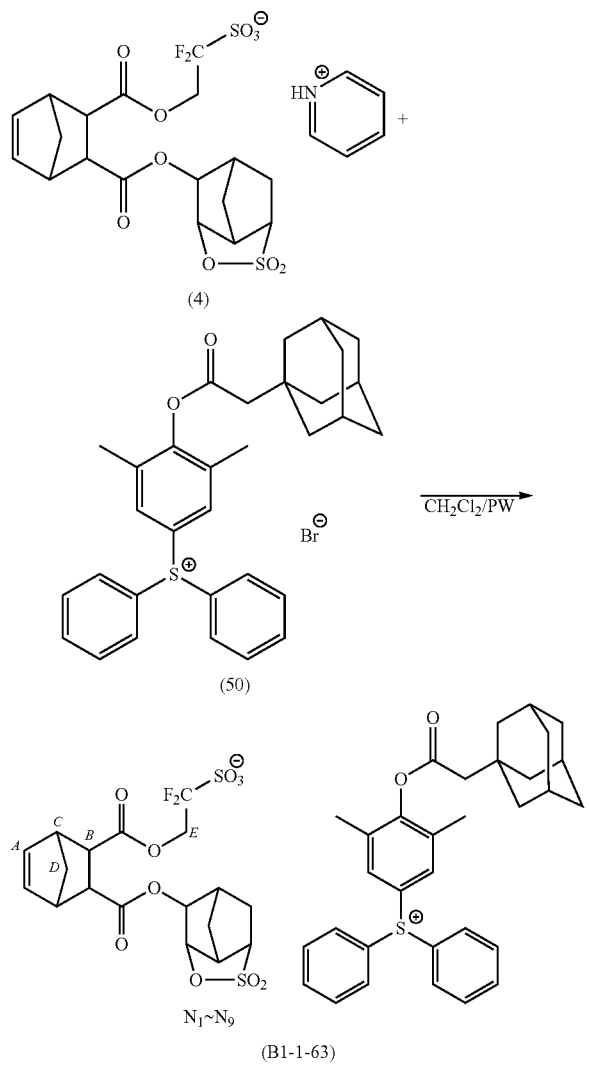

[Chemical Formula 143.]

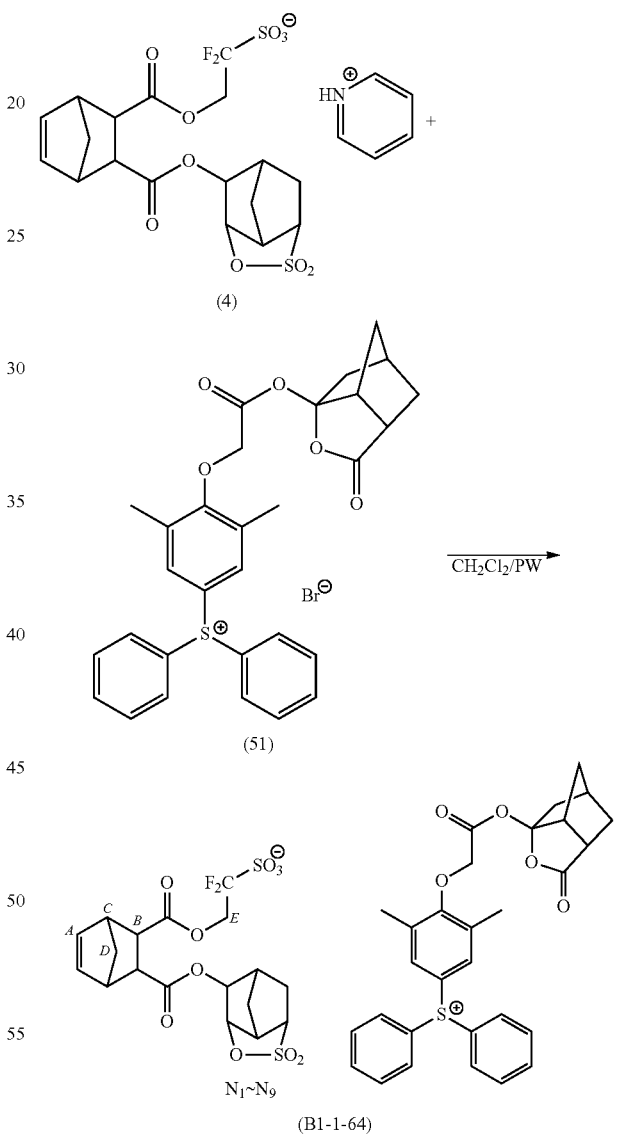

Example 64

Synthesis of Compound (B1-1-64)

The same procedure as in iii) of Example 1 was performed, except that a compound (51) was used instead of 4-methylphenyldiphenylsulfonium bromide, thereby obtaining a compound (B1-1-64) in the form of a white solid.

Example 65

Synthesis of Compound (B1-1-65)

The same procedure as in iii) of Example 1 was performed, except that a compound (52) was used instead of 4-methylphenyldiphenylsulfonium bromide, thereby obtaining a compound (B1-1-65) in the form of a white solid.

The obtained compound (B1-1-65) was analyzed by $^1$H-NMR and $^{19}$F-NMR, and the structure thereof was identified by the following results.

$^1$H-NMR (400 MHz, DMSO-d6): δ (ppm)=7.92-7.80 (m, 10H, ArH), 7.67 (s, 2H, ArH), 6.22 (m, 1H, A), 6.07 (m, 1H, A'), 4.76 (m, 1H, N1), 4.67-4.34 (m, 5H, E+N2+CationCH2), 3.87 (m, 1H, N3), 3.58-3.38 (m, 3H, B+N4), 3.11 (m, 2H, C), 2.39-2.35 (m, 7H, N5+CationCH3), 2.17-2.12 (m, 3H, N6+cyclohexyl), 1.95-1.66 (m, 5H, N7-9+CationCH2), 1.57-1.14 (m, 2H, D+cyclohexyl), 0.84 (t, 3H, CationCH3)

$^{19}$F-NMR (376 MHz, DMSO-d6): δ (ppm)=−118.5-118.9 (m, 2F)

[Chemical Formula 144.]

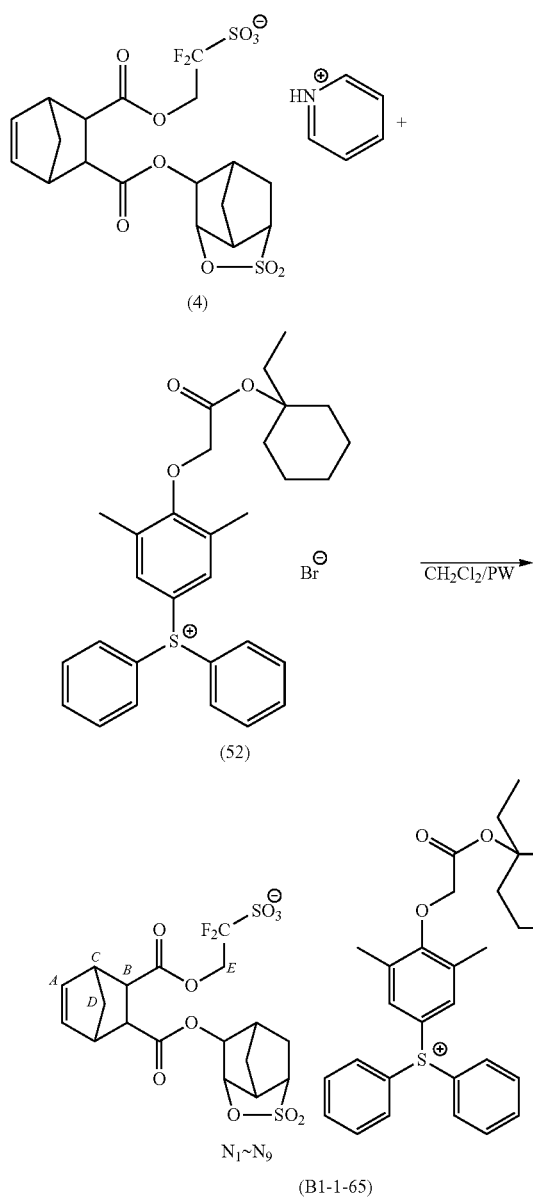

(B1-1-65)

Example 66

Synthesis of Compound (B1-1-66)

The same procedure as in iii) of Example 1 was performed, except that a compound (53) was used instead of 4-methylphenyldiphenylsulfonium bromide, thereby obtaining a compound (B1-1-66) in the form of a white solid.

The obtained compound (B1-1-66) was analyzed by $^1$H-NMR and $^{19}$F-NMR, and the structure thereof was identified by the following results.

$^1$H-NMR (400 MHz, DMSO-d6): δ (ppm)=8.44 (d, 1H, ArH), 8.22 (m, 2H, ArH), 7.89-7.73 (m, 13H, ArH), 7.50 (d, 1H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

[Chemical Formula 145.]

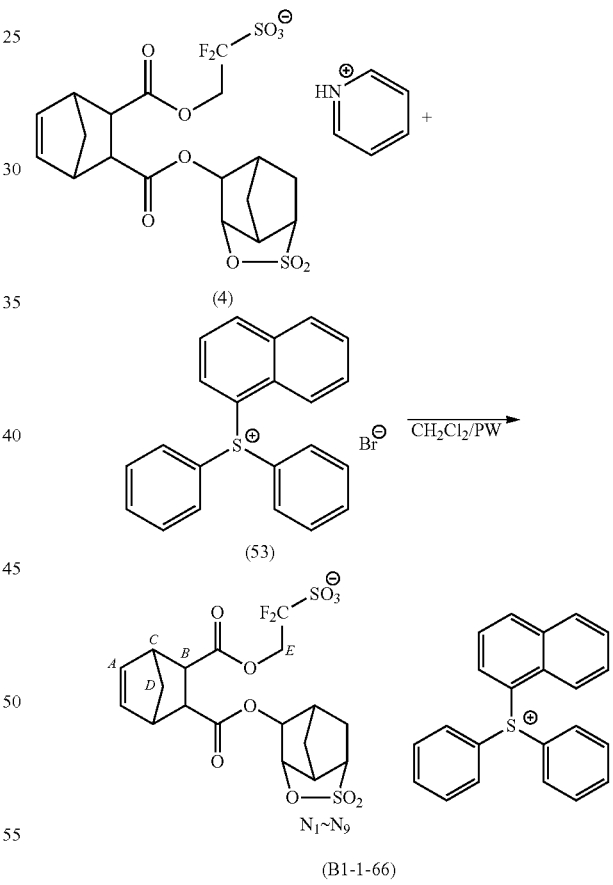

(B1-1-66)

Example 67

Synthesis of Compound (B1-1-67)

The same procedure as in iii) of Example 1 was performed, except that a compound (54) was used instead of 4-methylphenyldiphenylsulfonium bromide, thereby obtaining a compound (B1-1-67) in the form of a white solid.

The obtained compound (B1-1-67) was analyzed by ¹H-NMR and ¹⁹F-NMR, and the structure thereof was identified by the following results.

¹H-NMR (400 MHz, DMSO-d6): δ (ppm)=8.24 (d, 4H, ArH), 7.59 (t, 2H, ArH), 7.47 (t, 4H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

¹⁹F-NMR (376 MHz, DMSO-d6): δ (ppm)=−118.5-−118.9 (m, 2F)

[Chemical Formula 146.]

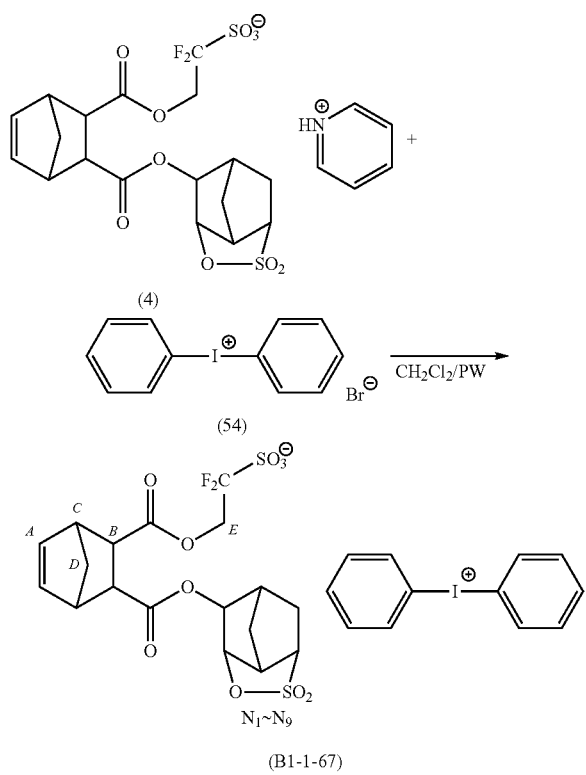

[Chemical Formula 147.]

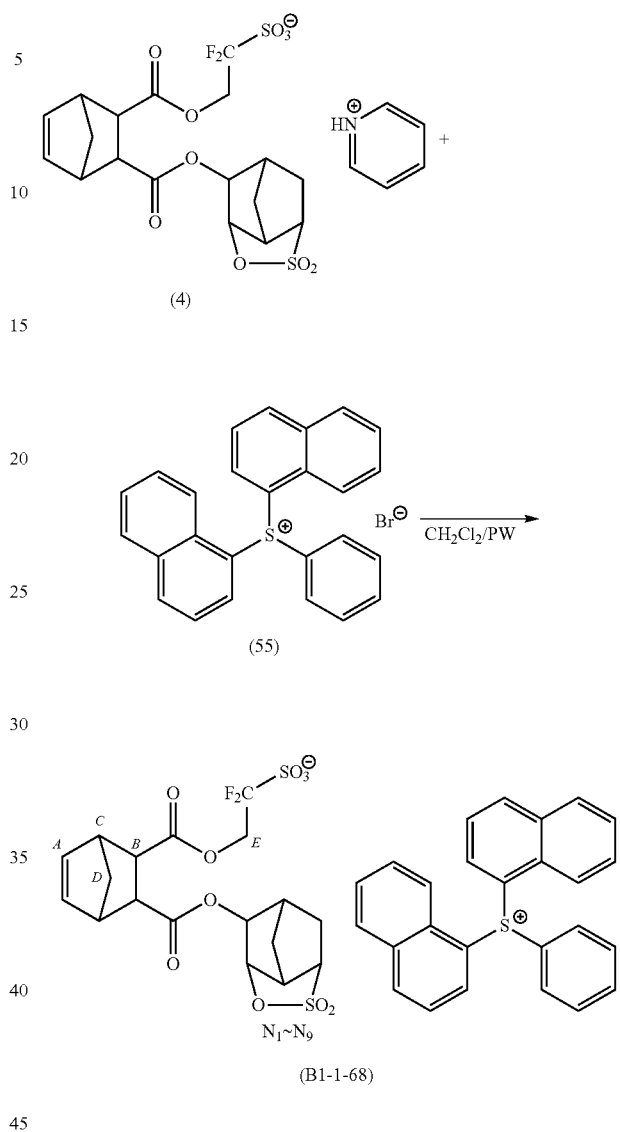

Example 68

Synthesis of Compound (B1-1-68)

The same procedure as in iii) of Example 1 was performed, except that a compound (55) was used instead of 4-methylphenyldiphenylsulfonium bromide, thereby obtaining a compound (B1-1-68) in the form of a white solid.

The obtained compound (B1-1-68) was analyzed by ¹H-NMR and ¹⁹F-NMR, and the structure thereof was identified by the following results.

¹H-NMR (400 MHz, DMSO-d6): δ (ppm)=8.55 (d, 2H, ArH), 8.38 (d, 2H, ArH), 8.32 (d, 2H, ArH), 8.03 (d, 2H, ArH), 7.97-7.93 (m, 1H, ArH), 7.88-7.82 (m, 8H, ArH), 7.55 (d, 2H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 2H, D)

¹⁹F-NMR (376 MHz, DMSO-d6): δ (ppm)=−118.5-−118.9 (m, 2F)

Example 69

Synthesis of Compound (B1-1-69)

The same procedure as in iii) of Example 1 was performed, except that a compound (56) was used instead of 4-methylphenyldiphenylsulfonium bromide, thereby obtaining a compound (B1-1-69) in the form of a white solid.

The obtained compound (B1-1-69) was analyzed by ¹H-NMR and ¹⁹F-NMR, and the structure thereof was identified by the following results.

¹H-NMR (400 MHz, DMSO-d6): δ (ppm)=6.22 (m, 1H, A), 6.07 (m, 1H, A'), 4.76 (m, 1H, N1), 4.65-4.34 (m, 5H, E+N2+CationCH2 (C=O)), 3.87 (m, 1H, N3), 3.59-3.36 (m, 7H, B+N4+CationSCH2), 3.11 (m, 2H, C), 2.37-1.56 (m, 26H, N5-9+Adamantane+CationCH2), 1.44-1.21 (m, 2H, D)

¹⁹F-NMR (376 MHz, DMSO-d6): δ (ppm)=−118.5-−118.9 (m, 2F)

[Chemical Formula 148.]

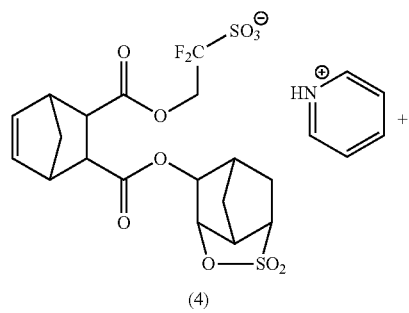

(4)

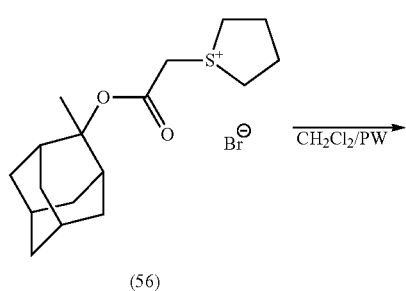

(56)

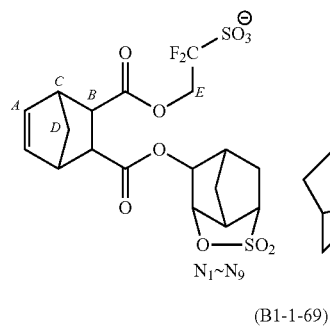

(B1-1-69)

Example 70

Synthesis of Compound (B1-1-70)

The same procedure as in iii) of Example 1 was performed, except that a compound (57) was used instead of 4-methylphenyldiphenylsulfonium bromide, thereby obtaining a compound (B1-1-70) in the form of a white solid.

The obtained compound (B1-1-70) was analyzed by $^{1}$H-NMR and $^{19}$F-NMR, and the structure thereof was identified by the following results.

$^{1}$H-NMR (400 MHz, DMSO-d6): δ (ppm)=7.75 (s, 2H, ArH), 6.22 (m, 1H, A), 6.07 (m, 1H, A'), 4.76 (m, 1H, N1), 4.65-4.34 (m, 3H, E+N2), 3.97-3.87 (m, 3H, N3+CationCH2), 3.79-3.72 (m, 2H, CationCH2), 3.58-3.38 (m, 3H, B+N4), 3.11 (m, 2H, C), 2.41-2.29 (m, 5H, N5+CationCH2), 2.19-1.64 (m, 25H, N6-9+CationCH3+Adamantane), 1.44-1.21 (m, 2H, D)

$^{19}$F-NMR (376 MHz, DMSO-d6): δ (ppm)=−118.5-−118.9 (m, 2F)

[Chemical Formula 149.]

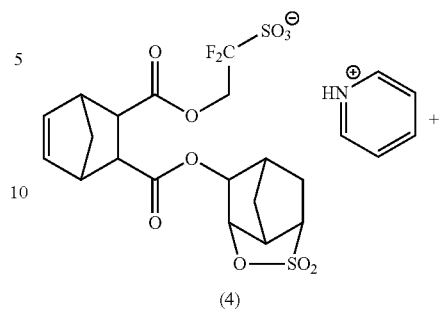

(4)

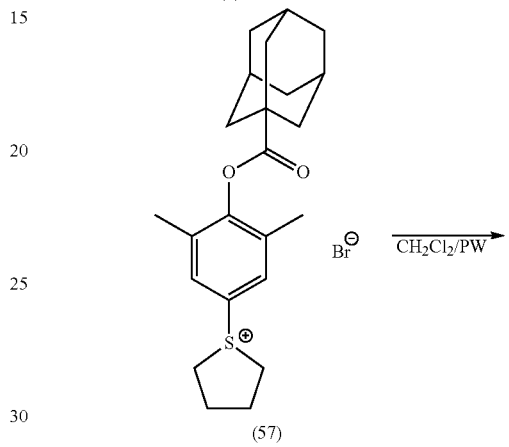

(57)

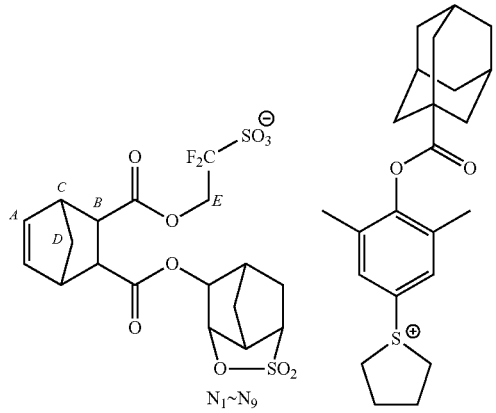

(B1-1-70)

Example 71

Synthesis of Compound (B1-1-71)

The same procedure as in iii) of Example 1 was performed, except that a compound (58) was used instead of 4-methylphenyldiphenylsulfonium bromide, thereby obtaining a compound (B1-1-71) in the form of a white solid.

The obtained compound (B1-1-71) was analyzed by $^{1}$H-NMR and $^{19}$F-NMR, and the structure thereof was identified by the following results.

$^{1}$H-NMR (400 MHz, DMSO-d6): δ (ppm)=7.82 (m, 2H, ArH), 6.22 (m, 1H, A), 6.07 (m, 1H, A'), 4.76 (m, 1H, N1), 4.65-4.34 (m, 3H, E+N2), 3.92-3.73 (m, 5H, N3+CationCH2), 3.58-3.38 (m, 3H, B+N4), 3.11 (m, 2H, C), 2.44-1.55 (m, 32H, N5-9+CationCH3+CationCH2+adamantane), 1.44-1.21 (m, 2H, D)

$^{19}$F-NMR (376 MHz, DMSO-d6): δ (ppm)=−118.5−−118.9 (m, 2F)

[Chemical Formula 150.]

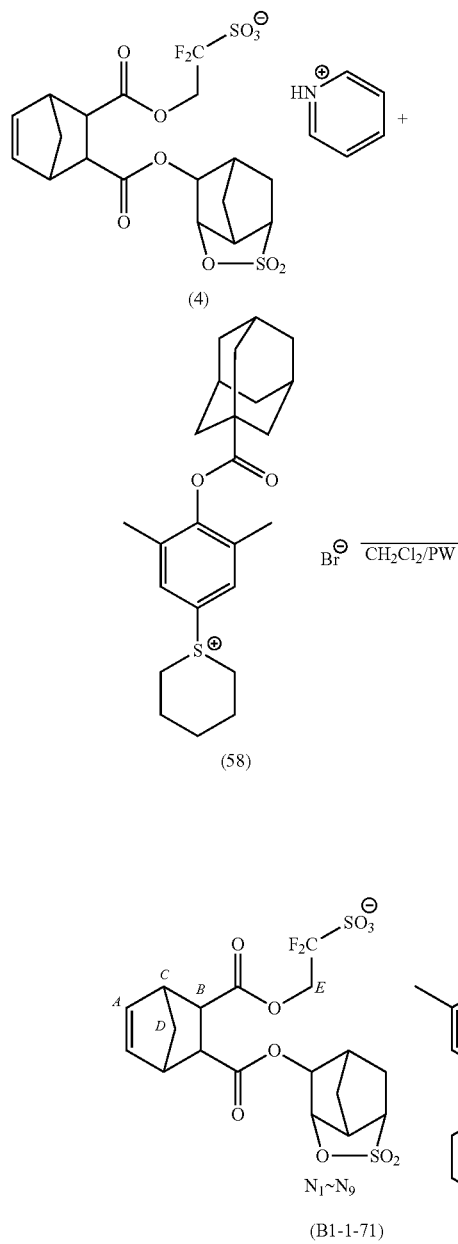

(B1-1-71)

Example 72

Synthesis of Compound (B1-1-72)

The same procedure as in iii) of Example 1 was performed, except that a compound (59) was used instead of 4-methylphenyldiphenylsulfonium bromide, thereby obtaining a compound (B1-1-72) in the form of a white solid.

The obtained compound (B1-1-72) was analyzed by $^1$H-NMR and $^{19}$F-NMR, and the structure thereof was identified by the following results.

$^1$H-NMR (400 MHz, DMSO-d6): δ (ppm)=8.23 (d, 4H, ArH), 7.98 (d, 4H, ArH), 6.22 (m, 1H, A), 6.07 (m, 1H, A'), 4.76 (m, 1H, N1), 4.65-4.34 (m, 3H, E+N2), 3.87 (m, 1H, N3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 20H, D+t-Butyl)

$^{19}$F-NMR (376 MHz, DMSO-d6): δ (ppm)=−118.5−−118.9 (m, 2F)

[Chemical Formula 151.]

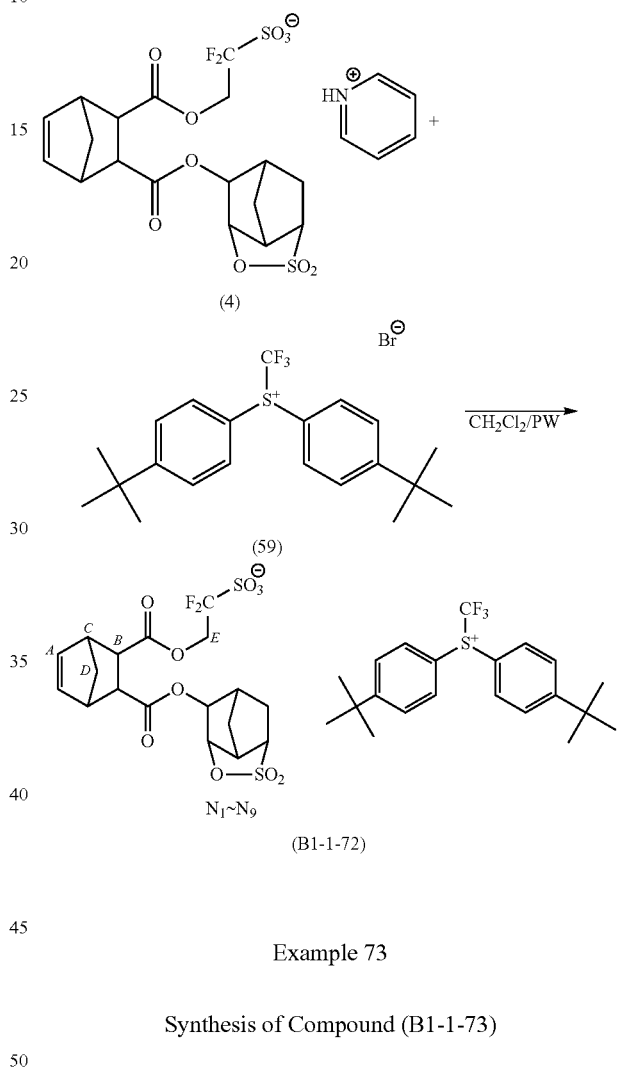

(B1-1-72)

Example 73

Synthesis of Compound (B1-1-73)

The same procedure as in iii) of Example 1 was performed, except that a compound (60) was used instead of 4-methylphenyldiphenylsulfonium bromide, thereby obtaining a compound (B1-1-73) in the form of a white solid.

The obtained compound (B1-1-73) was analyzed by $^1$H-NMR and $^{19}$F-NMR, and the structure thereof was identified by the following results.

$^1$H-NMR (400 MHz, DMSO-d6): δ (ppm)=7.98-7.77 (m, 10H, ArH), 7.64 (s, 2H, ArH), 6.22 (m, 1H, A), 6.07 (m, 1H, A'), 4.76 (m, 1H, N1), 4.65-4.34 (m, 5H, E+N2+CationCH2O), 3.87 (m, 1H, N3), 3.58-3.38 (m, 3H, B+N4), 3.11 (m, 2H, C), 2.41-2.34 (m, 7H, N5+CationCH3), 2.26-2.02 (m, 10H, N6+Adamantane), 1.89-1.66 (m, 9H, N7-9+Adamantane), 1.44-1.21 (m, 2H, D)

$^{19}$F-NMR (376 MHz, DMSO-d6): δ (ppm)=−118.5−−118.9 (m, 2F)

[Chemical Formula 152.]

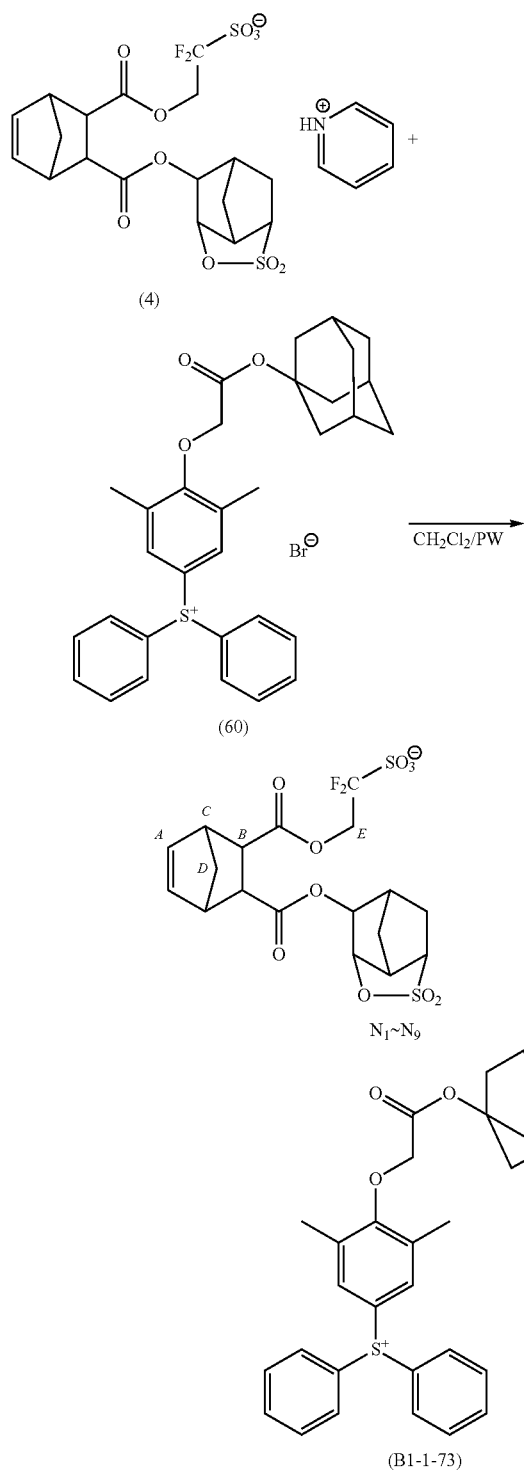

Example 74

Synthesis of Compound (B1-1-74)

The same procedure as in iii) of Example 1 was performed, except that a compound (61) was used instead of 4-methylphenyldiphenylsulfonium bromide, thereby obtaining a compound (B1-1-74) in the form of a white solid.

The obtained compound (B1-1-74) was analyzed by $^1$H-NMR and $^{19}$F-NMR, and the structure thereof was identified by the following results.

$^1$H-NMR (400 MHz, DMSO-d6): δ (ppm)=7.89-7.77 (m, 10H, ArH), 7.64 (s, 2H, ArH), 6.22 (m, 1H, A), 6.07 (m, 1H, A'), 5.70 (t, 1H, OCHC=O), 4.82-4.76 (m, 3H, N1+ArOCH2), 4.65-4.30 (m, 5H, E+N2+OCOCH2), 3.87 (m, 1H, N3), 3.58-3.38 (m, 3H, B+N4), 3.11 (m, 2H, C), 2.71-2.64 (m, 1H, OCH2CH2), 2.37-2.24 (m, 8H, N5+CationCH3+OCH2CH2), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5−−118.9 (m, 2F)

[Chemical Formula 153.]

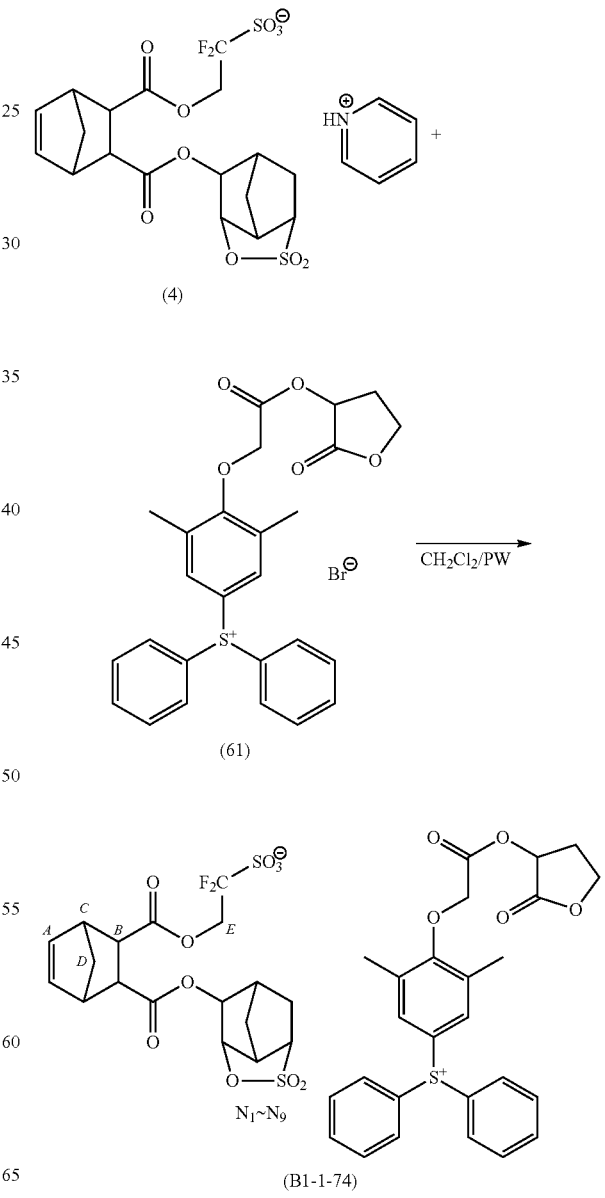

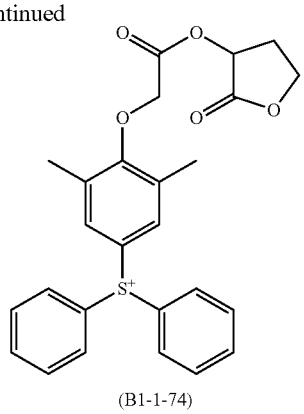

(B1-1-74)

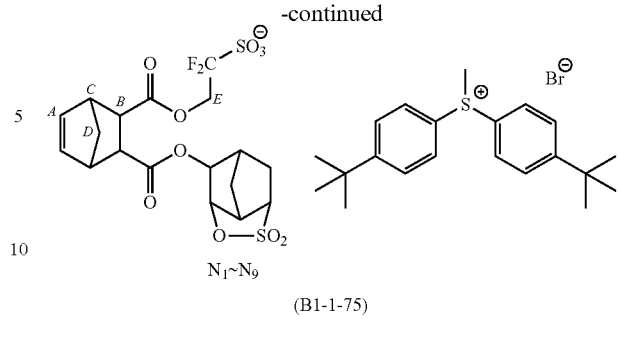

(B1-1-75)

Example 75

Synthesis of Compound (B1-1-75)

The same procedure as in iii) of Example 1 was performed, except that a compound (62) was used instead of 4-methylphenyldiphenylsulfonium bromide, thereby obtaining a compound (B1-1-75) in the form of a white solid.

The obtained compound (B1-1-75) was analyzed by $^1$H-NMR and $^{19}$F-NMR, and the structure thereof was identified by the following results. $^1$H-NMR (400 MHz, DMSO-d6): δ (ppm)=8.05 (d, 2H, ArH), 7.74 (d, 2H, ArH), 6.22 (m, 1H, A), 6.07 (m, 1H, A'), 4.76 (m, 1H, N1), 4.65-4.34 (m, 3H, E+N2), 3.89-3.84 (m, 4H, N3+S—CH3), 3.58-3.38 (m, 3H, B+N4), 3.11 (m, 2H, C), 2.37 (m, 1H, N5), 2.16 (m, 1H, N6), 1.89-1.66 (m, 3H, N7-9), 1.44-1.21 (m, 20H, D+t-Butyl)

$^{19}$F-NMR (376 MHz, DMSO-d6): δ (ppm)=−118.5−−118.9 (m, 2F)

Example 76

Synthesis of Compound (B1-1-76)

The same procedure as in iii) of Example 1 was performed, except that a compound (63) was used instead of 4-methylphenyldiphenylsulfonium bromide, thereby obtaining a compound (B1-1-76) in the form of a white solid.

The obtained compound (B1-1-76) was analyzed by $^1$H-NMR and $^{19}$F-NMR, and the structure thereof was identified by the following results.

$^1$H-NMR (400 MHz, DMSO-d6): δ (ppm)=8.41 (m, 2H ArH), 8.12 (d, 1H, ArH), 7.73-7.93 (m, 2H, ArH), 7.19 (d, 1H, ArH), 6.22 (m, 1H, A), 6.07 (m, 1H, A'), 5.23 (s, 2H, CationCH2), 4.95 (m, 1H, Adamantane), 4.76 (m, 1H, N1), 4.65-4.34 (m, 3H, E+N2), 4.03 (m, 2H, CH2S), 3.87 (m, 1H, N3), 3.75 (m, 2H, CH2S), 3.58-3.38 (m, 3H, B+N4), 3.11 (m, 2H, C), 2.43-2.25 (m, 5H, N5+CationCH2), 2.16 (m, 1H, N6), 1.99-1.21 (m, 19H, N7-9+D+Adamantane)

$^{19}$F-NMR (376 MHz, DMSO-d6): δ (ppm)=−118.5−−118.9 (m, 2F)

[Chemical Formula 154.]

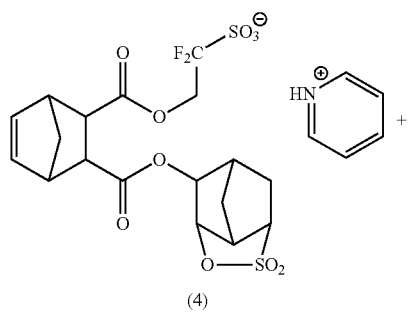

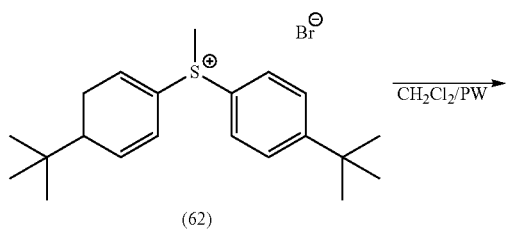

[Chemical Formula 155.]

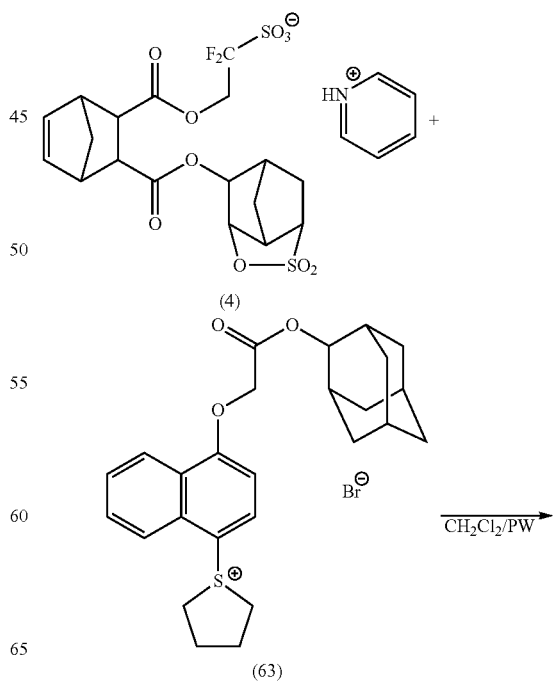

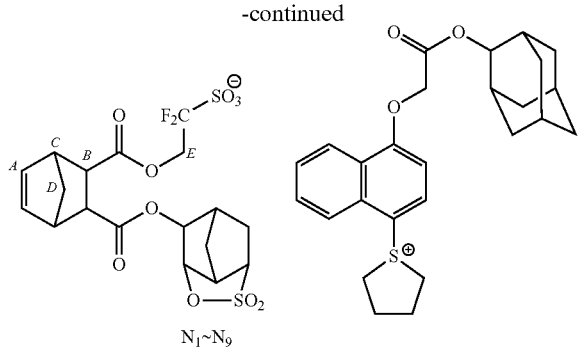

(B1-1-76)

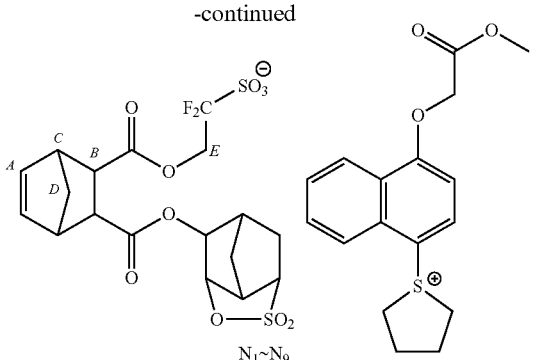

(B1-1-77)

Example 77

Synthesis of Compound (B1-1-77)

The same procedure as in iii) of Example 1 was performed, except that a compound (64) was used instead of 4-methylphenyldiphenylsulfonium bromide, thereby obtaining a compound (B1-1-77) in the form of a white solid.

The obtained compound (B1-1-77) was analyzed by $^1$H-NMR and $^{19}$F-NMR, and the structure thereof was identified by the following results.

$^1$H-NMR (400 MHz, DMSO-d6): δ (ppm)=8.42 (m, 2H ArH), 8.17 (d, 1H, ArH), 7.91-7.78 (m, 2H, ArH), 7.23 (d, 1H, ArH), 6.22 (m, 1H, A), 6.07 (m, 1H, A'), 5.26 (s, 2H, CationCH2), 4.76 (m, 1H, N1), 4.65-4.34 (m, 3H, E+N2), 4.19-3.75 (m, 8H, N3+SCH2+CationCH3), 3.58-3.38 (m, 3H, B+N4), 3.11 (m, 2H, C), 2.60-2.29 (m, 5H, N5+CationCH2), 2.16 (m, 1H, N6), 1.89-1.66 (m, 3H, N7-9), 1.44-1.21 (m, 2H, D)

$^{19}$F-NMR (376 MHz, DMSO-d6): δ (ppm)=−118.5-−118.9 (m, 2F)

[Chemical Formula 156.]

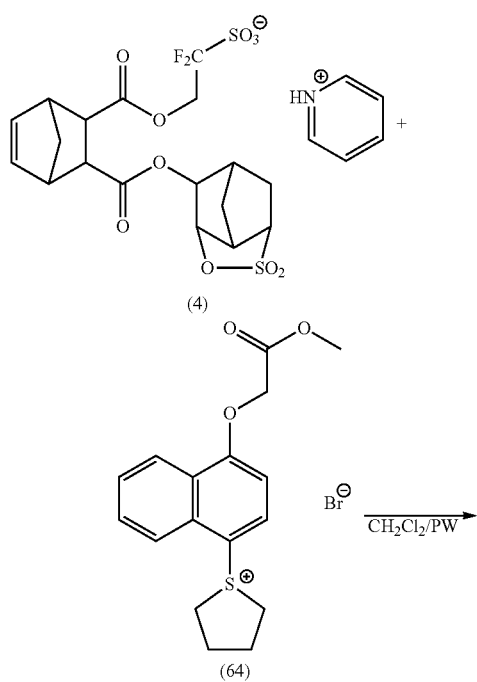

<Evaluation of Solubility of Compound in Organic Solvent>

Using the compounds and the organic solvents shown below, the solubility of a compound in an organic solvent was evaluated in the following manner.

Compound

The aforementioned compound (B1-1-1)

A compound (B2-3) represented by chemical formula shown below

[Chemical Formula 157.]

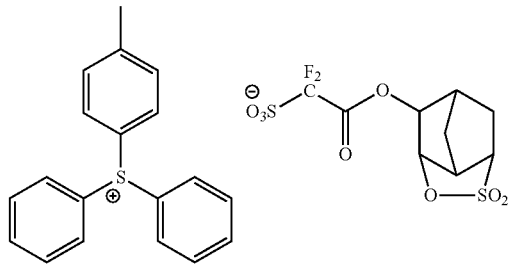

(B2-3)

Organic Solvent (S)-1: propylene glycol monomethyl ether (PGME)

(S)-2: propyleneglycol monomethyletheracetate (PGMEA).

(S)-3: cyclohexanone (S)-4: 4-Hydroxybutyric acid γ-lactone (S)-5: a mixed solvent of PGMEA/PGME=6/4 (weight ratio)

[Evaluation Method]

Each of the compound (B1-1-1) and the compound (B2-3) was added to each organic solvent, and whether or not it was dissolved at room temperature (23° C.) was confirmed. The results are shown in Table 1.

In Table 1, "10 wt %" indicates that a solution of the compound with a concentration of 10% by weight could be prepared. "3 wt %" indicates that a solution of the compound with a concentration of 3% by weight could be prepared. "<1 wt %" indicates that the compound could not be completely dissolved, and a solution of the compound with a concentration of 1% by weight could not be prepared.

TABLE 1

|   | Compound (B1-1-1) | Compound (B2-3) |
|---|---|---|
| (S)-1 | 10 wt % | <1 wt % |
| (S)-2 | <1 wt % | <1 wt % |
| (S)-3 | 10 wt % | 3 wt % |
| (S)-4 | 10 wt % | 10 wt % |
| (S)-5 | 10 wt % | <1 wt % |

From the results of Table 1, the compound (B1-1-1) exhibited excellent solubility in organic solvent (S)-1, (S)-3 and (S)-5, as compared to the compound (B2-3).

The reason why the compound (B1-1-1) exhibits such excellent solubility is presumed that, in the compound (B1-1-1), a divalent aliphatic group is introduced into the structure of the anion moiety.

Production of Resist Composition

Examples 78 to 81, Comparative Examples 3 and 4

The components shown in Table 2 were mixed together and dissolved to obtain positive resist compositions.

TABLE 2

|  | Component (A) | Component (B) | Component (D) | Component (E) | Component (S) | |
|---|---|---|---|---|---|---|
| Ex. 78 | (A)-1 [100] | (B)-1 [10.75] | (D)-1 [1.20] | (E)-1 [1.32] | (S)-6 [10.00] | (S)-5 [2120] |
| Comp. Ex. 3 | (A)-1 [100] | (B)-2 [10.42] | (D)-1 [1.20] | (E)-1 [1.32] | (S)-6 [10.00] | (S)-5 [2120] |
| Comp. Ex. 4 | (A)-1 [100] | (B)-3 [8.56] | (D)-1 [1.20] | (E)-1 [1.32] | (S)-6 [10.00] | (S)-5 [2120] |
| Ex. 79 | (A)-1 [100] | (B)-4 [10.28] | (D)-1 [1.20] | (E)-1 [1.32] | (S)-6 [10.00] | (S)-5 [2120] |
| Ex. 80 | (A)-1 [100] | (B)-5 [10.78] | (D)-1 [1.20] | (E)-1 [1.32] | (S)-6 [10.00] | (S)-5 [2120] |
| Ex. 81 | (A)-1 [100] | (B)-6 [10.31] | (D)-1 [1.20] | (E)-1 [1.32] | (S)-6 [10.00] | (S)-5 [2120] |

In Table 2, the reference characters indicate the following. Further, the values in brackets [ ] indicate the amount (in terms of parts by weight) of the component added.

(A)-1: a copolymer (A1-11-1) represented by chemical formula shown below Mw: 7,000, Mw/Mn: 1.80. In the chemical formula, the subscript numerals shown on the bottom right of the parentheses ( ) indicate the percentage (mol %) of the respective structural units.

[Chemical Formula 158.]

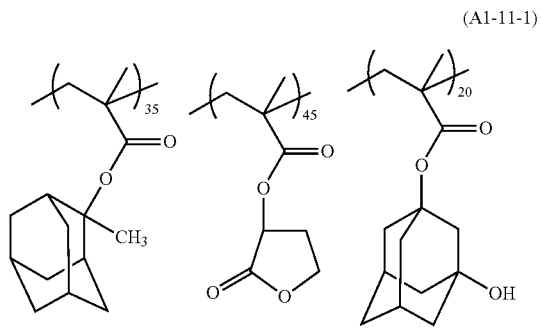

(A1-11-1)

(B)-1: the aforementioned compound (B1-1-1)
(B)-2: the aforementioned compound (B2-1)
(B)-3: the aforementioned compound (B2-2)
(B)-4: the aforementioned compound (B1-1-2)
(B)-5: the aforementioned compound (B1-1-3)
(B)-6: the aforementioned compound (B1-1-4)
(D)-1: tri-n-pentylamine
(E)-1: salicylic acid
(S)-6: γ-butyrolactone
(S)-5: a mixed solvent of PGMEA/PGME=6/4 (weight ratio)

<Evaluation of Lithography Properties and Shape of Resist Pattern>

Using the obtained positive resist compositions, resist patterns were formed in the following manner, and the following evaluations were conducted.

[Formation of Resist Pattern]

An organic anti-reflection film composition (product name: ARC-29A, manufactured by Brewer Science Ltd.) was applied to an 8-inch silicon wafer using a spinner, and the composition was then baked at 205° C. for 60 seconds, thereby forming an organic anti-reflection film having a film thickness of 82 nm.

Then, each positive resist composition was applied to the anti-reflection film using a spinner, and was then prebaked (PAB) on a hotplate at 110° C. for 60 seconds and dried, thereby forming a resist film having a film thickness of 150 nm.

Subsequently, the resist film was selectively irradiated with an ArF excimer laser (193 nm) through a mask pattern, using an ArF exposure apparatus NSR-5302A (manufactured by Nikon Corporation; NA (numerical aperture)=0.60, 2/3 annular illumination).

Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was washed for 30 seconds with pure water, followed by drying by shaking.

As a result, in each of the examples, a space and line resist pattern (hereafter, referred to as "SL pattern") in which spaces having a space width of 120 nm were provided at equal intervals (pitch: 240 nm) was formed on the resist film.

The optimum exposure dose Eop (mJ/cm$^2$) with which the SL pattern was formed was determined. The results are shown in Table 3.

[Evaluation of Line Width Roughness (LWR)]

LS patterns having a space width of 120 nm and a pitch of 240 nm were formed with the above Eop in the same manner as described above, and the space width at 400 points in the lengthwise direction of the space were measured using a measuring scanning electron microscope (SEM) (product name: S-9220, manufactured by Hitachi, Ltd.; acceleration voltage: 800V). From the results, the value of 3 times the standard deviation s (i.e., 3s) was determined, and the average of the 3s values at 5 points was calculated as a yardstick of LWR. The results are shown in Table 3.

The smaller this 3s value is, the lower the level of roughness of the line width, indicating that a SL pattern with a uniform width was obtained.

[Evaluation of Mask Error Factor (MEF)]

In the same manner as described above, with the above Eop, SL patterns were formed using a mask pattern targeting a space width of 120 nm and a pitch of 260 nm, and a mask pattern targeting a space width of 130 nm and a pitch of 260 nm, and the MEF value was calculated by the following formula. The results are shown in Table 3.

$$MEF = |CD_{130} - CD_{120}| / |MD_{130} - MD_{120}|$$

In the formula, $CD_{130}$ and $CD_{120}$ represent the respective space widths (nm) of the actual SL patterns respectively formed using the mask pattern targeting a space width of 130 nm and the mask pattern targeting a space width of 120 nm. $MD_{130}$ and $MD_{120}$ represent the respective target space widths (nm), meaning $MD_{130} = 130$, and $MD_{120} = 120$.

A MEF value closer to 1 indicates that a resist pattern faithful to the mask pattern was formed.

[Evaluation of Exposure Latitude (EL Margin)]

The exposure dose with which an SL pattern having a dimension of the target dimension (space width: 120 nm)±5% (i.e., 114 nm to 126 nm) was determined, and the EL margin (unit: %) was determined by the following formula. The results are shown in Table 3.

$$EL\ margin\ (\%) = (|E1 - E2| / Eop) \times 100$$

E1: Exposure dose (mJ/cm$^2$) with which an SL pattern having a space width of 114 nm was formed E2: Exposure dose (mJ/cm$^2$) with which an SL pattern having a line width of 126 nm was formed The larger the value of the "EL margin", the smaller the change in the pattern size by the variation of the exposure dose.

TABLE 3

|  | Ex. 78 | Comp. Ex. 3 | Comp. Ex. 4 | Ex. 79 | Ex. 80 | Ex. 81 |
|---|---|---|---|---|---|---|
| Eop (mJ/cm$^2$) | 57.5 | 48.3 | 39.9 | 55.0 | 54.1 | 53.1 |
| LWR (nm) | 9.3 | 11.6 | 12.2 | 9.6 | 10.1 | 10.3 |
| MEF | 1.58 | 2.30 | 2.35 | 1.78 | 1.74 | 1.82 |
| EL margin (%) | 9.14 | 7.74 | 7.29 | 8.81 | 8.77 | 8.56 |

As seen from the results shown in Table 3, as compared to the resist compositions of Comparative Examples 3 and 4, the resist compositions of Examples 78 to 81 exhibited excellent lithography properties such as LWR, MEF and EL margin, and a resist pattern having an excellent shape with reduced roughness could be formed.

Production of Resist Composition

Example 82, Comparative Examples 5 and 6

The components shown in Table 4 were mixed together and dissolved to obtain positive resist compositions.

TABLE 4

|  | Component (A) | Component (B) | | Component (E) | Component (F) | Component (S) | |
|---|---|---|---|---|---|---|---|
| Ex. 82 | (A)-2 [100] | (B)-7 [11.06] | (B)-10 [3.4] | (E)-1 [0.25] | (F)-1 [3.0] | (S)-6 [25] | (S)-5 [2400] |
| Comp. Ex. 5 | (A)-2 [100] | (B)-8 [8.91] | (B)-10 [3.4] | (E)-1 [0.25] | (F)-1 [3.0] | (S)-6 [25] | (S)-5 [2400] |
| Comp. Ex. 6 | (A)-2 [100] | (B)-9 [9.4] | (B)-10 [3.4] | (E)-1 [0.25] | (F)-1 [3.0] | (S)-6 [25] | (S)-5 [2400] |

In Table 4, the reference characters indicate the following. Further, the values in brackets [ ] indicate the amount (in terms of parts by weight) of the component added. (E)-1, (S)-5 and (S)-6 are the same as defined above. Further, the values in brackets [ ] indicate the amount (in terms of parts by weight) of the component added.

(A)-2: polymeric compound (A)-2 shown below (B)-7: the aforementioned compound (B1-1-5)

(B)-8: the aforementioned compound (B2-3)

(B)-9: compound (B)-9 shown below (B)-10: triphenylsulfonium d-camphor-10-sulfonate (F)-1: polymeric compound (F)-1 shown below

[Chemical Formula 159.]

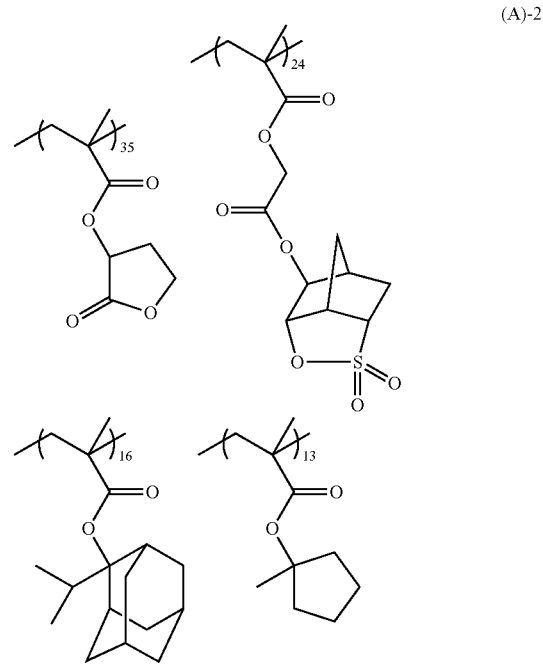

(A)-2

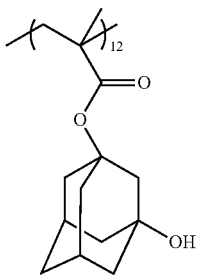

[Mw=6,900, Mw/Mn=1.61, the subscript numerals shown to the bottom right of the parentheses ( ) indicate the percentage (mol %) of the respective structural units within the copolymer.]

[Chemical Formula 160.]

(B)-9

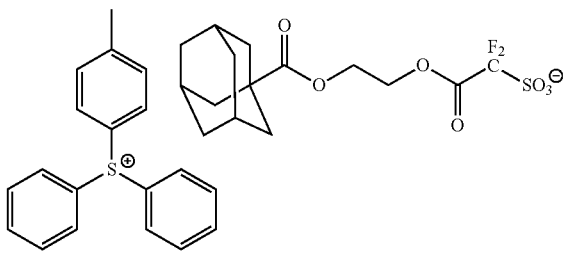

[Chemical Formula 161.]

(F)-1

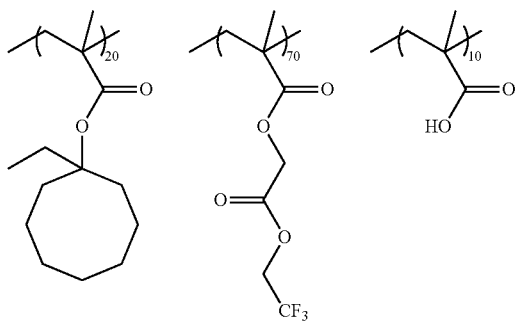

[Mw=20,000, Mw/Mn=1.5, the subscript numerals shown to the bottom right of the parentheses ( ) indicate the percentage (mol %) of the respective structural units within the copolymer.]

[Formation of Resist Pattern by Immersion Exposure]

An organic anti-reflection film composition (product name: ARC95, manufactured by Brewer Science Ltd.) was applied to an 12-inch silicon wafer using a spinner, and the composition was then baked at 205° C. for 90 seconds, thereby forming an organic anti-reflection film having a film thickness of 90 nm.

Then, each of the resist compositions of Example 82 and Comparative Examples 5 and 6 was applied to the organic anti-reflection film using a spinner, and was then prebaked (PAB) on a hotplate at 120° C. for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)=1.07, Crosspole w/POLANO; immersion medium: water).

Thereafter, a post exposure bake (PEB) treatment was conducted at 85° C. for 60 seconds, followed by alkali development for 40 seconds at 23° C. in a 2.38% by weight aqueous solution of tetramethylammonium hydroxide (TMAH). Then, the resist was washed for 30 seconds with pure water, followed by drying by shaking.

As a result, in each of the examples, a 1:1 line and space pattern (LS pattern) having a line width of 55 nm was formed.

The optimum exposure dose Eop (mJ/cm$^2$; sensitivity) with which the LS pattern was formed was determined. The results are shown in Table 5.

The LWR was evaluated in the same manner as described above. The results are shown in Table 5. EL and MEF were evaluated as follows. The results are shown in Table 5.

[EL]

55 nm LS patterns were formed in the same manner as described above, except that the exposure dose was changed at constant intervals. Then, a graph was plotted by taking the exposure dose on the horizontal axis and the size of the formed line on the vertical axis, and the gradient was determined by linear regression. Further, the absolute value of a value obtained by dividing the gradient by the Eop was determined, and the change in size per 1 mJ/cm$^2$ was determined. The smaller this value is, the smaller the influence by the variation in the exposure dose. In Table 5, the results are indicated under "EL".

[MEF]

With respect to the 55 nm LS patterns, with the above Eop, LS patterns with a pitch of 110 nm were formed using a mask pattern targeting a line pattern size of 50 to 60 nm (11 target sizes at intervals of 1 nm). The value of the mask error factor was determined as the gradient of a graph obtained by plotting the target size (nm) on the horizontal axis, and the actual diameter (nm) of the formed patterns on the vertical axis. A MEF value (gradient of the plotted line) closer to 1 indicates that a resist pattern faithful to the mask pattern was formed.

TABLE 5

|  | Eop (mJ/cm$^2$) | EL (nm/(mJ/cm$^2$)) | LWR (nm) | MEF |
|---|---|---|---|---|
| Ex. 82 | 36.4 | 1.49 | 4.37 | 2.52 |
| Comp. Ex. 5 | 28.3 | 1.90 | 4.59 | 2.63 |
| Comp. Ex. 6 | 22.4 | 2.86 | 4.94 | 3.03 |

Production of Resist Composition

Example 83, Comparative Example 7

The components shown in Table 6 were mixed together and dissolved to obtain positive resist compositions.

TABLE 6

|  | Component (A) | Component (B) | Component (D) | Component (E) | Component (S) | EL margin (%) |
|---|---|---|---|---|---|---|
| Ex. 83 | (A)-3 [100] | (B)-11 [46.0] | (D)-2 [2.0] | (E)-1 [0.8] | (S)-5 [3000] | 14 |
| Comp. Ex. 7 | (A)-3 [100] | (B)-12 [39.2] | (D)-2 [2.0] | (E)-1 [0.8] | (S)-5 [3000] | 8 |

In Table 6, the reference characters indicate the following. Further, the values in brackets [ ] indicate the amount (in terms of parts by weight) of the component added. (E)-1, (S)-5 and (S)-6 are the same as defined above. Further, the values in brackets [ ] indicate the amount (in terms of parts by weight) of the component added.
(A)-3: polymeric compound (A)-3 shown below
(B)-11: the aforementioned compound (B1-1-6)
(B)-12: compound (B)-12 shown below
(D)-2: tri-n-octylamine.

[Chemical Formula 162.]

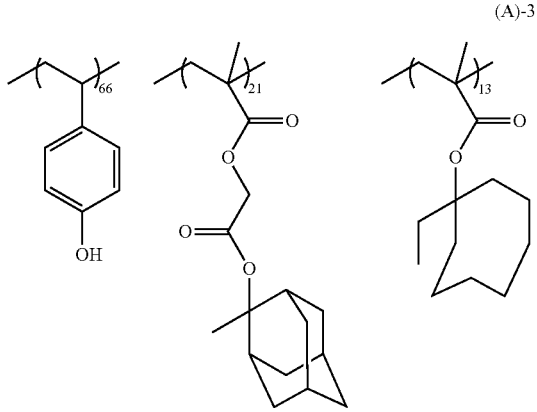

[Mw=7,000, Mw/Mn=1.7, the subscript numerals shown to the bottom right of the parentheses ( ) indicate the percentage (mol %) of the respective structural units within the copolymer.]

[Chemical Formula 163.]

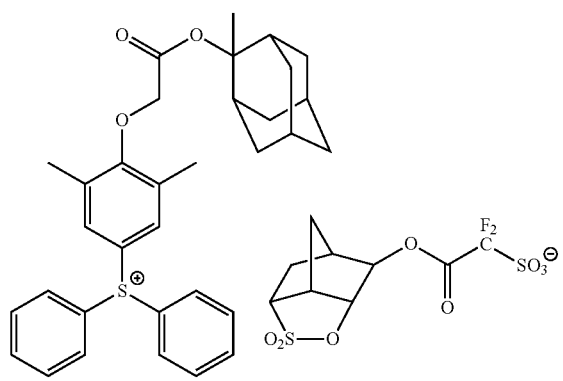

[Formation of Resist Pattern by EB Exposure]

Using a spinner, each resist composition of Example 83 and Comparative Example 7 was uniformly applied to an 8-inch silicon wafer that had been treated with hexamethyldisilazane (HMDS) at 90° C. for 36 seconds, and a bake treatment (PAB) was conducted at 100° C. for 60 seconds, thereby forming a resist film (film thickness: 100 nm). Subsequently, the resist film was subjected to drawing (exposure) using an electron beam lithography apparatus HL-800D (VSB) (manufactured by Hitachi, Ltd.), followed by a bake treatment (PEB) at 90° C. for 60 seconds. Then, development was conducted with a 2.38 wt % aqueous tetramethylammonium hydroxide (TMAH) solution (product name: NMD-3; manufactured by Tokyo Ohka Kogyo Co., Ltd.) at 23° C. for 60 seconds.

As a result, in each of the examples, a space and line pattern (SL pattern) having a space width of 50 nm and a pitch of 200 nm was formed.

Further, the ±10% EL margin (unit: %) was determined in the same manner as in [Evaluation of exposure latitude (EL margin)] described above. The results are shown in Table 6.

From the results shown in Tables 5 and 6, it can be seen that the resist composition of the present invention also exhibits excellent lithography properties in immersion exposure and EB exposure.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising a base component (A) which exhibits changed solubility in an alkali developing solution under action of acid and an acid-generator component (B) which generates acid upon exposure, the acid-generator component (B) comprising an acid generator (B1) comprising a compound represented by general formula (b1-1) shown below:

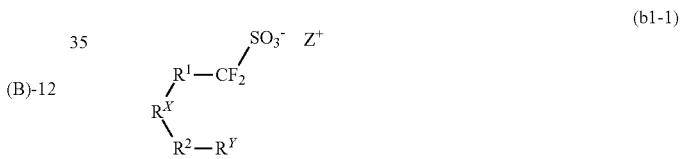

wherein $R^X$ represents a group selected from the group consisting of groups represented by the formulas shown below:

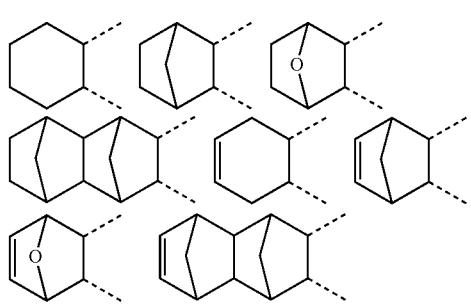

$R^Y$ represents a monovalent aliphatic group of 3 to 20 carbon atoms containing —S(=O)$_2$—; $R^1$ represents —C(=O)—O—$R^{92}$— ($R^{92}$ represents an alkylene group); $R^2$ represents —C(=O)—O—; and $Z^+$ represents a monovalent organic cation.

2. The resist composition according to claim 1, wherein $Z^+$ in general formula (b1-1) is an organic cation represented by general formula (b1-c1) shown below or general formula (b1-c2) shown below:

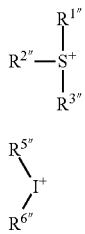

(b1-c1)

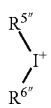

(b1-c2)

wherein each of $R^{1''}$ to $R^{3''}$, $R^{5''}$ and $R^{6''}$ independently represents an aryl group, alkyl group or alkenyl group which may have a substituent, provided that at least one of $R^{1''}$ to $R^{3''}$ represents an aryl group, and at least one of $R^{5''}$ and $R^{6''}$ represents an aryl group, and two of $R^{1''}$ to $R^{3''}$ may be mutually bonded to form a ring with the sulfur atom.

3. The resist composition according to claim 1, wherein the amount of the acid generator (B1), relative to 100 parts by weight of the base component (A) is within the range of 0.5 to 50 parts by weight.

4. The resist composition according to claim 1, wherein the base component (A) is a base component which exhibits increased solubility in an alkali developing solution under action of acid.

5. A method of forming a resist pattern, comprising: forming a resist film using a resist composition of claim 1; conducting exposure of the resist film; and alkali-developing the resist film to form a resist pattern.

6. The resist composition according to claim 1, wherein, in the general formula (b1-1), $R^Y$ represents a group selected from the group consisting of groups represented by the formulas shown below:

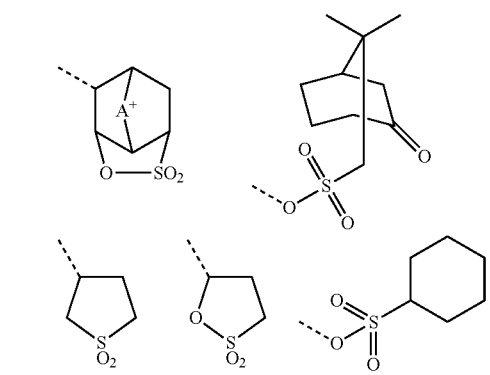

wherein A' represents an oxygen atom (—O—), a sulfur atom (—S—), or an alkylene group of 1 to 5 carbon atoms which contains an oxygen atom or a sulfur atom.

* * * * *